(12) United States Patent
Ohlmeyer et al.

(10) Patent No.: US 10,759,790 B2
(45) Date of Patent: *Sep. 1, 2020

(54) HETEROCYCLIC CONSTRAINED TRICYCLIC SULFONAMIDES AS ANTI-CANCER AGENTS

(71) Applicant: ICAHN SCHOOL OF MEDICINE AT MOUNT SINAI, New York, NY (US)

(72) Inventors: Michael Ohlmeyer, Plainsboro, NJ (US); Nilesh Zaware, Briarwood, NY (US)

(73) Assignee: Ichan School of Medicine at Mount Sinai, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/758,045

(22) PCT Filed: Sep. 8, 2016

(86) PCT No.: PCT/US2016/050688
§ 371 (c)(1),
(2) Date: Mar. 7, 2018

(87) PCT Pub. No.: WO2017/044569
PCT Pub. Date: Mar. 16, 2017

(65) Prior Publication Data
US 2018/0251456 A1    Sep. 6, 2018

Related U.S. Application Data

(60) Provisional application No. 62/216,172, filed on Sep. 9, 2015.

(51) Int. Cl.
| | | |
|---|---|---|
| C07D 413/04 | (2006.01) | |
| C07D 413/14 | (2006.01) | |
| C07D 401/04 | (2006.01) | |
| C07D 498/04 | (2006.01) | |
| C07D 403/04 | (2006.01) | |
| C07D 405/04 | (2006.01) | |

(52) U.S. Cl.
CPC ......... *C07D 413/04* (2013.01); *C07D 401/04* (2013.01); *C07D 403/04* (2013.01); *C07D 405/04* (2013.01); *C07D 413/14* (2013.01); *C07D 498/04* (2013.01)

(58) Field of Classification Search
CPC .................................................. C07D 413/04
See application file for complete search history.

(56) References Cited

U.S. PATENT DOCUMENTS

| | | |
|---|---|---|
| 4,634,766 A | 1/1987 | Atkinson et al. |
| 4,668,671 A | 5/1987 | Gribble et al. |
| 4,882,351 A | 11/1989 | Oshima et al. |
| 6,583,138 B1 | 6/2003 | Miyamoto et al. |
| 9,540,358 B2 | 1/2017 | Ohlmeyer et al. |
| 9,937,186 B2 * | 4/2018 | Ohlmeyer ............. C07C 311/29 |
| 2002/0103189 A1 | 8/2002 | Miyamoto et al. |
| 2008/0275023 A1 | 11/2008 | Guidi et al. |
| 2015/0376191 A1 | 12/2015 | Ohlmeyer et al. |
| 2017/0015625 A1 | 1/2017 | Ohlmeyer et al. |
| 2017/0015630 A1 | 1/2017 | Ohlmeyer et al. |

FOREIGN PATENT DOCUMENTS

| | | |
|---|---|---|
| CN | 102942562 A | 2/2013 |
| EA | 15779 B1 | 12/2011 |
| EP | 0679641 A1 | 11/1995 |
| EP | 0881220 A1 | 12/1998 |
| EP | 1481673 A1 | 12/2004 |
| WO | 2002/024657 A2 | 3/2002 |
| WO | 2004052847 A2 | 6/2004 |
| WO | 2006/066879 A2 | 6/2006 |

(Continued)

OTHER PUBLICATIONS

Silverman, R.B. The Organic Chemistry of Drug Design and Drug Action 1992, Academic: New York, p. 19.*

(Continued)

*Primary Examiner* — David K O'Dell
(74) *Attorney, Agent, or Firm* — Heslin Rothenberg Farley & Mesiti P.C.

(57) ABSTRACT

A genus of arylsulfonamide derivatives of heterocyclic constrained tricyclic compounds is disclosed. The compounds are of the following genus:

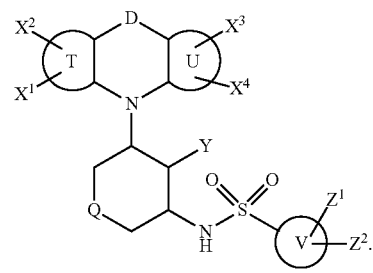

The compounds induce FOXO1 transcription factor translocation to the nucleus by modulating PP2A and, as a consequence, exhibit anti-proliferative effects. They are useful in the treatment of a variety of disorders, including as a therapy in cancer treatment, or used in combination with other drugs to restore sensitivity to chemotherapy where resistance has developed.

20 Claims, No Drawings

(56) References Cited

FOREIGN PATENT DOCUMENTS

| WO | 2006116157 A2 | 11/2006 |
|---|---|---|
| WO | 2006117183 A1 | 11/2006 |
| WO | 2008/121859 A1 | 10/2008 |
| WO | 2013025882 A2 | 2/2013 |
| WO | 2014031986 A1 | 2/2014 |
| WO | 2014130534 A1 | 8/2014 |
| WO | 2015/138500 A1 | 9/2015 |
| WO | 2015138496 A1 | 9/2015 |
| WO | 2015138500 A1 | 9/2015 |
| WO | 2017/024229 A1 | 2/2017 |
| WO | 2017/044567 A1 | 3/2017 |
| WO | 2017/044571 A1 | 3/2017 |
| WO | 2017/044572 A1 | 3/2017 |
| WO | 2017/044575 A1 | 3/2017 |

OTHER PUBLICATIONS

International Search Report & Written Opinion issued in PCT/US2016/050688, dated Oct. 26, 2016.
International Search Report & Written Opinion issued in PCT/US2015/019770, dated May 8, 2015.
RN 1350122-38-1 CAS Registry, entered STN: Dec. 7, 2011.
Extended EP Search Report for EP 12823881.3 dated Mar. 3, 2015.
International Search Report for PCT/US2012/051097 dated Feb. 20, 2013.
International Search Report for PCT/US2014/017127 dated May 20, 2014.
Alfredsson et al., "Mass Fragmentographic Analysis of Clomipramine and Its Mono-Demethylated Metabolite in Human Plasma" Psychopharmacology, 52, 25-30 (1977).
Midgley et al., "Synthesis of [13C$_2$]-Amitriptyline, Nortriptyline and Desmethynortriptyline" Journal of Labelled Compounds and Radiopharmaceuticals, vol. XV, pp. 511-521 (1978).
Hadrich et al., "Synthesis and Characterization of Fluorescent Ligands for the Norepinephrine Transporter: Potential Neuroblastoma Imaging Agents", Journal of Medicinal Chemistry, American Chemical Society, US, vol. 42, No. 16, Jul. 16, 1999 (Jul. 16, 1999), pp. 3101-3108, XP003003932, ISSN: 0022-2623, DOI: 10.1021/JM9811155.
Runyon et al., "Influence of Chain Length and N-Alkylation on the Selective Serotonin Receptor Ligand 9-(Aminomethyl)-9,10-dihydroanthracene", Bioorganic & Medicinal Chemistry Letters 11 (2001), 655-658.
Van Dort et al., Synthesis of $^{11}$C-Labeled Desipramine and its Metabolite 2-Hydroxydesipramine: Potential Radiotracers for PET Studies of the Norepinephrine Transporter, Nuclear Medicine & Biology, vol. 24, pp. 707-711, 1997.
Ilies et al., "Protease Inhibitors: Synthesis of Bacterial Collagenase and Matrix Metalloproteinase Inhibitors Incorporating Arylsulfonylureido and 5-Dibenzo-suberenyl/suberyl Moieties", Bioorganic & Medicinal Chemistry, 11 (2003) 2227-2239.
Yang et al., "Catalytic decarboxylative alkylation of B-keto acids with sulfonamides via the cleavage of carbon-nitrogen and carbon-carbon bonds," Chemical Communications, 2011 (published on Web: Jun. 22, 2011), vol. 47, No. 29, pp. 8343-8345.
Azuine et al., "Cancer chemopreventive effect of phenothiazines and related tri-heterocyclic analogues in the 12-0-tetradecanoylphorbol-13-acetate promoted Epstein-Barr virus early antigen activation and the mouse skin two-stage carcinogenes is models," Pharmacological Research, 2004, vol. 49, No. 2, pp. 161-169.
Ohshima, et al., "Non-Prostanoid Thromboxane A$_2$ Receptor Antagonists with a Dibenzoxepin Ring System. 2" J. Med. Chem, 1992, 35, 3402-3413.
Morak-Mlodawska et al., "Acyl and Sulfonyl Derivatives of 10-Aminoalkyl-2,7-Diazaphenothiazines#, Heterocycles", vol. 78, No. 5, 2009 pp. 1289-1298.
Alfonso et al., "Synthesis of a $C_{11}$ Spiropiperidino derivative of 8-Chloro-6,11-dihydro 5H-Benzo [5,6]cyclohepta[1,2-b]pyridine", Tetrahedron Letters 39, 1998, 7661-7664.
Kau et al., A chemical genetic screen identifies inhibitors of regulated nuclear export of a Forkhead transcription factor in PTEN-deficient tumor cells, Cancer Cell, XP008037524, Dec. 2003, pp. 463-476.
Jelen et al., "Synthesis of 6-Aminoalkyldiquino-1,4-Thiazines and Their Acyl and Sulfonyl Derivatives, Heterocycles", vol. 4, No. 4, XP055279565, 2008, pp. 859-870.
Pluta et al., "Anticancer activity of newly synthesized azaphenothiazines from NCI's anticancer screening bank#", Pharmaceutical Reports, 2010, 62, 319-332.
Motohashi et al., "Synthesis and Biological Activity of N-acylphenothiazines" International Journal of Antimicrobial Agents, 2000, pp. 203-207, vol. 14.
Database PubChemCompound, "N-[4-methoxy-3-(3-phenothiazin-l0-ylpropylsulfamoyl)phenyl]acetamide," URL: http://pubchem.ncbi.nlm.nih.gov/search/search.cgi, 2005-2009.
International Search Report for PCT/US2015/019764 dated May 8, 2015.
International Search Report for PCT/US2016/050685 dated Oct. 18, 2016.
International Search Report for PCT/US2016/050688 dated Oct. 18, 2016.
International Search Report for PCT/US2016/045779 dated Sep. 30, 2016.
International Search Report for PCT/US2016/050690 dated Oct. 18, 2016.
International Search Report for PCT/US2016/050696 dated Oct. 18, 2016.
International Search Report for PCT/US2016/050692 dated Oct. 18, 2016.
O'Brien et al., "cis- and trans-Stereoselective Epoxidation of N-protected 2-Cyclohexen-1-ylamines," Organic Letters, 2003, 14(23), 6012-6015.
Zhang et al., "Akt, FoxO and regulation of apoptosis" Biochimica et Biophysica Acta, 2011, vol. 1813, pp. 1978-1986.
Seidlova et al. "Neurotropic and psychotropic substances. XIII. Contributions to the synthesis of amitriptyline, nortriptyline and related substances," Protein Enginee, Oxford University Press, Surrey, GB, vol. 32, No. 8, Jan. 1, 1967, pp. 2826-2839. (In German).

* cited by examiner

HETEROCYCLIC CONSTRAINED TRICYCLIC SULFONAMIDES AS ANTI-CANCER AGENTS

CROSS REFERENCE TO RELATED APPLICATIONS

This application is a U.S. National Phase filing under 35 U.S.C. § 371 of International Application PCT/US2016/050688, filed Sep. 8, 2016, and published as WO 2017/044569 on Mar. 16, 2017. PCT/US2016/050688 claims priority of U.S. provisional application 62/216,172, filed Sep. 9, 2015. The entire contents of each of the prior applications are incorporated herein by reference.

FIELD OF THE INVENTION

The invention relates to the use of tricyclic chemical modulators of PP2A, comprising heterocyclic constrained tricyclic sulfonamides to treat diseases such as cancer, neurodegenerative disease and other disorders.

BACKGROUND

The FOXO (Forkhead transcription factors, Class 0) proteins are a group of transcription factors involved in control of a variety of physiological, metabolic and developmental pathways. They are downstream effectors in a number of signaling pathways including insulin and growth factor signaling; they are also regulated by oxidative stress and nutrient deprivation. Cellular processes affected by FOXO activity include cell cycle control, differentiation, proliferation and apoptosis. Disregulation of FOXO mediated processes has been implicated in a number of pathologies including tumorigenesis, inflammation, diabetes and neurodegenerative conditions amongst others. Activity of FOXO transcription factors are controlled in part by their subcellular localization, in particular their localization to the nucleus from the cytosol, and their subsequent transcriptional activation.

Four FOXO proteins designated FOXO1, FOXO3a, FOXO4 and FOXO6 are present in human cells and their activity is controlled by a variety of mechanisms including stability (proteolytic cleavage), sub-cellular localization and transcriptional activation. Activity of the first three members of the family is controlled by cytosolic-nuclear translocation.

FOXO1 regulates expression of a number of genes that play critical roles in cell cycle and apoptosis. A pivotal regulatory mechanism of FOXO is reversible phosphorylation, catalyzed by kinases and phosphatases. Phosphorylation of FOXO1 is associated with 14-3-3 binding and cytosolic localization, whereas dephosphorylated FOXO1 translocates to the nucleus and is transcriptionally active.

Protein phosphatase 2A is one of the four major serine threonine phosphatases and is implicated in the negative control of cell growth and division. Protein phosphatase 2A holoenzymes are heterotrimeric proteins composed of a structural subunit A, a catalytic subunit C, and a regulatory subunit B. The PP2A heterotrimeric protein phosphatase is a ubiquitous and conserved phosphatase with broad substrate specificity and diverse cellular functions. Among the targets of PP2A are proteins of oncogenic signaling cascades, such as Raf, MEK, and AKT.

PP2A interacts directly with FOXO1 and dephosphorylates FOXO1. Inhibition of PP2A phosphatases rescues FOXO1-mediated cell death by regulating the level of the pro-apoptotic protein BIM. In addition, PP2A directly regulates FOXO3a subcellular localization and transcriptional activation. Without wishing to be held to any particular theory, it may be that the compounds described herein promote apoptosis by acting on FOXO transcription factors via activation of PP2A.

Myc proteins (c-myc, Mycn and Mycl) target proliferative and apoptotic pathways vital for progression in cancer and it is overexpressed and deregulated in many human cancers. The control of Myc abundance through protein degradation has attracted considerable interest and Ser-62 phosphorylation by a number of kinases has been shown to stabilize the protein. PP2A is responsible for Ser-62 dephosphorylation which primes the protein for ubiquitylation and degradation, thus PP2A functions as a negative regulator of Myc.

Prostate cancer is the second leading cause of cancer death in men in America, behind lung cancer. According to the American Cancer Society, approximately 1 man in 36 will die of prostate cancer. Male hormones, specifically testosterone, fuel the growth of prostate cancer. By reducing the amount and activity of testosterone, the growth of advanced prostate cancer is slowed. Endocrine therapy, known as androgen ablation, is the first line of treatment for metastatic prostate cancer. Androgen deprivation therapy for metastatic prostate cancer results in tumor regression and symptomatic improvement in the majority of patients. However, metastatic prostate cancer inevitably progresses despite castrate levels of serum testosterone. Several new therapies have been approved for patients with castration-resistant prostate cancer (CRPC); however, none are curative and tumors ultimately develop resistance. To combat CRPC new approaches and novel therapies are required.

Breast cancer can affect both men and women. Breast cancer is the most prevalent cancer in women, after skin cancers, with about 1 in every 8 women expected to develop invasive breast cancer at some point. One subset of breast cancer expresses the androgen receptor (AR), which has been implicated as a therapeutic target in that subset. About 10-20% of breast cancers—more than one out of every 10—are found to be triple-negative. "Triple negative breast cancer" refers to a breast cancer that does not contain estrogen receptors, progesterone receptors, or human epidermal growth factor receptor 2 (HER2). This means that the growth of the cancer is not supported by the hormones estrogen and progesterone, nor by the presence of too many HER2 receptors. Therefore, triple-negative breast cancer does not respond to hormonal therapy (such as tamoxifen or aromatase inhibitors) or therapies that target HER2 receptors, such as Herceptin (chemical name: trastuzumab). While these tumors are often treatable, the chemotherapy is not targeted, and response durations are short. For doctors and researchers, there is intense interest in finding new medications that can treat breast cancer.

The compounds described herein exhibit anti-proliferative effects and are useful as monotherapy in cancer treatment. Additionally, they can be used in combination with other drugs to restore sensitivity to chemotherapy where resistance has developed.

SUMMARY OF THE INVENTION

A genus of heterocyclic constrained tricyclic arylsulfonamide derivatives has now been found that induce FOXO1 transcription factor translocation to the nucleus by modulating PP2A. The compounds described herein exhibit anti-proliferative effects, and are useful in the treatment of a variety of disorders, including as a monotherapy in cancer treatment, or used in combination with other drugs to restore sensitivity to chemotherapy where resistance has developed.

In a first aspect the invention relates to compounds of formula I:

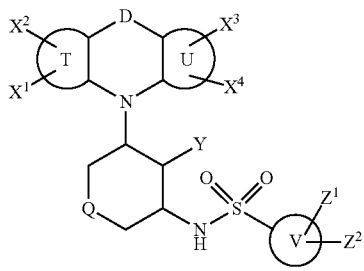

wherein:
D is selected from a direct bond, —O—, —CH$_2$O—, —OCH$_2$—, —C(=O)NR$^D$—, and —N(R$^D$)C(=O)—;
R$^D$ is selected from hydrogen and (C$_1$-C$_6$)alkyl;
T is a benzene ring or a five- or six-membered heteroaromatic ring;
U is a benzene ring or a five- or six-membered heteroaromatic ring;
X$^1$, X$^2$, X$^3$, and X$^4$ are independently selected in each instance from hydrogen, halogen, nitro, cyano, (C$_1$-C$_6$) alkyl, (C$_1$-C$_6$)haloalkyl, (C$_1$-C$_6$)haloalkoxy, (C$_1$-C$_6$) haloalkylthio, —NR$^1$R$^2$, —OR$^1$, —C(O)R$^1$, —OC(O)R$^1$, —C(O)NR$^1$R$^2$, —C(O)OR$^1$, —SR$^1$, —SO$_2$R$^1$, and —SO$_2$NR$^1$R$^2$;
R$^1$ and R$^2$ are independently selected in each instance from the group consisting of hydrogen and (C$_1$-C$_6$)alkyl;
Q is selected from —O—, S(O)$_n$—, and —NR—;
n is zero, 1 or 2;
R is selected from hydrogen, optionally substituted (C$_1$-C$_6$)alkyl, (C$_3$-C$_7$)cycloalkyl, aryl, or heteroaryl; —SO$_2$R$^3$; —SO$_2$N(R$^3$R$^4$); —C(=O)R$^5$; —C(=O)OR$^5$; or —C(=O)N(R$^3$R$^4$); wherein said substituents on the (C$_1$-C$_6$)alkyl, (C$_3$-C$_7$)cycloalkyl, aryl, or heteroaryl are selected from the group consisting of hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_3$-C$_7$)cycloalkyl, (C$_1$-C$_4$)haloalkyl, (C$_1$-C$_4$)haloalkoxy, and (C$_1$-C$_4$)alkoxy;
R$^3$ and R$^4$ are independently selected in each instance from hydrogen, (C$_1$-C$_6$)alkyl, aryl, and arylalkyl, wherein said aryl or the aryl of the arylalkyl is optionally substituted with hydroxy, halogen, cyano, nitro, amino, (C$_1$-C$_4$)alkylamino, (C$_1$-C$_4$)dialkylamino, C$_4$)acylamino, (C$_1$-C$_4$)alkylsulfonyl, (C$_1$-C$_4$)alkylthio, (C$_1$-C$_4$)alkyl, (C$_1$-C$_4$)haloalkyl, (C$_1$-C$_4$)haloalkoxy, or (C$_1$-C$_4$)alkoxy;
R$^5$ is selected from hydrogen, optionally substituted (C$_1$-C$_4$)alkyl, or optionally substituted aryl, wherein said optional substituents are selected from the group consisting of (C$_1$-C$_3$)alkyl, OR$^1$, NH$_2$, NHMe, N(Me)$_2$, and heterocycle;
Y is selected from hydrogen or hydroxyl;
V is selected from phenyl, a six-membered heteroaromatic ring, furan, and thiophene;
Z$^1$ and Z$^2$ are independently selected in each instance from the group consisting of hydrogen, halogen, nitro, cyano, azide, (C$_1$-C$_6$)alkyl, (C$_1$-C$_6$)haloalkyl, (C$_1$-C$_6$) haloalkoxy, —(C$_1$-C$_6$)haloalkylthio, —NR$^1$R$^2$, —NR$^1$C(O)R$^2$, —NR$^1$C(O)OR$^6$, —OR$^1$, —C(O)R', —OC(O)R$^1$, —C(O)NR$^1$R$^2$, —C(O)OR$^1$, —SR$^1$, —SO$_2$R$^1$, and —SO$_2$NR$^1$R$^2$; and R$^6$ is (C$_1$-C$_8$)hydrocarbon.

In a second aspect, the invention relates to methods and uses of the above-described compounds in medicine, particularly for the treatment of a disease chosen from (a) cancer; (b) diabetes; (c) autoimmune disease; (d) age onset proteotoxic disease; (e) mood disorder; (f) acne vulgaris; (g) solid organ transplant rejection; (h) graft vs. host disease; i) cardiac hypertrophy; j) viral infection; and (k) parasitic infection. These methods include administering to a patient a therapeutically effective amount of a compound described herein.

In a third aspect, the invention relates to a method for restoring sensitivity to one or more chemotherapeutic agents in the treatment of cancer. The method includes administering an effective amount of a compound described herein.

In a fourth aspect, the invention relates to a method for treating a disease or disorder in a patient where the disease or disorder involves the dysregulation of PP2A influenced signaling cascades such as the PI3K-AKT, MAP kinase and mTOR pathways. These methods include administering to a patient a therapeutically effective amount of a compound described herein.

In a fifth aspect, the invention relates to a method for treating a disease or disorder in a patient where the disease or disorder involves the dysregulation of a Myc dependent signaling pathway. These methods include administering to a patient a therapeutically effective amount of a compound described herein.

In a sixth aspect, the invention relates to pharmaceutical compositions comprising the compounds described herein.

DETAILED DESCRIPTION OF THE INVENTION

Substituents are generally defined when introduced and retain that definition throughout the specification and in all independent claims.

In a composition aspect, the invention relates to compounds of formula I:

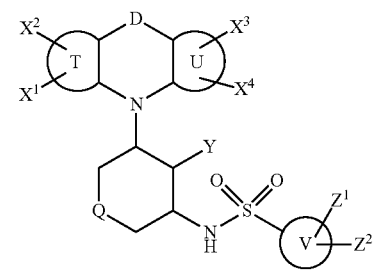

as described above.

In some embodiments, the invention relates to compounds of formula IIa or IIb:

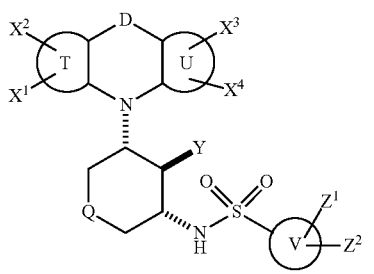

IIa

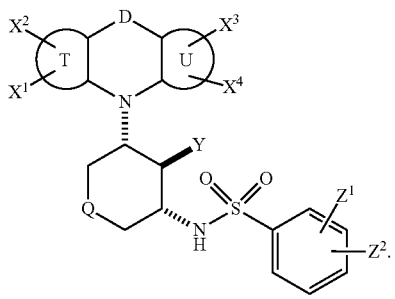

IIb

In some embodiments, the invention relates to compounds of formula IIIa, IIIb, IIIc, or IIId:

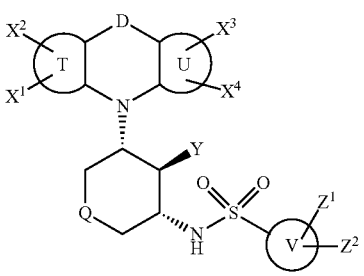

IIIa

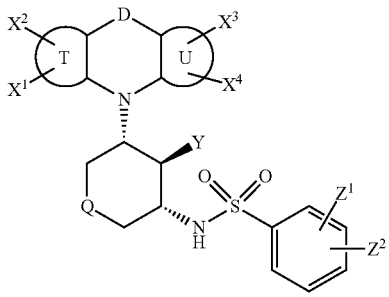

IIIb

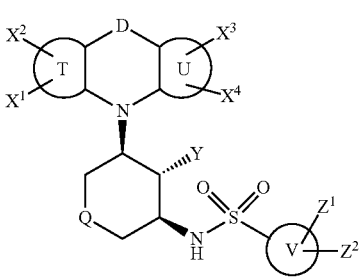

IIIc

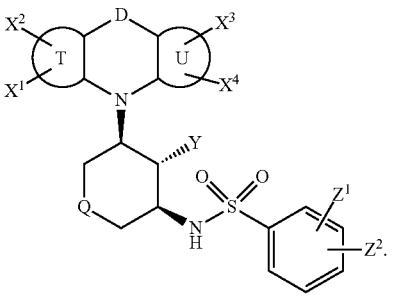

IIId

In the embodiments described below, the compound may be of formula I, IIa, IIb, IIIa, IIIb, IIIc, or IIId, unless otherwise indicated.

In some embodiments, D is a direct bond. In other embodiments, D is —O—. In still other embodiments, D is —CH$_2$O—. In yet other embodiments, D is —OCH$_2$—. In some embodiments, D is —C(=O)NR$^D$—. In other embodiments, D is —N(R$^D$)C(=O)—.

In some embodiments, R$^D$ is hydrogen. In other embodiments, R$^D$ is (C$_1$-C$_6$)alkyl.

In some embodiments, T is a benzene ring. In other embodiments, T is a five-membered heteroaromatic ring. In still other embodiments, T is a six-membered heteroaromatic ring.

In some embodiments, U is a benzene ring. In other embodiments, U is a five-membered heteroaromatic ring. In still other embodiments, U is a six-membered heteroaromatic ring.

In some embodiments, T and U are each independently selected from the group consisting of a benzene ring, furan, imidazole, isothiazole, isoxazole, oxadiazole, oxazole, pyran, pyrazine, pyrazole, pyridazine, pyridine, pyrimidine, pyrrole, thiadiazole, thiazine, thiazole, thiophene, triazine, and triazole. In some embodiments, T and U are each independently selected from a benzene ring, pyridine, pyrimidine, pyridazine, thiophene, thiazole, oxazole, imidazole, pyrrole, and furan. In some embodiments, one of T and U is a benzene ring, and the other of T and U is selected from a benzene ring, pyridine, pyrimidine, and thiophene. In still other embodiments, T and U are each independently selected from a benzene ring and pyridine. In some embodiments, at least one of T and U is a benzene ring. In other embodiments, T and U are both benzene rings.

In some embodiments, Y is hydroxyl. In other embodiments, Y is hydrogen.

In some embodiments V is phenyl. In other embodiments V is thiophene. In still other embodiments, V is furan. In yet other embodiments, V is a six-membered heteroaromatic ring. For instance, V may be pyridine, pyrimidine, or pyridazine.

In some embodiments, Q is —O—. In other embodiments, Q is —S—. In other embodiments, Q is —S(O)—. In other embodiments, Q is —S(O)$_2$—. In still other embodiments, Q is —NR—.

In some embodiments, R is hydrogen. In other embodiments, R is optionally substituted (C$_1$-C$_6$)alkyl. In still other embodiments, R is optionally substituted (C$_3$-C$_7$)cycloalkyl. In yet other embodiments, R is optionally substituted aryl. In further embodiments, R is optionally substituted heteroaryl. In these instances, the optional substituents available for the (C$_1$-C$_6$)alkyl, (C$_3$-C$_7$)cycloalkyl, aryl or heteroaryl may be one or more of hydroxy, halogen, cyano, nitro, amino, ($C_1$-$C_4$)alkylamino, ($C_1$-$C_4$)dialkylamino, ($C_1$-$C_4$)acylamino, ($C_1$-$C_4$)alkylsulfonyl, ($C_1$-$C_4$)alkylthio, ($C_1$-$C_4$)alkyl, ($C_3$-$C_7$)cycloalkyl, ($C_1$-$C_4$)haloalkyl, ($C_1$-$C_4$)haloalkoxy, and ($C_1$-$C_4$)alkoxy. In some embodiments, R is ($C_1$-$C_6$)alkyl optionally substituted with one or more of hydroxy, fluoro, or ($C_3$-$C_7$)cycloalkyl. In other embodiments, R is ($C_1$-$C_3$)alkyl optionally substituted with one or more of hydroxy or fluoro. In yet other embodiments, R is ($C_3$-$C_7$)cycloalkyl optionally substituted with one or more of hydroxy, methyl, or fluoro. In still other embodiments, R is aryl optionally substituted with one or more of hydroxy, methoxy, halogen, ($C_1$-$C_3$)haloalkyl, nitro, amino, or methyl. In further embodiments, R is phenyl optionally substituted with one or more of hydroxy, chloro, fluoro, methoxy, nitro, amino, trifluoromethyl, or methyl. In yet other embodiments, R is heteroaryl optionally substituted with one or more of hydroxy, methoxy, halogen, ($C_1$-$C_3$)haloalkyl, nitro, amino, or methyl. In some embodiments, R is a nitrogen-containing heteroaryl optionally substituted with one or two methyl groups. In some embodiments, R is —$SO_2R^3$. In other embodiments, R is —$SO_2NR^3R^4$. In still other embodiments, R is —C(=O)$R^5$. In some embodiments, R is —C(=O)O$R^5$. In yet other embodiments, R is —C(=O)N$R^3R^4$.

In some embodiments, $R^3$ and $R^4$ are independently selected in each instance from hydrogen, ($C_1$-$C_6$)alkyl, aryl, and arylalkyl. In some embodiments, the aryl or the aryl of the arylalkyl may be optionally substituted with hydroxy, halogen, cyano, nitro, amino, ($C_1$-$C_4$)alkylamino, ($C_1$-$C_4$)dialkylamino, ($C_1$-$C_4$)acylamino, ($C_1$-$C_4$)alkylsulfonyl, ($C_1$-$C_4$)alkylthio, ($C_1$-$C_4$)alkyl, ($C_1$-$C_4$)haloalkyl, ($C_1$-$C_4$)haloalkoxy, or ($C_1$-$C_4$)alkoxy. In some embodiments, $R^4$ is selected from hydrogen and methyl. In other embodiments, $R^3$ is selected from hydrogen, ($C_1$-$C_6$)alkyl, ($C_1$-$C_6$)haloalkyl, aryl, and arylalkyl. In some of these embodiments, the aryl or the aryl of the arylalkyl is optionally substituted with one or more of hydroxy, halogen, cyano, nitro, amino, ($C_1$-$C_4$)alkylamino, ($C_1$-$C_4$)dialkylamino, ($C_1$-$C_4$)acylamino, ($C_1$-$C_4$)alkylsulfonyl, ($C_1$-$C_4$)alkylthio, ($C_1$-$C_4$)alkyl, ($C_1$-$C_4$)haloalkyl, ($C_1$-$C_4$)haloalkoxy, and ($C_1$-$C_4$)alkoxy.

In some embodiments, $R^5$ is selected from hydrogen, optionally substituted ($C_1$-$C_4$)alkyl, or optionally substituted aryl. In some embodiments, the optional substituents are selected from ($C_1$-$C_3$)alkyl, $OR^1$, $NH_2$, NHMe, N(Me)$_2$, and heterocycle. In other embodiments, $R^5$ is selected from optionally substituted ($C_1$-$C_4$)alkyl or optionally substituted aryl, and the optional substituents are selected from one or more of OH, OMe, $NH_2$, NHMe, N(Me)$_2$, or heterocycle.

In some embodiments, R is —C(=O)$R^5$ and $R^5$ is selected from methyl, optionally substituted with $OR^1$, $NH_2$, NHMe, N(Me)$_2$, and heterocycle. In other embodiments, R is —C(=O)O$R^5$ and $R^5$ is selected from the group consisting of phenyl and ($C_1$-$C_4$)alkyl, each of which may be substituted with $OR^1$; in some of these embodiments, $R^1$ is hydrogen, while in other of these embodiments, $R^1$ is ($C_1$-$C_6$)alkyl. In still other embodiments, R is —$SO_2R^3$ and $R^3$ is selected from hydrogen, ($C_1$-$C_6$)alkyl, and aryl. In some of these embodiments, the aryl may be substituted with hydroxy, halogen, cyano, amino, or ($C_1$-$C_4$)alkoxy. In yet other embodiments, R is $SO_2NR^3R^4$; $R^3$ is selected from hydrogen, ($C_1$-$C_3$)alkyl, and optionally substituted aryl; and $R^4$ is hydrogen or methyl. In further embodiments, R is —C(=O)N$R^3R^4$; $R^3$ is selected from hydrogen, ($C_1$-$C_3$)alkyl, and aryl optionally substituted with hydroxy, halogen, cyano, amino, or methoxy; and $R^4$ is hydrogen or methyl.

In some embodiments, $X^1$, $X^2$, $X^3$, and $X^4$ are independently selected in each instance from hydrogen, halogen, nitro, cyano, ($C_1$-$C_6$)alkyl, ($C_1$-$C_6$)haloalkyl, ($C_1$-$C_6$)haloalkoxy, ($C_1$-$C_6$)haloalkylthio, —$NR^1R^2$, —$OR^1$, —C(O)$R^1$, —OC(O)$R^1$, —C(O)$NR^1R^2$, —C(O)$OR^1$, —$SR^1$, —$SO_2R^1$, and —$SO_2NR^1R^2$. In some embodiments, zero, one or two of $X^1$, $X^2$, $X^3$, and $X^4$ are independently selected in each instance from halogen and ($C_1$-$C_6$)haloalkyl, and the remainder are hydrogen. In other embodiments, one or two of $X^1$, $X^2$, $X^3$, and $X^4$ are independently selected in each instance from chloro, fluoro, and ($C_1$-$C_3$)fluoroalkyl, and the remainder are hydrogen.

In some embodiments, $R^1$ is hydrogen. In other embodiments, $R^1$ is ($C_1$-$C_6$)alkyl. In some embodiments, $R^2$ is hydrogen. In other embodiments, $R^2$ is ($C_1$-$C_6$)alkyl.

In some embodiments, $Z^1$ is selected from hydrogen, halogen, nitro, cyano, azide, ($C_1$-$C_6$)alkyl, ($C_1$-$C_6$)haloalkyl, ($C_1$-$C_6$)haloalkoxy, —($C_1$-$C_6$)haloalkylthio, —$NR^1R^2$, —$NR^1C(O)R^2$, —$NR^1C(O)OR^6$, —$OR^1$, —C(O)$R^1$, —OC(O)$R^1$, —C(O)$NR^1R^2$, —C(O)$OR^1$, —$SR^1$, —$SO_2R^1$, and —$SO_2NR^1R^2$. In some embodiments, $Z^2$ is selected from hydrogen, halogen, nitro, cyano, azide, ($C_1$-$C_6$)alkyl, ($C_1$-$C_6$)haloalkyl, ($C_1$-$C_6$)haloalkoxy, —($C_1$-$C_6$)haloalkylthio, —$NR^1R^2$, —$NR^1C(O)R^2$, —$NR^1C(O)OR^6$, —$OR^1$, —C(O)R', —OC(O)$R^1$, —C(O)$NR^1R^2$, —C(O)$OR^1$, —$SR^1$, —$SO_2$R', and —$SO_2NR^1R^2$. In other embodiments, $Z^1$ and $Z^2$ are independently selected in each instance from hydrogen, halogen, ($C_1$-$C_6$)haloalkyl, ($C_1$-$C_6$)alkoxy, and ($C_1$-$C_6$)haloalkoxy. In some embodiments, $Z^1$ is hydrogen and $Z^2$ is selected from hydrogen, halogen, ($C_1$-$C_6$)haloalkyl, ($C_1$-$C_6$)alkoxy, ($C_1$-$C_6$)haloalkoxy, and NHBoc. In some embodiments, $Z^1$ is hydrogen and $Z^2$ is hydrogen, fluoro, chloro, trifluoromethyl, methoxy, trifluoromethoxy, or NHBoc. In other embodiments, $Z^2$ is para to the attachment of ring V to the sulfonyl.

In some embodiments, $R^6$ is ($C_1$-$C_8$)hydrocarbon. In other embodiments, $R^6$ is ($C_1$-$C_6$)alkyl. In some embodiments, $R^6$ is t-butyl. In still other embodiments, $R^6$ is allyl. In yet other embodiments, $R^6$ is benzyl.

The person of skill will understand that, in some instances, $R^1$, $R^2$, $R^3$, $R^4$, and $R^5$ may not be hydrogen. For instance, when Q is NR, R is —$SO_2R^3$, and $R^3$ is hydrogen, the resulting moiety will be unstable. The circumstances under which a hydrogen atom would be inappropriate will be clear to the person of skill in the art.

In some embodiments, D and Q are each —O—, and the compound is of one of the formulae below:

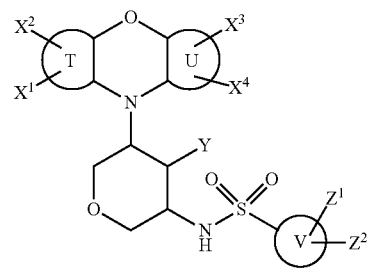

-continued

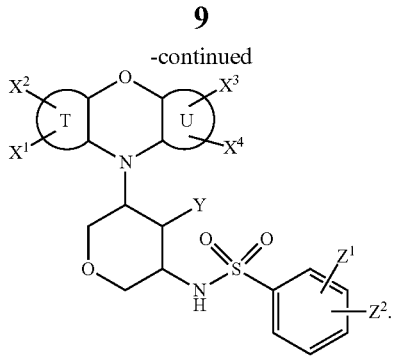

In some embodiments, D is —O— and Q is NR and the compound is of one of the formulae below:

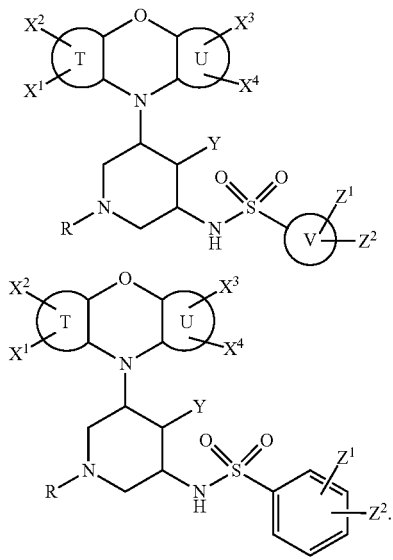

In some embodiments, D is a direct bond and Q is —O—, and the compound is of one of the formulae below:

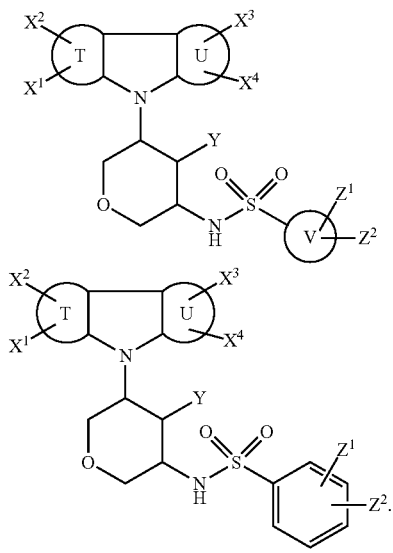

In some embodiments, D is a direct bond and Q is NR, and the compound is of one of the formulae below:

In some embodiments, $Z^1$ is hydrogen and $Z^2$ is selected from hydrogen, halogen, $(C_1-C_6)$haloalkyl, —$NR^1C(O)OR^6$, $(C_1-C_6)$alkoxy, or $(C_1-C_6)$haloalkoxy. In other embodiments, $Z^1$ is hydrogen and $Z^2$ is hydrogen, fluoro, chloro, trifluoromethyl, NHBoc, methoxy, or trifluoromethoxy. In still other embodiments, $Z^1$ is hydrogen and $Z^2$ is trifluoromethoxy.

In some embodiments of the foregoing subgenera, the relative configurations are such that the amine and the tricycle are both trans to the alcohol (Y), as shown above in, for instance, formula IIa. In this trans:trans subgroup, compounds can be either single enantiomers, like in formulae IIIa and IIIc, or a mixture of the two. If a mixture, the mixture will most commonly be racemic, but it need not be. Substantially pure single enantiomers of biologically active compounds such as those described herein often exhibit advantages over their racemic mixture.

In summary, the invention relates to:
[1]. A compound of formula I, IIa, IIb, IIc, IIIb, IIIc, or IIId.
[2]. A compound according to [1] above wherein D is a direct bond.
[3]. A compound according to [1] above wherein D is —O—.
[4]. A compound according to [1] above wherein D is —CH$_2$O—.
[5]. A compound according to [1] above wherein D is —OCH$_2$
[6]. A compound according to [1] above wherein D is —C(=O)NR$^D$—.
[7]. A compound according to [1] above wherein D is —N(R$^D$)C(=O)—
[8]. A compound according to any of [1] through [7] above wherein T and U are each independently selected from the group consisting of a benzene ring and pyridine.
[9]. A compound according to any of [1] through [7] above wherein at least one of T and U is a benzene ring.
[10]. A compound according to any of [1] through [7] above wherein both T and U are benzene rings.

[11]. A compound according to any of [1] through [10] above wherein Y is hydroxyl.

[12]. A compound according to any of [1] through [10] above wherein Y is hydrogen.

[13]. A compound according to any of [1] through [12] above wherein Q is —O—.

[14]. A compound according to any of [1] through [12] above wherein Q is —NR—.

[15]. A compound according to any of [1] through [12] above wherein Q is —S(O)$_n$—.

[16]. A compound according to any of [1] through [15] above, wherein zero, one or two of $X^1$, $X^2$, $X^3$, and $X^4$ are independently selected in each instance from halogen and ($C_1$-$C_6$)haloalkyl, and the remainder are hydrogen.

[17]. A compound according to any of [1] through [16] above, wherein zero, one or two of $X^1$, $X^2$, $X^3$, and $X^4$ are independently selected in each instance from chloro, fluoro, and ($C_1$-$C_3$)fluoroalkyl, and the remainder are hydrogen.

[18]. A compound according to any of [1] through [17] above, wherein $Z^1$ and $Z^2$ are independently selected in each instance from hydrogen, halogen, ($C_1$-$C_6$)haloalkyl, —$NR^1C(O)OR^6$, ($C_1$-$C_6$)alkoxy, and ($C_1$-$C_6$) haloalkoxy.

[19]. A compound according to any of [1] through [18] above, wherein $Z^1$ is hydrogen and $Z^2$ is selected from hydrogen, halogen, ($C_1$-$C_6$)haloalkyl, —$NR^1C(O)OR^6$, ($C_1$-$C_6$)alkoxy, and ($C_1$-$C_6$)haloalkoxy.

[20]. A compound according to any of [1] through [19] above, wherein Z' is hydrogen and $Z^2$ is hydrogen, fluoro, chloro, trifluoromethyl, —NHBoc, methoxy, or trifluoromethoxy.

[21]. A compound according to any of [1] through [20] above, wherein V is phenyl.

[22]. A compound according to any of [1] through [21] above, wherein $Z^2$ is para to the attachment of ring V to the sulfonyl.

The compounds described herein contain three or more asymmetric centers and may thus give rise to enantiomers, diastereomers, and other stereoisomeric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration. For example, the graphic representation

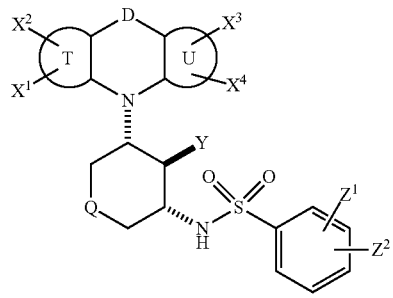

indicates either, or both, of the two trans:trans enantiomers:

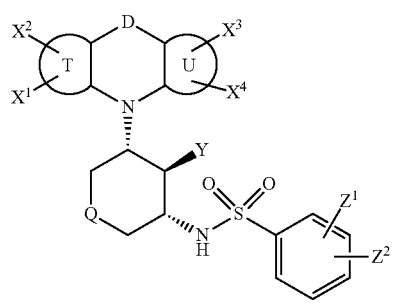

in any ratio, from pure enantiomers to racemates. The graphic representation:

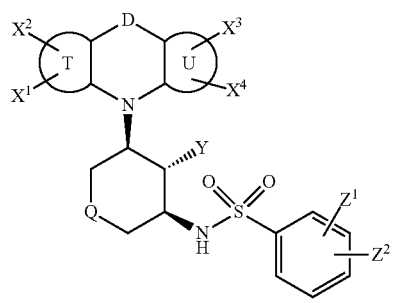

indicates a single enantiomer of unknown absolute stereochemistry, i.e. it could be either of the two preceding structures, as a substantially pure single enantiomer. And, finally, the representation:

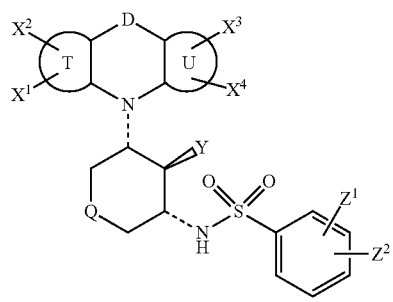

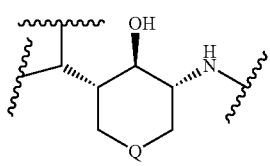

indicates a pure (1R,2R,6S)-2-amino-6-(C-attached tricycle) heterocyclyl-4-ol. For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers. In the text describing the stereochemistry of the examples, the convention of Chemical Abstracts is used. Thus "(1R,2R,6S)-rel-" indicates that the three chiral centers are in that relative relationship, which would be depicted in a structural diagram by solid bold and dashed lines, whereas "(1R,2R,6S)" without the "rel" indicates a single enantiomer of that absolute configuration, which would be depicted in a structural diagram by solid and broken wedges.

It may be found upon examination that certain species and genera are not patentable to the inventors in this application. In this case, the exclusion of species and genera in applicants' claims are to be considered artifacts of patent prosecution and not reflective of the inventors' concept or description of their invention, which encompasses all members of the genus 1 that are not in the public's possession.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt form thereof, and a pharmaceutically acceptable carrier or diluent.

While it may be possible for the compounds of formula I to be administered as the raw chemical, it is preferable to present them as a pharmaceutical composition. According to a further aspect, the present invention provides a pharmaceutical composition comprising a compound of formula I or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2$H, $^3$H, $^{13}$C, $^{14}$C, $^{15}$N, $^{35}$S, $^{18}$F, and $^{36}$Cl, respectively. Compounds that contain those radioisotopes and/or other radioisotopes of other atoms are within the scope of this invention. Tritiated, i.e. $^3$H, and carbon-14, i.e., $^{14}$C, radioisotopes are particularly preferred for their ease in preparation and detectability. Compounds that contain isotopes $^{11}$C, $^{13}$N, $^{15}$O and $^{18}$F are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating cancer in a patient, the method comprising administering to the patient a therapeutically effective amount of a compound of formula I. In some embodiments, the cancer is characterized by dysregulation of the PI3K-AKT-FOXO signaling pathway. For example, the cancer can be selected from the group consisting of: ovarian, pancreatic, renal cell, breast, prostate, lung, hepatocellular carcinoma, glioma, leukemia, lymphoma, colorectal cancers, and sarcomas.

In some embodiments, the method further comprises administering one or more additional cancer chemotherapeutic agents. In some embodiments, the one or more additional cancer chemotherapeutic agents are EGFR inhibitors.

In some embodiments, the cancer is chemotherapy resistant cancer. In some embodiments, the method further comprises administering one or more cancer chemotherapeutic agents. In some embodiments, the one or more cancer chemotherapeutic agents are EGFR inhibitors.

In some embodiments, administration of a compound of formula I can restore sensitivity to one or more chemotherapeutic agents in a patient wherein the patient has developed a resistance to the one or more chemotherapeutic agents. More particularly, cancers that may be treated by the compounds, compositions and methods described herein include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue.

The compounds described herein can also be administered in combination with existing methods of treating cancers, for example by chemotherapy, irradiation, or surgery. Thus, there is further provided a method of treating cancer comprising administering an effective amount of a compound according to formula I to a patient, wherein a therapeutically effective amount of one or more additional cancer chemotherapeutic agents are administered to the patient.

Also provided herein is a method for treating diabetes in a patient, the method comprising administering to the patient a therapeutically effective amount of a compound of formula I.

Further provided herein is a method for treating an autoimmune disease in a patient, the method comprising administering to the patient a therapeutically effective amount of a compound of formula I. The autoimmune disease can be, for example, inflammatory bowel disease (IBD). Immune responses are constantly and tightly regulated and one important cellular component in maintaining self tolerance (i.e., prevention of autoimmunity) and tolerance of benign commensal gut flora are regulatory T cells (Treg). Treg can be subdivided into multiple phenotypes, but the most common are CD4+CD25+ T cells that express the transcription factor Foxp3. Foxp3 is a direct transcriptional target of FOXO proteins, particularly FOXO1 and FOXO3. Thus activation of FOXO proteins in naïve T-cells promotes and directs differentiation to maintain a population of Treg cells.

Acute immune mediated rejection and chronic immune mediated rejection are key obstacles to successful solid organ transplantation. It is believed that these forms of rejection can be prevented/overcome by amplifying Treg number and or function. Similarly, a common and morbid complication of allogeneic hematopoietic cell transplants (Allo-HCT) used to treat various malignant and non-malignant conditions, is graft versus host disease, in which the transplanted immune cells from the donor damage multiple organs in the recipient (most notably skin, gut, and liver). Increasing experimental and clinical data indicate that Tregs can be harnessed to prevent and or treat this disease process.

Thus compounds of the present invention are useful in treatment of autoimmune and related diseases, by activating FOXO proteins and inducing T cell differentiation to Tregs. Compounds may be administered therapeutically to subjects directly, or alternatively, T cells may be collected from a subject and differentiated ex vivo to Tregs as described by Taylor et al. [*Blood* 99, 3493-3499 (2002)].

Aspects of the invention include methods for treatment of autoimmune disease characterized by deficiency in Treg function comprising administering a therapeutically useful amount of compound of formula I. The method can also include extraction of naïve T-cells from a patient, differentiation of T-cells to Tregs ex vivo by treatment with a compound of formula I, optionally supplemented with an HDACi, followed by administration of Tregs to patient with optional separation of compound of formula I from Tregs prior to their administration. As stated above, autoimmune diseases that can be so treated include IBD, solid organ transplant rejection, and GvHD in allo-HCT In some embodiments, the compounds can be administered to a patient to treat an autoimmune disorder, for example, Addison's disease, Amyotrophic Lateral Sclerosis, celiac disease, Crohn's disease, diabetes, eosinophilic fasciitis, Guillain-Barré syndrome (GBS), Graves' disease, Lupus erythematosus, Miller-Fisher syndrome, psoriasis, rheumatoid arthritis, ulcerative colitis, and vasculitis. In some embodiments, the compound provided herein can be used for treating a disease or disorder in a patient wherein the disease or disorder involves excessive or unregulated cellular proliferation, the method comprising administering to the patient a therapeutically effective amount of a compound of formula I. Also provided herein is a method for treating a disease or disorder in a patient where the disease or disorder involves the dysregulation of the pi3K-AKT-FOXO signaling pathway, the method comprising administering to the patient a therapeutically effective amount of a compound of formula I.

Further provided herein is a method for treating a disease in a patient wherein the disease is characterized by proteotoxicity, including age onset proteotoxicity leading to neurodegeneration, the method comprising administering to the patient a therapeutically effective amount of a compound of formula I. Hyperphosphorylated Tau has been implicated as the pathogenic protein in several neurodegenerative diseases and furthermore PP2A has been shown to be an important phosphatase in reversing aberrant phosphorylation of Tau; see for example Ludovic Martin et al., Tau protein phosphatases in Alzheimer's disease: The leading role of PP2A in Ageing Research Reviews 12 (2013) 39-49; Miguel Medina and Jesus Avila, Further understanding of tau phosphorylation: implications for therapy in Expert Rev. Neurotherapy, 15(1), 115-112 (2015) and Michael Voronkov et al., Phosphoprotein phosphatase 2A: a novel druggable target for Alzheimer's disease in Future Med Chem. 2011 May, 3(7) 821-833. Hyperphosphorylated alpha-Synuclein is a second exemplar of a toxic protein, and again PP2A has been shown to reverse its aberrantly phosphorylated state; see for example Kang-Woo Lee et al., Enhanced Phosphatase Activity Attenuates alpha-Synucleinopathy in a Mouse Model in Neurobiology of Disease, May 11, 2011, 31(19) 6963-6971. In some embodiments, the disease is selected from the group consisting of: Alzheimer's disease, Parkinson's disease, Huntington's disease, amyotrophic lateral sclerosis, frontotemporal dementia, progressive supranuclear palsy, corticobasal degeneration and Pick's disease.

The compounds provided herein may further be used in a method for treating a mood disorder in a patient by administering to the patient a therapeutically effective amount of a compound of formula I. In some embodiments, the mood disorder is stress-induced depression.

Also provided herein is a method for treating acne vulgaris in a patient by administering to the patient a therapeutically effective amount of a compound of formula I.

Further provided herein is a method for treating cardiac hypertrophy in a patient by administering to the patient a therapeutically effective amount of a compound of formula I. In some embodiments, the cardiac hypertrophy is associated with a disease selected from hypertension, myocardial infarction, and valvular heart disease.

The compounds provided herein may further be used in a method for treating a viral infection in a patient by administering to the patient a therapeutically effective amount of a compound of formula I. Examples of viruses that may cause viral infections to be treated include, but are not limited to: a polyomavirus, such as John Cunningham Virus (JCV), Simian virus 40 (SV40), or BK Virus (BKV); influenza, Human Immunodeficiency Virus type 1 (HIV-1), Human Papilloma Virus (HPV), adenovirus, Epstein-Barr Virus (EBV), Hepatitis C Virus (HCV), Molluscum contagiosum virus (MCV); Human T-lymphotropic virus type 1 HTLV-1), Herpes Simplex Virus type 1 (HSV-1), cytomegalovirus (CMV), hepatitis B virus, Bovine papillomavirus (BPV-1), human T-cell lymphotropic virus type 1, Japanese encephalitis virus, respiratory syncytial virus (RSV), and West Nile virus.

Further provided herein is a method for treating a parasitic infection in a patient by administering to the patient a therapeutically effective amount of a compound of formula I. Examples of parasites that may cause parasitic infections to be treated include, but are not limited to, *Plasmodium* and *Theileria*.

PP2A enzymes are involved in the regulation of cell transcription, cell cycle, and viral transformation. Many viruses, including cytomegalovirus, parainfluenza, DNA tumor viruses, and HIV-1, utilize different approaches to exploit PPA2 in order to modify, control, or inactivate cellular activities of the host [Garcia et al., Microbes and Infection, 2, 2000, 401-407]. Therefore, the compounds provided herein may further be used in a method for treating a viral infection in a patient by administering to the patient a therapeutically effective amount of a compound of formula I. Examples of viruses that may cause viral infections to be treated include, but are not limited to: a polyomavirus, such as John Cunningham Virus (JCV), Simian virus 40 (SV40), or BK Virus (BKV); influenza, Human Immunodeficiency Virus type 1 (HIV-1), Human Papilloma Virus (HPV), adenovirus, Epstein-Barr Virus (EBV), Hepatitis C Virus (HCV), Molluscum contagiosum virus (MCV); Human T-lymphotropic virus type 1 HTLV-1), Herpes Simplex Virus type 1 (HSV-1), cytomegalovirus (CMV), hepatitis B virus, Bovine papillomavirus (BPV-1), human T-cell lymphotropic virus type 1, Japanese encephalitis virus, respiratory syncytial virus (RSV), and West Nile virus.

Serine/Threonine phosphatases, including PP2A are involved in modulation of synaptic plasticity (D. G. Winder and J. D. Sweatt, Nature Reviews Neuroscience, vol 2, July 2001, pages 461-474). Persistently decreased PP2A activity is associated with maintenance of Long Term Potentiation (LTP) of synapses, thus treatment PP2A activators such as those described here may reverse synaptic LTP. Psychostimulant drugs of abuse such as cocaine and methamphetamine are associated with deleterious synaptic LTP (L. Mao et al, Neuron 67, Sep. 9, 2010 and A. Stipanovich et al, Nature vol 453, 2008, pages 879-884), which may underlie the pathology of addiction and relapse therefore PP2A activators described here may be useful as treatments for psychostimulant abuse.

Abnormalities in synaptic structure and signaling are linked to autistic spectrum disorder, see for example, Y Chen et al., CTTNBP2, but not CTTNBP2NL, regulates dendritic spinogenesis and synaptic distribution of the striatin-PP2A complex, Molecular Biology of the Cell, 23, Nov. 15, 2012, 4383-4392. PP2A has been shown to be important in normal development of dendritic spines, and treatment with compounds of the present invention may ameliorate or reverse autistic spectrum disorder.

Abbreviations and Definitions

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

The following abbreviations and terms have the indicated meanings throughout:

Ac=acetyl
Aq=aqueous
Boc=t-butyloxy carbonyl
Bu=butyl
c-=cyclo
DBA=dibenzylideneacetone
DCM=dichloromethane=methylene chloride=$CH/C_{12}$
DMF=N,N-dimethylformamide
eq. or equiv.=equivalent(s)
Et=ethyl
GC=gas chromatography
h=hour(s)
KHMDS=Potassium bis(trimethylsilyl)amide
mCPBA=meta-Chloroperoxybenzoic acid
Me=methyl
mesyl=methanesulfonyl
min.=minute(s)
NMO or NMMO=N-methylmorpholine oxide
Pg=protecting group
Ph=phenyl
RT=room temperature
sat'd or sat.=saturated
t- or tert=tertiary
TFA=trifluoroacetic acid
THF=tetrahydrofuran
tosyl=p-toluenesulfonyl As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

The terms "administer", "administering" or "administration" in reference to a dosage form of the invention refers to the act of introducing the dosage form into the system of subject in need of treatment. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The term "modulate" with respect to a FOXO transcription factor protein refers to activation of the FOXO transcription factor protein and its biological activities associated with the FOXO pathway. Modulation of FOXO transcription factor proteins includes up-regulation (i.e., agonizing, activation or stimulation). The mode of action of a FOXO modulator can be direct, e.g., through binding to the FOXO transcription factor protein as a ligand. The modulation can also be indirect, e.g., through binding to and/or modifying another molecule which otherwise binds to and activates the FOXO transcription factor protein.

Throughout this specification the terms and substituents retain their definitions.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

The term "halogen" means fluorine, chlorine, bromine or iodine atoms. In one embodiment, halogen may be a fluorine or chlorine atom.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl[—C(═O)O-alkyl], alkoxycarbonylamino[HNC(═O)O-alkyl], aminocarbonyl (also known as carboxamido) [—C(═O)NH$_2$], alkylaminocarbonyl[—C(═O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In preferred embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino, and benzyloxy.

Substituents R″ are generally defined when introduced and retain that definition throughout the specification and in all independent claims.

EXAMPLES

| Compound No. | Structure |
|---|---|
| 1 | 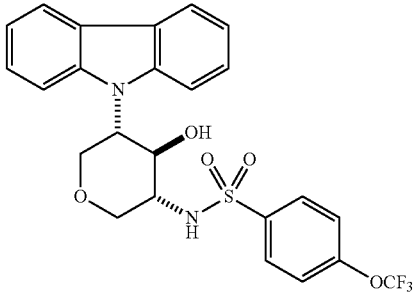 |
| 2 | 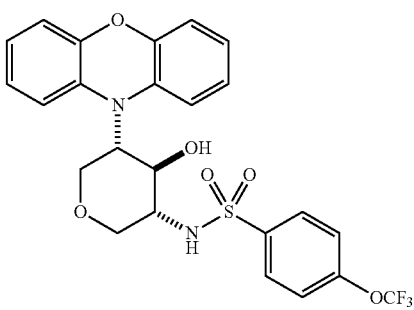 |
| 2a | 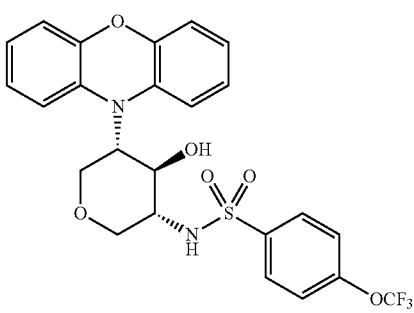 [SMILES: O=S(=O)(N[C@@H]1COC[C@H](N2c3ccccc3Oc3ccccc32)[C@H]1O)c1ccc(OC(F)(F)F)cc1] |
| 2b | 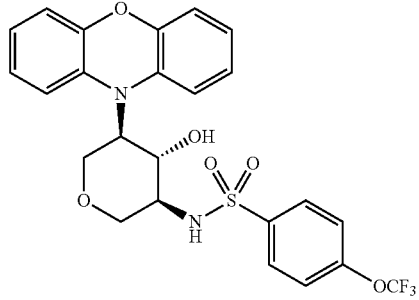 [SMILES: O=S(=O)(N[C@H]1COC[C@@H](N2c3ccccc3Oc3ccccc32)[C@@H]1O)c1ccc(OC(F)(F)F)cc1] |
| 3 | 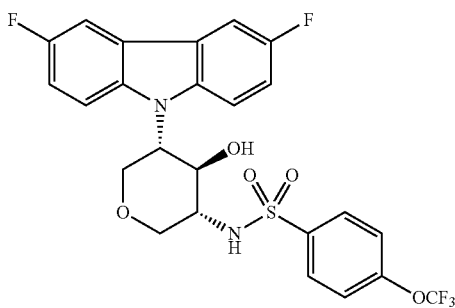 [SMILES: O=S(=O)(N[C@@H]1COC[C@H](n2c3ccc(F)cc3c3cc(F)ccc32)[C@H]1O)c1ccc(OC(F)(F)F)cc1] |
| 4 | 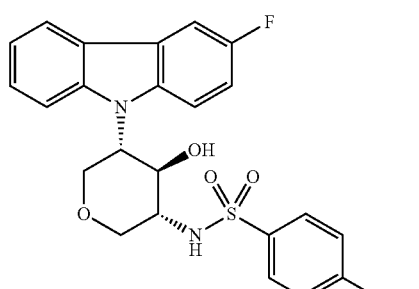 |
| 5 | 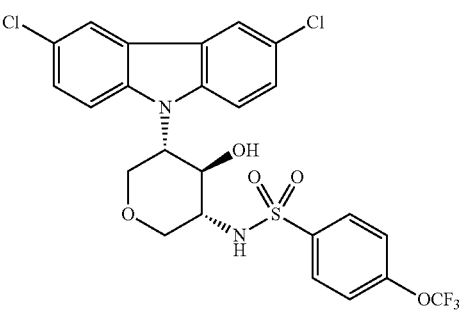 [SMILES: O=S(=O)(N[C@@H]1COC[C@H](n2c3ccc(Cl)cc3c3cc(Cl)ccc32)[C@H]1O)c1ccc(OC(F)(F)F)cc1] |
| 6 | 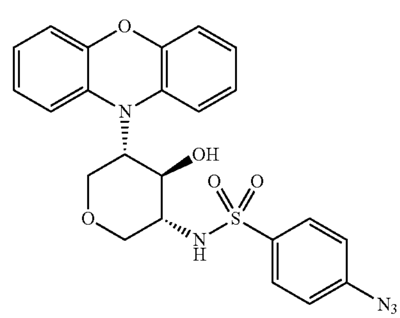 [SMILES: [N-]=[N+]=Nc1ccc(S(=O)(=O)N[C@@H]2COC[C@H](N3c4ccccc4Oc4ccccc43)[C@H]2O)cc1] |

-continued

| Compound No. | Structure |
|---|---|
| 7 | phenoxazine with F, linked to tetrahydropyran bearing OH and NH-SO2-C6H4-OCF3 |
| 8 | phenoxazine with CF3, linked to tetrahydropyran bearing OH and NH-SO2-C6H4-OCF3 |
| 9 | pyrido-phenoxazine with F, linked to tetrahydropyran bearing OH and NH-SO2-C6H4-OCF3 |
| 10 | 3,7-difluoro phenoxazine, linked to tetrahydropyran bearing OH and NH-SO2-C6H4-OCF3 |
| 11 | phenoxazine with F, linked to tetrahydropyran bearing OH and NH-SO2-C6H4-OCF3 |

| Compound No. | Structure |
|---|---|
| 12 | 3,7-dichloro phenoxazine, linked to tetrahydropyran bearing OH and NH-SO2-C6H4-OCF3 |
| 13 | phenoxazine with Cl, linked to tetrahydropyran bearing OH and NH-SO2-C6H4-OCF3 |
| 14 | 3,7-bis(trifluoromethyl) phenoxazine, linked to tetrahydropyran bearing OH and NH-SO2-C6H4-OCF3 |
| 15 | phenoxazine with CF3, linked to tetrahydropyran bearing OH and NH-SO2-C6H4-OCF3 |
| 16 | phenoxazine linked to N-Boc piperidine bearing OH and NH-SO2-C6H4-OCF3 |

-continued

| Compound No. | Structure |
|---|---|
| 17 | phenoxazine-piperidine(HN)-OH-NHSO2-C6H4-OCF3 |
| 18 | phenoxazine-piperidine(N-Ac)-OH-NHSO2-C6H4-OCF3 |
| 16a | phenoxazine-piperidine(N-Boc)-OH-NHSO2-C6H4-OCF3 |
| 16b | phenoxazine-piperidine(N-Boc)-OH-NHSO2-C6H4-OCF3 |
| 17a | phenoxazine-piperidine(NH)-OH-NHSO2-C6H4-OCF3 |

-continued

| Compound No. | Structure |
|---|---|
| 17b | phenoxazine-piperidine(NH)-OH-NHSO2-C6H4-OCF3 |
| 19a | phenoxazine-piperidine(N-Me)-OH-NHSO2-C6H4-OCF3 |
| 19b | phenoxazine-piperidine(N-Me)-OH-NHSO2-C6H4-OCF3 |
| 18a | phenoxazine-piperidine(N-Ac)-OH-NHSO2-C6H4-OCF3 |
| 18b | phenoxazine-piperidine(N-Ac)-OH-NHSO2-C6H4-OCF3 |

-continued
| Compound No. | Structure |
|---|---|
| 20a | 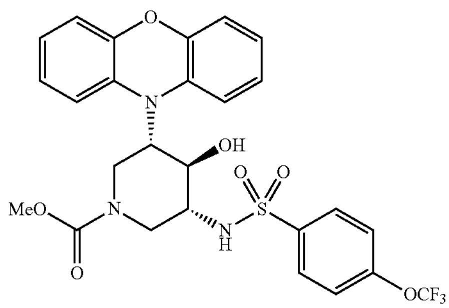 [SMILES: COC(=O)N1C[C@@H](NS(=O)(=O)c2ccc(OC(F)(F)F)cc2)[C@H](O)[C@@H](N2c3ccccc3Oc3ccccc32)C1] |
| 20b | 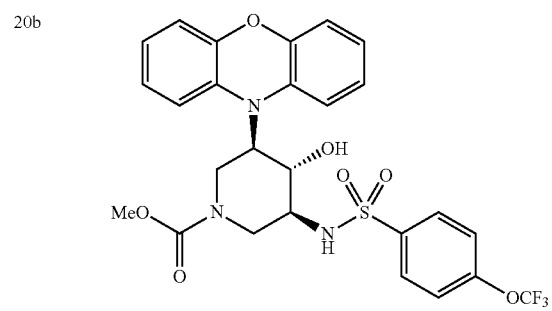 |
| 21 | 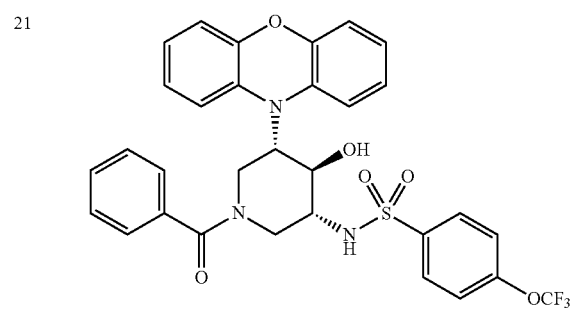 |
| 22 | 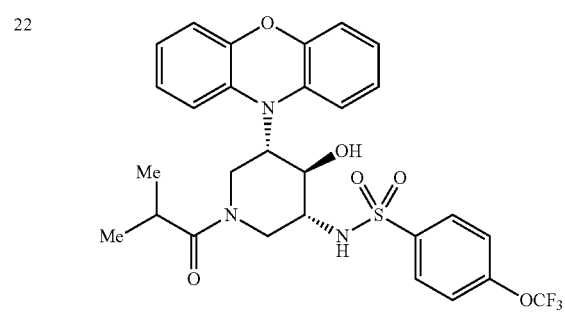 |
| 23 | 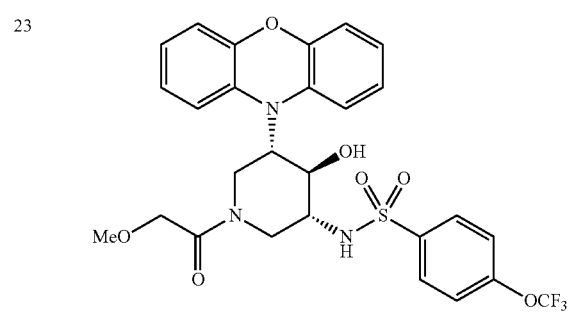 |
-continued
| Compound No. | Structure |
|---|---|
| 24 | 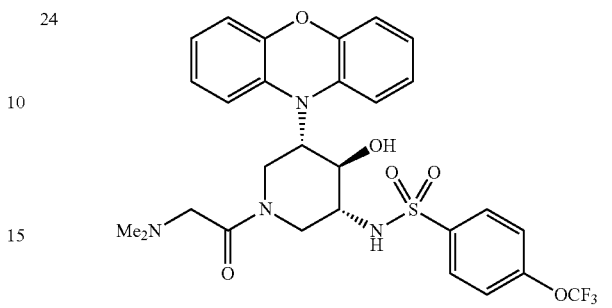 |
| 25 | 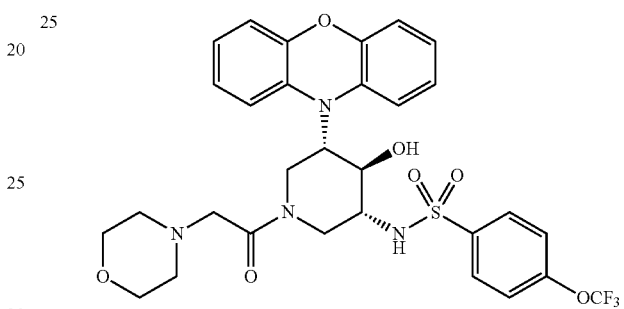 |
| 26 | 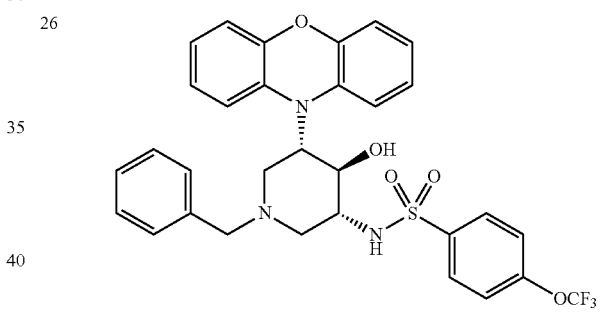 |
| 27 | 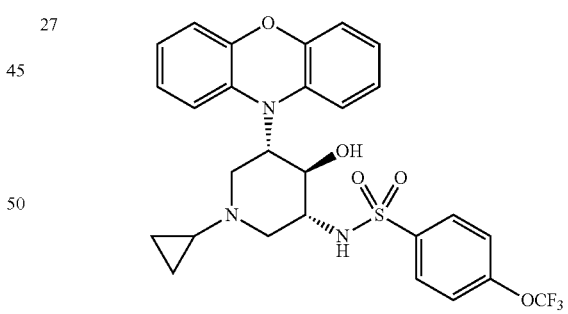 |
| 28 | 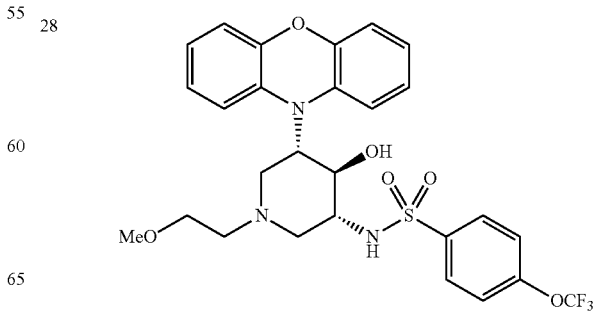 |

| Compound No. | Structure |
|---|---|
| 29 | 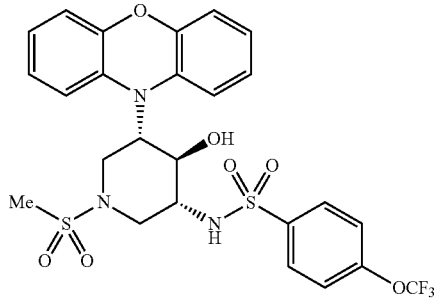 [SMILES: CS(=O)(=O)N1C[C@@H](NS(=O)(=O)c2ccc(OC(F)(F)F)cc2)[C@H](O)[C@@H](N2c3ccccc3Oc3ccccc32)C1] |
| 30 | 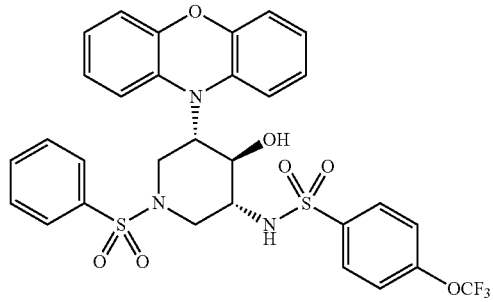 [SMILES: O=S(=O)(N[C@@H]1CN(S(=O)(=O)c2ccccc2)C[C@H](N2c3ccccc3Oc3ccccc32)[C@H]1O)c1ccc(OC(F)(F)F)cc1] |
| 31 | 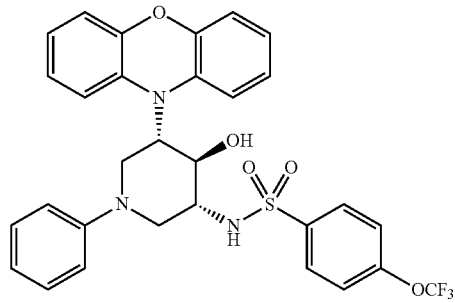 [SMILES: O=S(=O)(N[C@@H]1CN(c2ccccc2)C[C@H](N2c3ccccc3Oc3ccccc32)[C@H]1O)c1ccc(OC(F)(F)F)cc1] |
| 32 | 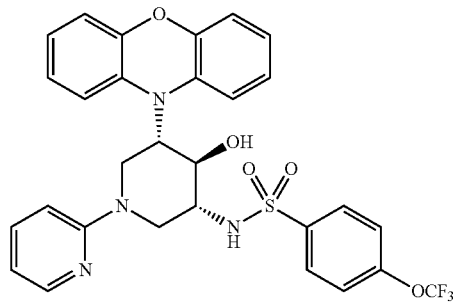 [SMILES: O=S(=O)(N[C@@H]1CN(c2ccccn2)C[C@H](N2c3ccccc3Oc3ccccc32)[C@H]1O)c1ccc(OC(F)(F)F)cc1] |
| 33 | 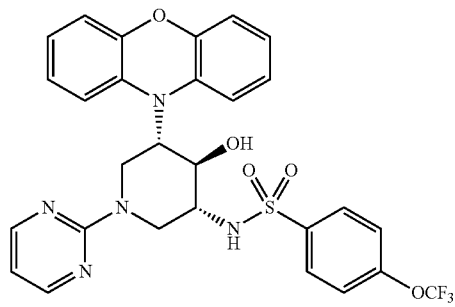 [SMILES: O=S(=O)(N[C@@H]1CN(c2ncccn2)C[C@H](N2c3ccccc3Oc3ccccc32)[C@H]1O)c1ccc(OC(F)(F)F)cc1] |
| Compound No. | Structure |
|---|---|
| 34 | 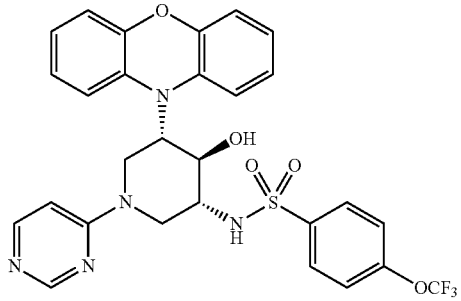 [SMILES: O=S(=O)(N[C@@H]1CN(c2ccncn2)C[C@H](N2c3ccccc3Oc3ccccc32)[C@H]1O)c1ccc(OC(F)(F)F)cc1] |
| 35 | 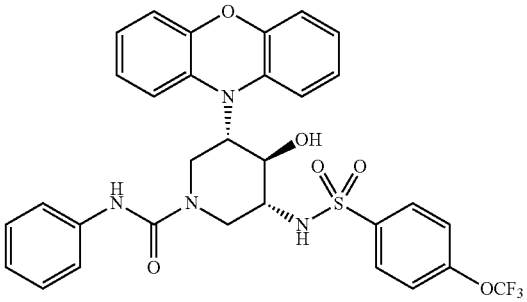 [SMILES: O=C(Nc1ccccc1)N1C[C@@H](NS(=O)(=O)c2ccc(OC(F)(F)F)cc2)[C@H](O)[C@@H](N2c3ccccc3Oc3ccccc32)C1] |
| 36 | 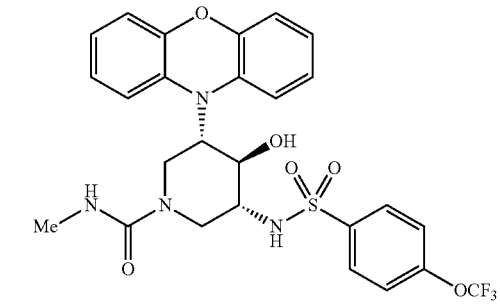 [SMILES: CNC(=O)N1C[C@@H](NS(=O)(=O)c2ccc(OC(F)(F)F)cc2)[C@H](O)[C@@H](N2c3ccccc3Oc3ccccc32)C1] |
| 37 | 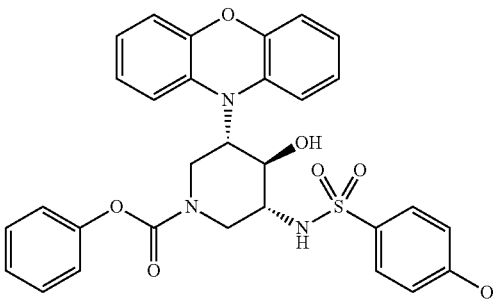 |
| 38 | 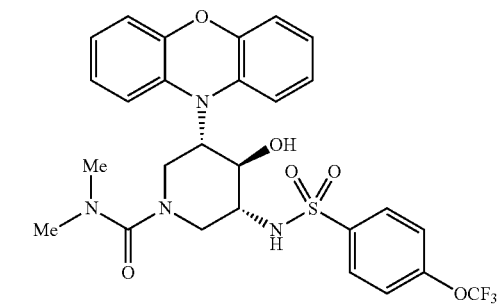 [SMILES: CN(C)C(=O)N1C[C@@H](NS(=O)(=O)c2ccc(OC(F)(F)F)cc2)[C@H](O)[C@@H](N2c3ccccc3Oc3ccccc32)C1] |

| Compound No. | Structure |
|---|---|
| 39 | 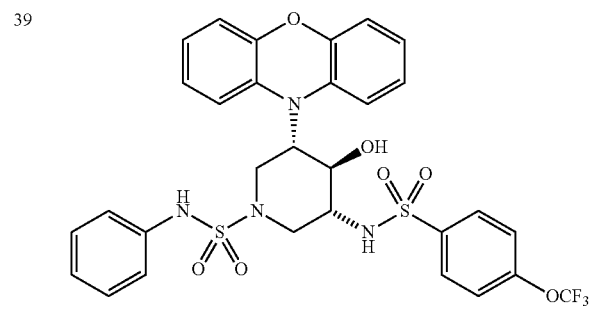 |
| 40 | 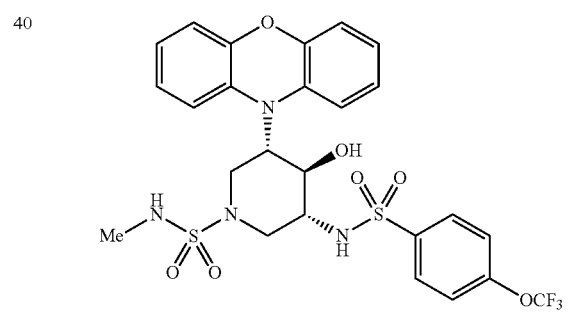 |
| 41 | 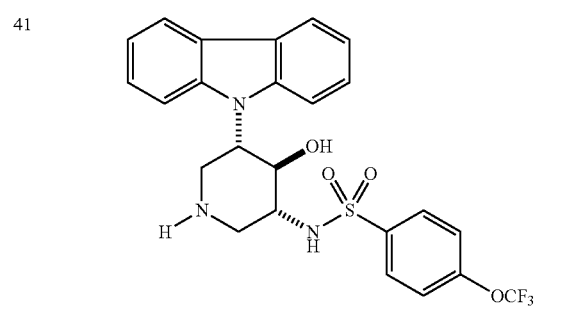 |
| 41a | 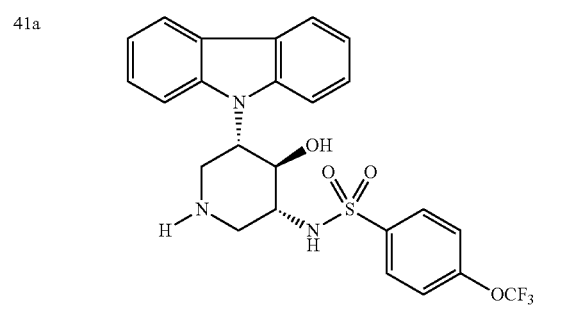 |
| 41b | 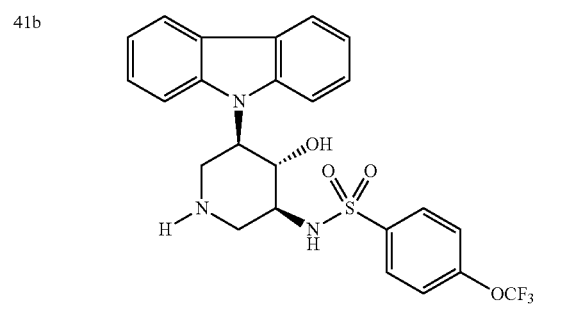 |
| Compound No. | Structure |
|---|---|
| 42 | 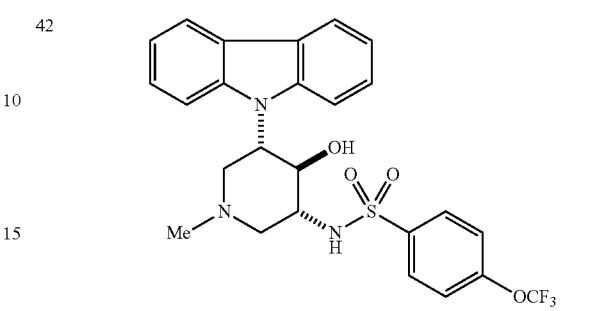 |
| 42a | 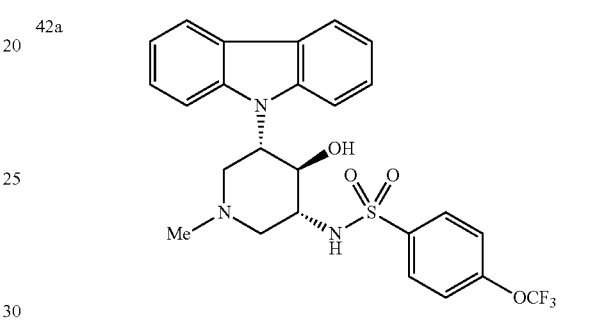 |
| 42b |  |
| 43 | 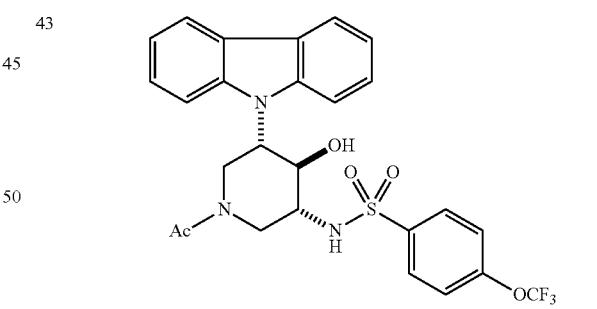 |
| 43a | 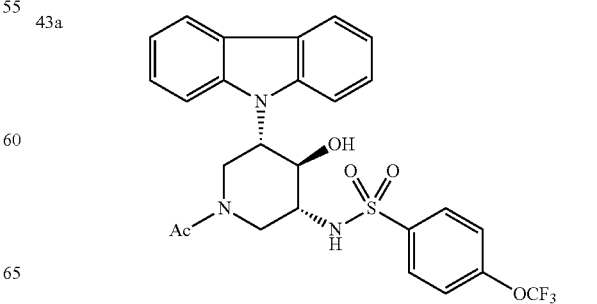 |

TABLE-continued
| Compound No. | Structure |
|---|---|
| 43b | 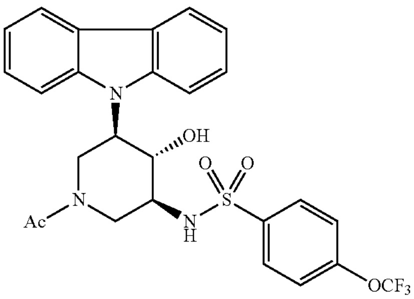 [SMILES: CC(=O)N1C[C@H](NS(=O)(=O)c2ccc(OC(F)(F)F)cc2)[C@@H](O)[C@H](n2c3ccccc3c3ccccc32)C1] |
| 44 | 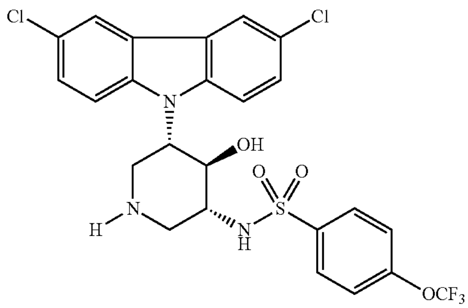 [SMILES: O=S(=O)(N[C@@H]1CNC[C@H](n2c3ccc(Cl)cc3c3cc(Cl)ccc32)[C@H]1O)c1ccc(OC(F)(F)F)cc1] |
| 45 | 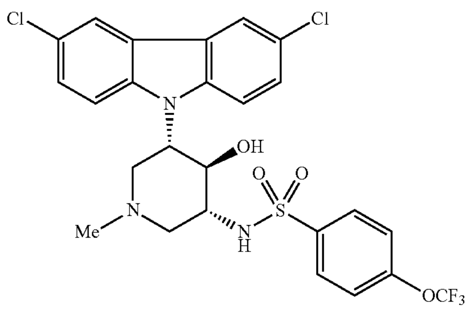 |
| 46 | 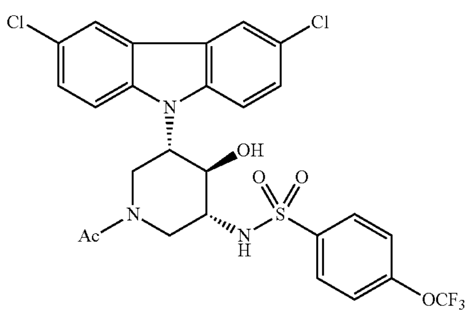 |
| 47 | 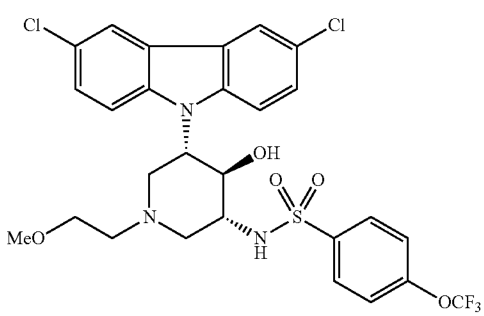 [SMILES: COCCN1C[C@@H](NS(=O)(=O)c2ccc(OC(F)(F)F)cc2)[C@H](O)[C@@H](n2c3ccc(Cl)cc3c3cc(Cl)ccc32)C1] |
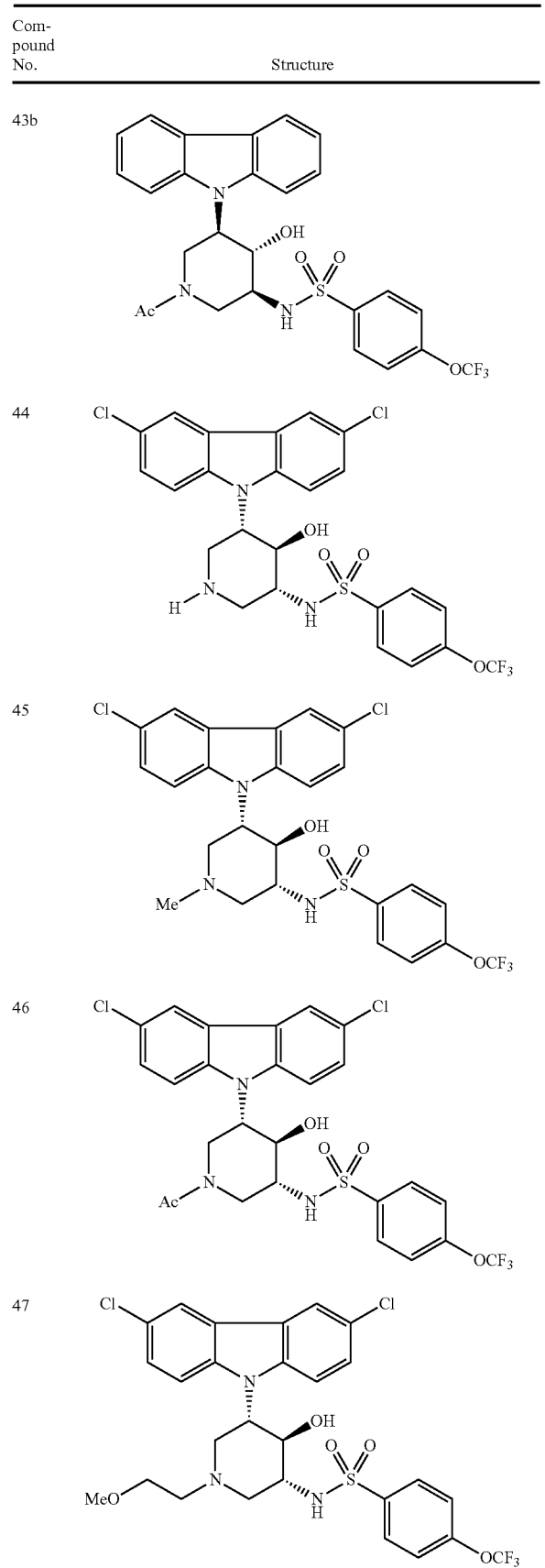
TABLE-continued
| Compound No. | Structure |
|---|---|
| 48 | 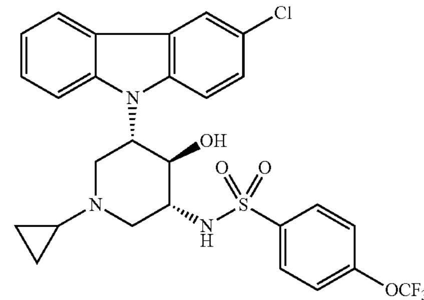 [SMILES: O=S(=O)(N[C@@H]1CN(C2CC2)C[C@H](n2c3ccccc3c3cc(Cl)ccc32)[C@H]1O)c1ccc(OC(F)(F)F)cc1] |
| 49 | 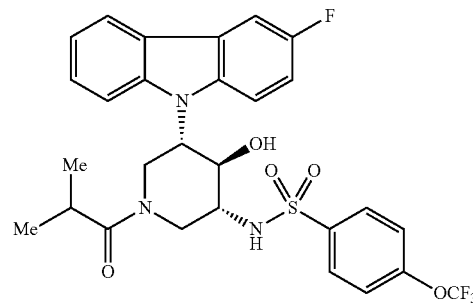 [SMILES: CC(C)C(=O)N1C[C@@H](NS(=O)(=O)c2ccc(OC(F)(F)F)cc2)[C@H](O)[C@@H](n2c3ccccc3c3cc(F)ccc32)C1] |
| 50 | 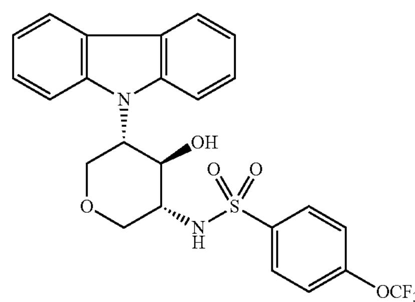 |
| 51 | 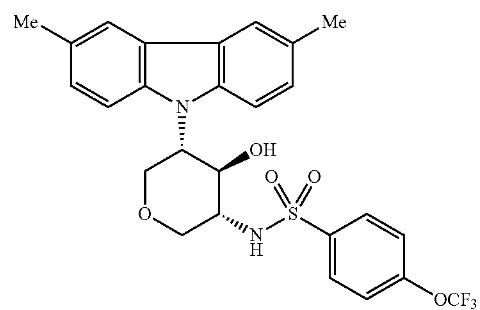 [SMILES: Cc1ccc2c(c1)c1cc(C)ccc1n2[C@H]1COC[C@@H](NS(=O)(=O)c2ccc(OC(F)(F)F)cc2)[C@@H]1O] |
| 52a | 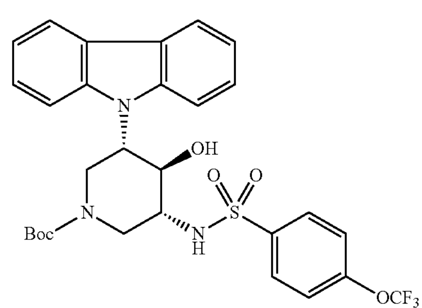 [SMILES: CC(C)(C)OC(=O)N1C[C@@H](NS(=O)(=O)c2ccc(OC(F)(F)F)cc2)[C@H](O)[C@@H](n2c3ccccc3c3ccccc32)C1] |
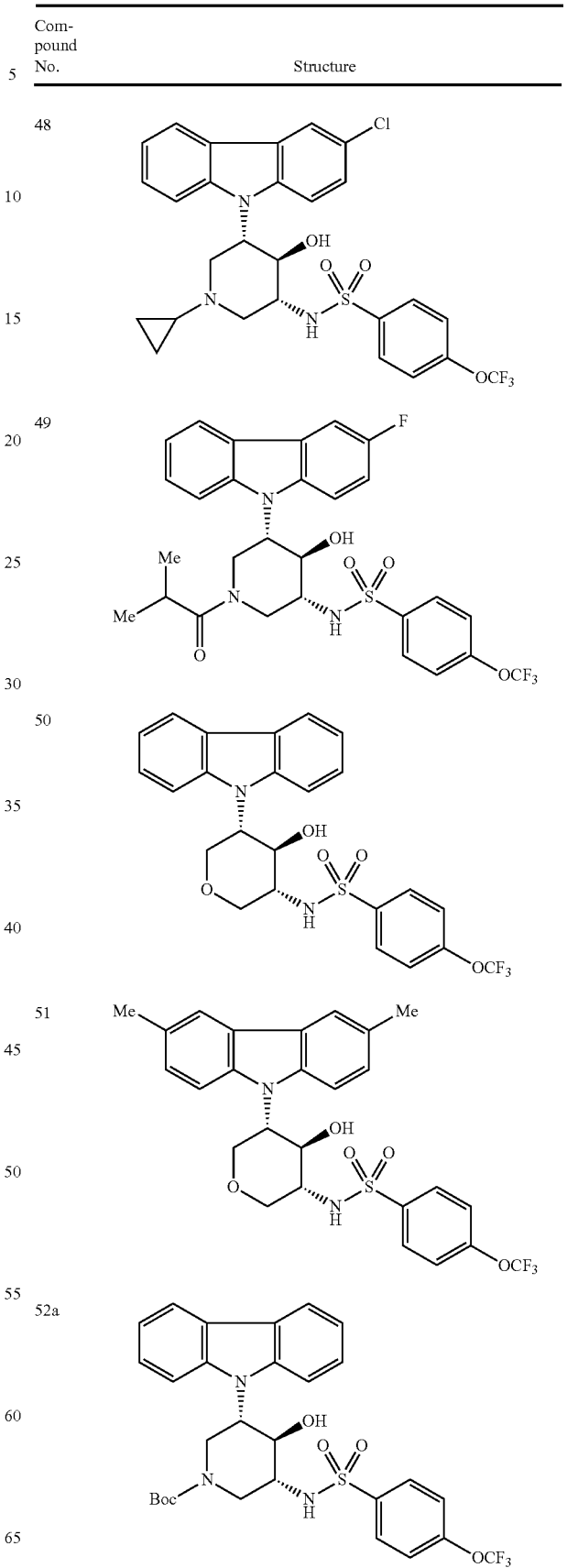

| Compound No. | Structure |
|---|---|
| 53a | 3-tBu carbazole-N-piperidine (HN), 4-OH, 3-NHSO₂-C₆H₄-4-OCF₃ |
| 52b | carbazole-N-piperidine (N-Boc), 4-OH, 3-NHSO₂-C₆H₄-4-OCF₃ |
| 53b | 3-tBu carbazole-N-piperidine (HN), 4-OH, 3-NHSO₂-C₆H₄-4-OCF₃ |
| 52 | carbazole-N-piperidine (N-Boc), 4-OH, 3-NHSO₂-C₆H₄-4-OCF₃ |
| 54 | 3,6-diF carbazole-N-piperidine (N-Boc), 4-OH, 3-NHSO₂-C₆H₄-4-OCF₃ |
| 55 | 3,6-diF carbazole-N-piperidine (HN), 4-OH, 3-NHSO₂-C₆H₄-4-OCF₃ |
| 56 | 3,6-diCl carbazole-N-piperidine (N-Boc), 4-OH, 3-NHSO₂-C₆H₄-4-OCF₃ |
| 44 | 3,6-diCl carbazole-N-piperidine (HN), 4-OH, 3-NHSO₂-C₆H₄-4-OCF₃ |
| 57 | 3,7-bis(CF₃) phenoxazine-N-piperidine (N-Boc), 4-OH, 3-NHSO₂-C₆H₄-4-OCF₃ |
| 58 | 3,7-bis(CF₃) phenoxazine-N-piperidine (HN), 4-OH, 3-NHSO₂-C₆H₄-4-OCF₃ |

| Compound No. | Structure |
|---|---|
| 60 | (phenoxazine-N-tetrahydropyran with OH and NHSO₂-phenyl) |
| 61 | (phenoxazine-N-tetrahydropyran with OH and NHSO₂-C₆H₄-Cl (para)) |
| 62 | (phenoxazine-N-tetrahydropyran with OH and NHSO₂-(5-chlorothiophen-2-yl)) |
| 63 | (phenoxazine-N-tetrahydropyran with OH and NHSO₂-(6-trifluoromethylpyridin-3-yl)) |
| 64 | (phenoxazine-N-tetrahydropyran with OH and NHSO₂-C₆H₄-Cl (meta)) |
| 65 | (phenoxazine-N-tetrahydropyran with OH and NHSO₂-C₆H₄-Cl (ortho)) |
| 66 | (phenoxazine-N-tetrahydropyran with OH and NHSO₂-C₆H₄-NHBoc (para)) |
| 67 | (phenoxazine-N-tetrahydropyran with OH and NHSO₂-C₆H₄-NH₂ (para)) |
| 68 | (phenoxazine-N-tetrahydropyran with OH and NHSO₂-C₆H₄-NHBoc (meta)) |
| 69 | (phenoxazine-N-tetrahydropyran with OH and NHSO₂-C₆H₄-NH₂ (meta)) |

| Compound No. | Structure |
|---|---|
| 70 | 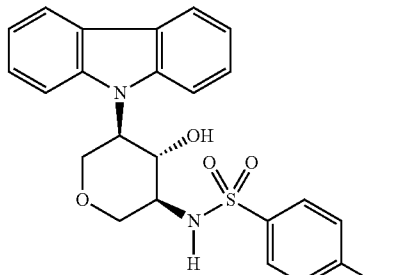 |
| 71 | 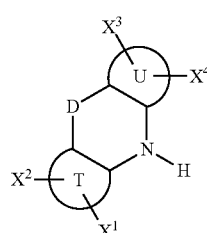 |

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1st Ed., Oxford University Press, 2000; and in *March's Advanced Organic chemistry: Reactions, Mechanisms, and Structure*, 5th Ed., Wiley-Interscience Publication, 2001.

Many compounds described herein may be prepared by the schemes shown in U.S. Provisional Application US 62/201,819, which is incorporated herein by reference. In general, compounds can be prepared by:

(a) reacting a compound of formula XII

XII

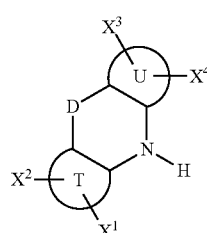

with a compound of formula XIII

XIII

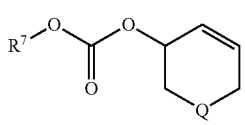

wherein $R^7$ is $(C_1-C_4)$alkyl, in the presence of a palladium catalyst to provide a product of formula XIV

XIV

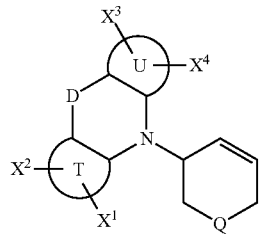

and oxidizing the product of formula XIV with osmium tetroxide to provide the cis diol XV or with meta chloroperbenzoic acid followed by hydrolysis of the resulting epoxide to provide the trans diol XVI:

XV

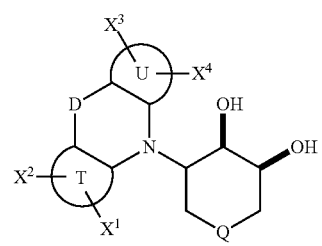

XIV

If a chiral palladium catalyst is used in the initial step to make XIV, the stereochemistry can thus be controlled for all products downstream.

The diol of formula XV/XVI

XV/XVI

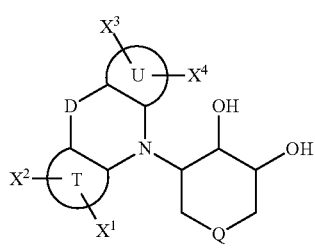

may be reacted with thionyl chloride or a sulfonyl chloride, such as methanesulfonyl chloride, to provide a sulfonylated product; and the sulfonylated product may be reacted with an alkali metal azide to provide a 3-azido-4-hydroxy-5-(heteroaryl)heterocycle of formula VI:

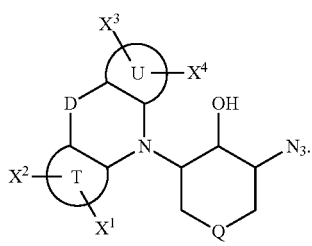

The azide may be reduced to provide the corresponding amine XVIII:

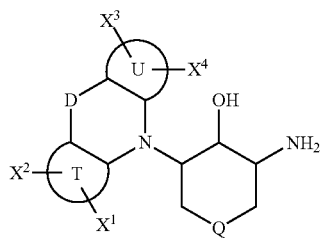

A convenient reducing agent is triphenyl phosphine, but there are many procedures known to persons of skill that may be employed for reducing an azide to an amine. The amine XVIII may be reacted with the appropriate sulfonyl chloride to provide the products described herein in which Y is OH and Q is oxygen. When Q is NR, the compounds may be made in the same fashion as above but with R initially being a protecting group, such as t-Boc or Cbz. The protecting group is then cleaved after synthesis is complete, and the resulting NH condensed with any acylating or alkylating agent needed by procedures well-known in the art. Introduction of aryl or heteroaryl moieties onto the ring nitrogen may be achieved by $SN_{Ar}$ substitution reactions for electron deficient aromatic systems such 4-nitrophenyl or electrophilic heteroaromatic systems such as 4-pyrimidinyl systems. More generally arylation or heteroarylation of the ring nitrogen may be achieved by palladium mediated N-aryl amination: the Buchwald-Hartwig reaction, see for example N. Marion et al, in "Modified (NHC)Pd(allyl)C$_1$(NHC)N-Heterocyclic Carbene) Complexes for Room-Temperature Suzuki-Miyaura and Buchwald-Hartwig Reactions" J. Am. Chem. Soc. 2006, 128, 4101 or J. P. Wolfe et al in "Rational Development of Practical Catalysts for Aromatic Carbon-Nitrogen Bond Formation. Examples as applied to compounds of the present invention are shown in the scheme below:

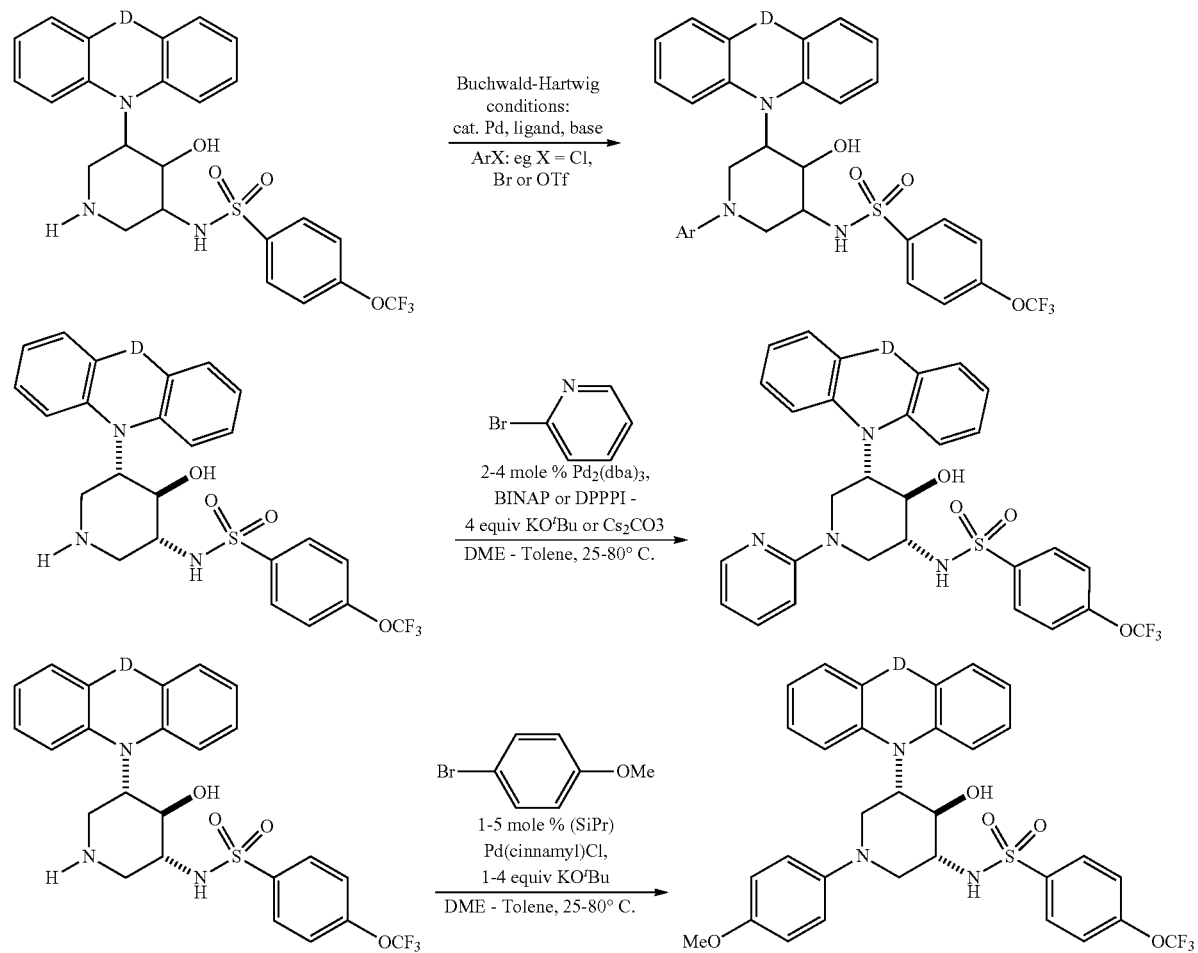

When Q is sulfur, the ring will either start out in the sulfone oxidation state or it will be oxidized to the sulfone when dihydroxylating the allylic olefin. The foregoing scheme produces sulfonamide products of the (1S,2S,3R)-re/configuration. When products of other relative configurations are desired, the cycloalkene may be oxidized with reagents, such as meta-chloroperbenzoic acid and others well-known to persons of skill in the art, and the resulting epoxide opened in a trans sense.)

When compounds in which Y is hydrogen are desired, the olefin XIV may be treated with a sterically hindered hydroborating agent such as 9-BBN or the like, followed by oxidation of the alkyboron to the alcohol with an oxidant such as N-methylmorpholine-N-oxide or aqueous hydrogen peroxide. The alcohol intermediate is converted to leaving group such as the mesylate and displaced with azide. This is carried forward to the target compound by reduction and reaction with the appropriate aryl sulfonyl chloride. This process is illustrated in the scheme below:

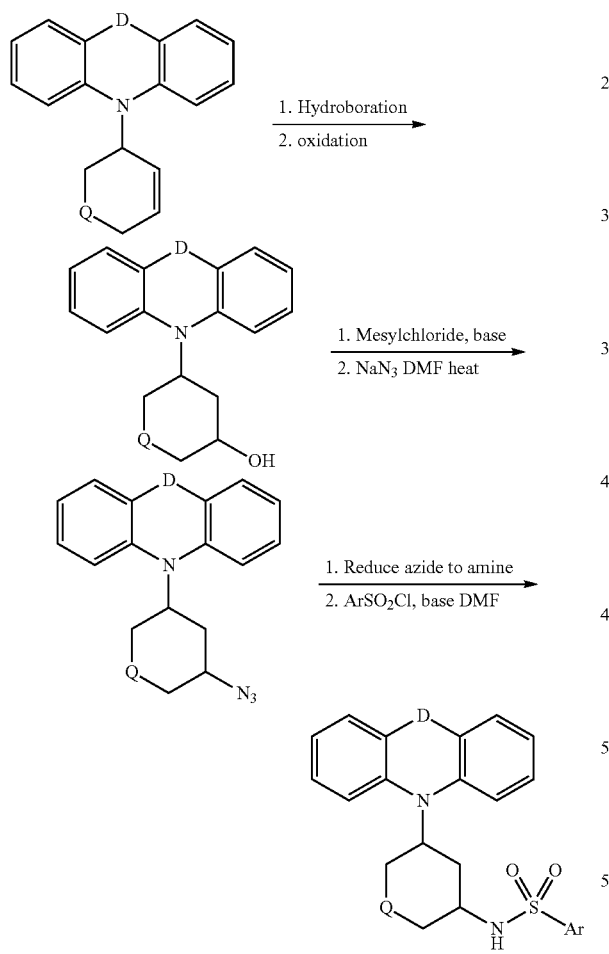

For example:
Alternatively compounds in which Y=H may be accessed via radical mediated deoxgenation processes as described in, for example, W. Hartwig in "Modern Methods For The Radical Deoxgenation of Alcohols", Tetrahedron Vol. 39, No. 16, page 2609 (1983). One example of this type of transformation as applied to compounds of the present invention (Barton-McCombie conditions) is shown below:

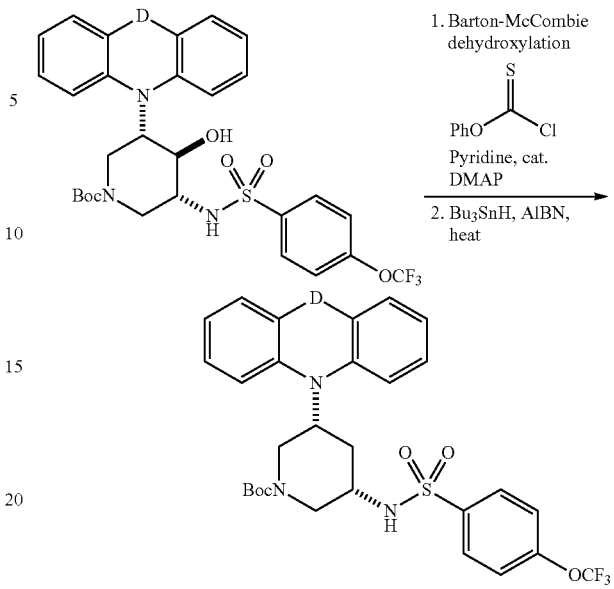

Exemplary syntheses are presented below:

Synthesis of Tert-butyl (3,6-dihydro-2H-pyran-3-yl) carbonate

Katcher et al:

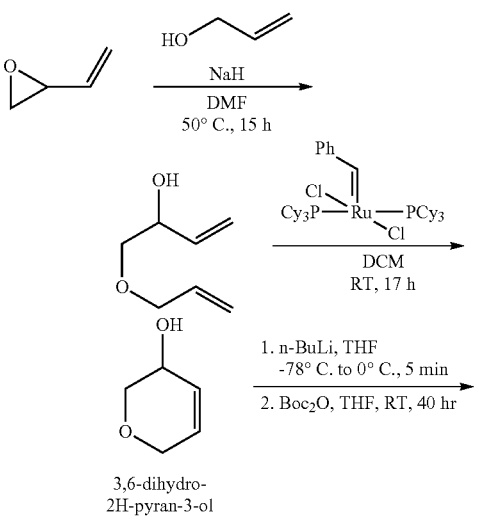

3,6-dihydro-2H-pyran-3-ol

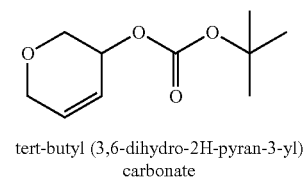

tert-butyl (3,6-dihydro-2H-pyran-3-yl) carbonate 3,6-dihydro-2H-pyran-3-ol is a known compound and was synthesized according to Katcher et al. J. Am. Chem. Soc., 2010, 132 (49), pp 17402-17404. It may be converted to tert-butyl (3,6-dihydro-2H-pyran-3-yl) carbonate: to a solution of 3,6-dihydro-2H-pyran-3-ola 1 (1.00 g, 9.98 mmol) in THF (33 mL) was added n-butyllithium (2.5 M in hexanes, 3.95 mL, 9.98 mmol) at −78° C. The resulting solution was warmed to 0° C. and stirred for 5 min prior to addition of di-tertbutyl dicarbonate (2.38 g, 10.9 mmol) in THF (17 mL). The reaction was warmed to RT, stirred for 40 h. The reaction was then quenched with water, extracted with ethyl acetate, washed with brine, concentrated, and the residue purified by flash chromatography (SiO$_2$, 0%-3% ethyl acetate-hexanes) to afford tert-butyl cyclohex-2-en-1-yl carbonate 2 (1.39 g, 70%) as a colorless oil. TLC solvent: 7:1 hexane-ethylacetate (P-anisaldehdye used for staining). 1H NMR (600 MHz, CDCl3) δ 6.04 (1H, d, J=10.2 Hz), 5.94-5.92 (1H, m), 4.88 (1H, bs), 4.19-4.16 (1H, m), 4.06-4.03 (1H, m), 3.93-3.91 (1H, m), 3.80 (1H, dd, J=12.6, 1.8 Hz), 1.46 (9H, s); 13C NMR (150 MHz, MeOD) δ 153.2, 132.4, 122.4, 82.4, 67.5, 65.1, 41.7, 27.9.

The analogous sulfur based heterocycles may be accessed using prop-2-ene-1-thiol in an analogous scheme, with optional oxidation to the sulfoxide or sulfone:

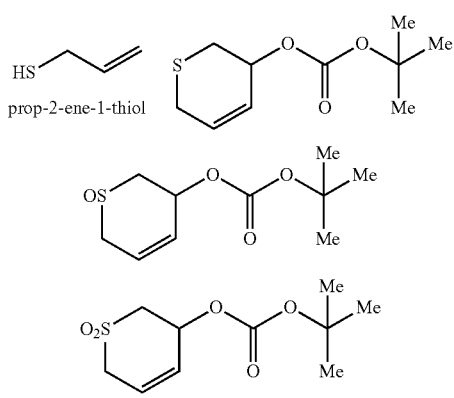

An alternative route to tert-butyl (3,6-dihydro-2H-pyran-3-yl) carbonate is to establish the pyran ring system via an Achmatowicz furanylcarbinol rearrangement and perform functional group interconversions as shown in the scheme below:

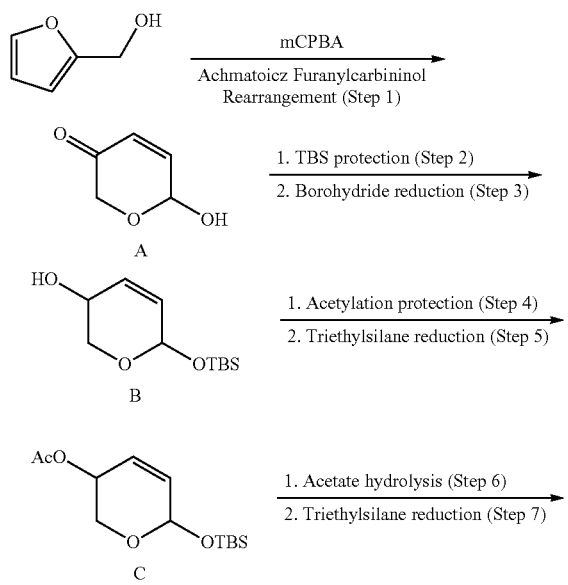

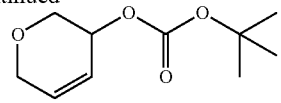

tert-butyl (3,6-dihydro-2H-pyran-3-yl) carbonate

Step 1: m-CPBA (3000 g, 17.4 mol, 1.72 eq) was added to a solution of furfuryl alcohol (1000 g, 10.2 mol, 1.0 eq) in DCM (15 L) at 0° C. The mixture was stirred at 0° C. for 3 h. The solid was filtered and the filtrate was concentrated under vacuum to give intermediate A (630 g, ~54%) as yellow solid. Step 2: To a solution of compound A (630 g, 5.52 mol, 1.0 eq) in DCM under N$_2$ was cooled to −78° C. 2,6-Lutidine (828 g, 7.73 mol, 1.4 eq) was then added in one portion, followed by slowly addition of t-butyldimethylsilyltrifluoromethanesulfonate (1750 g, 6.62 mol, 1.2 eq). The reaction was allowed to slowly warm to 0° C. over 4 h. The reaction was then quenched by addition of 6 L of water. The organic phase was washed with 10% citric acid and brine. The organic layer was then dried over Na$_2$SO$_4$, filtered and condensed to give yellow oil, which was purified on silica gel (PE:EA=40:1-20:1) to give a TBS protected intermediate (900 g, ~71.4%) as a yellow oil. This intermediate was carried into step 3: (675.0 g, 2.96 mol, 1.0 eq) and CeCl$_3$.7H$_2$O (1101 g, 2.96 mol, 1.0 eq) in MeOH was cooled to −20° C. Then NaBH$_4$ (123 g, 3.25 mol, 1.1 eq) was added portion wise. The mixture was stirred at −20° C. for 30 min, and quenched with acetone (~1350 mL) and stirred at RT (room temperature) for 1 h. The solvent was removed under reduced pressure. Brine was added and the slurry was transferred to a separatory funnel. The mixture was extracted with DCM (thick emulsion formed) three times. The combined organic layers were dried over Na$_2$SO$_4$, filtered and condensed to give crude intermediate B (424 g, ~62%) as a tan colored oil. Step 4: To a solution of intermediate B (424 g, 1.84 mol, 1.0 eq) and TEA (372 g, 3.68 mol, 2.0 eq) in DCM (4 L) was added acetic anhydride (939 g, 9.2 mol, 5.0 eq), and the solution was stirred at RT overnight. MeOH (95 mL) was added and the mixture was stirred at RT for 30 min before adding water and transferring to a separatory funnel. The organic layer was washed with water and brine, dried over Na$_2$SO$_4$, filtered and condensed. The crude material was purified on a silica gel column (PE:EA=30:1-15:1-10:1) to give an acetylated intermediate (320 g, ~64%) as a pale yellow oil. This intermediate was reduced in step 5: (320 g, 1.17 mol, 1.0 eq) was dissolved in DCM (3 L), placed under a nitrogen atmosphere, and cooled to −30° C. (dry ice/acetone). Triethylsilane (272 g, 2.34 mol, 2.0 eq) was then added slowly via syringe, followed by drop wise addition of BF$_3$Et$_2$O (179 ml, 1.2 eq). The reaction was kept under nitrogen and slowly allowed to warm. After 1 h, the reaction mixture was quenched by additions of saturated sodium bicarbonate. After transferring to a separatory funnel, the organic layer was washed with water and brine, dried over sodium sulfate, filtered and condensed. The crude material was purified on a silica gel column (PE:EA=20:1-10:1-5:1). Evaporation of clean fractions gave intermediate C (140 g, yield-84%) as a colorless oil. Step 6: To a solution of intermediate C (140, 0.98 mol, 1.0 eq) in methanol was added 30% sodium methoxide (35 mL) in methanol. The solution was allowed to stir at room temperature. After 30 min, TLC showed complete conversion to product. Evaporation of the solvent gave 3,6-dihydro-2H-pyran-3-ol (100 g, ~83%) as a colorless oil. This was Boc activated in step 7:(100 g, 1.0 eq) in THF was added K$_2$CO$_3$ (140 g, 1.01 mol, 1.23 eq), Boc$_2$O (210 g, 0.96 mol, 1.17 eq), and DMAP (7 g, 0.06 mol). The resulting solution was stirred at RT for 3 h. After evaporation of the solvent under reduced pressure, the residue was purified by flash chromatography (PE: EA=30:1) to afford tert-butyl cyclohex-2-en-1-yl carbonate (105 g, ~64%) as a colorless oil.
Scheme for Synthesis of Example 1
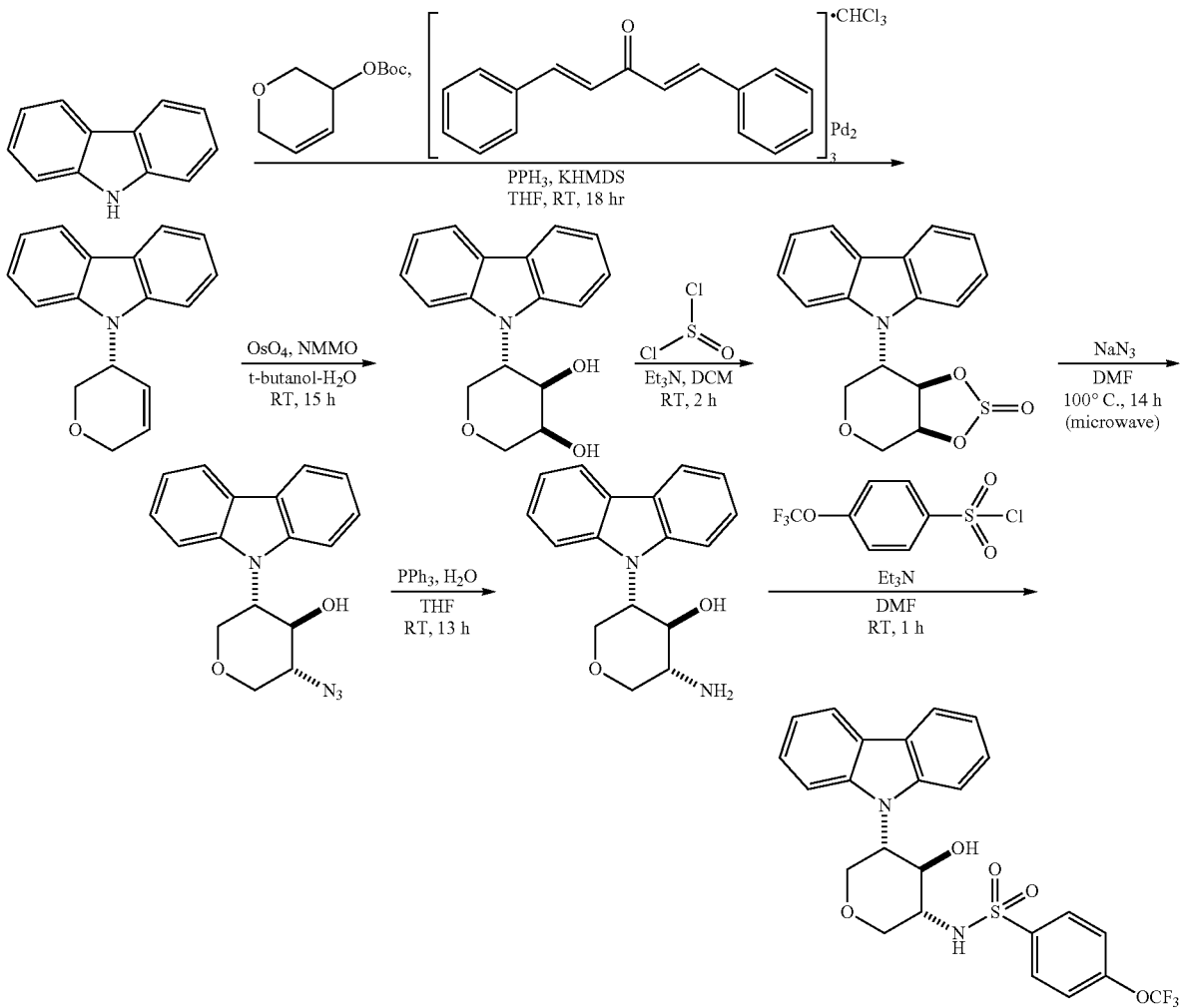
Experimental
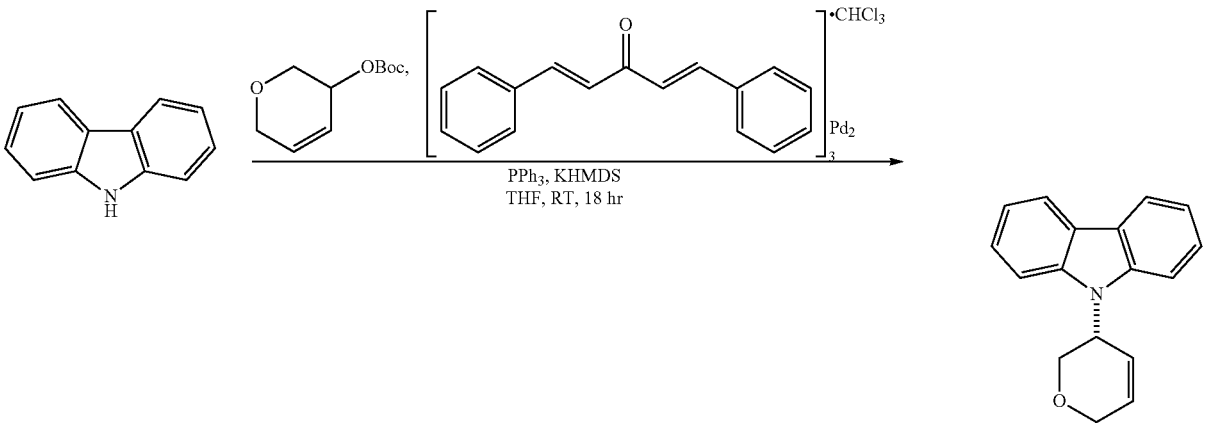

Rac-9-(3,6-dihydro-2H-pyran-3-yl)-9H-carbazole

A 20 mL Biotage microwave reaction vial (vial A) was charged with Pd$_2$.dba$_3$. CHCl$_3$ (0.103 g, 0.100 mmol), and triphenyl phosphine (0.078 g, 0.300 mmol). The vial was sealed, evacuated and backfilled with argon three times. Dry degassed dichloromethane (6.0 mL) was added to this vial, and the mixture was stirred at RT (room temperature) for 60 min. A separate 20 mL Biotage® microwave reaction vial (vial B) was charged with 9H-carbazole (0.334 g, 2.00 mmol) and dry degassed dichloromethane (5.0 mL), followed by potassium bis(trimethylsilyl)amide (2.00 mL, 2.00 mmol, 1 M solution in THF), and the mixture was stirred at RT for 60 min. After stirring for 60 min, Rac-tert-butyl (3,6-dihydro-2H-pyran-3-yl) carbonate (0.480 g, 2.40 mmol) was added to vial A, all its contents were transferred to vial B, and the reaction mixture was stirred at RT for 18 h. At this point, the reaction mixture was evaporated onto silica gel and subjected to column chromatography (SiO$_2$; 1% ethylacetate in hexanes) to afford title compound (0.148 g, 30%). $^1$H NMR (600 MHz, CDCl$_3$) δ 8.12 (2H, d, J=7.8 Hz), 7.60 (2H, d, J=6.6 Hz), 7.45 (2H, t, J=7.2 Hz), 7.26 (2H, d, J=7.2 Hz), 6.23 (1H, d, J=10.2 Hz), 6.16 (1H, d, J=10.2 Hz), 5.46 (1H, br s), 4.47 (1H, d, J=19.2 Hz), 4.37 (1H, d, J=16.8 Hz), 4.19-4.11 (2H, m); $^{13}$C NMR (150 MHz, CDCl$_3$) δ 140.2, 129.6, 126.5, 125.8, 123.5, 120.5, 119.3, 110.1, 66.3, 65.4, 49.0; LCMS m/z 250.1226 ([M+H$^+$], C$_{17}$H$_{16}$NO requires 250.1227).

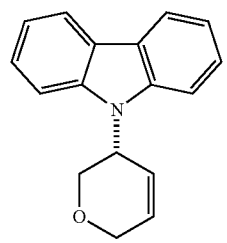

Rac-(3S,4R,5S)-5-(9H-carbazol-9-yl)tetrahydro-2H-pyran-3,4-diol

Reaction was done in two 0.130 g batches of Rac-9-(3,6-dihydro-2H-pyran-3-yl)-9H-carbazole: A solution of Rac-9-(3,6-dihydro-2H-pyran-3-yl)-9H-carbazole (0.130 g, 0.521 mmol), 4-methylmorpholine N-oxide monohydrate (0.067 g, 0.573 mmol), and osmium tetroxide (0.052 mL, 0.005 mmol, 2.5% in tert-butanol) in tert-butanol (1.00 mL) and water (0.10 mL), was stirred at RT for 15 h. Reaction mixture from both batches were treated with solid sodium bisulfite, stirred for 1 h, evaporated on to silica, and purified by flash chromatography (SiO$_2$, 0%-70% ethyl acetate-hexanes) to afford title compound (0.037 g, 11%). $^1$H NMR (600 MHz, CDCl$_3$) δ 8.11 (2H, br s), 7.55-7.46 (2H, m), 7.27 (2H, t, J=7.8 Hz), 5.04 (1H, d, J=3.6 Hz), 4.78 (1H, d, J=10.2 Hz), 4.28-4.21 (3H, m), 4.09-4.08 (1H, m), 3.79 (1H, d, J=12.6 Hz), 2.75 (1H, br s), 2.20 (1H, br s); $^{13}$C NMR (150 MHz, CDCl$_3$) δ 141.9, 138.7, 126.3, 125.8, 121.0, 120.3, 111.2, 109.1, 70.8, 69.0, 68.8, 67.1, 54.4; LCMS m/z 284.1285 ([M+H$^+$], C$_{17}$H$_{18}$NO$_3$ requires 284.1282).

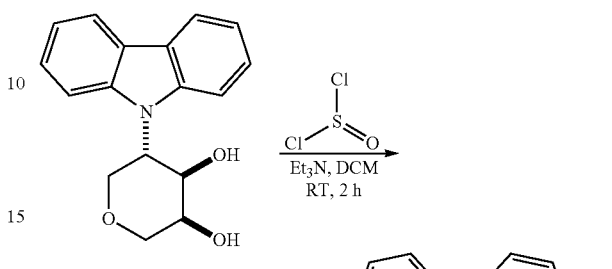

Rac-(3aS,7S,7aR)-7-(9H-carbazol-9-yl)tetrahydro-3aH-[1,3,2]dioxathiolo[4,5-c]pyran 2-oxide A solution of Rac-(3S,4R,5S)-5-(9H-carbazol-9-yl)tetrahydro-2H-pyran-3,4-diol (0.257 g, 0.907 mmol) in dichloromethane (2.00 mL) was cooled to 0° C., treated with triethylamine (1.00 mL, 7.26 mmol), then thionyl chloride (0.197 mL, 2.72 mmol) was added drop-wise. The reaction mixture was warmed to room temperature, stirred for 2 h, partitioned between dichloromethane and water. The organic layer was concentrated to give a residue, which was subjected to column chromatography (SiO$_2$, 17% ethylacetate in hexanes) to afford the title compound (0.277 g, 93%). $^1$H NMR (600 MHz, CDCl$_3$) δ as a mixture of sulfur diastereomers 8.14 (2H, d, J=7.8 Hz), 7.48-7.47 (2H, m), 7.40 (2H, d, J=8.4 Hz), 7.31-7.28 (2H, m), 5.76-5.74 & 5.55-5.53 (1H, m), 5.72-5.68 & 4.79-4.74 (1H, m), 5.23 & 4.81 (1H, d, J=4.8 Hz), 4.33-4.24 (1H, m), 4.19-4.05 (3H, m); LCMS m/z 330.0782 ([M+H$^+$], C$_{17}$H$_{16}$NO$_4$S requires 330.0795).

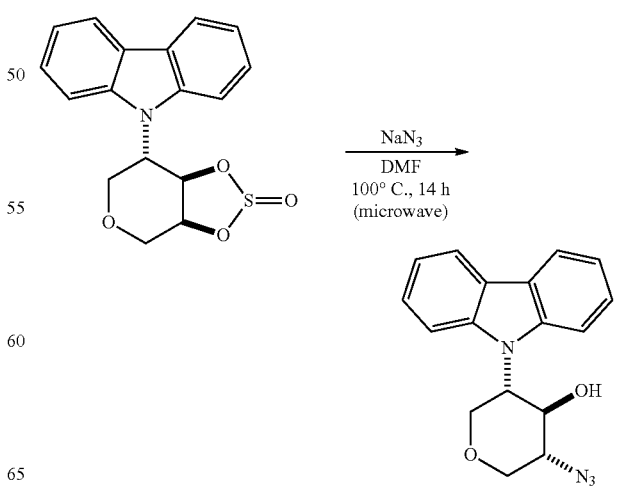

Rac-(3R,4R,5S)-3-azido-5-(9H-carbazol-9-yl)tetrahydro-2H-pyran-4-ol

A solution of Rac-(3aS,7S,7aR)-7-(9H-carbazol-9-yl)tetrahydro-3aH-[1,3,2]dioxathiolo[4,5-c]pyran 2-oxide (0.277 g, 0.841 mmol) in DMF (1.0 mL) was treated with sodium azide (0.066 g, 1.00 mmol), and heated to 100° C. in a microwave for 14 h. The reaction mixture was treated with sat. aq. $NH_4C_1$, extracted with ethylacetate, washed with brine, concentrated, purified by column chromatography ($SiO_2$, 6%-13% ethylacetate-hexanes) to afford the title compound (0.140 g, 54%). $^1$H NMR (600 MHz, $CDCl_3$) δ 8.11 (2H, dd, J=24.0, 7.8 Hz), 7.53-7.49 (3H, m), 7.44 (1H, t, J=7.8 Hz), 7.29=7.27 (2H, m), 4.71-4.65 (2H, m), 4.25 (1H, t, J=11.4 Hz), 4.14 (1H, dd, J=12.0, 5.4 Hz), 4.01-3.99 (1H, m), 3.80-3.76 (1H, m), 3.39 (1H, t, J=11.4 Hz), 2.15 (1H, br s); $^{13}$C NMR (150 MHz, $CDCl_3$) δ 141.6, 138.3, 126.5, 125.9, 124.6, 123.1, 121.1, 120.4, 120.1, 119.9, 111.1, 109.0, 72.7, 69.1, 67.1, 62.8, 57.9; LCMS m/z 309.1345 ([M+H$^+$], $C_{17}H_{17}N_4O_2$ requires 309.1347).

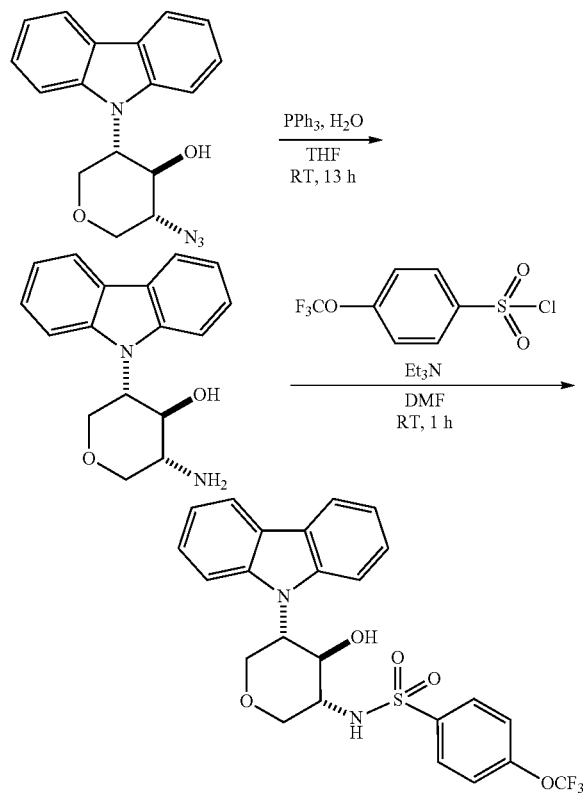

Rac-N-(3R,4R,5S)-5-(9H-carbazol-9-yl)-4-hydroxytetrahydro-2H-pyran-3-yl)-4-(trifluoromethoxy)benzenesulfonamide (Example 1)

A solution of Rac-(3R,4R,5S)-3-azido-5-(9H-carbazol-9-yl)tetrahydro-2H-pyran-4-ol (0.130 g, 0.422 mmol) in THF (1.40 mL) was cooled to 0° C., treated with $PPh_3$ (0.121 g, 0.464 mmol), $H_2O$ (0.001 mL, 0.055 mmol), and stirred for 13 h at room temperature. The solution was concentrated to dryness, dissolved in a minimal amount of dichloromethane and purified by flash chromatography ($SiO_2$, 100% hexanes, 50% ethyl acetate-hexanes, 5%, methanol-dichlormethane, 17:2:1 dichloromethane:methanol:35% ammonium hydroxide) to afford slightly crude Rac-(3R,4S,5S)-3-amino-5-(9H-carbazol-9-yl)tetrahydro-2H-pyran-4-ol (0.120 g) which was taken to the next step without further purification.

A solution of Rac-(3R,4S,5S)-3-amino-5-(9H-carbazol-9-yl)tetrahydro-2H-pyran-4-ol (0.120 g, 0.425 mmol) in DMF (1.40 mL) was cooled to 0° C., treated with triethylamine (0.236 mL, 1.70 mmol), and 4-(trifluoromethoxy)benzene-1-sulfonyl chloride (0.079 mL, 0.468 mmol). The mixture was warmed to room temperature, and stirred for 1 h. The mixture was partitioned between water and ethylacetate. The organic layer was washed with brine, and concentrated in vacuo. The residue was dissolved in a minimal amount of dichloromethane and purified by flash chromatography (Sift, 17%-20% ethylacetate-hexanes) to afford the title compound (0.157 g, 74% over two steps). $^1$H NMR (600 MHz, $CDCl_3$) δ 8.09 (1H, d, J=6.6 Hz), 8.02 (1H, d, J=6.0 Hz), 7.85 (2H, d, J=7.8 Hz), 7.50 (1H, d, J=7.2 Hz), 7.38-7.33 (3H, m), 7.25-7.21 (4H, m), 5.44 (1H, br s), 4.52 (2H, br s), 4.18 (1H, br s), 4.12-4.10 (1H, m), 3.93 (1H, d, J=10.2 Hz), 3.38 (2H, br s), 2.19 (1H, br s); $^{13}$C NMR (150 MHz, $CDCl_3$) δ 152.5, 141.5, 138.2, 137.9, 129.5, 126.4, 125.8, 124.5, 122.9, 121.0, 120.3, 120.0, 119.8, 111.2, 109.0, 70.7, 70.0, 67.0, 58.0, 56.4; LCMS m/z 507.1189 ([M+H$^+$], $C_{24}H_{22}F_3N_2O_5S$ requires 507.1197).

Scheme for Synthesis of (Example 3)

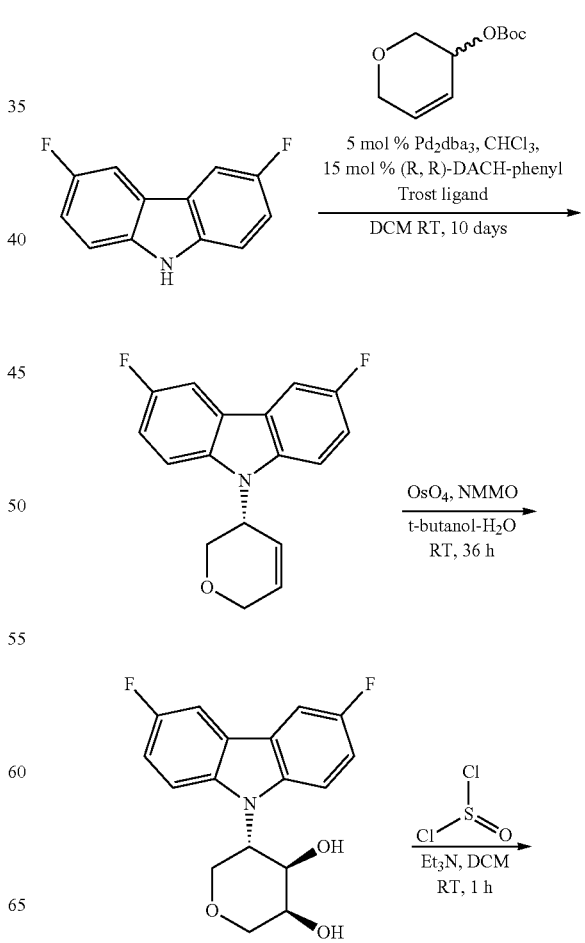

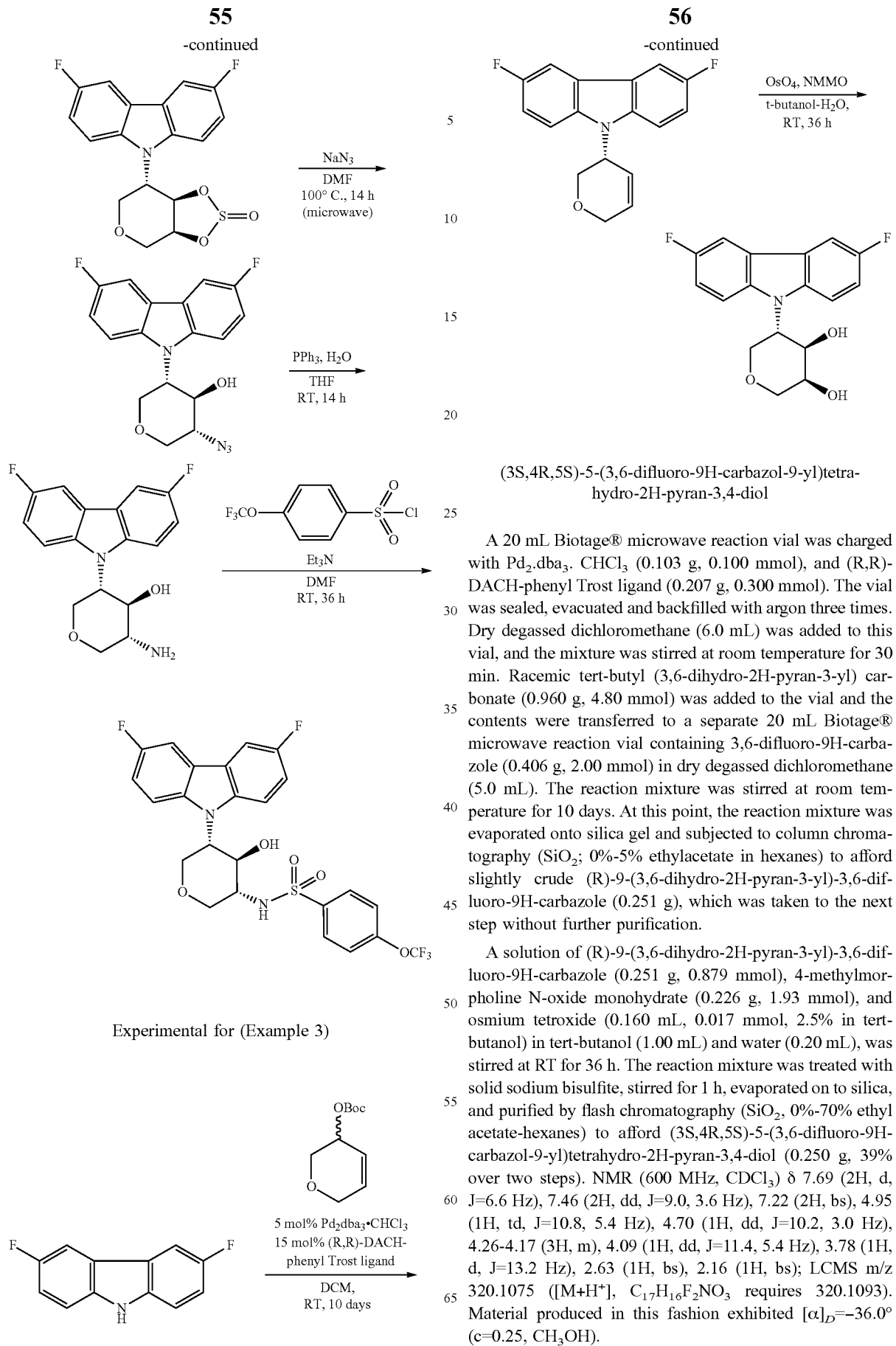

(3S,4R,5S)-5-(3,6-difluoro-9H-carbazol-9-yl)tetrahydro-2H-pyran-3,4-diol

A 20 mL Biotage® microwave reaction vial was charged with Pd$_2$.dba$_3$. CHCl$_3$ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 3,6-difluoro-9H-carbazole (0.406 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO$_2$; 0%-5% ethylacetate in hexanes) to afford slightly crude (R)-9-(3,6-dihydro-2H-pyran-3-yl)-3,6-difluoro-9H-carbazole (0.251 g), which was taken to the next step without further purification.

A solution of (R)-9-(3,6-dihydro-2H-pyran-3-yl)-3,6-difluoro-9H-carbazole (0.251 g, 0.879 mmol), 4-methylmorpholine N-oxide monohydrate (0.226 g, 1.93 mmol), and osmium tetroxide (0.160 mL, 0.017 mmol, 2.5% in tert-butanol) in tert-butanol (1.00 mL) and water (0.20 mL), was stirred at RT for 36 h. The reaction mixture was treated with solid sodium bisulfite, stirred for 1 h, evaporated on to silica, and purified by flash chromatography (SiO$_2$, 0%-70% ethyl acetate-hexanes) to afford (3S,4R,5S)-5-(3,6-difluoro-9H-carbazol-9-yl)tetrahydro-2H-pyran-3,4-diol (0.250 g, 39% over two steps). NMR (600 MHz, CDCl$_3$) δ 7.69 (2H, d, J=6.6 Hz), 7.46 (2H, dd, J=9.0, 3.6 Hz), 7.22 (2H, bs), 4.95 (1H, td, J=10.8, 5.4 Hz), 4.70 (1H, dd, J=10.2, 3.0 Hz), 4.26-4.17 (3H, m), 4.09 (1H, dd, J=11.4, 5.4 Hz), 3.78 (1H, d, J=13.2 Hz), 2.63 (1H, bs), 2.16 (1H, bs); LCMS m/z 320.1075 ([M+H$^+$], C$_{17}$H$_{16}$F$_2$NO$_3$ requires 320.1093). Material produced in this fashion exhibited [α]$_D$=−36.0° (c=0.25, CH$_3$OH).

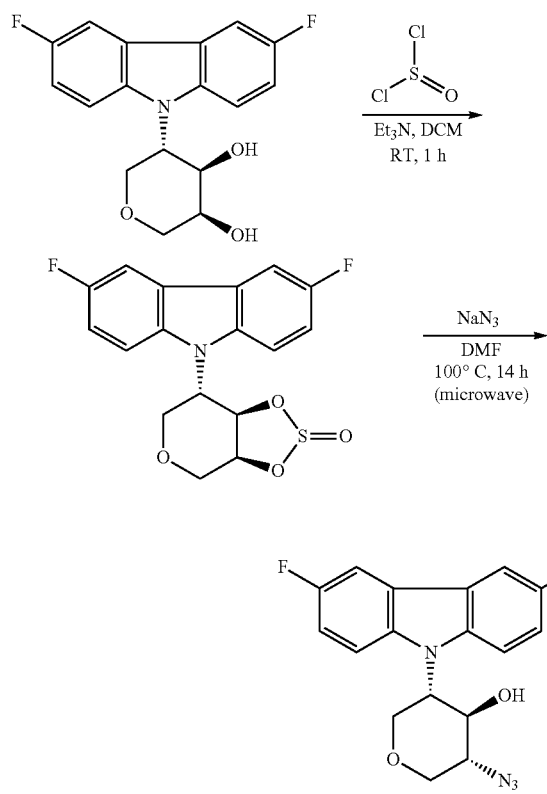
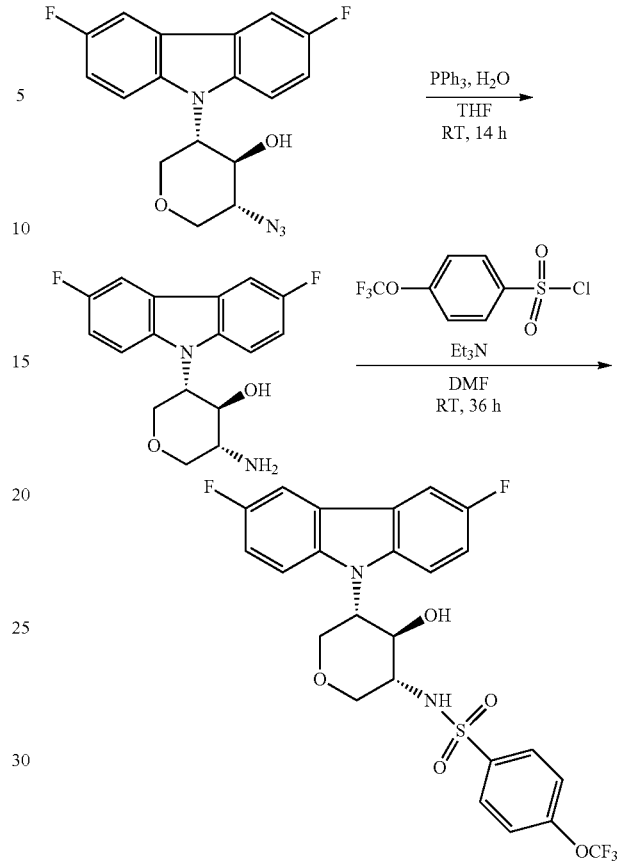

(3R,4R,5S)-3-azido-5-(3,6-difluoro-9H-carbazol-9-yl)tetrahydro-2H-pyran-4-ol

A solution of (3S,4R,5S)-5-(3,6-difluoro-9H-carbazol-9-yl)tetrahydro-2H-pyran-3,4-diol (0.250 g, 0.783 mmol) in dichloromethane (10.0 mL) was cooled to 0° C., treated with triethylamine, then slowly, over an extended period of time thionyl chloride (0.170 mL, 2.35 mmol) was added. The reaction mixture was warmed to room temperature, stirred for 1 h, partitioned between dichloromethane and water. The organic layer was concentrated to give a residue which was subjected to column chromatography (SiO$_2$, 17% ethylacetate in hexanes) to afford slightly crude (3aS,7S,7aR)-7-(3, 6-difluoro-9H-carbazol-9-yl)tetrahydro-3aH-[1,3,2]dioxathiolo[4,5-c]pyran 2-oxide (0.223 g), which was taken to the next step without further purification.

A solution of (3aS,7S,7aR)-7-(3,6-difluoro-9H-carbazol-9-yl)tetrahydro-3aH-[1,3,2]dioxathiolo[4,5-c]pyran 2-oxide (0.223 g, 0.610 mmol) in DMF (2.0 mL) was treated with sodium azide (0.170 g, 1.83 mmol), and heated to 100° C. in a microwave for 14 h. The reaction mixture was treated with sat. aq. NH$_4$C$_1$, extracted with ethylacetate, washed with brine, concentrated, purified by column chromatography (SiO$_2$, 6%-13% ethylacetate-hexanes) to afford (3R,4R,5S)-3-azido-5-(3,6-difluoro-9H-carbazol-9-yl)tetrahydro-2H-pyran-4-ol (0.128 g, 48% over two steps). $^1$H NMR (600 MHz, CDCl$_3$) δ 7.69 (2H, ddd, J=25.8, 8.4, 2.4 Hz), 7.46-7.42 (2H, m), 7.27-7.18 (2H, m), 4.64-4.57 (2H, m), 4.23-4.19 (2H, m), 4.05 (1H, dd, J=11.4, 5.4 Hz), 3.83-3.79 (1H, m), 3.41 (1H, t, J=11.4 Hz), 2.18 (1H, bs); LCMS m/z 345.1149 ([M+H$^+$], C$_{17}$H$_{15}$F$_2$N$_4$O$_2$ requires 345.1158).

N-((3R,4R,5S)-5-(3,6-difluoro-9H-carbazol-9-yl)-4-hydroxytetrahydro-2H-pyran-3-yl)-4-(trifluoromethoxy)benzenesulfonamide (Example 3):

A solution of 3-azido-5-(3,6-difluoro-9H-carbazol-9-yl)tetrahydro-2H-pyran-4-ol (0.128 g, 0.372 mmol) in THF (2.25 mL) was cooled to 0° C., treated with PPh$_3$ (0.107 g, 0.408 mmol), H$_2$O (0.001 mL, 0.055 mmol), and stirred for 14 h at room temperature. The solution was concentrated to dryness, dissolved in a minimal amount of dichloromethane and purified by flash chromatography (SiO$_2$, 100% hexanes, 50% ethyl acetate-hexanes, 5%, methanol-dichlormethane, 17:2:1 dichloromethane:methanol:35% ammonium hydroxide) to afford slightly crude (3R,4S,5S)-3-amino-5-(3,6-difluoro-9H-carbazol-9-yl)tetrahydro-2H-pyran-4-ol (0.109 g) which was taken to the next step without further purification.

A solution of (3R,4S,5S)-3-amino-5-(3,6-difluoro-9H-carbazol-9-yl)tetrahydro-2H-pyran-4-ol (0.109 g, 0.342 mmol) in DMF (2.0 mL) was cooled to 0° C., treated with triethylamine (0.190 mL, 1.37 mmol), and 4-(trifluoromethoxy)benzene-1-sulfonyl chloride (0.063 mL, 0.377 mmol). The mixture was warmed to room temperature, and stirred for 36 h. The mixture was partitioned between water and ethylacetate. The organic layer was washed with brine, and concentrated in vacuo. The residue was dissolved in a minimal amount of dichloromethane and purified by flash chromatography (SiO$_2$, 17%-20% ethylacetate-hexanes) to afford N-((3R,4R,5S)-5-(3,6-difluoro-9H-carbazol-9-yl)-4-hydroxytetrahydro-2H-pyran-3-yl)-4-(trifluoromethoxy)benzenesulfonamide (0.068 g, 34% over two steps). $^1$H NMR (600 MHz, MeOD) δ 8.02 (2H, d, J=8.4 Hz), 7.80 (1H, d, J=7.8 Hz), 7.74 (1H, d, J=7.2 Hz), 7.67 (1H, dd, J=9.0, 4.2 Hz), 7.54 (1H, dd, J=9.0, 4.2 Hz), 7.42 (2H, d, J=8.4 Hz), 7.20 (2H, t, J=8.4 Hz), 4.61 (1H, td, J=11.4, 6.0 Hz), 4.44 (1H, t, J=9.6 Hz), 4.24 (1H, t, J=12.0 Hz), 4.03 (1H, dd, J=10.8, 4.2 Hz), 3.92 (1H, dd, J=11.4, 5.4 Hz), 3.50-3.42 (2H, m); $^{13}$C NMR (150 MHz, MeOD) δ 129.3, 120.8, 114.0, 113.8, 113.4, 113.3, 112.2, 110.5, 106.0, 105.9, 105.3, 70.4, 70.0, 66.8, 58.6, 56.9; LCMS m/z 543.0990 ([M+H$^+$], C$_{24}$H$_{20}$F$_5$N$_2$O$_5$S requires 543.1008). Material produced in this fashion exhibited [α]$_D$=−40.0° (c=0.25, CH$_3$OH). The enantiomeric identity and purity was also confirmed by analytical chiral HPLC>99% (CHIRALPAK® OZ-H column, 70:30 hexanes-EtOH, 1.0 mL/min, retention times: 5.74 min Scheme for Synthesis of Example 4

Experimental for Synthesis of Example 4

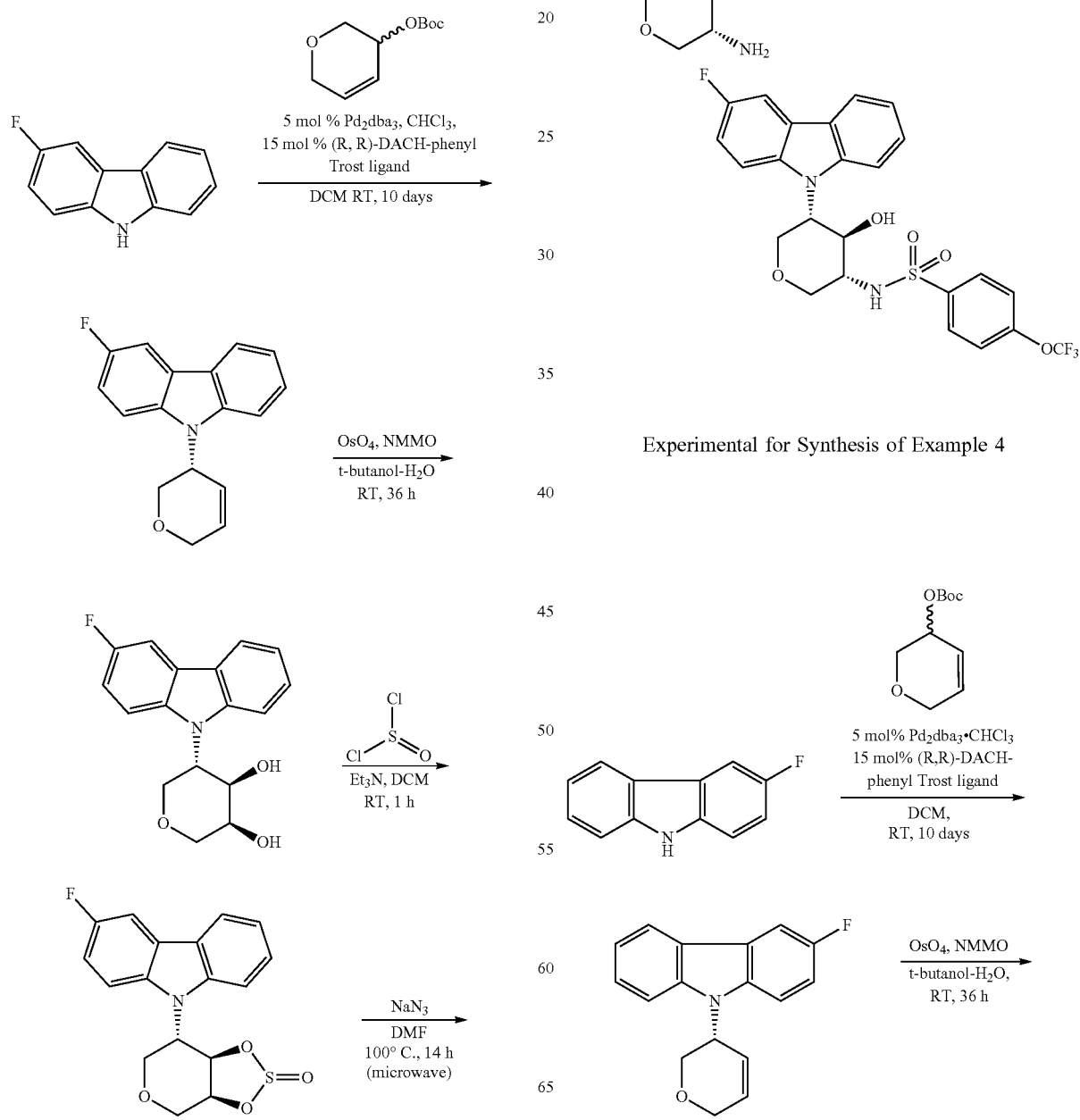

-continued

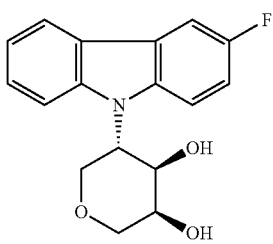

(3S,4R,5S)-5-(3-fluoro-9H-carbazol-9-yl)tetrahydro-2H-pyran-3,4-diol

A 20 mL Biotage® microwave reaction vial was charged with Pd$_2$.dba$_3$. CHCl$_3$ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 3-fluoro-9H-carbazole (0.370 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO$_2$; 0%-5% ethylacetate in hexanes) to afford slightly crude (R)-9-(3,6-dihydro-2H-pyran-3-yl)-3-fluoro-9H-carbazole (0.403 g), which was taken to the next step without further purification.

A solution of (R)-9-(3,6-dihydro-2H-pyran-3-yl)-3-fluoro-9H-carbazole (0.403 g, 1.50 mmol), 4-methylmorpholine N-oxide monohydrate (0.386 g, 3.30 mmol), and osmium tetroxide (0.320 mL, 0.030 mmol, 2.5% in tert-butanol) in tert-butanol (2.00 mL) and water (0.40 mL), was stirred at RT for 36 h. The reaction mixture was treated with solid sodium bisulfite, stirred for 1 h, evaporated on to silica, and purified by flash chromatography (SiO$_2$, 0%-70% ethyl acetate-hexanes) to afford (3S,4R,5S)-5-(3-fluoro-9H-carbazol-9-yl)tetrahydro-2H-pyran-3,4-diol (0.339 g, 68% over two steps). $^1$H NMR (600 MHz, CDCl$_3$) δ 8.04 (1H, d, J=6.6 Hz), 7.75 (1H, d, J=6.0 Hz), 7.53-7.43 (3H, m), 7.25 (1H, t, J=6.6 Hz), 7.19 (1H, bs), 4.98 (1H, bs), 4.72 (1H, bs), 4.24-4.18 (3H, m), 4.07 (1H, dd, J=11.4, 5.4 Hz), 3.76 (1H, d, J=13.2 Hz), 2.69 (1H, bs), 2.21 (1H, bs); LCMS m/z 302.1180 ([M+H$^+$], C$_{17}$H$_{17}$FNO$_3$ requires 302.1187). Material produced in this fashion exhibited [α]D=−32.0° (c=0.25, CH$_3$OH).

-continued

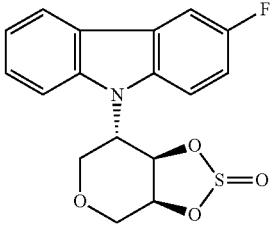

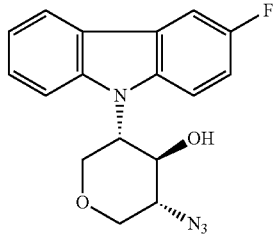

(3R,4R,5S)-3-azido-5-(3-fluoro-9H-carbazol-9-yl)tetrahydro-2H-pyran-4-ol

A solution of (3S,4R,5S)-5-(3-fluoro-9H-carbazol-9-yl)tetrahydro-2H-pyran-3,4-diol (0.339 g, 1.12 mmol) in dichloromethane (10.0 mL) was cooled to 0° C., treated with triethylamine, then slowly, over an extended period of time thionyl chloride (0.244 mL, 3.37 mmol) was added. The reaction mixture was warmed to room temperature, stirred for 1 h, partitioned between dichloromethane and water. The organic layer was concentrated to give a residue which was subjected to column chromatography (SiO$_2$, 17% ethylacetate in hexanes) to afford slightly crude (3aS,7S,7aR)-7-(3-fluoro-9H-carbazol-9-yl)tetrahydro-3aH-[1,3,2]dioxathiolo[4,5-c]pyran 2-oxide (0.224 g), which was taken to the next step without further purification.

A solution of (3aS,7S,7aR)-7-(3-fluoro-9H-carbazol-9-yl)tetrahydro-3aH-[1,3,2]dioxathiolo[4,5-c]pyran 2-oxide (0.224 g, 0.645 mmol) in DMF (2.0 mL) was treated with sodium azide (0.125 g, 1.93 mmol), and heated to 100° C. in a microwave for 14 h. The reaction mixture was treated with sat. aq. NH$_4$C$_1$, extracted with ethylacetate, washed with brine, concentrated, purified by column chromatography (SiO$_2$, 6%-13% ethylacetate-hexanes) to afford (3R,4R,5S)-3-azido-5-(3-fluoro-9H-carbazol-9-yl)tetrahydro-2H-pyran-4-ol (0.085 g, 23% over two steps). $^1$H NMR (600 MHz, CDCl$_3$) δ 8.05 (1H, dd, J=24.0, 7.8 Hz), 7.75 (1H, ddd, J=27.0, 8.4, 2.4 Hz), 7.53-7.49 (2H, m), 7.47-7.41 (1H, m), 7.28-7.19 (2H, m), 4.71-4.60 (2H, m), 4.29-4.18 (2H, m), 4.04 (1H, dd, J=12.0, 4.8 Hz), 3.84-3.79 (1H, m), 3.42 (1H, td, J=11.4, 4.8 Hz), 2.18 (1H, bs); $^{13}$C NMR (150 MHz, CDCl$_3$) δ 127.1, 126.5, 120.1, 119.9, 111.2, 109.3, 69.1, 67.1, 58.2, 57.9; LCMS m/z 327.1244 ([M+H$^+$], C$_{17}$H$_{16}$FN$_4$O$_2$ requires 327.1252).

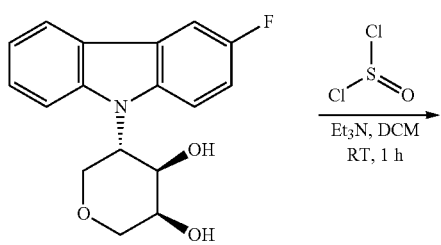

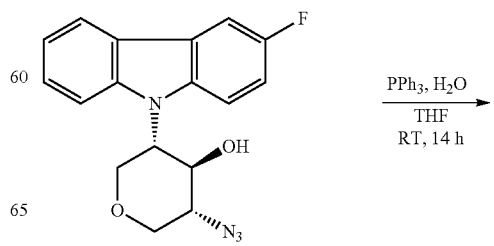

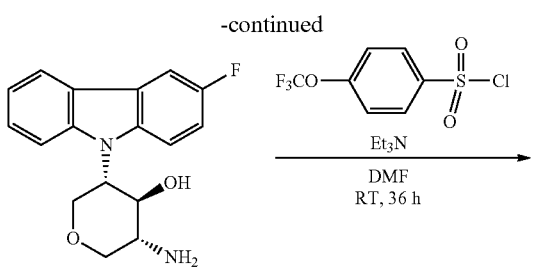

N-((3R,4R,5S)-5-(3-fluoro-9H-carbazol-9-yl)-4-hydroxytetrahydro-2H-pyran-3-yl)-4-(trifluoromethoxy)benzenesulfonamide (Example 4)

A solution of (3R,4R,5S)-3-azido-5-(3-fluoro-9H-carbazol-9-yl)tetrahydro-2H-pyran-4-ol (0.085 g, 0.260 mmol) in THF (2.25 mL) was cooled to 0° C., treated with PPh$_3$ (0.075 g, 0.286 mmol), H$_2$O (0.001 mL, 0.055 mmol), and stirred for 14 h at room temperature. The solution was concentrated to dryness, dissolved in a minimal amount of dichloromethane and purified by flash chromatography (SiO$_2$, 100% hexanes, 50% ethyl acetate-hexanes, 5%, methanol-dichlormethane, 17:2:1 dichloromethane:methanol:35% ammonium hydroxide) to afford slightly crude (3R,4S,5S)-3-amino-5-(3-fluoro-9H-carbazol-9-yl)tetrahydro-2H-pyran-4-ol (0.082 g) which was taken to the next step without further purification.

A solution of (3R,4S,5S)-3-amino-5-(3-fluoro-9H-carbazol-9-yl)tetrahydro-2H-pyran-4-ol (0.082 g, 0.273 mmol) in DMF (2.0 mL) was cooled to 0° C., treated with triethylamine (0.151 mL, 1.09 mmol), and 4-(trifluoromethoxy)benzene-1-sulfonyl chloride (0.050 mL, 0.300 mmol). The mixture was warmed to room temperature, and stirred for 36 h. The mixture was partitioned between water and ethylacetate. The organic layer was washed with brine, and concentrated in vacuo. The residue was dissolved in a minimal amount of dichloromethane and purified by flash chromatography (SiO$_2$, 17%-20% ethylacetate-hexanes) to afford N-((3R,4R,5S)-5-(3-fluoro-9H-carbazol-9-yl)-4-hydroxytetrahydro-2H-pyran-3-yl)-4-(trifluoromethoxy)benzenesulfonamide (0.056 g, 41% over two steps). $^1$HNMR (600 MHz, MeOD) δ 8.00 (1H, dd, J=35.4, 7.8 Hz), 7.92 (2H, d, J=9.0 Hz), 7.75 (1H, ddd, J=45.0, 8.4, 1.8 Hz), 7.51-7.38 (2H, m), 7.32 (2H, d, J=7.2 Hz), 7.25-7.21 (2H, m), 7.19-7.09 (1H, m), 5.21 (1H, dd, J=40.8, 4.8 Hz), 4.55-4.44 (2H, m), 4.23-4.15 (2H, m), 3.96 (1H, dd, J=11.4, 4.2 Hz), 3.46-3.39 (2H, m), 2.28-2.26 (1H, m); $^{13}$C NMR (150 MHz, CDCl$_3$) δ 152.6, 137.9, 129.6, 127.1, 126.5, 121.4, 121.1, 120.6, 120.1, 119.9, 114.3, 114.1, 111.5, 111.2, 109.7, 109.2, 70.9, 70.1, 67.0, 58.4, 56.4; LCMS m/z 525.1105 ([M+H$^+$], C$_{24}$H$_{21}$F$_4$N$_2$O$_5$S requires 525.1102). Material produced in this fashion exhibited [α]$_D$=−12.0° (c=0.25, CH$_3$OH). The enantiomeric identity and purity was also confirmed by analytical chiral HPLC>99% (CHIRALPAK® OZ-H column, 70:30 hexanes-EtOH, 1.0 mL/min, retention times: 5.74 min Scheme for the Synthesis of Example 5

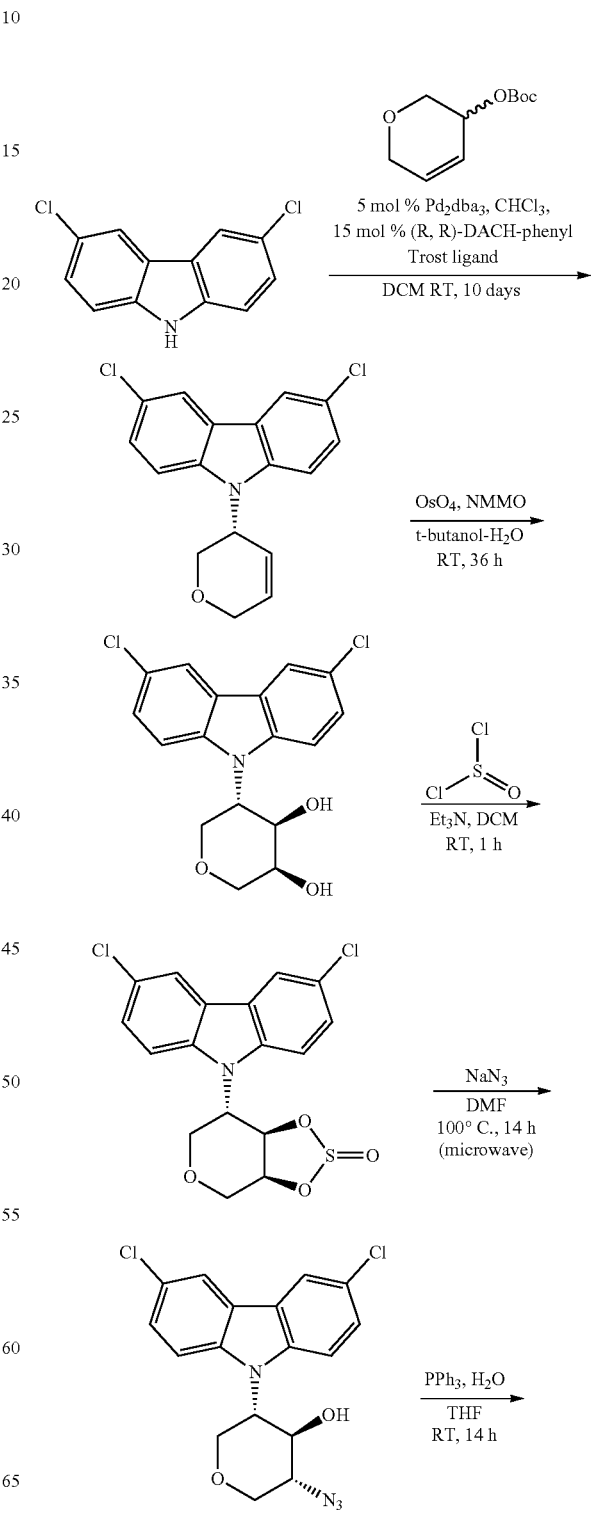

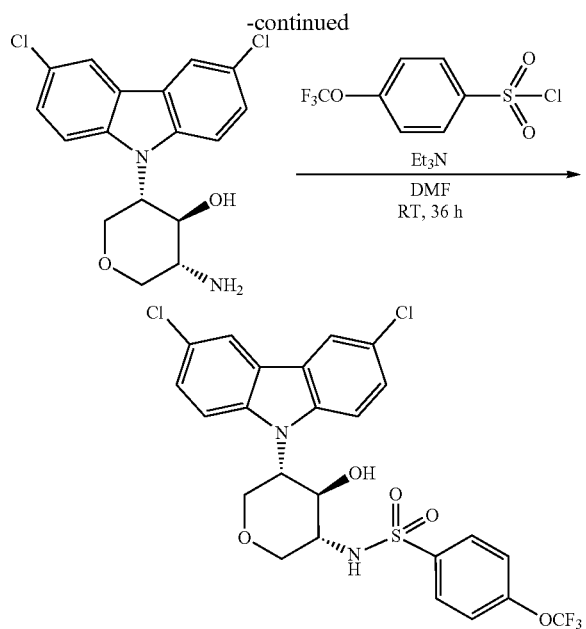

Experimental for Synthesis of Example 5

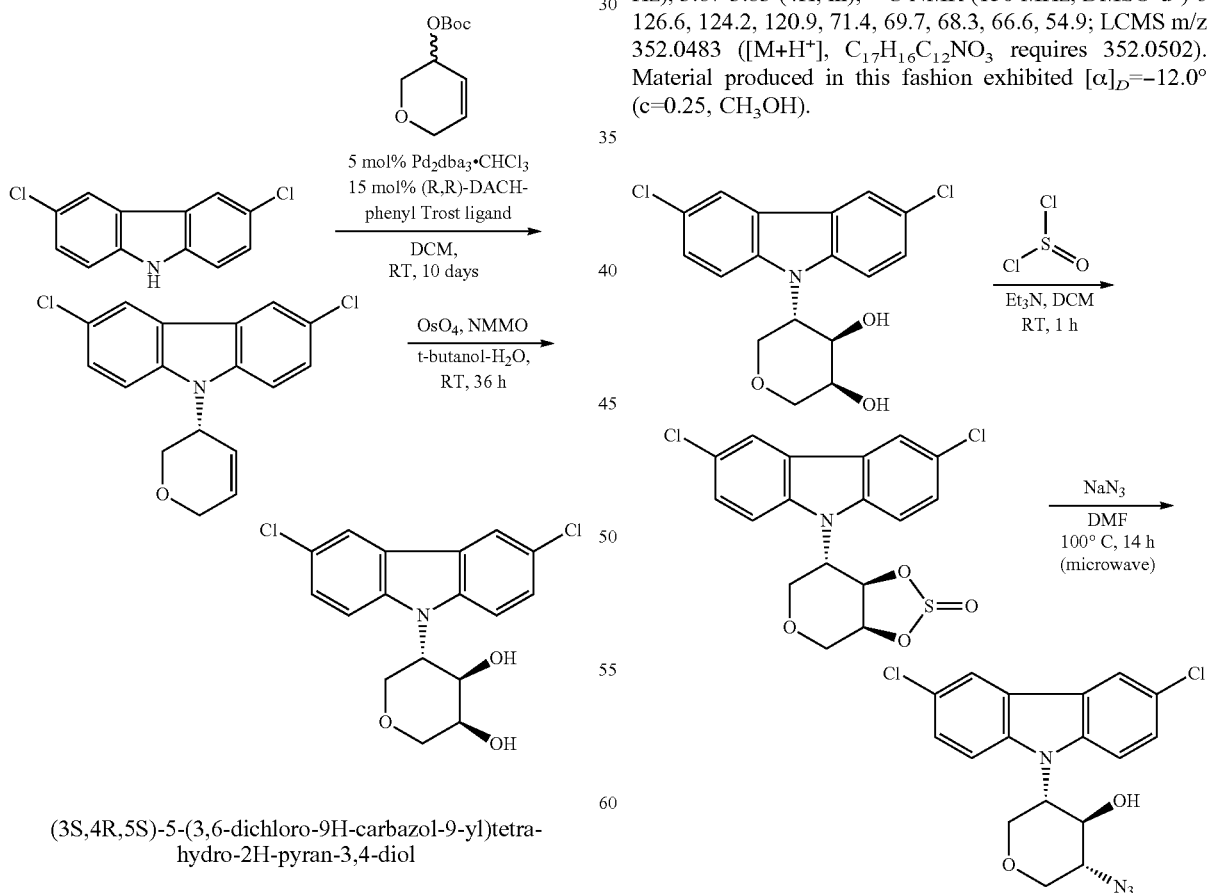

(3S,4R,5S)-5-(3,6-dichloro-9H-carbazol-9-yl)tetrahydro-2H-pyran-3,4-diol

A 20 mL Biotage® microwave reaction vial was charged with Pd$_2$.dba$_3$. CHCl$_3$ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 3,6-dichloro-9H-carbazole (0.472 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO$_2$; 0%-5% ethylacetate in hexanes) to afford slightly crude (R)-3,6-dichloro-9-(3,6-dihydro-2H-pyran-3-yl)-9H-carbazole (0.582 g) which was taken to the next step without further purification.

A solution of (R)-3,6-dichloro-9-(3,6-dihydro-2H-pyran-3-yl)-9H-carbazole (0.582 g, 1.80 mmol), 4-methylmorpholine N-oxide monohydrate (0.464 g, 3.96 mmol), and osmium tetroxide (0.370 mL, 0.036 mmol, 2.5% in tert-butanol) in tert-butanol (3.00 mL) and water (0.60 mL), was stirred at RT for 36 h. The reaction mixture was treated with solid sodium bisulfite, stirred for 1 h, evaporated on to silica, and purified by flash chromatography (SiO$_2$, 0%-70% ethyl acetate-hexanes) to afford (3S,4R,5S)-5-(3,6-dichloro-9H-carbazol-9-yl)tetrahydro-2H-pyran-3,4-diol (0.488 g, 69% over two steps). $^1$H NMR (600 MHz, DMSO-d$^6$) δ 8.33 (2H, bs), 7.78 (2H, bs), 7.45 (2H, bs), 4.93 (1H, d, J=4.8 Hz), 4.90-4.85 (2H, m), 4.54-4.50 (1H, m), 4.11 (1H, t, J=10.8 Hz), 3.87-3.83 (4H, m); $^{13}$C NMR (150 MHz, DMSO-d$^6$) δ 126.6, 124.2, 120.9, 71.4, 69.7, 68.3, 66.6, 54.9; LCMS m/z 352.0483 ([M+H$^+$], C$_{17}$H$_{16}$C$_{12}$NO$_3$ requires 352.0502). Material produced in this fashion exhibited [α]$_D$=−12.0° (c=0.25, CH$_3$OH).

(3R,4R,5S)-3-azido-5-(3,6-dichloro-9H-carbazol-9-yl)tetrahydro-2H-pyran-4-ol A solution of (3S,4R,5S)-5-(3,6-dichloro-9H-carbazol-9-yl)tetrahydro-2H-pyran-3,4-diol (0.488 g, 1.53 mmol) in dichloromethane (10.0 mL) was cooled to 0° C., treated with triethylamine, then slowly, over an extended period of time thionyl chloride (0.334 mL, 4.60 mmol) was added. The reaction mixture was warmed to room temperature, stirred for 1 h, partitioned between dichloromethane and water. The organic layer was concentrated to give a residue which was subjected to column chromatography (SiO$_2$, 17% ethylacetate in hexanes) to afford slightly crude (3aS,7S,7aR)-7-(3,6-dichloro-9H-carbazol-9-yl)tetrahydro-3aH-[1,3,2]dioxathiolo[4,5-c]pyran 2-oxide (0.540 g), which was taken to the next step without further purification.

A solution of (3aS,7S,7aR)-7-(3,6-dichloro-9H-carbazol-9-yl)tetrahydro-3aH-[1,3,2]dioxathiolo[4,5-c]pyran 2-oxide (0.540 g, 1.36 mmol) in DMF (3.0 mL) was treated with sodium azide (0.264 g, 4.06 mmol), and heated to 100° C. in a microwave for 14 h. The reaction mixture was treated with sat. aq. NH$_4$C$_1$, extracted with ethylacetate, washed with brine, concentrated, purified by column chromatography (SiO$_2$, 6%-13% ethylacetate-hexanes) to afford (3R,4R,5S)-3-azido-5-(3,6-dichloro-9H-carbazol-9-yl)tetrahydro-2H-pyran-4-ol (0.309 g, 53% over two steps). $^1$H NMR (600 MHz, CDCl$_3$) δ 8.01 (2H, dd, J=24.6, 1.8 Hz), 7.48-7.40 (4H, m), 4.63 (1H, td, J=10.8, 5.4 Hz), 4.56 (1H, t, J=9.0 Hz), 4.22-4.18 (2H, m), 4.04 (1H, dd, J=11.4, 5.4 Hz), 3.81-3.77 (1H, m), 3.41 (1H, t, J=12.0 Hz), 2.23 (1H, bs); $^{13}$C NMR (150 MHz, CDCl$_3$) δ 137.1, 127.3, 126.6, 126.0, 124.9, 123.3, 121.0, 120.3, 112.1, 110.4, 72.7, 69.1, 67.1, 63.0, 58.0; LCMS m/z 377.0550 ([M+H$^+$], C$_{17}$H$_{15}$Cl$_2$N$_4$O$_2$ requires 377.0567).

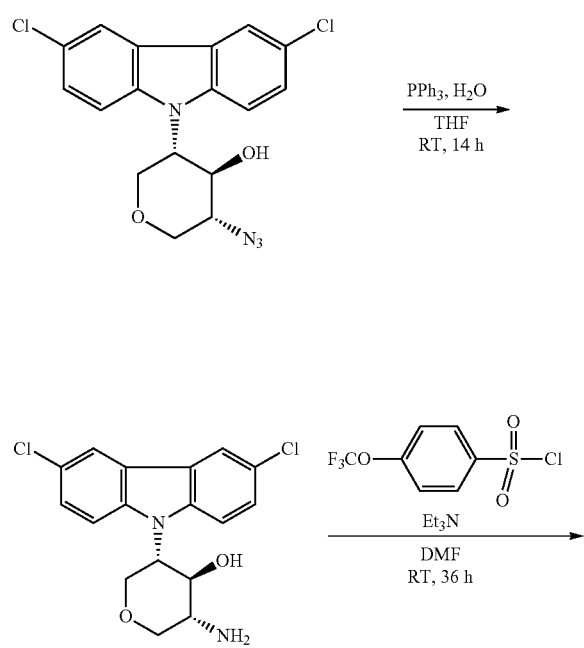

N-((3R,4R,5S)-5-(3,6-dichloro-9H-carbazol-9-yl)-4-hydroxytetrahydro-2H-pyran-3-yl)-4-(trifluoromethoxy)benzenesulfonamide (Example 5)

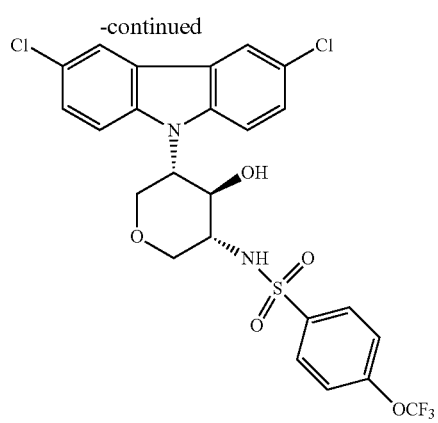

A solution of (3R,4R,5S)-3-azido-5-(3-fluoro-9H-carbazol-9-yl)tetrahydro-2H-pyran-4-ol (0.309 g, 0.819 mmol) in THF (2.25 mL) was cooled to 0° C., treated with PPh$_3$ (0.236 g, 0.901 mmol), H$_2$O (0.001 mL, 0.055 mmol), and stirred for 14 h at room temperature. The solution was concentrated to dryness, dissolved in a minimal amount of dichloromethane and purified by flash chromatography (SiO$_2$, 100% hexanes, 50% ethyl acetate-hexanes, 5%, methanol-dichloromethane, 17:2:1 dichloromethane:methanol:35% ammonium hydroxide) to afford slightly crude (3R,4S,5S)-3-amino-5-(3,6-dichloro-9H-carbazol-9-yl)tetrahydro-2H-pyran-4-ol (0.231 g) which was taken to the next step without further purification.

A solution of (3R,4S,5S)-3-amino-5-(3,6-dichloro-9H-carbazol-9-yl)tetrahydro-2H-pyran-4-ol (0.231 g, 0.657 mmol) in DMF (2.0 mL) was cooled to 0° C., treated with triethylamine (0.366 mL, 2.63 mmol), and 4-(trifluoromethoxy)benzene-1-sulfonyl chloride (0.122 mL, 0.723 mmol). The mixture was warmed to room temperature, and stirred for 36 h. The mixture was partitioned between water and ethylacetate. The organic layer was washed with brine, and concentrated in vacuo. The residue was dissolved in a minimal amount of dichloromethane and purified by flash chromatography (SiO$_2$, 17%-20% ethylacetate-hexanes) to afford N-((3R,4R,5S)-5-(3,6-dichloro-9H-carbazol-9-yl)-4-hydroxytetrahydro-2H-pyran-3-yl)-4-(trifluoromethoxy)benzenesulfonamide (0.174 g, 37% over two steps). $^1$H NMR (600 MHz, CDCl$_3$) δ 7.99-7.95 (4H, m), 7.42-7.34 (5H, m), 7.29-7.26 (1H, m), 5.11 (1H, bs), 4.48 (2H, bs), 4.23-4.15 (2H, m), 4.00-3.98 (1H, m), 3.47-3.43 (2H, m), 2.29 (1H, bs); $^{13}$C NMR (150 MHz, CDCl$_3$) δ 129.6, 127.3, 126.6, 121.2, 120.3, 112.1, 110.4, 71.0, 70.1, 67.0, 58.3, 56.5; LCMS m/z 575.0369 ([M+H$^+$], C$_{24}$H$_{20}$Cl$_2$F$_3$N$_2$O$_5$S requires 575.0417). Material produced in this fashion exhibited [α]$_D$+12.0° (c=0.25, CH$_3$OH). The enantiomeric identity and purity was also confirmed by analytical chiral HPLC>99% (CHIRALPAK® OZ-H column, 70:30 hexanes-EtOH, 1.0 mL/min, retention times: 6.63 min.

Synthesis of Pyran Constrained Phenoxazines
Scheme for Synthesis of Example 2
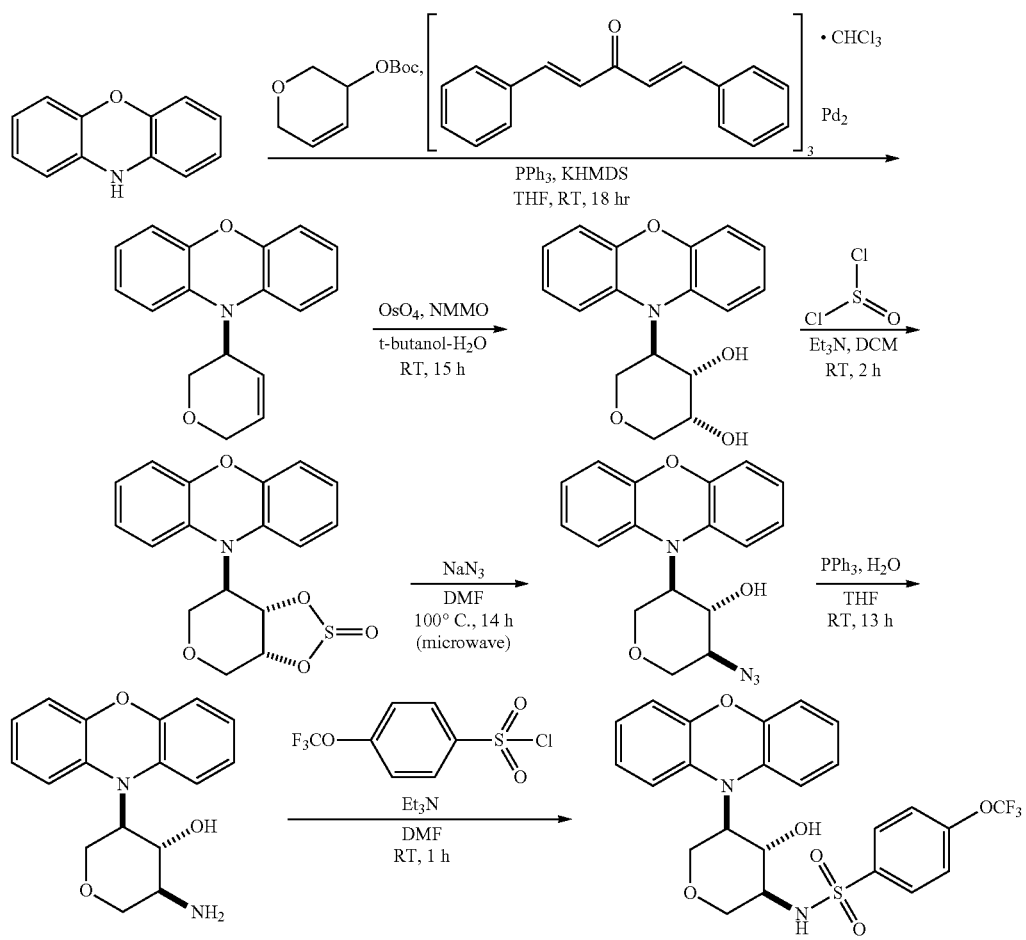
Experimental for Synthesis of Example 2
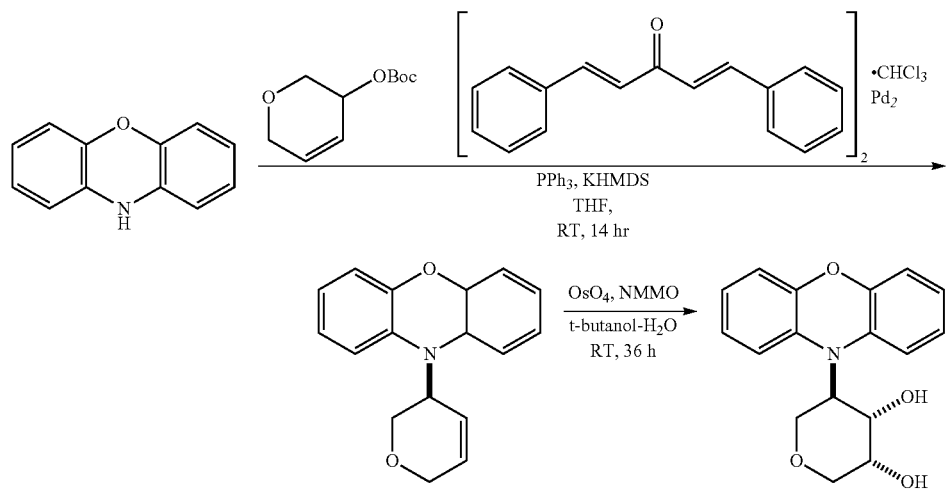

5-(10H-phenoxazin-10-yl)tetrahydro-2H-pyran-3,4-diol

A 20 ml Biotage® microwave reaction vial (Vial A) was charged with $Pd_2.dba_3 \cdot CHCl_3$ (0.103 g, 0.10 mmol), and triphenylphosphine (0.078 g, 0.30 mmol). The vial was sealed, evacuated and backfilled with argon three times. Dry degassed THF (6.00 mL) was added to this vial, and the mixture was stirred at room temperature for 60 min. In a separate 20 mL Biotage® microwave reaction vial (Vial B), 10H-phenoxazine (0.366 g, 2.00 mmol) was added. The vial was sealed, evacuated and backfilled with argon three times. Dry degassed THF (5.00 mL) was added, and Potassium bis(trimethylsilyl)amide solution (1.0 M in THF, 1.00 mL, 2.00 mmol) was added drop wise at RT and the mixture was stirred for 60 min. Following this tert-butyl (5,6-dihydro-2H-pyran-2-yl) carbonate (0.960 g, 4.80 mmol), and the contents of vial B were transferred to vial A in this sequence. The reaction mixture was stirred at room temperature for 14 h. At this point, the reaction mixture was evaporated onto silica gel and purified by flash chromatography ($SiO_2$, 0%-5% ethyl acetate-hexanes) to afford crude 10-(3,6-dihydro-2H-pyran-3-yl)-10H-phenoxazine (0.442 g), which was taken to the next step without further purification. LCMS m/z 266.1203 ([M+H$^+$], $C_{17}H_{16}NO_2$ requires 266.1176).

A solution of 10-(3,6-dihydro-2H-pyran-3-yl)-10H-phenoxazine (0.398 g, 1.50 mmol), 4-methylmorpholine N-oxide (0.386 g, 3.30 mmol), and osmium tetroxide (0.320 mL, 0.030 mmol, 2.5% in tert-butanol) in tert-butanol (2.0 mL) and water (0.4 mL), was stirred at RT for 36 h. The reaction mixture was treated with solid sodium bisulfite for 1 h, dichloromethane and silica were added, the mixture was concentrated and purified by flash chromatography ($SiO_2$, 20%-66% ethyl acetate-hexanes) to afford 5-(10H-phenoxazin-10-yl)tetrahydro-2H-pyran-3,4-diol (0.235 g, 52% over two steps). $^1$H NMR (600 MHz, MeOD) δ 7.00-6.98 (2H, m), 6.91-6.89 (2H, m), 6.83-6.81 (2H, m), 6.74 (2H, dd, J=8.4, 1.2 Hz), 4.26 (1H, dd, J=10.2, 3.0 Hz), 4.10-4.03 (2H, m), 3.93 (1H, bs), 3.89 (1H, d, J=12.6 Hz), 3.75 (1H, t, J=10.8 Hz), 3.58 (1H, d, J=12.6 Hz); $^{13}$C NMR (150 MHz, MeOD) δ 149.5, 135.4, 123.4, 122.6, 118.3, 115.5, 71.0, 70.2, 68.7, 68.4, 62.5; HRMS calcd for $C_{17}H_{18}NO_4$ [M+H$^+$] 300.1230, found 300.1203. Material produced in this fashion exhibited [α]$_D$=+0.05 (c=1.0, $CH_2Cl_2$).

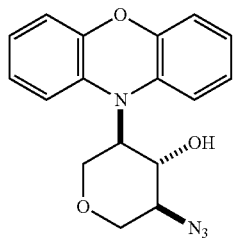

3-azido-5-(10H-phenoxazin-10-yl)tetrahydro-2H-pyran-4-ol

A solution of 5-(10H-phenoxazin-10-yl)tetrahydro-2H-pyran-3,4-diol (0.235 g, 0.785 mmol) in dichloromethane (2.0 mL) under argon was cooled to 0° C., and treated with triethylamine (0.870 mL, 6.28 mmol). Following this thionyl chloride (0.171 mL, 2.36 mmol) was added very slowly over 5 min. The reaction mixture was warmed to RT, and stirred for 2 h. The reaction mixture was partitioned between dichloromethane and water, concentrated to obtain a residue which was purified by flash chromatography ($SiO_2$, 17% ethylacetate-hexanes) to afford crude 7-(10H-phenoxazin-10-yl)tetrahydro-3aH-[1,3,2]dioxathiolo[4,5-c]pyran 2-oxide (0.394 g) which was taken to the next step without further purification. LCMS m/z 346.0737 ([M+H$^+$], $C_{17}H_{16}NO_5S$ requires 346.0744).

A solution of 7-(10H-phenoxazin-10-yl)tetrahydro-3aH-[1,3,2]dioxathiolo[4,5-c]pyran 2-oxide (0.349 g, 1.01 mmol) in DMF (3.0 mL) was treated with sodium azide (0.170 g, 1.84 mmol), and heated to 100° C. in a microwave for 14 h. Sat. aq. $NH_4Cl$ was added, mixture was extracted with ethylacetate, washed with brine (100 mL×4), concentrated, and purified by flash chromatography ($SiO_2$, 6%-13% ethylacetate-hexanes) to afford 4-azido-2-(10H-phenoxazin-10-yl)tetrahydro-2H-pyran-3-ol (0.244 g, 96% over two steps). $^1$H NMR (600 MHz, MeOD) δ 6.96 (2H, dd, J=8.4, 1.8 Hz), 6.92 (2H, td, J=7.8, 1.8 Hz), 6.84 (2H, td, J=7.8, 1.2 Hz), 6.76 (2H, dd, J=7.8, 1.2 Hz), 4.13-4.08 (2H, m), 3.94 (1H, dd, J=11.4, 5.4 Hz), 3.78 (1H, t, J=11.4 Hz), 3.67 (1H, td, J=10.2, 4.8 Hz), 3.52 (1H, ddd, J=9.0, 5.4, 3.6 Hz), 3.16 (1H, t, J=10.8 Hz); $^{13}$C NMR (150 MHz, MeOD) δ 149.5, 135.1, 123.5, 122.9, 118.4, 115.7, 72.1, 68.6, 68.5, 66.7, 64.3; ESI-HRMS calcd for $C_{17}H_{17}N_4O_3$ [M+H$^+$] 325.1295, found 325.1290.

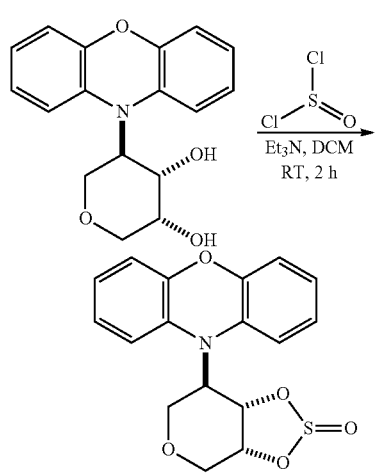

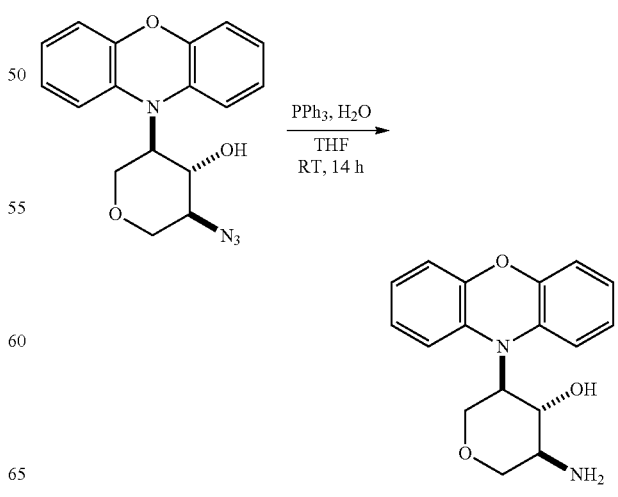

3-amino-5-(10H-phenoxazin-10-yl)tetrahydro-2H-pyran-4-ol

A solution of 3-azido-5-(10H-phenoxazin-10-yl)tetrahydro-2H-pyran-4-ol (0.207 g, 0.638 mmol) in THF (2.25 mL) was cooled to 0° C., treated with triphenylphosphine (0.184 g, 0.702 mmol), water (0.001 mL, 0.055 mmol), and stirred for 14 h at RT. The solution was concentrated to dryness, dissolved in a minimal amount of CH$_2$Cl2 and purified by flash chromatography (SiO$_2$, 100% hexanes, 50% ethyl acetate-hexanes, 5%, methanol-dichlormethane, 17:2:1 dichloromethane:methanol:35% ammonium hydroxide) to afford 3-amino-5-(10H-phenoxazin-10-yl)tetrahydro-2H-pyran-4-ol (0.097 g, 51%). $^1$HNMR (600 MHz, MeOD) δ 6.97 (2H, dd, J=7.8, 1.2 Hz), 6.91 (2H, td, J=7.8, 1.2 Hz), 6.83 (2H, td, J=7.8, 1.2 Hz), 6.76 (2H, dd, J=7.8, 1.2 Hz), 4.10 (1H, dd, J=11.4, 4.8 Hz), 3.95-3.88 (2H, m), 3.81 (1H, t, J=11.4 Hz), 5.13 (1H, td, J=11.4, 4.8 Hz), 3.18 (1H, t, J=10.8 Hz), 2.82-2.79 (1H, m); $^{13}$C NMR NMR (150 MHz, MeOD) δ 149.5, 135.2, 123.5, 122.7, 118.3, 115.6, 73.1, 70.9, 68.7, 66.8, 55.2; ESI-HRMS calcd for C$_{17}$H$_{19}$N$_2$O$_3$ [M+H$^+$] 299.1390, found 299.1382.

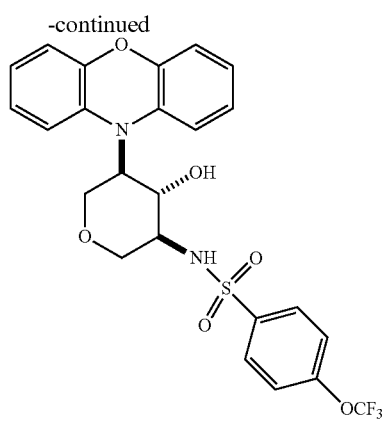

N-(4-hydroxy-5-(10H-phenoxazin-10-yl)tetrahydro-2H-pyran-3-yl)-4-(trifluoromethoxy)benzenesulfonamide (Example 2)

A solution of 3-amino-5-(10H-phenoxazin-10-yl)tetrahydro-2H-pyran-4-ol (0.095 g, 0.318 mmol) in DMF (1.5 mL) was cooled to 0° C., treated with triethylamine (0.177 mL, 1.27 mmol), and 4-(trifluoromethoxy)benzene-1-sulfonyl chloride (0.059 mL, 0.350 mmol). The mixture was warmed to RT, and stirred for 16 h. The mixture was partitioned between water (10 mL) and CH$_2$Cl$_2$ (10 mL). The organic layer was washed with saturated aqueous NaCl (30 mL×5), and concentrated in vacuo. The residue was dissolved in a minimal amount of CH$_2$Cl$_2$ and purified by flash chromatography (SiO$_2$, 25 g, 17%-20% ethylacetate-hexanes) to afford N-(4-hydroxy-5-(10H-phenoxazin-10-yl)tetrahydro-2H-pyran-3-yl)-4-(trifluoromethoxy)benzenesulfonamide (0.116 g, 70%). $^1$H NMR (600 MHz, MeOD) δ 7.98 (2H, d, J=9.0 Hz), 7.40 (2H, d, J=8.4 Hz), 6.91-6.87 (4H, m), 6.82 (2H, td, J=7.8, 1.8 Hz), 6.74-6.73 (2H, m), 4.06 (I H, dd, J=11.4, 4.8 Hz), 4.00 (1H, t, J=9.6 Hz), 3.85 (1H, dd, J=10.2, 4.2 Hz), 3.73 (1H, t, J=11.4 Hz), 3.57 (1H, td, J=10.8, 4.8 Hz), 3.23-3.15 (2H, m); $^{13}$C NMR (150 MHz, MeOD) δ 151.8, 149.5, 140.3, 135.0, 129.3, 123.5, 122.9, 120.8, 118.4, 115.7, 70.3, 69.9, 68.6, 67.2, 57.3; ESI-HRMS calcd for C$_{24}$H$_{22}$F$_3$N$_2$O$_6$S [M+H$^+$] 523.1145, found 523.1130.

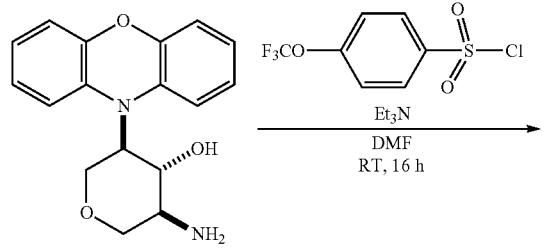

Scheme for Synthesis of Example 2a

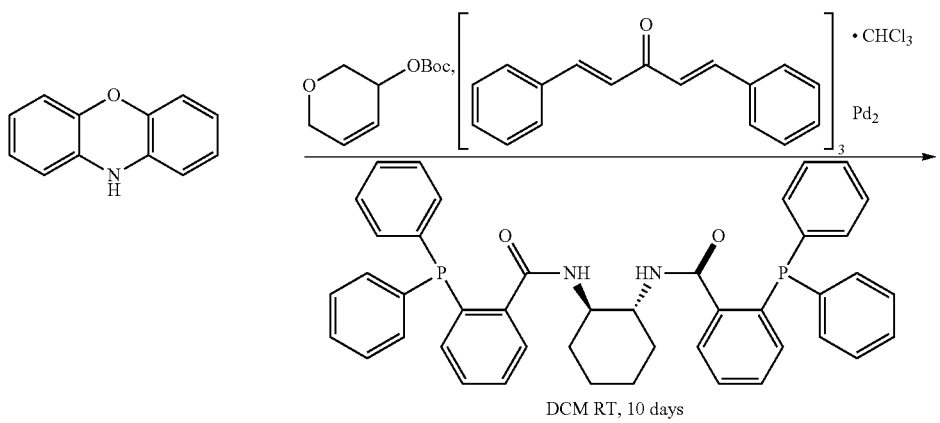

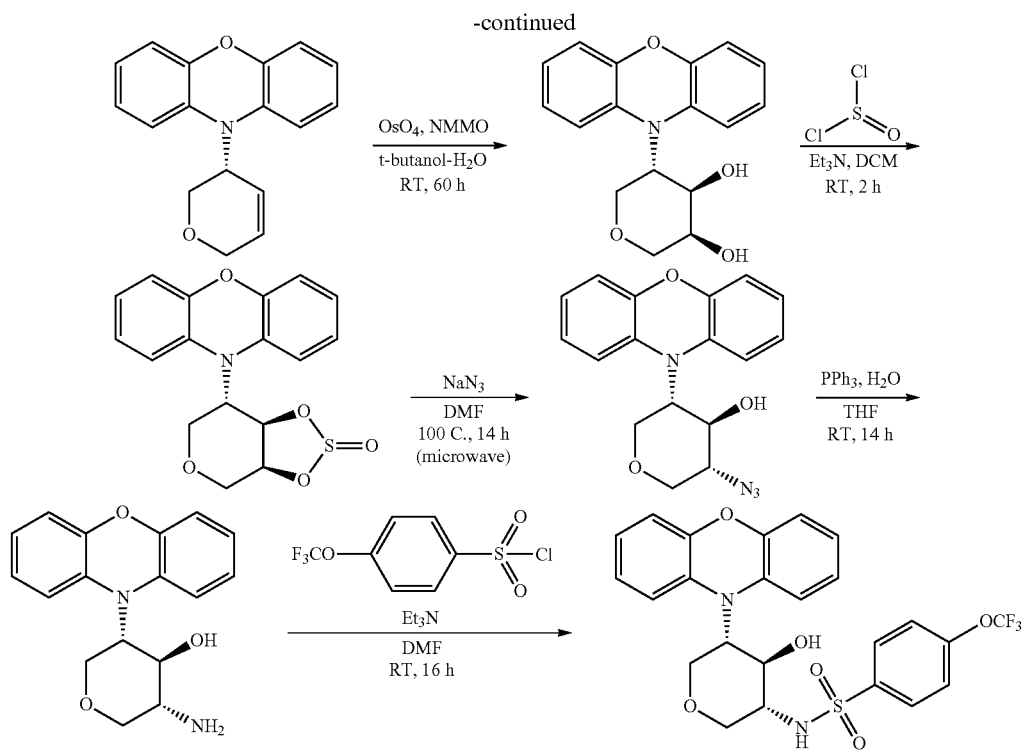

Experimental for Synthesis of Example 2a

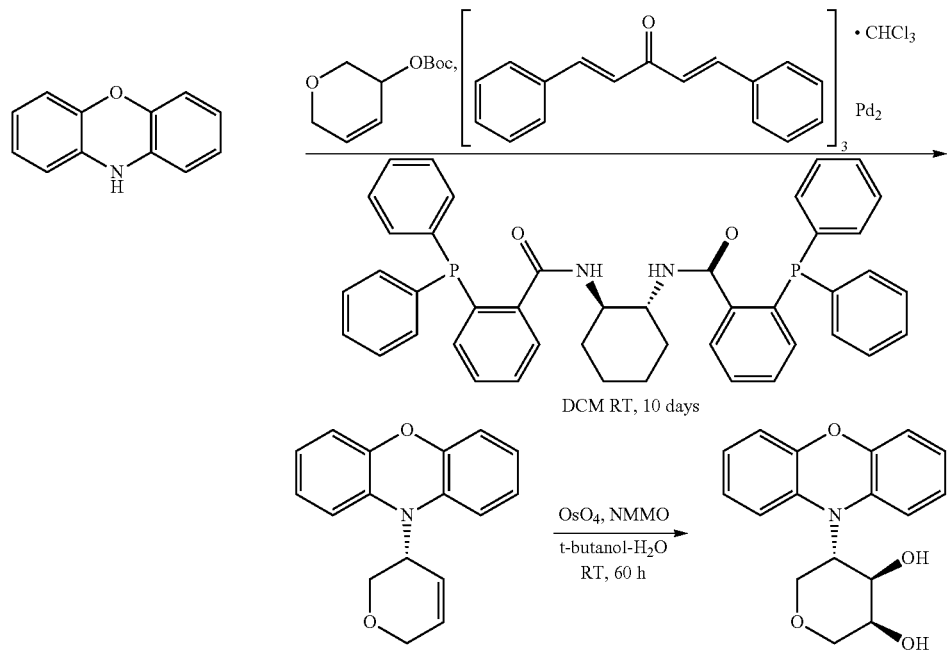

(3S,4R,5S)-5-(10H-phenoxazin-10-yl)tetrahydro-2H-pyran-3,4-diol

A 20 mL Biotage® microwave reaction vial was charged with Pd$_2$.dba$_3$. CHCl$_3$ (0.103 g, 0.10 mmol), and (R,R)-DACH-phenyl Trost ligand (0.207 g, 0.30 mmol). The vial was sealed, evacuated and backfilled with argon three times. Dry degassed dichloromethane (6.0 mL) was added to this vial, and the mixture was stirred at room temperature for 60 min. Tert-butyl cyclohex-2-en-1-yl carbonate (0.960 g, 4.80 mmol) was added to the vial and the contents were transferred to a separate 20 mL Biotage® microwave reaction vial containing 10H-phenoxazine (0.366 g, 2.00 mmol) in dry degassed dichloromethane (5.0 mL). The reaction mixture was stirred at room temperature for 10 days. At this point, the reaction mixture was evaporated onto silica gel and subjected to flash chromatography (SiO$_2$; 0%-5% ethylacetate-hexanes) to afford crude (R)-10-(cyclohex-2-en-1-yl)-10H-phenoxazine (0.538 g), which was taken to the next step without further purification. LCMS m/z 266.1155 ([M+H$^+$], C$_{17}$H$_{16}$NO$_2$ requires 266.1176).

A solution of (R)-10-(cyclohex-2-en-1-yl)-10H-phenoxazine (0.538 g, 2.02 mmol), 4-methylmorpholine N-oxide (0.522 g, 4.46 mmol), and osmium tetroxide (0.410 mL, 0.040 mmol, 2.5% in tert-butanol) in tert-butanol (2.70 mL) and water (0.54 mL), was stirred at RT for 60 h. The reaction mixture was treated with solid sodium bisulfite for 1 h, dichloromethane and silica were added, the mixture was concentrated and purified by flash chromatography (SiO$_2$, 20%-66% ethyl acetate-hexanes) to afford (3S,4R,5S)-5-(10H-phenoxazin-10-yl)tetrahydro-2H-pyran-3,4-diol (0.492 g, 82% over two steps). $^1$H NMR (600 MHz, MeOD) δ 6.99-6.98 (2H, m), 6.90 (2H, td, J=7.2, 0.6 Hz), 6.83-6.81 (2H, m), 6.74 (2H, dd, J=7.8, 0.6 Hz), 4.25 (1H, dd, J=10.2, 3.0 Hz), 4.10-4.03 (2H, m), 3.93 (1H bs), 3.89 (1H, d, J=12.6 Hz), 3.75 (1H, t, J=10.8 Hz), 3.57 (1H, d, J=12.0 Hz); $^{13}$C NMR (150 MHz, MeOD) δ 149.5, 135.4, 123.4, 122.6, 118.3, 115.5, 71.0, 70.2, 68.7, 68.4, 62.5; ESI-HRMS calcd for C$_{17}$H$_{18}$NO$_4$ [M+H$^+$] 300.1230, found 300.1202. Material produced in this fashion exhibited [α]$_D$=+0.30 (c=1.0, CH$_2$Cl$_2$).

this thionyl chloride (0.335 mL, 4.62 mmol) was added very slowly over 5 min. The reaction mixture was warmed to RT, and stirred for 2 h. The reaction mixture was partitioned between dichloromethane and water, concentrated to obtain a residue which was purified by flash chromatography (SiO$_2$, 17%-25% ethylacetate-hexanes) to afford crude (3aS,7S,7aR)-7-(10H-phenoxazin-10-yl)tetrahydro-4H-[1,3,2]dioxathiolo[4,5-c]pyran 2-oxide (0.478 g) which was taken to the next step without further purification. LCMS m/z 346.0730 ([M+H$^+$], C$_{17}$H$_{16}$NO$_5$S requires 346.0744).

A solution of (3aS,7S,7aR)-7-(10H-phenoxazin-10-yl)tetrahydro-4H-[1,3,2]dioxathiolo[4,5-c]pyran 2-oxide (0.478 g, 1.38 mmol) in DMF (3.0 mL) was treated with sodium azide (0.269 g, 4.14 mmol), and heated to 100° C. in a microwave for 14 h. Sat. aq. NH$_4$C$_1$ was added, mixture was extracted with ethylacetate, washed with brine (100 mL×4), concentrated, and purified by flash chromatography (SiO$_2$, 6%-13% ethylacetate-hexanes) to afford (3R,4R,5S)-3-azido-5-(10H-phenoxazin-10-yl)tetrahydro-2H-pyran-4-ol (0.247 g, 49% over two steps). $^1$H NMR (600 MHz, MeOD) δ 6.96 (2H, dd, J=7.8, 1.2 Hz), 6.92 (2H, td, J=7.2, 1.2 Hz), 6.84 (2H, td, J=7.8, 1.8 Hz), 6.76 (2H, dd, J=7.8, 1.2 Hz), 4.13-4.07 (2H, m), 3.93 (1H, J=11.4, 5.4 Hz), 3.77 (1H, t, J=11.4 Hz), 3.67 (1H, td, J=10.8, 4.8 Hz), 3.53-3.49 (1H, m), 3.16 (1H, t, J=11.4 Hz); $^{13}$C NMR NMR (150 MHz, MeOD) δ 149.5, 135.1, 123.5, 122.9, 118.4, 115.7, 72.1, 68.6, 68.5, 66.7, 64.3; ESI-HRMS calcd for C$_{17}$H$_{17}$N$_4$O$_3$ [M+H$^+$] 325.1295, found 325.1284.

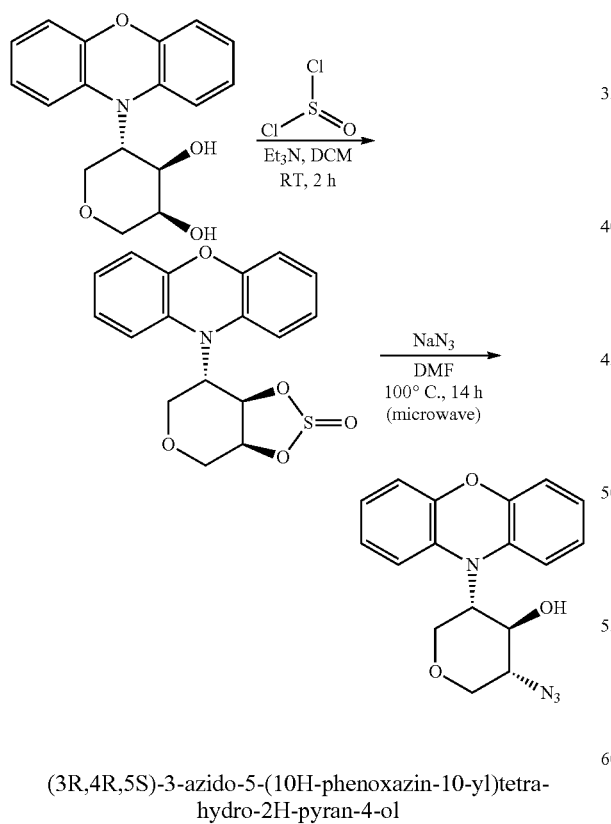

(3R,4R,5S)-3-azido-5-(10H-phenoxazin-10-yl)tetrahydro-2H-pyran-4-ol

A solution of (3S,4R,5S)-5-(10H-phenoxazin-10-yl)tetrahydro-2H-pyran-3,4-diol (0.462 g, 1.54 mmol) in dichloromethane (10.0 mL) under argon was cooled to 0° C., and treated with triethylamine (1.69 mL, 12.3 mmol). Following

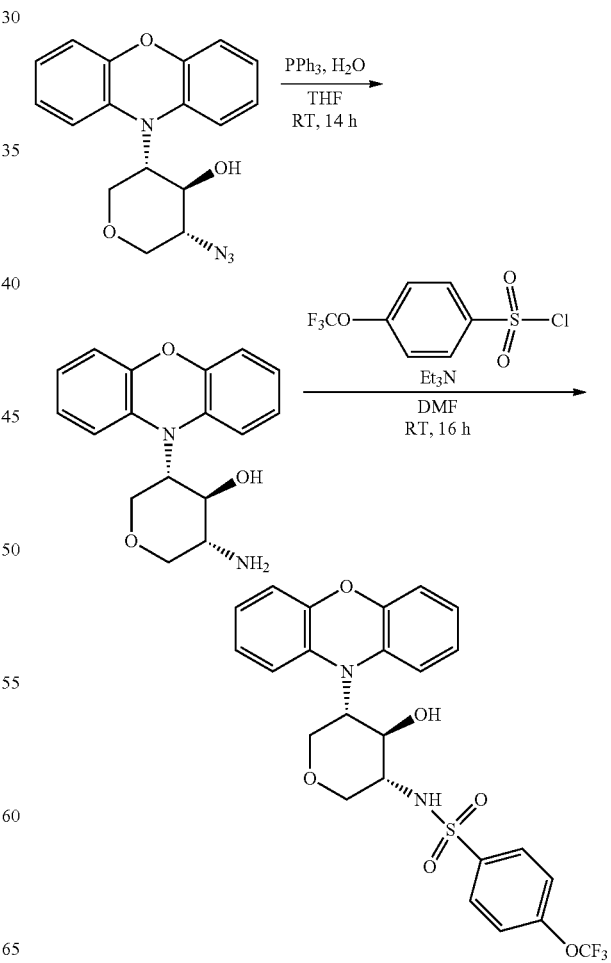

N-((3R,4R,5S)-4-hydroxy-5-(10H-phenoxazin-10-yl)tetrahydro-2H-pyran-3-yl)-4-(trifluoromethoxy)benzenesulfonamide (Example 2a)

A solution of (3R,4R,5S)-3-azido-5-(10H-phenoxazin-10-yl)tetrahydro-2H-pyran-4-ol (0.246 g, 0.758 mmol) in THF (2.70 mL) was cooled to 0° C., treated with triphenylphosphine (0.219 g, 0.834 mmol), water (0.001 mL, 0.055 mmol), and stirred for 14 h at RT. The solution was concentrated to dryness, dissolved in a minimal amount of $CH_2Cl_2$ and purified by flash chromatography ($SiO_2$, 100% hexanes, 50% ethyl acetate-hexanes, 5%, methanol-dichlormethane, 17:2:1 dichloromethane:methanol:35% ammonium hydroxide) to afford crude (3R,4S,5S)-3-amino-5-(10H-phenoxazin-10-yl)tetrahydro-2H-pyran-4-ol (0.226 g) which was taken to the next step without further purification. LCMS calcd for $C_{17}H_{19}N_2O_3$ [M+H$^+$] 299.1390, found 299.3586.

A solution of (3R,4S,5S)-3-amino-5-(10H-phenoxazin-10-yl)tetrahydro-2H-pyran-4-ol (0.226 g, 0.758 mmol) in DMF (5.0 mL) was cooled to 0° C., treated with triethylamine (0.422 mL, 3.03 mmol), and 4-(trifluoromethoxy)benzene-1-sulfonyl chloride (0.141 mL, 0.834 mmol). The mixture was warmed to RT, and stirred for 16 h. The mixture was partitioned between water (10 mL) and $CH_2Cl_2$ (10 mL). The organic layer was washed with saturated aqueous NaCl (30 mL×5), and concentrated in vacuo. The residue was dissolved in a minimal amount of $CH_2Cl_2$ and purified by flash chromatography ($SiO_2$, 25 g, 17%-20% ethylacetate-hexanes) to afford N-((3R,4R,5S)-4-hydroxy-5-(10H-phenoxazin-10-yl)tetrahydro-2H-pyran-3-yl)-4-(trifluoromethoxy)benzenesulfonamide (0.195 g, 49% over two steps). $^1$H NMR (600 MHz, MeOD) δ 7.98 (2H, d, J=9.0 Hz), 7.41 (2H, d, J=8.4 Hz), 6.922-6.88 (4H, m), 6.82 (2H, td, J=7.8, 1.8 Hz), 6.74-6.73 (2H, m), 4.07 (1H, dd, J=11.4, 4.2 Hz), 4.00 (1H, t, J=9.6 Hz), 3.85 (1H, dd, J=9.6, 3.0 Hz), 3.73 (1H, t, J=12.0 Hz), 3.58 (1H, td, J=10.8, 4.8 Hz), 3.23-3.15 (2H, m); $^{13}$C NMR (150 MHz, MeOD) δ 151.8, 149.5, 140.3, 135.0, 129.3, 123.4, 122.8, 120.8, 118.4, 115.6, 70.3, 69.9, 68.6, 67.2, 57.3; ESI-HRMS calcd for $C_{24}H_{22}F_3N_2O_6S$ [M+H$^+$] 523.1145, found 523.1147. Material produced in this fashion exhibited [α]$_D$=+0.17 (c=1.0, $CH_2Cl_2$). The enantiomeric identity and purity was also confirmed by analytical chiral HPLC>99% (CHIRALPAK® OZ-H column, 70:30 hexanes-EtOH, 1.0 mL/min, retention time: 5.53 min.

Scheme for Synthesis of Example 2b

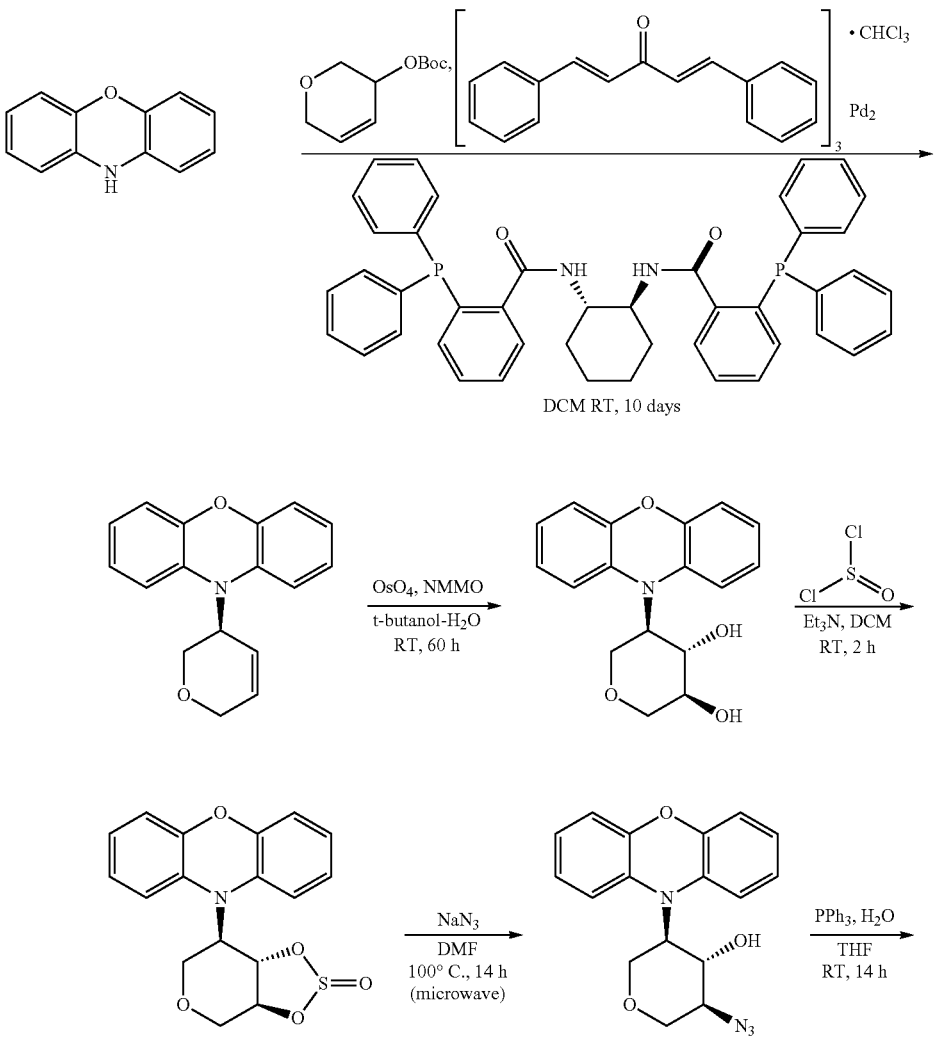

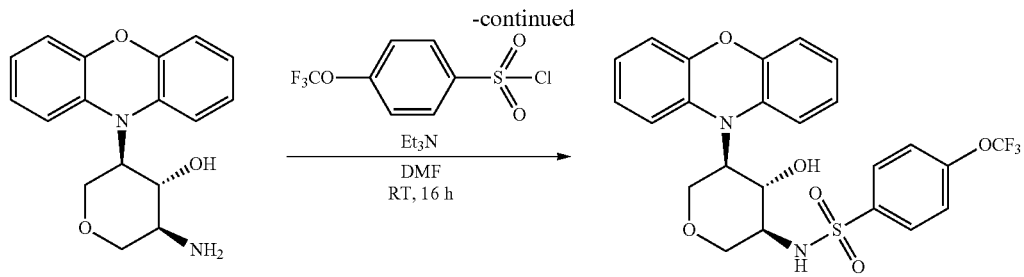

Experimental for Synthesis of Example 2b

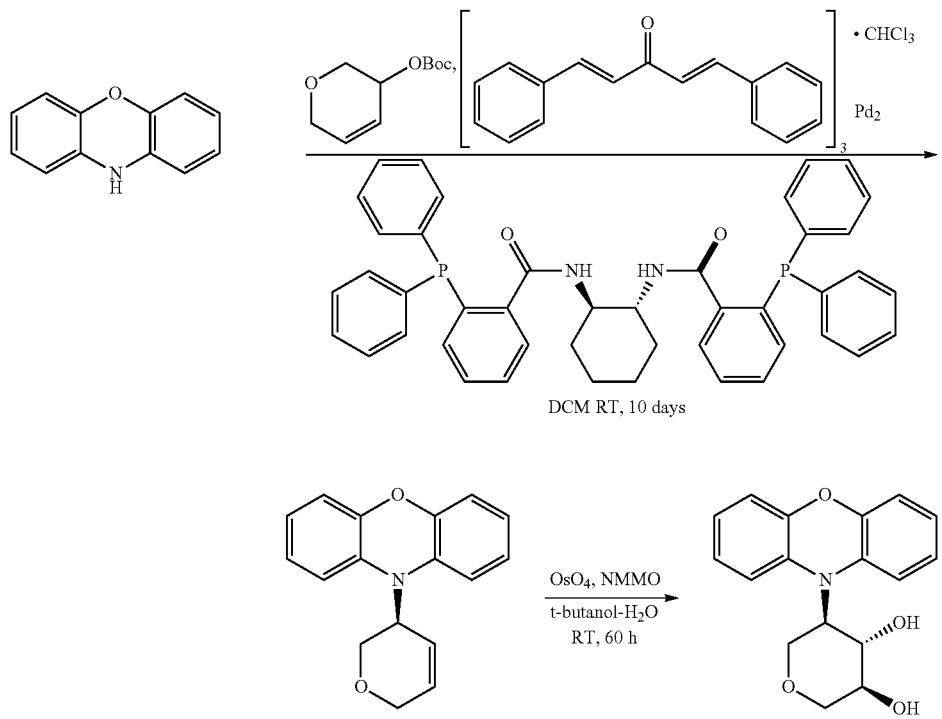

(3R,4S,5R)-5-(10H-phenoxazin-10-yl)tetrahydro-2H-pyran-3,4-diol

A 20 mL Biotage® microwave reaction vial was charged with Pd$_2$.dba$_3$. CHCl$_3$ (0.103 g, 0.10 mmol), and (S,S)-DACH-phenyl Trost ligand (0.207 g, 0.30 mmol). The vial was sealed, evacuated and backfilled with argon three times. Dry degassed dichloromethane (6.0 mL) was added to this vial, and the mixture was stirred at room temperature for 60 min. Tert-butyl cyclohex-2-en-1-yl carbonate (0.960 g, 4.80 mmol) was added to the vial and the contents were transferred to a separate 20 mL Biotage® microwave reaction vial containing 10H-phenoxazine (0.366 g, 2.00 mmol) in dry degassed dichloromethane (5.0 mL). The reaction mixture was stirred at room temperature for 10 days. At this point, the reaction mixture was evaporated onto silica gel and subjected to flash chromatography (SiO$_2$; 0%-5% ethylacetate-hexanes) to afford crude (S)-10-(cyclohex-2-en-1-yl)-10H-phenoxazine (0.550 g), which was taken to the next step without further purification. LCMS m/z 266.1465 ([M+H$^+$], C$_{17}$H$_{16}$NO$_2$ requires 266.1176).

A solution of (S)-10-(cyclohex-2-en-1-yl)-10H-phenoxazine (0.550 g, 2.07 mmol), 4-methylmorpholine N-oxide (0.534 g, 4.56 mmol), and osmium tetroxide (0.420 mL, 0.040 mmol, 2.5% in tert-butanol) in tert-butanol (2.75 mL) and water (0.55 mL), was stirred at RT for 60 h. The reaction mixture was treated with solid sodium bisulfite for 1 h, dichloromethane and silica were added, the mixture was concentrated and purified by flash chromatography (SiO$_2$, 20%-66% ethyl acetate-hexanes) to afford (3R,4S,5R)-5-(10H-phenoxazin-10-yl)tetrahydro-2H-pyran-3,4-diol (0.483 g, 81% over two steps). $^1$H NMR (600 MHz, MeOD) δ 6.99-6.98 (2H, m), 6.90 (2H, td, J=7.8, 1.2 Hz), 6.83-6.81 (2H, m), 6.74 (2H, dd, J=7.8, 1.2 Hz), 4.25 (1H, dd, J=10.2, 3.0 Hz), 4.10-4.03 (2H, m), 3.93 (1H, bs), 3.89 (1H, d, J=12.6 Hz), 3.75 (1H, t, J=10.8 Hz), 3.57 (1H, d, J=12.0 Hz); $^{13}$C NMR (150 MHz, MeOD) δ 149.5, 135.4, 123.4, 122.6, 118.3, 115.5, 71.0, 70.2, 68.7, 68.4, 62.5; ESI-HRMS calcd for C$_{17}$H$_{18}$NO$_4$ [M+H$^+$] 300.1230, found 300.1227. Material produced in this fashion exhibited [α]$_D$=−0.36 (c=1.0, CH$_2$Cl$_2$).

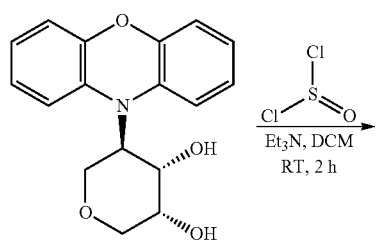

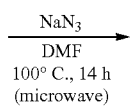

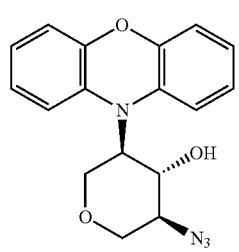

(3S,4S,5R)-3-azido-5-(10H-phenoxazin-10-yl)tetrahydro-2H-pyran-4-ol: A solution of (3R,4S,5R)-5-(10H-phenoxazin-10-yl)tetrahydro-2H-pyran-3,4-diol (0.453 g, 1.51 mmol) in dichloromethane (10.0 mL) under argon was cooled to 0° C., and treated with triethylamine (1.67 mL, 12.1 mmol). Following this thionyl chloride (0.329 mL, 4.54 mmol) was added very slowly over 5 min. The reaction mixture was warmed to RT, and stirred for 2 h. The reaction mixture was partitioned between dichloromethane and water, concentrated to obtain a residue which was purified by flash chromatography (SiO$_2$, 17%-25% ethylacetate-hexanes) to afford crude (3aR,7R,7aS)-7-(10H-phenoxazin-10-yl)tetrahydro-4H-[1,3,2]dioxathiolo[4,5-c]pyran 2-oxide (0.496 g) which was taken to the next step without further purification. LCMS m/z 346.0545 ([M+H$^+$], C$_{17}$H$_{16}$NO$_5$S requires 346.0744).

A solution of (3aR,7R,7aS)-7-(10H-phenoxazin-10-yl)tetrahydro-4H-[1,3,2]dioxathiolo[4,5-c]pyran 2-oxide (0.496 g, 1.44 mmol) in DMF (3.0 mL) was treated with sodium azide (0.280 g, 4.32 mmol), and heated to 100° C. in a microwave for 14 h. Sat. aq. NH$_4$C$_1$ was added, mixture was extracted with ethylacetate, washed with brine (100 mL×4), concentrated, and purified by flash chromatography (SiO$_2$, 6%-13% ethylacetate-hexanes) to afford (3S,4S,5R)-3-azido-5-(10H-phenoxazin-10-yl)tetrahydro-2H-pyran-4-ol (0.180 g, 38% over two steps). $^1$H NMR (600 MHz, MeOD) δ 6.97-6.95 (2H, m), 6.93-6.91 (2H, m), 6.86-6.83 (2H, m), 6.76 (2H, dd, J=7.8, 1.2 Hz), 4.13-4.08 (2H, m), 3.94 (1H, dd, J=11.4, 4.8 Hz), 3.78 (1H, t, J=11.4 Hz), 3.67 (1H, td, J=11.4, 5.4 Hz), 3.54-3.50 (1H, m), 3.16 (1H, t, J=11.4 Hz); $^{13}$C NMR (150 MHz, MeOD) δ 149.5, 135.1, 123.5, 122.9, 118.4, 115.7, 72.1, 68.6, 68.5, 66.7, 64.3; ESI-HRMS calcd for C$_{17}$H$_{17}$N$_4$O$_3$ [M+H$^+$] 325.1295, found 325.1292.

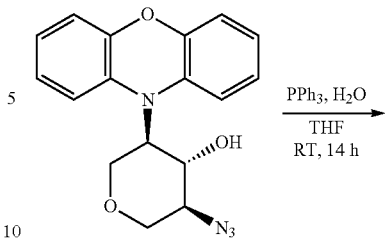

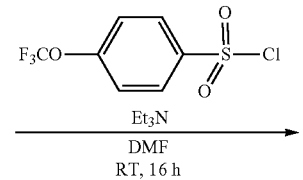

N-((3S,4S,5R)-4-hydroxy-5-(10H-phenoxazin-10-yl)tetrahydro-2H-pyran-3-yl)-4-(trifluoromethoxy)benzenesulfonamide A solution of (3S,4S,5R)-3-azido-5-(10H-phenoxazin-10-yl)tetrahydro-2H-pyran-4-ol (0.165 g, 0.508 mmol) in THF (2.00 mL) was cooled to 0° C., treated with triphenylphosphine (0.146 g, 0.559 mmol), water (0.001 mL, 0.055 mmol), and stirred for 14 h at RT. The solution was concentrated to dryness, dissolved in a minimal amount of CH$_2$Cl$_2$ and purified by flash chromatography (SiO$_2$, 100% hexanes, 50% ethyl acetate-hexanes, 5%, methanol-dichloromethane, 17:2:1 dichloromethane:methanol:35% ammonium hydroxide) to afford crude (3S,4R,5R)-3-amino-5-(10H-phenoxazin-10-yl)tetrahydro-2H-pyran-4-ol (0.151 g) which was taken to the next step without further purification. LCMS calcd for C$_{17}$H$_{19}$N$_2$O$_3$ [M+H$^+$] 299.1390, found 299.1397.

A solution of (3S,4R,5R)-3-amino-5-(10H-phenoxazin-10-yl)tetrahydro-2H-pyran-4-ol (0.151 g, 0.506 mmol) in DMF (5.0 mL) was cooled to 0° C., treated with triethylamine (0.282 mL, 2.02 mmol), and 4-(trifluoromethoxy)benzene-1-sulfonyl chloride (0.094 mL, 0.556 mmol). The mixture was warmed to RT, and stirred for 16 h. The mixture was partitioned between water (10 mL) and CH$_2$Cl$_2$ (10 mL). The organic layer was washed with saturated aqueous NaCl (30 mL×5), and concentrated in vacuo. The residue was dissolved in a minimal amount of CH$_2$Cl$_2$ and purified by flash chromatography (SiO$_2$, 25 g, 17%-20% ethylacetate-hexanes) to afford N-((3S,4S,5R)-4-hydroxy-5-(10H- phenoxazin-10-yl)tetrahydro-2H-pyran-3-yl)-4-(trifluoromethoxy)benzenesulfonamide (0.140 g, 53% over two steps). $^{1}$H NMR (600 MHz, MeOD) δ 7.98 (2H, d, J=9.0 Hz), 7.41 (2H, d, J=8.4 Hz), 6.95-6.87 (4H, m), 6.83-6.80 (2H, m), 6.74-6.73 (2H, m), 4.06 (1H, dd, J=10.8, 4.8 Hz), 4.00 (1H, t, J=9.6 Hz), 3.85 (1H, dd, J=9.6, 3.0 Hz), 3.73 (1H, t, J=11.4 Hz), 3.58 (1H, td, J=10.8, 4.8 Hz), 3.24-3.15 (2H, m); $^{13}$C NMR (150 MHz, MeOD) δ 151.8, 149.5, 140.3, 135.0, 129.3, 123.5, 122.9, 123.5, 122.9, 120.8, 118.4, 115.7, 70.3, 69.9, 68.6, 67.2, 57.3; ESI-HRMS calcd for $C_{24}H_{22}F_3N_2O_6S$ [M+H$^{+}$] 523.1145, found 523.1146. Material produced in this fashion exhibited [α]$_D$=−0.23 (c=1.0, $CH_2Cl_2$). The enantiomeric identity and purity was also confirmed by analytical chiral HPLC>99% (CHIRALPAK® OZ-H column, 70:30 hexanes-EtOH, 1.0 mL/min, retention time: 6.43 min.

Gram Scale Synthesis of Example 2a hexanes) to afford crude (R)-10-(cyclohex-2-en-1-yl)-10H-phenoxazine (8.57 g), which was taken to the next step without further purification.

The reaction was done in two batches:

Batch 1: A solution of (R)-10-(cyclohex-2-en-1-yl)-10H-phenoxazine (4.56 g, 17.2 mmol), 4-methylmorpholine N-oxide (4.43 g, 37.8 mmol), and osmium tetroxide (3.50 mL, 0.344 mmol, 2.5% in tert-butanol) in tert-butanol (2.00 mL) and water (0.40 mL), was stirred at RT for 36 h. The reaction mixture was treated with solid sodium bisulfite for 1 h, dichloromethane and silica were added, the mixture was concentrated to make a silica gel plug.

Batch 2: A solution of (R)-10-(cyclohex-2-en-1-yl)-10H-phenoxazine (4.01 g, 15.1 mmol), 4-methylmorpholine N-oxide (3.90 g, 33.3 mmol), and osmium tetroxide (3.07 mL, 0.302 mmol, 2.5% in tert-butanol) in tert-butanol (2.00 mL) and water (0.40 mL), was stirred at RT for 36 h. The reaction mixture was treated with solid sodium bisulfite for

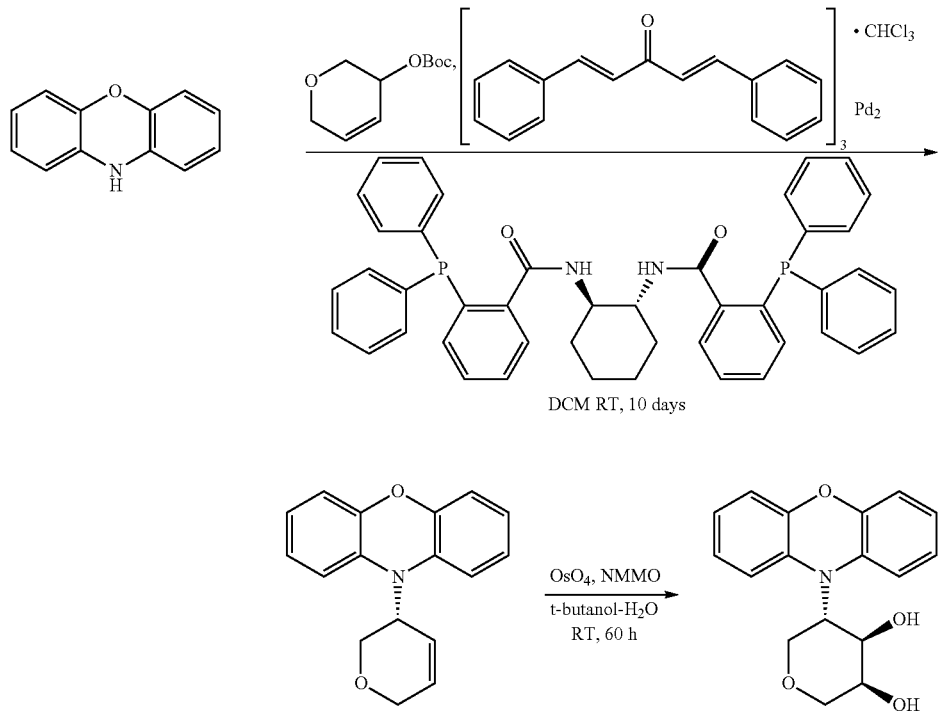

(3S,4R,5S)-5-(10H-phenoxazin-10-yl)tetrahydro-2H-pyran-3,4-diol: A 350 mL chem. Glass® pressure vessel was charged with Pd$_2$.dba$_3$. CHCl$_3$ (1.58 g, 1.53 mmol), and (R,R)-DACH-phenyl Trost ligand (3.17 g, 4.59 mmol). The vessel was sealed, evacuated and backfilled with argon three times. Dry degassed dichloromethane (85.0 mL) was added and the mixture was stirred at room temperature for 60 min. Tert-butyl cyclohex-2-en-1-yl carbonate (14.7 g, 73.4 mmol) was added to the vial and the contents were transferred to a separate 20 mL Biotage® microwave reaction vial containing 10H-phenoxazine (5.60 g, 30.6 mmol) in dry degassed dichloromethane (85.0 mL). The reaction mixture was stirred at room temperature for 10 days. At this point, the reaction mixture was evaporated onto silica gel and subjected to flash chromatography (SiO$_2$; 0%-5% ethylacetate- 1 h, dichloromethane and silica were added, the mixture was concentrated to make a silica gel plug.

Silica gel plugs from batch 1 and 2 were combined and purified by flash chromatography (Sift, 20%-66% ethyl acetate-hexanes) to afford (3S,4R,5S)-5-(10H-phenoxazin-10-yl)tetrahydro-2H-pyran-3,4-diol (9.14 g, 92% over two steps). $^{1}$H NMR (600 MHz, MeOD) δ 6.99-6.98 (2H, m), 6.90 (2H, td, J=7.2, 0.6 Hz), 6.83-6.81 (2H, m), 6.74 (2H, dd, J=7.8, 0.6 Hz), 4.25 (1H, dd, J=10.2, 3.0 Hz), 4.10-4.03 (2H, m), 3.93 (1H bs), 3.89 (1H, d, J=12.6 Hz), 3.75 (1H, t, J=10.8 Hz), 3.57 (1H, d, J=12.0 Hz); $^{13}$C NMR (150 MHz, MeOD) δ 149.5, 135.4, 123.4, 122.6, 118.3, 115.5, 71.0, 70.2, 68.7, 68.4, 62.5; ESI-HRMS calcd for $C_{17}H_{18}NO_4$ [M+H$^{+}$] 300.1230, found 300.1202.

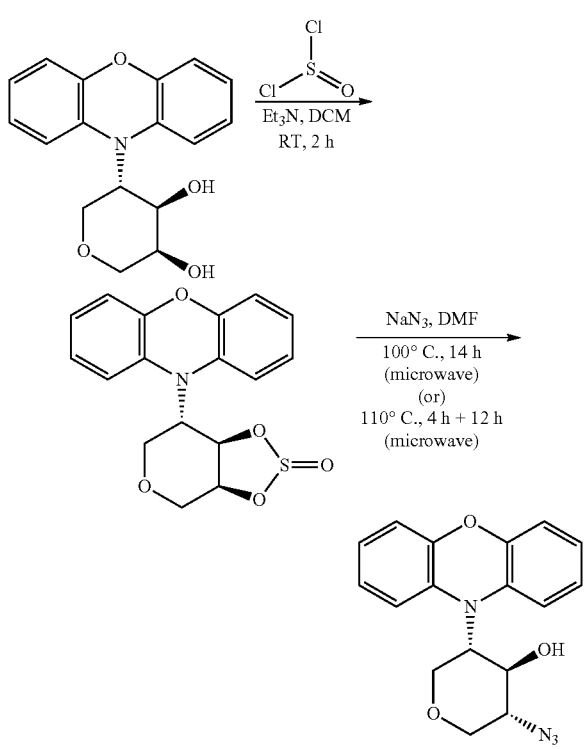

(3R,4R,5S)-3-azido-5-(10H-phenoxazin-10-yl)tetra-hydro-2H-pyran-4-ol

The reaction was done in two batches:

Batch 1: A solution of (3S,4R,5S)-5-(10H-phenoxazin-10-yl)tetrahydro-2H-pyran-3,4-diol (4.45 g, 3.95 mmol) in dichloromethane (50.0 mL) under argon was cooled to 0° C., and treated with triethylamine (21.5 mL, 155 mmol). Following this thionyl chloride (4.21 mL, 58.2 mmol) was added very slowly over 10 min. The reaction mixture was warmed to RT, and stirred for 2 h. The reaction mixture was partitioned between dichloromethane and water, concentrated to obtain a residue.

Batch 2: A solution of (3S,4R,5S)-5-(10H-phenoxazin-10-yl)tetrahydro-2H-pyran-3,4-diol (3.95 g, 13.2 mmol) in dichloromethane (50.0 mL) under argon was cooled to 0° C., and treated with triethylamine (14.6 mL, 105 mmol). Following this thionyl chloride (2.87 mL, 39.6 mmol) was added very slowly over 10 min. The reaction mixture was warmed to RT, and stirred for 2 h. The reaction mixture was partitioned between dichloromethane and water, concentrated to obtain a residue.

Residues from batches 1 and 2 were combined and purified by flash chromatography (SiO$_2$, 17% ethylacetate-hexanes) to afford crude (3aS,7S,7aR)-7-(10H-phenoxazin-10-yl)tetrahydro-4H-[1,3,2]dioxathiolo[4,5-c]pyran 2-oxide (7.45 g) which was taken to the next step without further purification.

The reaction was done in two batches:

Batch 1: A solution of (3aS,7S,7aR)-7-(10H-phenoxazin-10-yl)tetrahydro-4H-[1,3,2]dioxathiolo[4,5-c]pyran 2-oxide (7.45 g, 21.5 mmol) in DMF (11.0 mL) was treated with sodium azide (4.22 g, 64.7 mmol), and heated to 100° C. in a microwave for 14 h. Sat. aq. NH$_4$Cl was added, mixture was extracted with ethylacetate, washed with brine (100 mL×4), concentrated, and purified by flash chromatography (SiO$_2$, 6%-13% ethylacetate-hexanes) to afford (3R,4R,5S)-3-azido-5-(10H-phenoxazin-10-yl)tetrahydro-2H-pyran-4-ol (2.08 g). 4.53 g of starting material sulfide was recovered which was used in batch 2.

Batch 2: A solution of (3aS,7S,7aR)-7-(10H-phenoxazin-10-yl)tetrahydro-4H-[1,3,2]dioxathiolo[4,5-c]pyran 2-oxide (4.53 g, 13.1 mmol) in DMF (9.0 mL) was treated with sodium azide (2.56 g, 39.3 mmol), and heated to 110° C. in a microwave for 4 h; pressure was released from the vial and it was reheated at 110° C. in a microwave for 12 h. Sat. aq. NH$_4$Cl was added, mixture was extracted with ethylacetate, washed with brine (100 mL×4), concentrated, and purified by flash chromatography (SiO$_2$, 6%-13% ethylacetate-hexanes) to afford (3R,4R,5S)-3-azido-5-(10H-phenoxazin-10-yl)tetrahydro-2H-pyran-4-ol (2.67 g).

The combined yield from batch 1 and 2 gave the title compound in 52% yield (4.75 g). $^1$H NMR (600 MHz, MeOD) δ 6.96 (2H, dd, J=7.8, 1.2 Hz), 6.92 (2H, td, J=7.2, 1.2 Hz), 6.84 (2H, td, J=7.8, 1.8 Hz), 6.76 (2H, dd, J=7.8, 1.2 Hz), 4.13-4.07 (2H, m), 3.93 (1H, J=11.4, 5.4 Hz), 3.77 (1H, t, J=11.4 Hz), 3.67 (1H, td, J=10.8, 4.8 Hz), 3.53-3.49 (1H, m), 3.16 (1H, t, J=11.4 Hz); $^{13}$C NMR (150 MHz, MeOD) δ 149.5, 135.1, 123.5, 122.9, 118.4, 115.7, 72.1, 68.6, 68.5, 66.7, 64.3; ESI-HRMS calcd for $C_{12}H_{17}N_4O_3$ [M+H$^+$] 325.1295, found 325.1284.

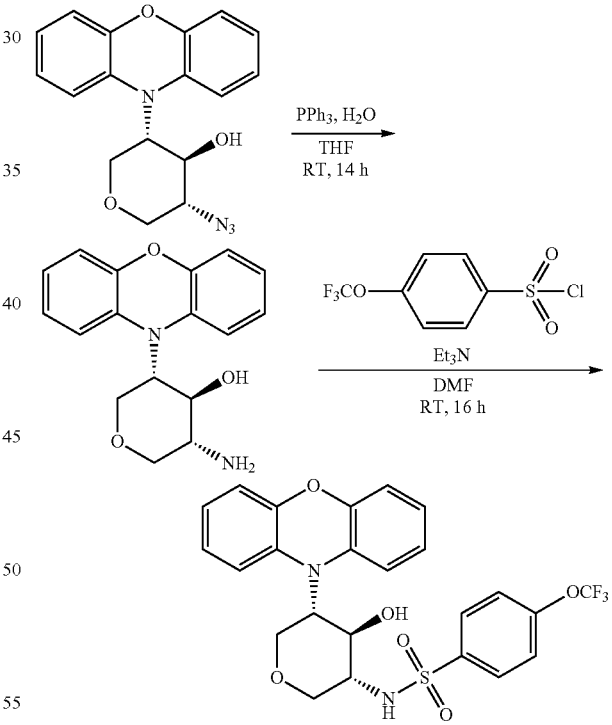

N-((3R,4R,5S)-4-hydroxy-5-(10H-phenoxazin-10-yl)tetrahydro-2H-pyran-3-yl)-4-(trifluoromethoxy)benzenesulfonamide The reaction was done in two batches:

Batch 1: A solution of (3R,4R,5S)-3-azido-5-(10H-phenoxazin-10-yl)tetrahydro-2H-pyran-4-ol (2.08 g, 6.40 mmol) in THF (22.5 mL) was cooled to 0° C., treated with triphenylphosphine (1.85 g, 7.05 mmol), water (0.009 mL, 0.512 mmol), and stirred for 14 h at RT. The solution was concentrated to dryness to obtain residue.

Batch 2: A solution of (3R,4R,5S)-3-azido-5-(10H-phenoxazin-10-yl)tetrahydro-2H-pyran-4-ol (2.67 g, 8.23 mmol) in THF (29.0 mL) was cooled to 0° C., treated with triphenylphosphine (2.38 g, 9.06 mmol), water (0.012 mL, 0.650 mmol), and stirred for 14 h at RT. The solution was concentrated to dryness to obtain residue.

Combined residues from batches 1 and 2 were dissolved in a minimal amount of $CH_2Cl_2$ and purified by flash chromatography ($SiO_2$, 100% hexanes, 50% ethyl acetate-hexanes, 5%, methanol-dichloromethane, 17:2:1 dichloromethane:methanol:35% ammonium hydroxide) to afford crude (3R,4S,5S)-3-amino-5-(10H-phenoxazin-10-yl)tetrahydro-2H-pyran-4-ol (3.95 g) which was taken to the next step without further purification.

A solution of (3R,4S,5S)-3-amino-5-(10H-phenoxazin-10-yl)tetrahydro-2H-pyran-4-ol (2.00 g, 6.70 mmol) in DMF (20.0 mL) was cooled to 0° C., treated with triethylamine (3.73 mL, 26.8 mmol), and 4-(trifluoromethoxy)benzene-1-sulfonyl chloride (1.25 mL, 7.37 mmol). The mixture was warmed to RT, and stirred for 16 h. The mixture was partitioned between water and $CH_2Cl_2$. The organic layer was washed with saturated aqueous NaCl (30 mL×5), and concentrated in vacuo. The residue was dissolved in a minimal amount of $CH_2Cl_2$ and purified by flash chromatography ($SiO_2$, 17%-20% ethylacetate-hexanes) to afford N-((3R,4R,5S)-4-hydroxy-5-(10H-phenoxazin-10-yl)tetrahydro-2H-pyran-3-yl)-4-(trifluoromethoxy)benzenesulfonamide (3.16 g, 80% over two steps). $^1$H NMR (600 MHz, MeOD) δ 7.98 (2H, d, J=9.0 Hz), 7.41 (2H, d, J=8.4 Hz), 6.922-6.88 (4H, m), 6.82 (2H, td, J=7.8, 1.8 Hz), 6.74-6.73 (2H, m), 4.07 (1H, dd, J=11.4, 4.2 Hz), 4.00 (1H, t, J=9.6 Hz), 3.85 (1H, dd, J=9.6, 3.0 Hz), 3.73 (1H, t, J=12.0 Hz), 3.58 (1H, td, J=10.8, 4.8 Hz), 3.23-3.15 (2H, m); $^{13}$C NMR (150 MHz, MeOD) δ 151.8, 149.5, 140.3, 135.0, 129.3, 123.4, 122.8, 120.8, 118.4, 115.6, 70.3, 69.9, 68.6, 67.2, 57.3; ESI-HRMS calcd for $C_{24}H_{22}F_3N_2O_6S$ [M+H$^+$] 523.1145, found 523.1149. Material produced in this fashion exhibited $[α]_D$=+13.0 (c=1.0, $CH_3OH$).

Piperidine Constraint

Experimental

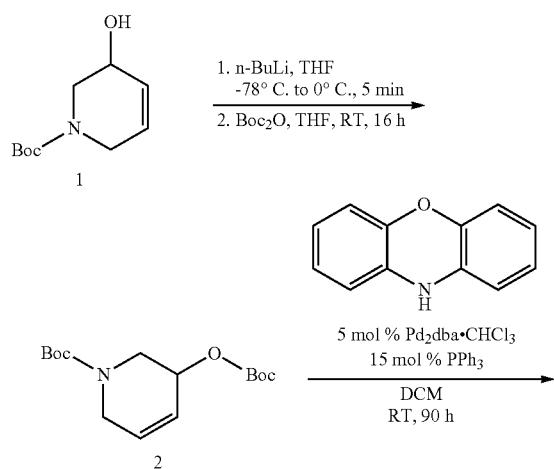

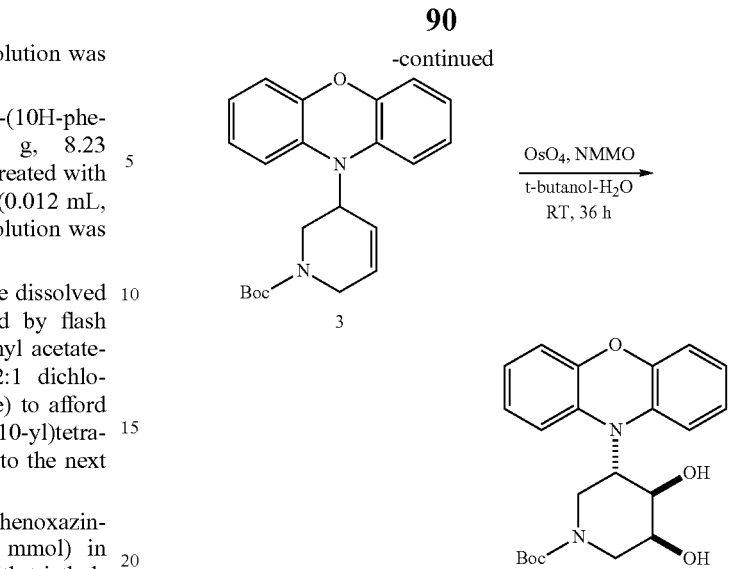

Rac-(3S,4R,5S)-tert-butyl 3,4-dihydroxy-5-(10H-phenoxazin-10-yl)piperidine-1-carboxylate (SM-2)

To a solution of tert-butyl 5-hydroxy-5,6-dihydropyridine-1(2H)-carboxylate 1 (10.0 g, 50.1 mmol) in THF (160 mL) was added n-butyllithium (2.5 M in hexanes, 19.8 mL, 2.50 mmol) at −78° C. The resulting solution was warmed to 0° C. and stirred for 5 min prior to addition of di-tert-butyl dicarbonate (12.0 g, 55.1 mmol) in THF (80.0 mL). The reaction was warmed to RT, stirred for 16 h. The reaction was then quenched with water, extracted with ethyl acetate, washed with brine, concentrated, and the residue purified by flash chromatography ($SiO_2$, 0%-3% ethyl acetate-hexanes) to afford slightly crude tert-butyl 5-((tert-butoxycarbonyl)oxy)-5,6-dihydropyridine-1(2H)-carboxylate 2 (15.3 g) as a colorless oil which was taken to the next step without further purification.

A 350 mL chem. Glass® pressure vessel was charged with $Pd_2.dba_3 \cdot CHCl_3$ (1.11 g, 1.07 mmol, 5 mol %), and triphenylphosphine (0.841 g, 3.21 mmol, 15 mol %). The vessel was sealed, evacuated and backfilled with argon three times. Dry degassed dichloromethane (60.0 mL) was added, and the mixture was stirred at room temperature for 60 min. Racemic tert-butyl cyclohex-2-en-1-yl carbonate (15.3 g, 51.1 mmol) was added followed by 10H-phenoxazine (3.92 g, 21.4 mmol) in dry degassed dichloromethane (50.0 mL). The reaction mixture was sealed and stirred at room temperature for 90 h. At this point, the reaction mixture was evaporated onto silica gel and subjected to column chromatography ($SiO_2$; 0%-5% ethylacetate in hexanes) to afford crude tert-butyl 5-(10H-phenoxazin-10-yl)-5,6-dihydropyridine-1(2H)-carboxylate 3 (8.10 g) which was taken to the next step without purification.

A solution of tert-butyl 5-(10H-phenoxazin-10-yl)-5,6-dihydropyridine-1(2H)-carboxylate 3 (8.10 g, 22.2 mmol), 4-methylmorpholine N-oxide monohydrate (5.73 g, 48.9 mmol), and osmium tetroxide (9.90 mL, 0.978 mmol, 2.5% in tert-butanol) in tert-butanol (48.6 mL) and water (6.10 mL), was stirred at RT for 36 h. The reaction mixture was treated with solid sodium bisulfite solution, stirred for 1 h, evaporated on to silica and purified by flash chromatography ($SiO_2$, 0%-70% ethyl acetate-hexanes) to afford the title compound SM-2 (7.20 g, 85% over two steps from phenoxazine). $^1$H NMR (600 MHz, MeOD) δ 7.01 (2H, bs), 6.90

(2H, bs), 6.82-6.75 (4H, m), 4.36-4.12 (3H, m), 3.99-3.96 (2H, m), 3.14 (1H, d, J=11.4 Hz), 3.04-2.91 (1H, m), 1.46 (9H, s); $^{13}$C NMR (150 MHz, MeOD) δ 156.5, 149.6, 135.3, 123.5, 122.7, 118.2, 115.6, 80.1, 69.5, 61.7, 48.8, 45.9, 45.1, 27.4; LCMS m/z 399.1914 ([M+H$^+$], $C_{22}H_{27}N_2O_5$ requires 399.1915).

Rac-(3S,4R,5S)-tert-butyl 3,4-dihydroxy-5-(10H-phenoxazin-10-yl)piperidine-1-carboxylate (SM-2), 6.12 g, was resolved into it's enantiomers by preparative chiral HPLC using CHIRALPAK® AD-H eluting with hexane:ethanol:methanol 90:8:2 to give 2.9 g of a first eluting enantiomer, named SM-2a with 99.7% ee and 2.8 g of a second eluting enantiomer, named SM-2b in 99.8% ee, both obtained as off-white foams. Optical purity was confirmed by analytical chiral HPLC using CHIRALPAK® IF-3 4.6 mm diameter× 150 mm length, 3 micron particle size, column, with mobile phase 90:10:0.1 hexanes-EtOH-diethylamine and flow rate 1.0 mL/min. SM-2a eluted at 7.0 min and SM-2b eluted at 8.4 min, both with >99% ee.

SM-2a exhibited optical rotation of $[α]_D$=−37.0 (c=1.0, CH$_3$OH) and $[α]_D$=−33.0 (c=1.0, CH$_2$Cl$_2$).

SM-2b exhibited optical rotation of $[α]_D$=+37.0 (c=1.0, CH$_3$OH) and $[α]_D$=+32.0 (c=1.0, CH$_2$Cl$_2$).

(3S,4R,5S)-tert-butyl 3,4-dihydroxy-5-(10H-phenoxazin-10-yl)piperidine-1-carboxylate can also be obtained via an asymmetric synthesis:

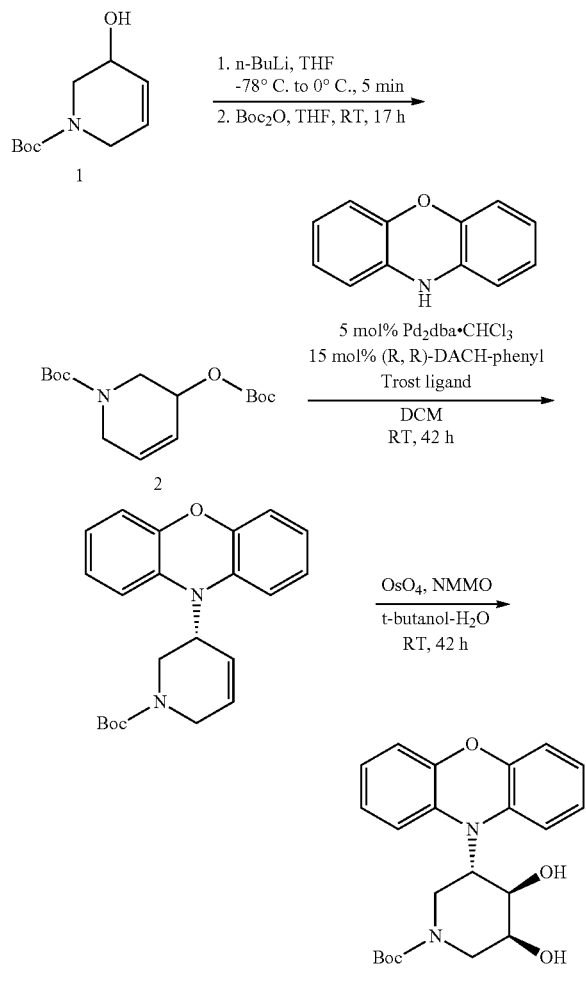

To a solution of tert-butyl 5-hydroxy-5,6-dihydropyridine-1(2H)-carboxylate 1 (0.500 g, 2.50 mmol) in THF (8.0 mL) was added n-butyllithium (2.5 M in hexanes, 0.99 mL, 2.50 mmol) at −78° C. The resulting solution was warmed to 0° C. and stirred for 5 min prior to addition of di-tert-butyl dicarbonate (0.600 g, 2.76 mmol) in THF (4.0 mL). The reaction was warmed to RT, stirred for 17 h. The reaction was then quenched with water, extracted with ethyl acetate, washed with brine, concentrated, and the residue purified by flash chromatography (SiO$_2$, 0%-3% ethyl acetate-hexanes) to afford crude tert-butyl 5-((tert-butoxycarbonyl)oxy)-5,6-dihydropyridine-1(2H)-carboxylate 2 (0.825 g) as a colorless oil which was taken to the next step without further purification.

A 5 mL Biotage® microwave reaction vial was charged with Pd$_2$.dba$_3$. CHCl$_3$ (0.025 g, 0.024 mmol), and (R,R)-DACH-phenyl Trost ligand (0.052 g, 0.075 mmol). The vial was sealed, evacuated and backfilled with argon three times. Dry degassed dichloromethane (1.25 mL) was added to this vial, and the mixture was stirred at room temperature for 30 min. Racemic tert-butyl cyclohex-2-en-1-yl carbonate (0.359 g, 1.20 mmol) was added to the vial and the contents were transferred to a separate 5 mL Biotage® microwave reaction vial containing 10H-phenoxazine (0.092 g, 0.50 mmol) in dry degassed dichloromethane (1.50 mL). The reaction mixture was stirred at room temperature for 10 days. At this point, the reaction mixture was evaporated onto silica gel and subjected to column chromatography (SiO$_2$; 0%-5% ethylacetate in hexanes) to afford crude (R)-tert-butyl 5-(10H-phenoxazin-10-yl)-5,6-dihydropyridine-1 (2H)-carboxylate, (0.141 g) which was taken to the next step without purification.

A solution of (R)-tert-butyl 5-(10H-phenoxazin-10-yl)-5,6-dihydropyridine-1(2H)-carboxylate, (0.126 g, 0.346 mmol), 4-methylmorpholine N-oxide monohydrate (0.089 g, 0.761 mmol), and osmium tetroxide (0.080 mL, 0.007 mmol, 2.5% in tert-butanol) in tert-butanol (2.0 mL) and water (0.40 mL), was stirred at RT for 42 h. The reaction mixture was treated with solid sodium bisulfite solution, stirred for 1 h, evaporated on to silica and purified by flash chromatography (SiO$_2$, 0%-70% ethyl acetate-hexanes) to afford (R)-tert-butyl 5-(10H-phenoxazin-10-yl)-5,6-dihydropyridine-1(2H)-carboxylate SM-2b (0.091 g, 51% over two steps from phenoxazine). $^1$H NMR (600 MHz, MeOD) δ 7.02 (2H, bs), 6.91 (2H, bs), 6.83-6.76 (4H, bs), 4.34-4.12 (3H, m), 4.00-3.97 (2H, m), 3.19-3.15 (1H, m), 3.06-2.93 (1H, m), 1.46 (9H, bs); $^{13}$C NMR (150 MHz, MeOD) δ 147.5, 134.1, 128.1, 123.4, 121.8, 115.5, 114.8, 80.5, 53.8, 43.4, 42.7, 42.0, 40.7, 27.4; LCMS m/z 399.1909 ([M+H$^+$], $C_{22}H_{27}N_2O_5$ requires 399.1915). Identity and optical purity was shown by analytical chiral HPLC>99% using CHIRALPAK® IF-3 4.6 mm diameter×150 mm length, 3 micron particle size column, with mobile phase 90:10:0.1 hexanes-EtOH-diethylamine at flow rate 1.0 mL/min, with material from the above procedure eluting at 8.4 min, ie identical the enantiomer, SM-2b obtained from the resolution above.

Use of the (S,S)-DACH-phenyl Trost ligand in a procedure analogous to that above will lead to the other enantiomer: SM-2a.

Absolute stereochemistry is assigned by analogy with the known stereochemical outcome of the DACH-phenyl Trost ligand palladium mediated asymmetric allylation process using tert-butyl cyclohex-2-en-1-yl carbonate as an electrophile and phenoxazine as a nucleophile, as described in patent filing PCT/US2015/019770.

Synthesis of Examples 16, 17 and 18

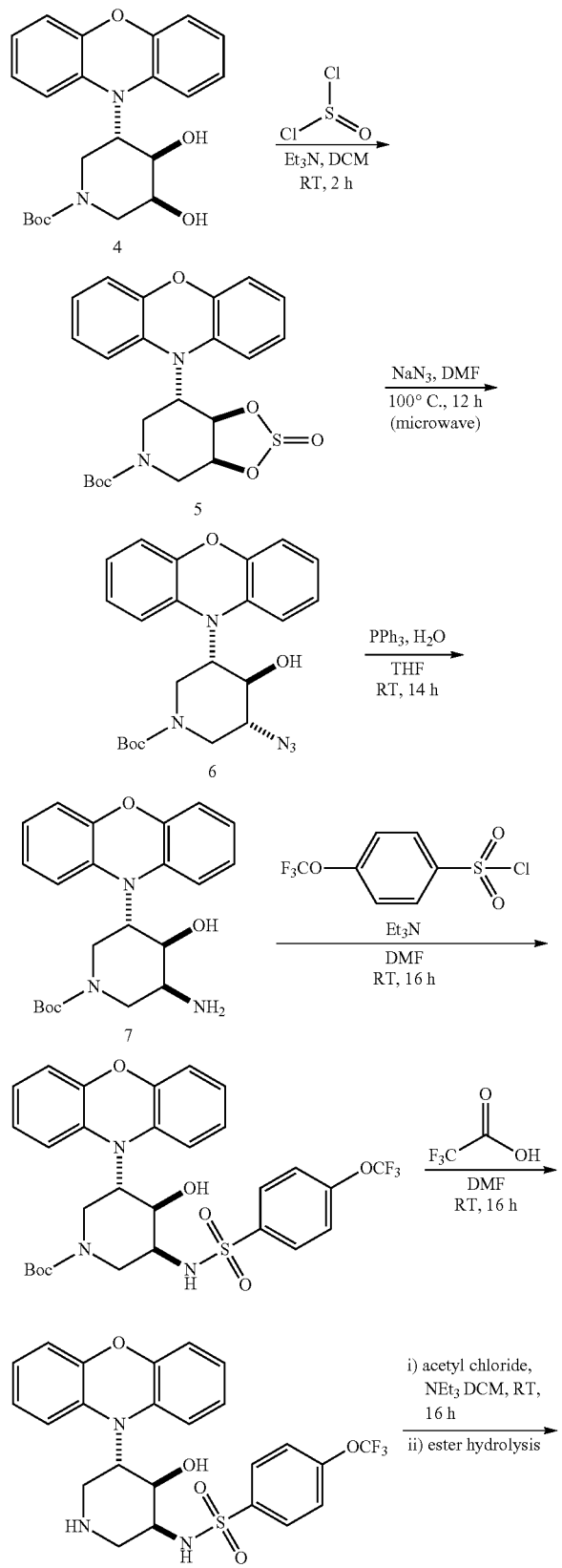

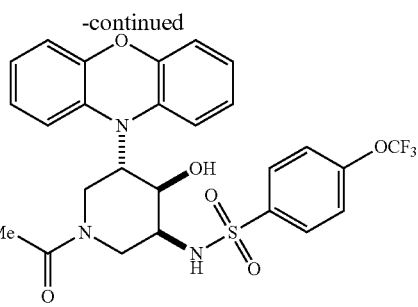

Experimental

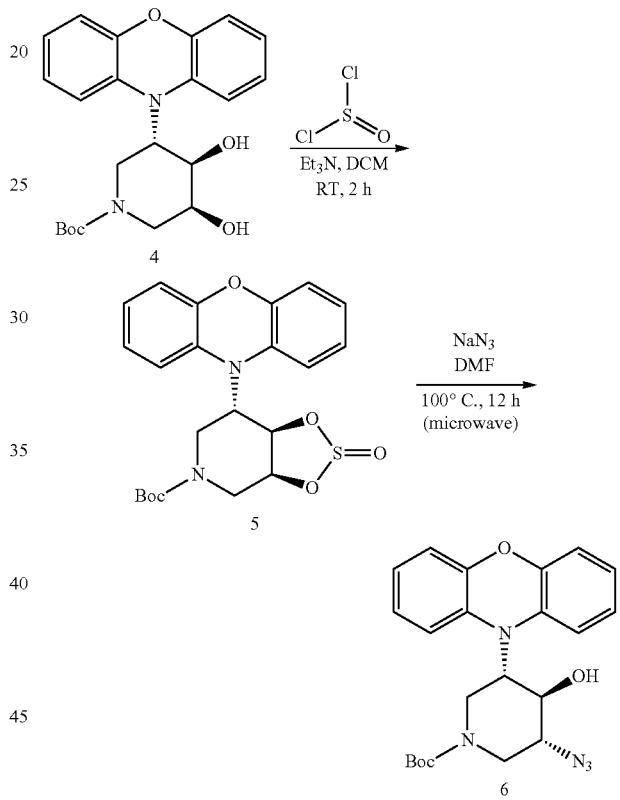

Rac-(3R,4R,5S)-tert-butyl 3-azido-4-hydroxy-5-(10H-phenoxazin-10-yl)piperidine-1-carboxylate (6)

Rac-(3S,4R,5S)-tert-butyl 3,4-dihydroxy-5-(10H-phenoxazin-10-yl)piperidine-1-carboxylate 4 (1.00 g, 2.5 mmol), and triethylamine (2.77 mL, 20.0 mmol) in dichloromethane (20.0 mL) was cooled to 0° C. Thionyl chloride (0.544 mL, 7.50 mmol) was added slowly. The reaction mixture was warmed to RT, stirred for 2 h, partitioned between dichloromethane and water. Organic layer was concentrated and the residue obtained was purified by flash chromatography (SiO$_2$, 17% ethyl acetate-hexanes) to afford crude Rac-(3 aS,7S,7aR)-tert-butyl 7-(10H-phenoxazin-10-yl)tetrahydro-[1,3,2]dioxathiolo[4,5-c]pyridine-5(6H)-carboxylate 2-oxide 5 (0.373 g) which was taken to the next step without further purification.

A solution of Rac-(3aS,7S,7aR)-tert-butyl 7-(10H-phenoxazin-10-yl)tetrahydro-[1,3,2]dioxathiolo[4,5-c]pyridine-5(6H)-carboxylate 2-oxide 5 (0.373 g, 0.839 mmol), sodium azide (0.164 g, 2.52 mmol) in DMF (1.0 mL) in 5 mL Biotage® microwave reaction vial was heated at 100° C. in a Biotage Initiator® microwave reactor for 12 h. The reaction mixture was treated with sat. aq. NH$_4$C$_1$, extracted with ethylacetate, washed with brine, concentrated, purified by column chromatography (SiO$_2$, 6%-13% ethylacetate-hexanes) to afford the title compound 6 (0.205 g, 33% over two steps). $^1$H NMR (600 MHz, MeOD) δ 6.99 (2H, bs), 6.94-6.80 (6H, m), 4.33-4.13 (2H, m), 3.48-3.35 (2H, m), 3.25-3.24 (2H, m), 2.78-2.65 (1H, m), 1.47 (9H, s); $^{13}$C NMR (150 MHz, MeOD) δ 154.9, 149.6, 123.5, 123.1, 118.3, 115.8, 81.0, 72.6, 66.5, 63.7, 45.9, 27.3; LCMS m/z 424.1987 ([M+H$^+$], C$_{22}$H$_{26}$N$_5$O$_4$ requires 424.1980).

droxy-5-(10H-phenoxazin-10-yl)piperidine-1-carboxylate 7 (0.321 g) which was taken to the next step without further purification.

A solution of Rac-(3R,4S,5S)-tert-butyl 3-amino-4-hydroxy-5-(10H-phenoxazin-10-yl)piperidine-1-carboxylate 7 (0.321 g, 0.807) in DMF (2.60 mL) was cooled to 0° C., treated with Et$_3$N (0.449 mL, 3.23 mmol), and 4-(trifluoromethoxy)benzene-1-sulfonyl chloride (0.150 mL, 0.888 mmol). The mixture was warmed to RT, and stirred for 16 h. The mixture was partitioned between water (10 mL) and CH$_2$Cl$_2$ (10 mL). The organic layer was washed with saturated brine (30 mL×5) to remove DMF, and concentrated in vacuo. The residue was dissolved in a minimal amount of CH$_2$Cl$_2$ and purified by flash chromatography (SiO$_2$, 0%-33% ethylacetate-hexanes) to afford the title compound Example 16 (0.183 g, 61% over two steps). $^1$H NMR (600 MHz, MeOD) δ 8.00 (2H, d, J=8.4 Hz), 7.42 (2H, d, J=8.4 Hz), 6.95-6.76 (8H, m), 4.29-4.03 (3H, m), 3.42 (1H, bs), 3.16 (1H, t, J=12.6 Hz), 3.10-3.08 (1H, m), 2.73-2.60 (1H, m), 1.43 (9H, s); $^{13}$C NMR (150 MHz, MeOD) δ 155.0, 151.8, 149.4, 140.4, 134.9, 129.2, 123.5, 123.0, 120.9, 118.4, 115.7, 80.7, 70.3, 66.9, 65.9, 57.0, 27.3; LCMS m/z 622.1839 ([M+H$^+$], C$_{29}$H$_{31}$F$_3$N$_3$O$_7$S requires 622.1830).

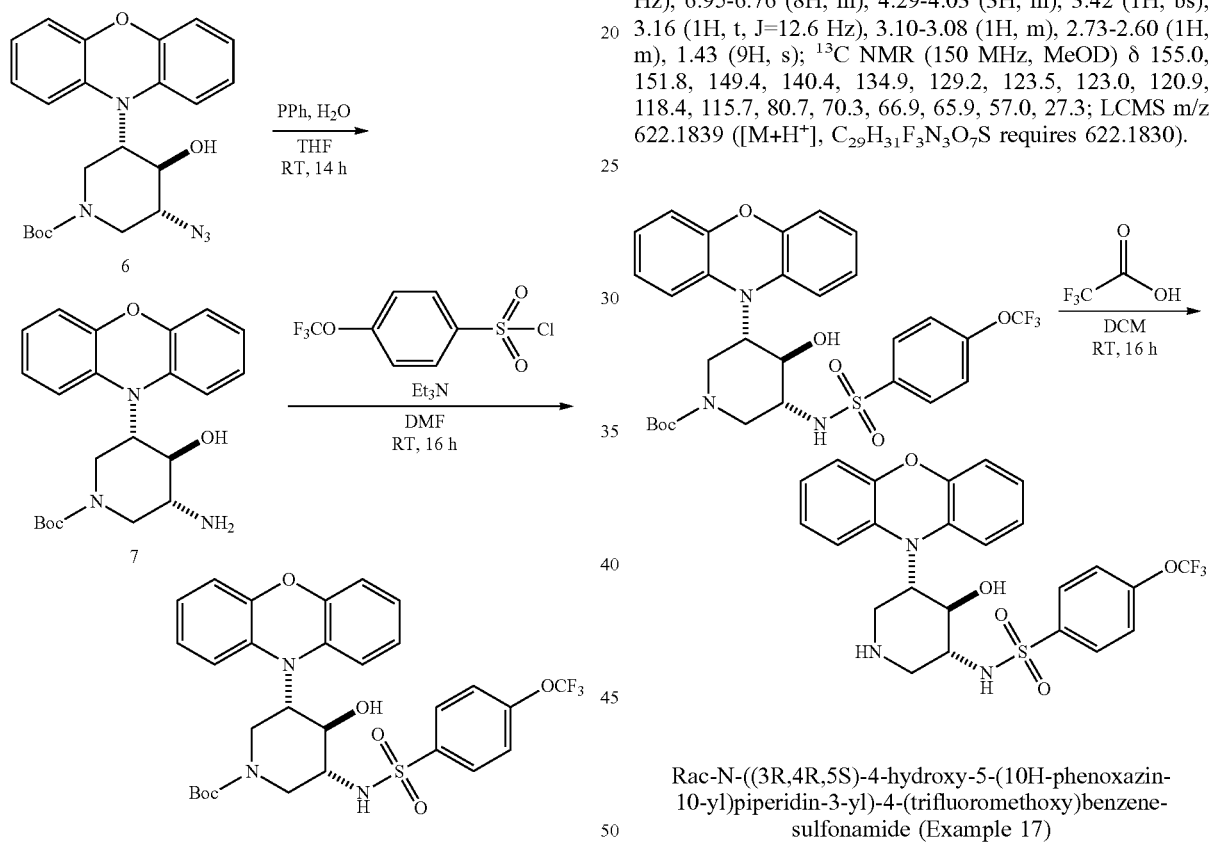

Rac-(3S,4R,5R)-tert-butyl 4-hydroxy-3-(10H-phenoxazin-10-yl)-5-(4-(trifluoromethoxy)phenylsulfonamido)piperidine-1-carboxylate (Example 16)

A solution of Rac-(3R,4R,5S)-tert-butyl 3-azido-4-hydroxy-5-(10H-phenoxazin-10-yl)piperidine-1-carboxylate 6 (0.205 g, 0.372 mmol) in THF (2.25 mL) was cooled to 0° C., treated with PPh$_3$ (0.140 g, 0.533 mmol), H$_2$O (0.001 mL, 0.055 mmol), and stirred for 14 h at room temperature. The solution was concentrated to dryness, dissolved in a minimal amount of dichloromethane and purified by flash chromatography (SiO$_2$, 100% hexanes, 50% ethyl acetate-hexanes, 5%, methanol-dichloromethane, 17:2:1 dichloromethane:methanol:35% ammonium hydroxide) to afford slightly crude Rac-(3R,4S,5S)-tert-butyl 3-amino-4-hy- Rac-N-((3R,4R,5S)-4-hydroxy-5-(10H-phenoxazin-10-yl)piperidin-3-yl)-4-(trifluoromethoxy)benzenesulfonamide (Example 17)

A solution of Rac-(3S,4R,5R)-tert-butyl 4-hydroxy-3-(10H-phenoxazin-10-yl)-5-(4-(trifluoromethoxy)phenylsulfonamido)piperidine-1-carboxylate Example 16 (0.153 g, 0.246 mmol), trifluoroacetic acid (0.117 mL, 1.52 mmol) in dichloromethane (1.0 mL) were stirred at RT for 16 h. Dichloromethane (5 mL) was added and the mixture was concentrated on rotavapor at 45° C. to remove trifluoroacetic acid. More dichloromethane and silica were added and mixture was concentrated to make a dry plug which was purified by flash chromatography (SiO$_2$, 50% ethyl acetate-hexanes, 17:2:1 dichloromethane:methanol:35% ammonium hydroxide) to afford title compound Example 17 (0.090 g, 70%). $^1$H NMR (600 MHz, MeOD) δ 8.00 (2H, d, J=8.4 Hz), 7.43 (2H, d, J=8.4 Hz), 6.94-6.73 (8H, m), 3.94 (1H, t, J=9.6 Hz), 3.52-3.48 (1H, m), 3.15 (2H, dd, J=10.8, 4.2 Hz), 3.02-3.00 (1H, m), 2.92 (1H, t, J=12.0 Hz), 2.41

(1H, t, J=12.6 Hz); δ 151.8, 149.5, 140.6, 135.1, 129.3, 123.4, 122.7, 120.8, 118.4, 115.6, 71.1, 68.1, 58.4, 50.3; LCMS m/z 522.1302 ([M+H⁺], C$_{24}$H$_{23}$F$_3$N$_3$O$_5$S requires 522.1306).

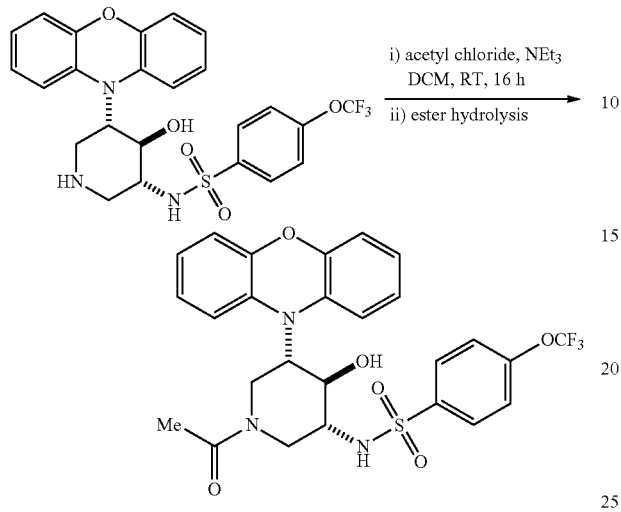

Rac-N-((3R,4R,5S)-1-acetyl-4-hydroxy-5-(10H-phenoxazin-10-yl)piperidin-3-yl)-4-(trifluoromethoxy)benzenesulfonamide (Example 18)

A solution of Rac-N-((3R,4R,5S)-4-hydroxy-5-(10H-phenoxazin-10-yl)piperidin-3-yl)-4-(trifluoromethoxy)benzenesulfonamide Example 17 (0.035 g, 0.067 mmol), acetyl chloride (0.006 mL, 0.080 mmol), and triethylamine (0.023 mL, 0.167 mmol) in dichloromethane (1.20 mL) was stirred at RT for 24 h. The reaction was washed with sat. aq. NaHCO$_3$ solution. The organic layer was concentrated to give a residue. Residue was stirred in EtOH (0.2 mL) with 1N NaOH (0.2 mL) for 56 h at RT, followed by 3 h at 100° C. The residue was purified by flash chromatography (SiO$_2$, 0%-33% ethylacetate-hexanes) to afford the title compound Example 18 (0.020 g, 53%). $^1$H NMR (600 MHz, MeOD) δ 8.01 (2H, d, J=9.0 Hz), 7.41 (2H, d, J=7.8 Hz), 6.97-6.73 (8H, m), 4.73-4.57 (1H, m), 4.12-3.93 (2H, m), 3.54-3.42 (1H, m), 3.09-3.07 (3H, m), 2.05 (3H, s); $^{13}$C NMR (150 MHz, MeOD) δ 170.7, 151.8, 149.3, 140.1, 134.9, 129.4, 123.5, 122.7, 120.9, 117.8, 115.7, 70.1, 65.4, 57.2, 50.4, 43.5, 19.8; LCMS m/z 564.1412 ([M+H⁺], C$_{26}$H$_{25}$F$_3$N$_3$O$_6$S requires 564.1411).

Synthesis of Examples 16b, 17b, 18b, 20b, and 19b

Scheme for the Synthesis of Examples 16b, 17b, 18b, 20b, and 19b

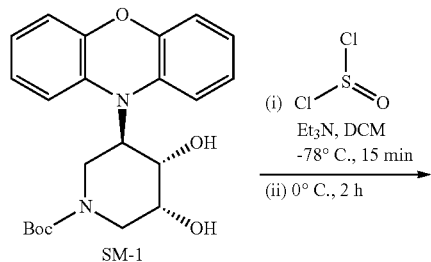

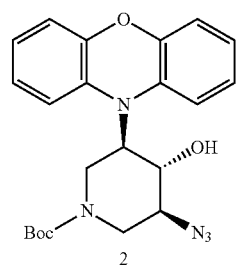

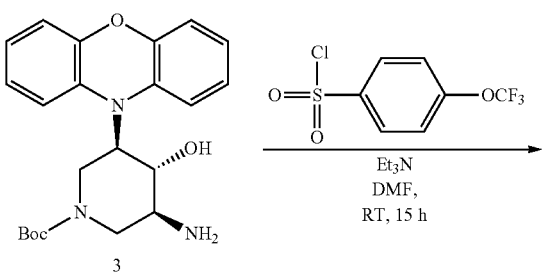

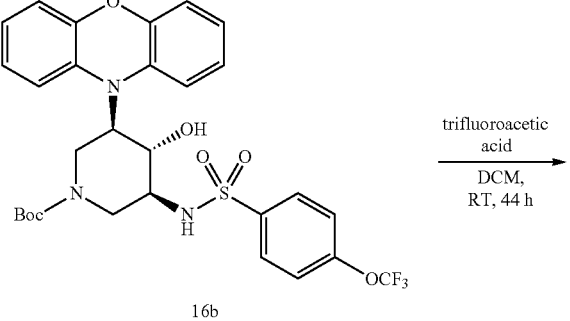

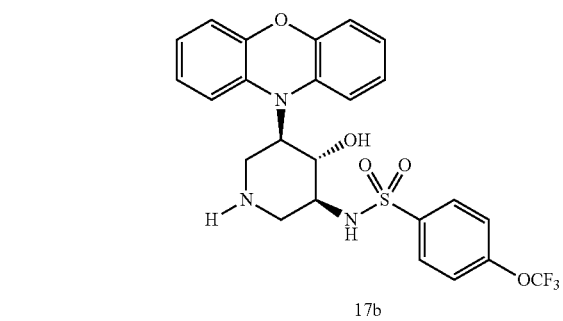 [SMILES: CN1C[C@H](NS(=O)(=O)c2ccc(OC(F)(F)F)cc2)[C@@H](O)[C@H](N2c3ccccc3Oc3ccccc32)C1]

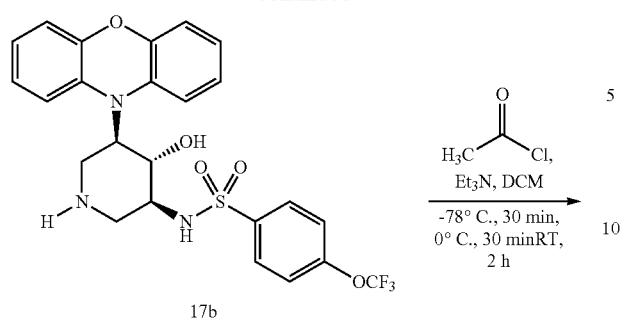

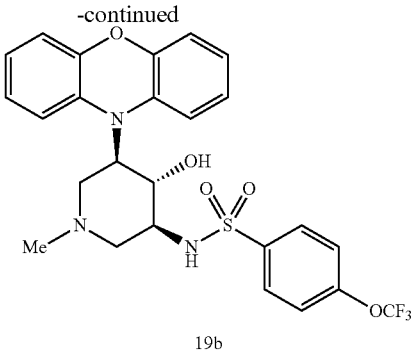

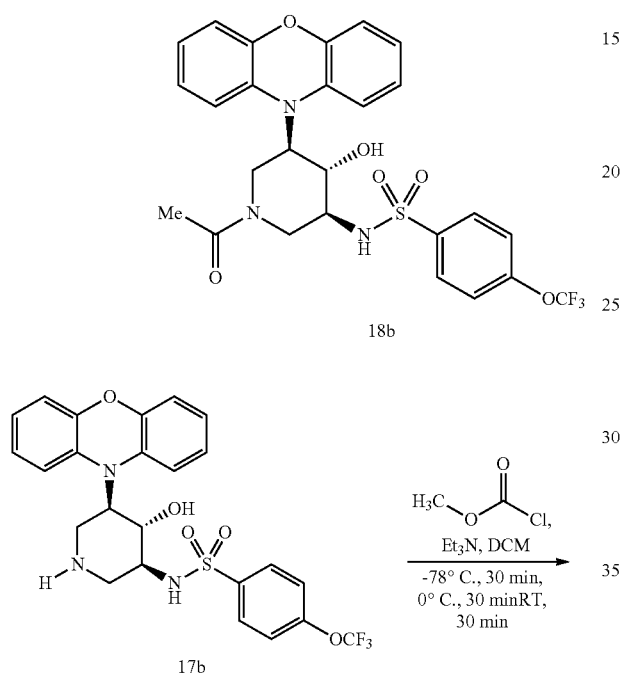

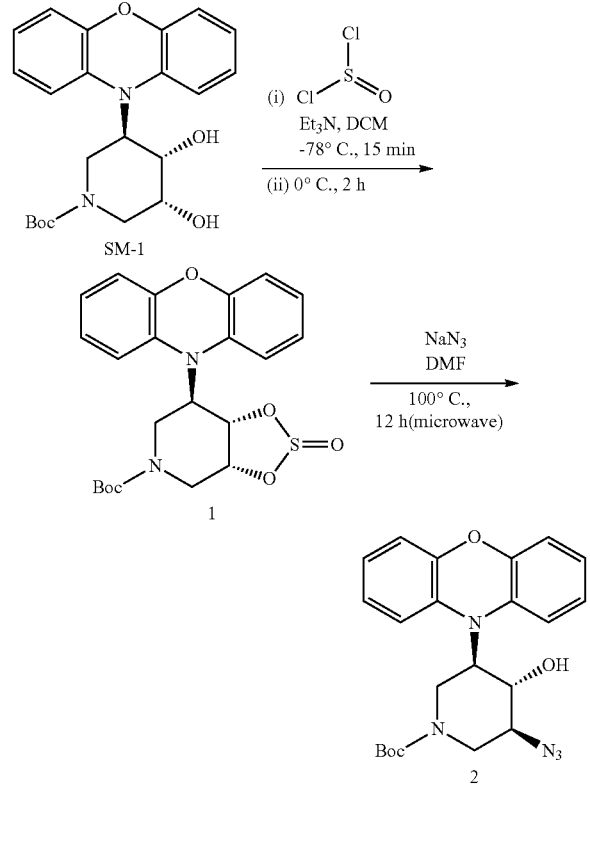

(3S,4S,5R)-tert-butyl 3-azido-4-hydroxy-5-(10H-phenoxazin-10-yl)piperidine-1-carboxylate (2)

(3R,4S,5R)-tert-butyl 3,4-dihydroxy-5-(10H-phenoxazin-10-yl)piperidine-1-carboxylate SM-1 (2.85 g, 7.15 mmol), and triethylamine (7.92 mL, 57.2 mmol) in dichloromethane (80.0 mL) was cooled to −78° C. Thionyl chloride (0.778 mL, 10.7 mmol) was added slowly. The reaction mixture was stirred at −78° C. for 15 min, warmed to 0° C., stirred for 2 h, partitioned between dichloromethane and water. Organic layer was concentrated and the residue obtained was purified by flash chromatography (SiO$_2$, 17%-25% ethyl acetate-hexanes) to afford crude (3aR,7R,7aS)-tert-butyl 7-(10H-phenoxazin-10-yl)tetrahydro-[1,3,2]dioxathiolo[4,5-c]pyridine-5(6H)-carboxylate 2-oxide 1 (2.87 g) which was taken to the next step without further purification.

A solution of (3aR,7R,7aS)-tert-butyl 7-(10H-phenoxazin-10-yl)tetrahydro-[1,3,2]dioxathiolo[4,5-c]pyridine-5(6H)-carboxylate 2-oxide 1 (2.87 g, 6.46 mmol), sodium azide (1.26 g, 19.4 mmol) in DMF (5.0 mL) in a 20 mL Biotage® microwave reaction vial was heated at 100° C. in a Biotage Initiator® microwave reactor for 12 h. The reaction mixture was treated with sat. aq. NH$_4$C$_1$, extracted with ethylacetate, washed with brine, concentrated, purified by column chromatography (SiO$_2$, 6%-13% ethylacetate-hexanes) to afford the title compound 2 (1.57 g, 52% over two steps). $^1$H NMR (600 MHz, MeOD) δ 6.99 (2H, d, J=7.2 Hz), 6.93 (2H, t, J=7.2 Hz), 6.86 (2H, br s), 6.79 (2H, br s), 4.33-4.26 (1H, m), 4.13-4.08 (2H, m), 3.48 (1H, br s), 3.39-3.35 (1H, m), 3.22 (1H, br s), 2.74-2.64 (1H, m), 1.46 (9H, s); $^{13}$C NMR (150 MHz, MeOD) δ 154.9, 149.6, 134.9, 123.5, 123.1, 118.3, 115.8, 81.0, 72.6, 66.5, 65.6, 63.7, 46.4, 45.9, 45.7, 45.1, 27.3; LCMS m/z 424.1983 ([M+H+], C$_{22}$H$_{26}$N$_5$O$_4$ requires 424.1980).

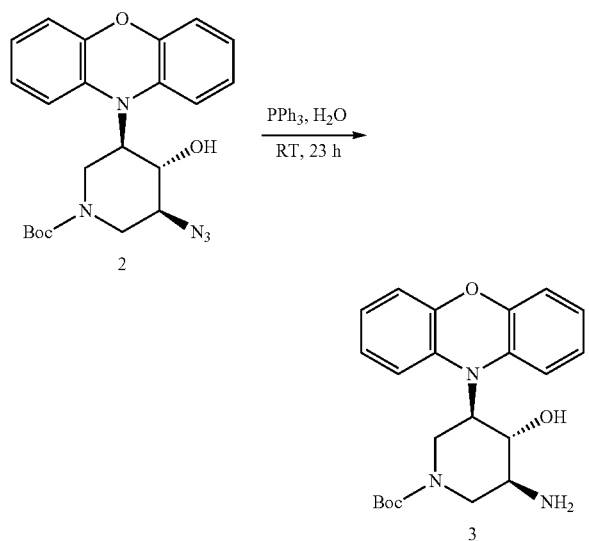

(3S,4R,5R)-tert-butyl 3-amino-4-hydroxy-5-(10H-phenoxazin-10-yl)piperidine-1-carboxylate (3)

A solution of (3S,4S,5R)-tert-butyl 3-azido-4-hydroxy-5-(10H-phenoxazin-10-yl)piperidine-1-carboxylate 2 (1.54 g, 3.63 mmol) in THF (16.5 mL) was cooled to 0° C., treated with PPh$_3$ (1.05 g, 4.00 mmol), H$_2$O (0.005 mL, 0.291 mmol), and stirred for 23 h at room temperature. The solution was concentrated to dryness, dissolved in a minimal amount of dichloromethane and purified by flash chromatography (SiO$_2$, 100% hexanes, 50% ethyl acetate-hexanes, 5%, methanol-dichloromethane, 17:2:1 dichloromethane:methanol:35% ammonium hydroxide) to afford title compound 3 (1.35 g, 94%). $^1$H NMR (600 MHz, MeOD) δ 7.00 (2H, d, J=7.8 Hz), 6.92 (2H, t, J=7.2 Hz), 6.85 (2H, br s), 6.79 (2H, br s), 4.34-4.28 (1H, m), 4.14 (1H, d, J=10.8 Hz), 3.92 (1H, t, J=9.0 Hz), 3.45 (1H, br s), 3.23 (1H, t, J=12.0 Hz), 2.66-2.58 (2H, m), 1.45 (9H, s); $^{13}$C NMR (150 MHz, MeOD) δ 135.1, 123.5, 122.9, 122.6, 118.3, 117.9, 115.7, 80.6, 73.5, 66.7, 65.8, 54.6, 45.3, 27.3; LCMS m/z 398.2074 ([M+H$^+$], C$_{22}$H$_{28}$N$_3$O$_4$ requires 398.2075).

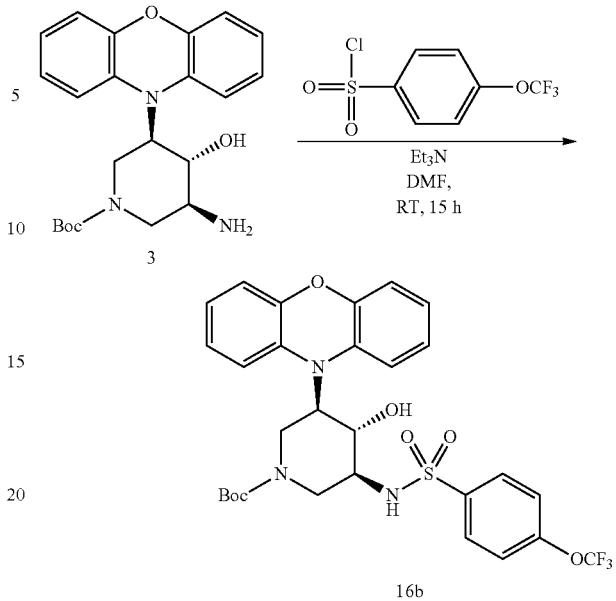

(3R,4S,5S)-tert-butyl 4-hydroxy-3-(10H-phenoxazin-10-yl)-5-(4-(trifluoromethoxy)phenylsulfonamido)piperidine-1-carboxylate (Example 16b)

A solution of (3S,4R,5R)-tert-butyl 3-amino-4-hydroxy-5-(10H-phenoxazin-10-yl)piperidine-1-carboxylate 3 (1.35 g, 3.39) in DMF (11.0 mL) was cooled to 0° C., treated with Et$_3$N (1.89 mL, 13.5 mmol), and 4-(trifluoromethoxy)benzene-1-sulfonyl chloride (0.633 mL, 3.72 mmol). The mixture was warmed to RT, and stirred for 15 h. The mixture was partitioned between water and CH$_2$Cl$_2$. The organic layer was washed with saturated brine (30 mL×5) to remove DMF, and concentrated in vacuo. The residue was dissolved in a minimal amount of CH$_2$Cl$_2$ and purified by flash chromatography (SiO$_2$, 0%-33% ethylacetate-hexanes) to afford the title compound Example 16b (1.74 g, 82%). $^1$H NMR (600 MHz, MeOD) δ 8.00 (2H, d, J=8.4 Hz), 7.42 (2H, d, J=8.4 Hz), 6.95-6.89 (4H, m), 6.84 (2H, br s), 6.77 (2H, br s), 4.28-4.24 (1H, m), 4.14 (1H, d, J=10.2 Hz), 4.02 (1H, br s), 3.42 (1H, br s), 3.16 (1H, t, J=12.6 Hz), 3.10-3.05 (1H, m), 2.73-2.59 (1H, m), 1.44 (9H, s); $^{13}$C NMR (150 MHz, MeOD) δ 151.8, 149.4, 140.4, 134.9, 129.2, 123.5, 122.8, 120.9, 117.9, 115.7, 80.7, 70.3, 66.9, 65.9, 57.0, 45.2, 27.3; LCMS m/z 622.1831 ([M+H$^+$], C$_{29}$H$_{31}$F$_3$N$_3$O$_7$S requires 622.1830). Material produced in this fashion exhibited [α]$_D$=−20.0° (c=1.0, CH$_3$OH).

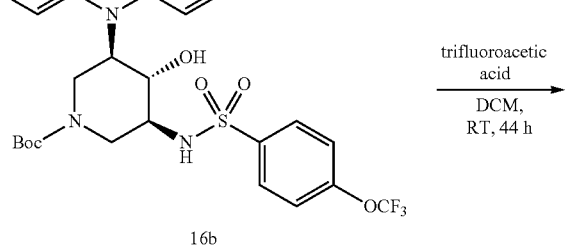

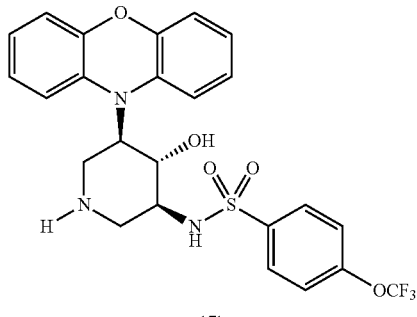

17b

N-((3S,4S,5R)-4-hydroxy-5-(10H-phenoxazin-10-yl) piperidin-3-yl)-4-(trifluoromethoxy)benzenesulfonamide (Example 17b)

A solution of (3R,4S,5S)-tert-butyl 4-hydroxy-3-(10H-phenoxazin-10-yl)-5-(4-(trifluoromethoxy)phenylsulfonamido)piperidine-1-carboxylate Example 16b (1.60 g, 2.57 mmol), trifluoroacetic acid (1.22 mL, 15.9 mmol) in dichloromethane (3.0 mL) were stirred at RT for 44 h. Dichloromethane was added and the mixture was concentrated on rotavapor at 45° C. to remove trifluoroacetic acid. More dichloromethane and silica were added and mixture was concentrated to make a dry plug which was purified by flash chromatography (SiO$_2$, 50% ethyl acetate-hexanes, 17:2:1 dichloromethane:methanol:35% ammonium hydroxide) to afford title compound Example 17b (1.31 g, 98%). $^1$H NMR (600 MHz, MeOD) δ 8.00 (2H, d, J=9.0 Hz), 7.41 (2H, d, J=8.4 Hz), 6.93 (2H, d, J=7.8 Hz), 6.87 (2H, t, J=8.4 Hz), 6.81 (2H, t, J=7.8 Hz), 6.73 (2H, d, J=7.8 Hz), 3.97 (1H, t, J=9.6 Hz), 3.53 (1H, td, J=11.4, 4.2 Hz), 3.23-3.19 (2H, m), 3.08 (1H, dd, J=12.6, 4.2 Hz), 2.98 (1H, t, J=12.6 Hz), 2.50 (1H, t, J=12.6 Hz); $^{13}$C NMR (150 MHz, MeOD) δ 151.8, 149.5, 140.4, 134.9, 129.3, 123.5, 122.9, 120.9, 118.5, 115.7, 70.8, 67.5, 57.8, 49.8, 47.1; LCMS m/z 522.1305 ([M+H$^+$], C$_{24}$H$_{23}$F$_3$N$_3$O$_5$S requires 522.1306). Material produced in this fashion exhibited [α]$_D$=−3.0° (c=1.0, CH$_3$OH).

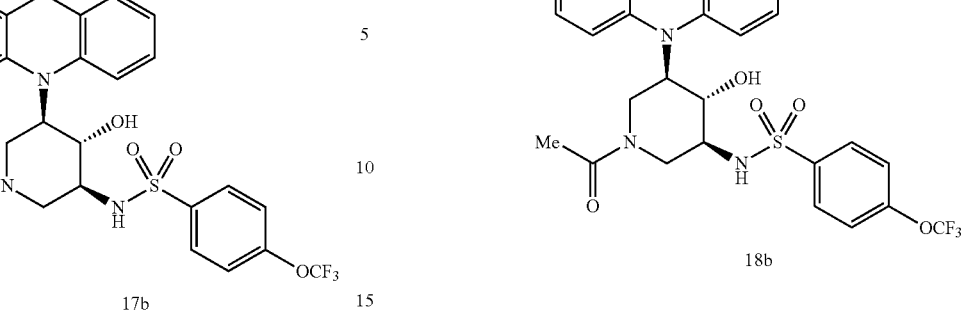

18b

N-((3S,4S,5R)-1-acetyl-4-hydroxy-5-(10H-phenoxazin-10-yl)piperidin-3-yl)-4-(trifluoromethoxy)benzenesulfonamide (Example 18b)

A solution of N-((3S,4S,5R)-4-hydroxy-5-(10H-phenoxazin-10-yl)piperidin-3-yl)-4-(trifluoromethoxy)benzenesulfonamide Example 17b (0.200 g, 0.384 mmol) and triethylamine (0.080 mL, 0.576 mmol) in dichloromethane (3.60 mL) was cooled to −78° C. Acetyl chloride (0.025 mL, 0.345 mmol) was added slowly. The reaction mixture was stirred at −78° C. for 30 min, 0° C. for 30 min, RT for 2 h, concentrated on rotavapor at 45° C. to remove acetyl chloride. The residue obtained was purified by flash chromatography (SiO$_2$, 0%-66% ethyl acetate-hexanes), triturated with 1:1 ethyl acetate-hexanes to afford title compound Example 18b (0.110 g, 51%) as a white powder. $^1$H NMR (600 MHz, MeOD) reported as 2:1 mixture of rotamers δ 8.02-7.99 (2H, m), 7.41 (2H, d, J=8.4 Hz), 6.95-6.73 (11H, m), 1H (4.72, dt, J=11.4, 2.4 Hz; 4.62-4.55, m), 4.11-4.08 (1H, m), 4.04-4.00 (1H, m), 3.95-3.93 (1H, m), 3.53-3.51 (1H, m), 1H (3.42, td, J=11.4, 4.2 Hz; 2.44, t, J=11.4 Hz), 3.14-3.03 (3H, m), 3H (2.05, s; 2.04, s); LCMS m/z 564.1407 ([M+H$^+$], C$_{26}$H$_{25}$F$_3$N$_3$O$_6$S requires 564.1411). Material produced in this fashion exhibited [α]$_D$=−34.0° (c=1.0, CH$_3$OH).

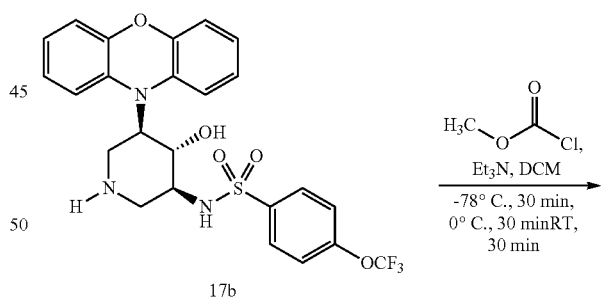

17b

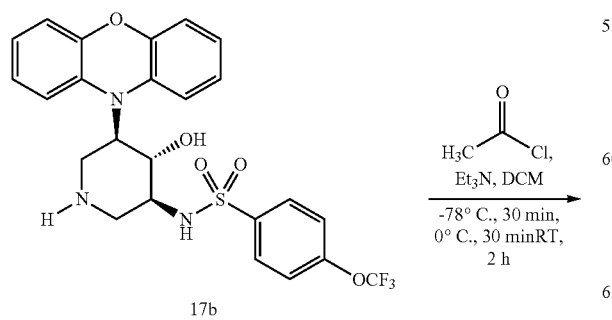

17b

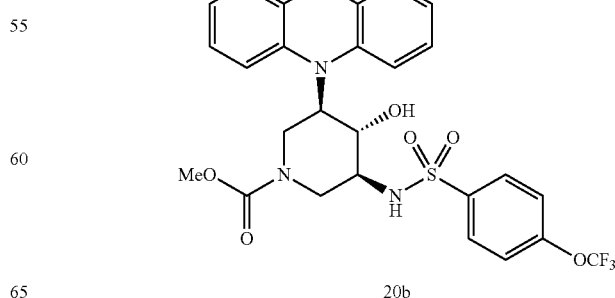

20b

(3R,4S,5S)-methyl 4-hydroxy-3-(10H-phenoxazin-10-yl)-5-(4-(trifluoromethoxy)phenylsulfonamido)piperidine-1-carboxylate (Example 20b)

A solution of N-((3S,4S,5R)-4-hydroxy-5-(10H-phenoxazin-10-yl)piperidin-3-yl)-4-(trifluoromethoxy)benzenesulfonamide Example 17b (0.200 g, 0.384 mmol) and triethylamine (0.080 mL, 0.576 mmol) in dichloromethane (3.60 mL) was cooled to −78° C. Methyl chloroformate (0.027 mL, 0.345 mmol) was added slowly. The reaction mixture was stirred at −78° C. for 30 min, 0° C. for 30 min, RT for 30 min, concentrated on rotavapor. The residue obtained was purified by flash chromatography (SiO$_2$, 0%-66% ethyl acetate-hexanes), triturated with 9:1 ether-hexanes to afford title compound Example 20b (0.130 g, 59%) as a white powder. $^1$H NMR (600 MHz, MeOD) δ 8.00 (2H, d, J=8.4 Hz), 7.43 (2H, d, J=8.4 Hz), 6.92-6.88 (4H, m), 6.82 (2H, d, J=7.8 Hz), 6.75 (2H, d, J=7.8 Hz), 4.32-4.23 (1H, m), 4.02 (2H, t, J=10.2 Hz), 3.69 (3H, s), 3.47 (1H, td, J=15.6, 4.8 Hz), 3.22-3.11 (2H, m), 2.72 (1H, br s); $^{13}$C NMR (150 MHz, MeOD) δ 151.8, 149.4, 140.3, 134.9, 129.3, 123.5, 122.8, 120.9, 118.0, 115.7, 70.3, 65.9, 56.8, 52.4, 45.6; LCMS m/z 580.1363 ([M+H$^+$], C$_{26}$H$_{25}$F$_3$N$_3$O$_7$S requires 580.1360). Material produced in this fashion exhibited [α]$_D$=−28.0° (c=1.0, CH$_3$OH).

N-((3S,4S,5R)-4-hydroxy-1-methyl-5-(10H-phenoxazin-10-yl)piperidin-3-yl)-4-(trifluoromethoxy)benzenesulfonamide (Example 19b)

A solution of formaldehyde (0.032 mL, 0.384 mmol, 37% by weight) in trifluoroethanol (2.50 ml) was stirred at 40° C. for 5 min. After this, N-((3S,4S,5R)-4-hydroxy-5-(10H-phenoxazin-10-yl)piperidin-3-yl)-4-(trifluoromethoxy)benzenesulfonamide Example 17b (0.200 g, 0.384 mmol) was added, and the mixture was stirred for 5 min more at 40° C. Following this sodium borohydride (0.017 g, 0.461 mmol) was added and the reaction was stirred in a sealed vessel at 80° C. for 2 h. Reaction mixture was concentrated and purified by flash chromatography (SiO$_2$, 0%-66% ethyl acetate-hexanes) to afford title compound Example 19b (0.119 g, 58%). $^1$H NMR (600 MHz, MeOD) δ 8.00 (2H, d, J=8.4 Hz), 7.43 (2H, d, J=8.4 Hz), 6.94 (2H, d, J=7.8 Hz), 6.89 (2H, d, J=7.2 Hz), 6.75 (2H, d, J=7.8 Hz), 3.85 (1H, t, J=10.2 Hz), 3.59 (1H, td, J=11.4, 4.2 Hz), 3.23 (1H, td, J=10.8, 4.8 Hz), 3.04 (1H, d, J=9.6 Hz), 2.89 (1H, dd, J=11.4, 2.4 Hz), 2.45 (1H, t, J=11.4 Hz), 2.27 (3H, s), 2.00 (1H, t, J=11.4 Hz); $^{13}$C NMR (150 MHz, MeOD) δ 151.8, 148.7, 140.4, 135.0, 129.3, 123.4, 122.9, 120.8, 118.7, 115.6, 70.4, 66.7, 60.0, 57.0, 56.8, 44.3; LCMS m/z 536.1460 ([M+H$^+$], C$_{25}$H$_{25}$F$_3$N$_3$O$_5$S requires 536.1462). Material produced in this fashion exhibited [α]$_C$ =+8.0° (c=1.0, CH$_3$OH).

Synthesis of Examples 16a, 17a, 18a, 20a, and 19a

Scheme for the Synthesis of Examples 16a, 17a, 18a, 20a, and 19a

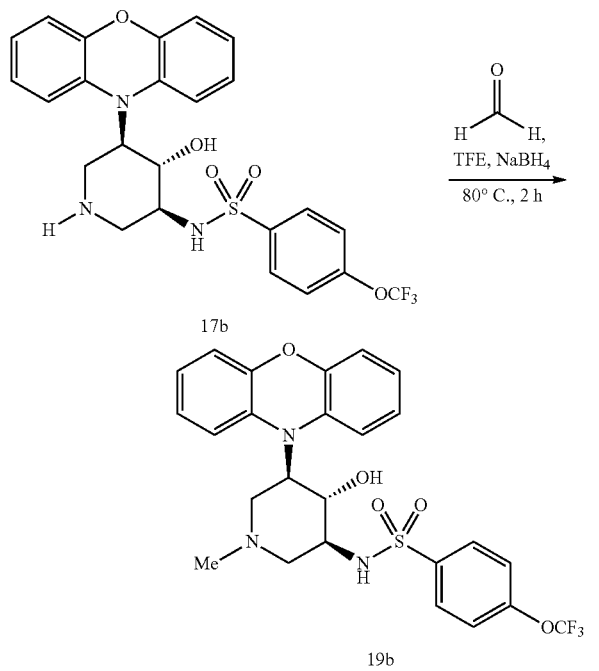

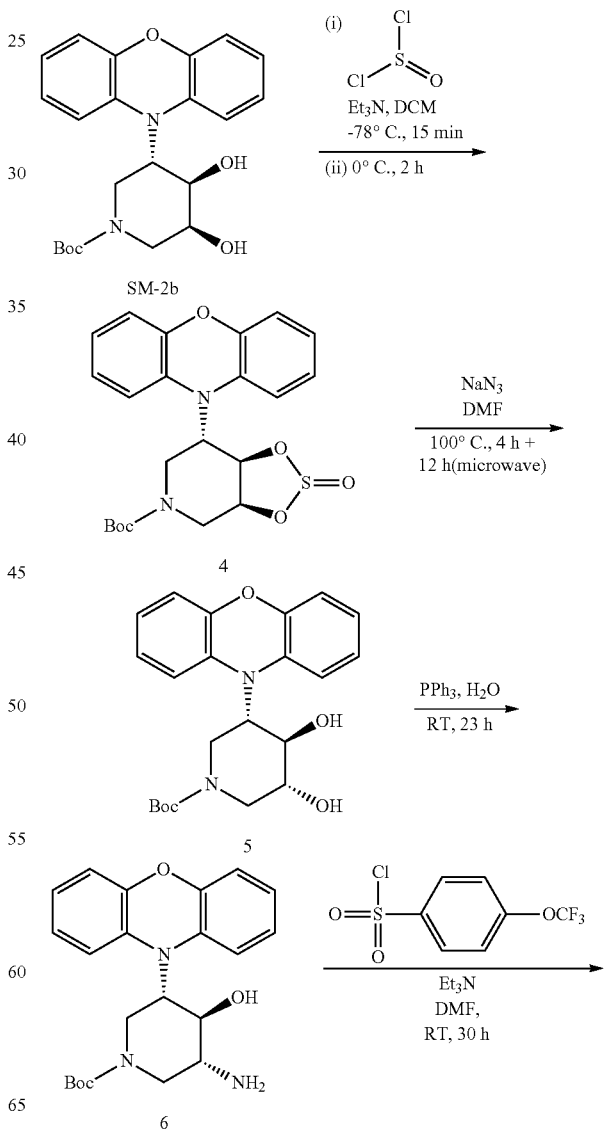

107
-continued

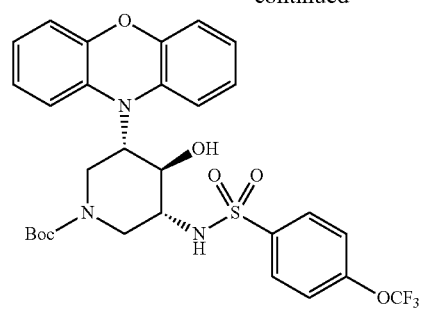
16a trifluoroacetic acid
DCM, RT, 44 h →

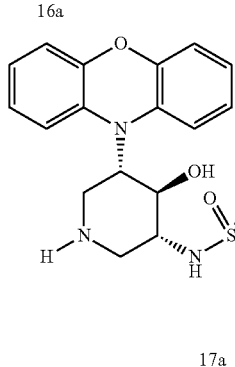
17a

17a + H₃C−C(O)−Cl, Et₃N, DCM
−78° C., 30 min, 0° C. 30 min RT, 2 h →

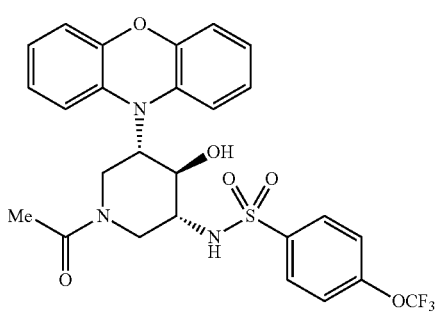
18a

17a + H₃C−O−C(O)−Cl, Et₃N, DCM
−78° C., 30 min, 30 min →

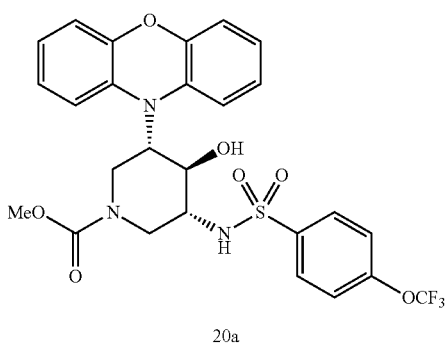
20a

108
-continued

17a + HCHO, TFE, NaBH₄
−80° C., 2 h →

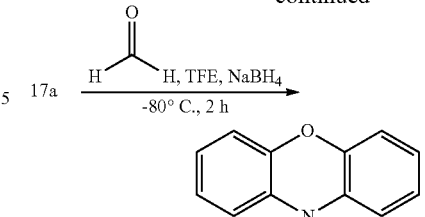
19a

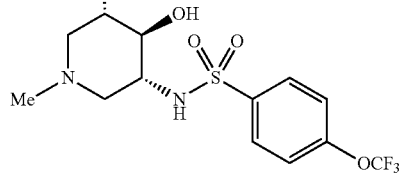
SM-2b (i) SOCl₂, Et₃N, DCM, −78° C., 15 min
(ii) 0° C., 2 h →

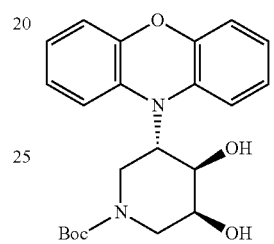
4

NaN₃, DMF
100° C., 4 h + 12 h (microwave) →

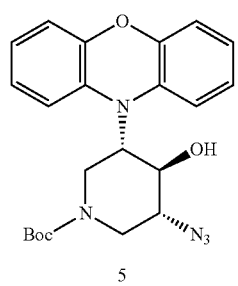
5

(3R,4R,5S)-tert-butyl 3-azido-4-hydroxy-5-(10H-phenoxazin-10-yl)piperidine-1-carboxylate (5)

(3S,4R,5S)-tert-butyl 3,4-dihydroxy-5-(10H-phenoxazin-10-yl)piperidine-1-carboxylate SM-2b (2.75 g, 6.90 mmol), and triethylamine (7.65 mL, 55.2 mmol) in dichloromethane (80.0 mL) was cooled to −78° C. Thionyl chloride (0.751 mL, 10.4 mmol) was added slowly. The reaction mixture was stirred at −78° C. for 15 min, warmed to 0° C., stirred for 2 h, partitioned between dichloromethane and water. Organic layer was concentrated and the residue obtained was purified by flash chromatography (SiO₂, 17%-25% ethyl acetate-hexanes) to afford crude (3aS,7S,7aR)-tert-butyl 7-(10H-phenoxazin-10-yl)tetrahydro-[1,3,2]dioxathiolo[4,5-c]pyridine-5(6H)-carboxylate 2-oxide 4 (2.47 g) which was taken to the next step without further purification.

A solution of (3 aS,7S,7aR)-tert-butyl 7-(10H-phenoxazin-10-yl)tetrahydro-[1,3,2]dioxathiolo[4,5-c]pyridine-5 (6H)-carboxylate 2-oxide 4 (2.47 g, 5.56 mmol), sodium azide (1.08 g, 16.7 mmol) in DMF (5.0 mL) in a 20 mL Biotage® microwave reaction vial was heated at 100° C. in a Biotage Initiator® microwave reactor for 4 h, pressure was released, vial was sealed with a new cap, heating at 100° C. was continued for 12 h more. The reaction mixture was treated with sat. aq. NH$_4$C$_1$, extracted with ethylacetate, washed with brine, concentrated, purified by column chromatography (SiO$_2$, 6%-13% ethylacetate-hexanes) to afford the title compound 5 (1.65 g, 57% over two steps). $^1$H NMR (600 MHz, MeOD) δ 6.99-6.79 (8H, m), 4.33-4.07 (3H, m), 3.48 (1H, br s), 3.37 (1H, br s), 3.21 (1H, br s), 2.73-2.63 (1H, m), 1.46 (9H, s); $^{13}$C NMR (150 MHz, MeOD) δ 154.9, 149.6, 134.9, 123.5, 123.1, 118.3, 115.8, 81.0, 72.6, 66.5, 65.6, 63.7, 46.4, 45.9, 45.7, 45.1, 27.3; LCMS m/z 424.4 ([M+H$^+$], C$_{22}$H$_{26}$N$_5$O$_4$ requires 424.2).

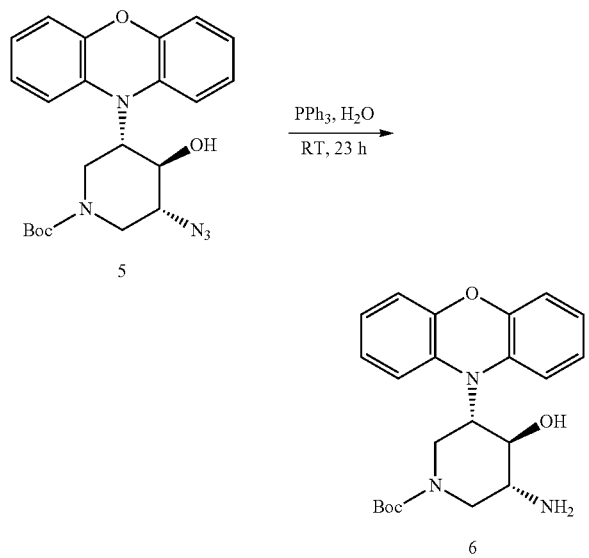

(3R,4S,5S)-tert-butyl 3-amino-4-hydroxy-5-(10H-phenoxazin-10-yl)piperidine-1-carboxylate (6)

A solution of (3R,4R,5S)-tert-butyl 3-azido-4-hydroxy-5-(10H-phenoxazin-10-yl)piperidine-1-carboxylate 5 (1.54 g, 3.63 mmol) in THF (16.5 mL) was cooled to 0° C., treated with PPh$_3$ (1.05 g, 4.00 mmol), H$_2$O (0.005 mL, 0.291 mmol), and stirred for 23 h at room temperature. The solution was concentrated to dryness, dissolved in a minimal amount of dichloromethane and purified by flash chromatography (SiO$_2$, 100% hexanes, 50% ethyl acetate-hexanes, 5%, methanol-dichloromethane, 17:2:1 dichloromethane:methanol:35% ammonium hydroxide) to afford title compound 6 (1.35 g, 94%). $^1$H NMR (600 MHz, MeOD) δ 7.00-6.79 (8H, m), 4.34-4.28 (1H, m), 4.15 (1H, br s), 3.92 (1H, t, J=9.0 Hz), 3.45 (1H, br s), 3.22 (1H, t, J=12.6 Hz), 2.67 (2H, br s), 1.45 (9H, s); $^{13}$C NMR (150 MHz, MeOD) δ 155.0, 149.6, 135.1, 132.5, 131.9, 128.7, 123.5, 122.9, 118.3, 117.9, 115.7, 80.6, 73.5, 66.7, 65.8, 54.6, 45.3, 27.3; LCMS m/z 398.5 ([M+H$^+$], C$_{22}$H$_{28}$N$_3$O$_4$ requires 398.2).

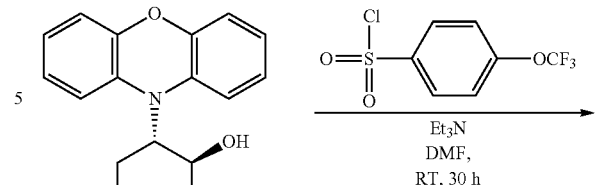

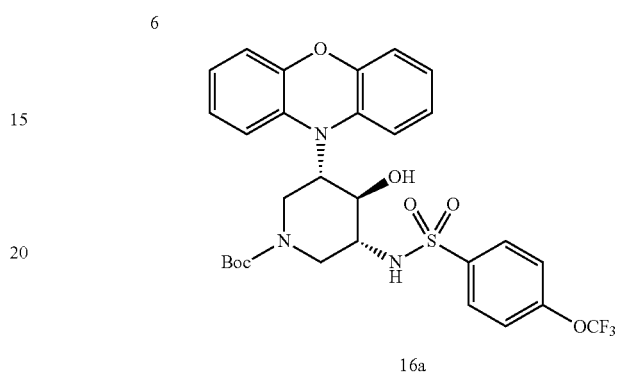

(3S,4R,5R)-tert-butyl 4-hydroxy-3-(10H-phenoxazin-10-yl)-5-(4-(trifluoromethoxy)phenylsulfonamido)piperidine-1-carboxylate (Example 16a)

A solution of (3R,4S,5S)-tert-butyl 3-amino-4-hydroxy-5-(10H-phenoxazin-10-yl)piperidine-1-carboxylate 6 (1.35 g, 3.39) in DMF (11.0 mL) was cooled to 0° C., treated with Et$_3$N (1.89 mL, 13.5 mmol), and 4-(trifluoromethoxy)benzene-1-sulfonyl chloride (0.633 mL, 3.72 mmol). The mixture was warmed to RT, and stirred for 30 h. The mixture was partitioned between water and CH$_2$Cl$_2$. The organic layer was washed with saturated brine (30 mL×5) to remove DMF, and concentrated in vacuo. The residue was dissolved in a minimal amount of CH$_2$Cl$_2$ and purified by flash chromatography (SiO$_2$, 0%-33% ethylacetate-hexanes) to afford the title compound Example 16a (1.96 g, 93%). $^1$H NMR (600 MHz, MeOD) δ 8.00 (2H, d, J=6.6 Hz), 7.43 (2H, d, J=7.8 Hz), 6.94-6.77 (8H, m), 4.28-4.24 (1H, m), 4.13 (1H, br s), 4.02 (1H, br s), 3.41 (1H, br s), 3.17 (1H, t, J=12.6 Hz), 3.10-3.05 (1H, m), 2.73-2.59 (1H, m), 1.44 (9H, s); $^{13}$C NMR (150 MHz, MeOD) δ 151.8, 149.4, 146.7, 140.5, 134.9, 129.2, 123.5, 120.9, 118.4, 118.0, 115.7, 80.7, 70.3, 66.8, 65.9, 56.9, 45.3, 27.3; LCMS m/z 622.4 ([M+H$^+$], C$_{29}$H$_{31}$F$_3$N$_3$O$_7$S requires 622.2). Material produced in this fashion exhibited [α]$_D$=+15.0° (c=1.0, CH$_3$OH).

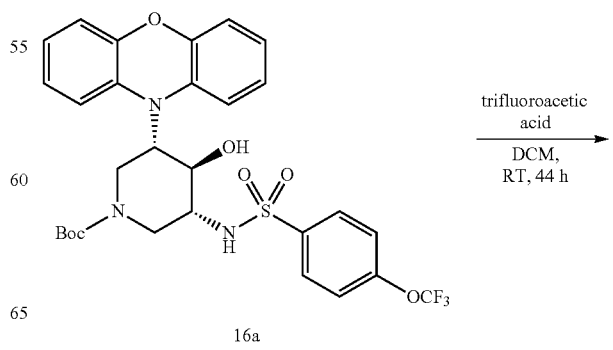

111
-continued

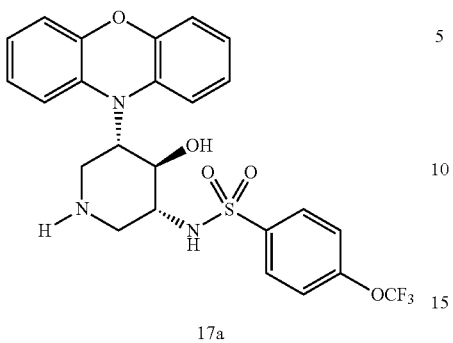

17a

N-((3R,4R,5S)-4-hydroxy-5-(10H-phenoxazin-10-yl)piperidin-3-yl)-4-(trifluoromethoxy)benzenesulfonamide (Example 17a)

A solution of (3S,4R,5R)-tert-butyl 4-hydroxy-3-(10H-phenoxazin-10-yl)-5-(4-(trifluoromethoxy)phenylsulfonamido)piperidine-1-carboxylate Example 16a (1.80 g, 2.89 mmol), trifluoroacetic acid (1.37 mL, 17.9 mmol) in dichloromethane (3.0 mL) were stirred at RT for 44 h. Dichloromethane was added and the mixture was concentrated on rotavapor at 45° C. to remove trifluoroacetic acid. More dichloromethane and silica were added and mixture was concentrated to make a dry plug which was purified by flash chromatography (SiO$_2$, 50% ethyl acetate-hexanes, 17:2:1 dichloromethane:methanol:35% ammonium hydroxide) to afford title compound Example 17a (1.49 g, 99%). $^1$H NMR (600 MHz, MeOD) δ 8.01 (2H, d, J=7.2 Hz), 7.42 (2H, d, J=7.8 Hz), 6.94 (2H, d, J=7.2 Hz), 6.89 (2H, t, J=7.8 Hz), 6.83 (2H, t, J=7.2 Hz), 6.75 (2H, d, J=7.8 Hz), 3.97 (1H, t, J=9.6 Hz), 3.56-3.55 (1H, m), 3.25-3.23 (2H, m), 3.13-3.11 (1H, m), 3.01 (1H, t, J=12.0 Hz), 2.54 (1H, t, J=11.4 Hz); $^{13}$C NMR (150 MHz, MeOD) δ 151.8, 149.6, 140.4, 134.9, 129.3, 123.5, 123.0, 120.8, 118.6, 115.7, 70.8, 67.4, 57.6, 49.6, 46.9; LCMS m/z 522.4 ([M+H$^+$], C$_{24}$H$_{23}$F$_3$N$_3$O$_5$S requires 522.1). Material produced in this fashion exhibited [α]$_D$=+3.0° (c=1.0, CH$_3$OH).

112
-continued

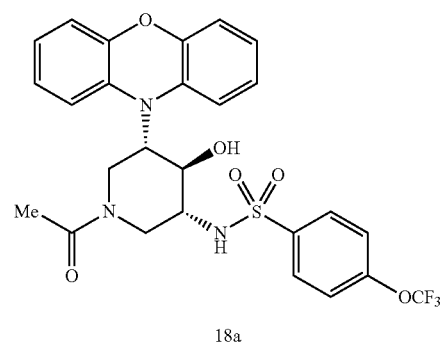

18a

N-((3R,4R,5S)-1-acetyl-4-hydroxy-5-(10H-phenoxazin-10-yl)piperidin-3-yl)-4-(trifluoromethoxy)benzenesulfonamide (Example 18a)

A solution of N-((3R,4R,5S)-4-hydroxy-5-(10H-phenoxazin-10-yl)piperidin-3-yl)-4-(trifluoromethoxy)benzenesulfonamide Example 17a (0.250 g, 0.479 mmol) and triethylamine (0.100 mL, 0.718 mmol) in dichloromethane (4.50 mL) was cooled to −78° C. Acetyl chloride (0.030 mL, 0.431 mmol) was added slowly. The reaction mixture was stirred at −78° C. for 30 min, 0° C. for 30 min, RT for 2 h, concentrated on rotavapor at 45° C. to remove acetyl chloride. The residue obtained was purified by flash chromatography (SiO$_2$, 0%-66% ethyl acetate-hexanes), triturated with 1:1 ethyl acetate-hexanes to afford title compound Example 18a (0.138 g, 55%) as a white powder. $^1$H NMR (600 MHz, MeOD) reported as 2:1 mixture of rotamers δ 8.02-7.99 (2H, m), 7.41 (2H, d, J=7.8 Hz), 6.96-6.76 (11H, m), 1H (4.71, d, J=10.8 Hz; 4.59, d, J=10.2 Hz), 4.12-4.08 (1H, m), 4.03-3.99 (1H, m), 3.93 (1H, d, J=12.0 Hz), 3.56-3.51 (1H, m), 1H (3.44-3.40, m; 2.44, t, J=12.0 Hz), 3.15-3.04 (3H, m), 3H (2.03, s; 2.00, s); LCMS m/z 564.3 ([M+H$^+$], C$_{26}$H$_{25}$F$_3$N$_3$O$_6$S requires 564.1). Material produced in this fashion exhibited [α]$_D$=+30.0° (c=1.0, CH$_3$OH).

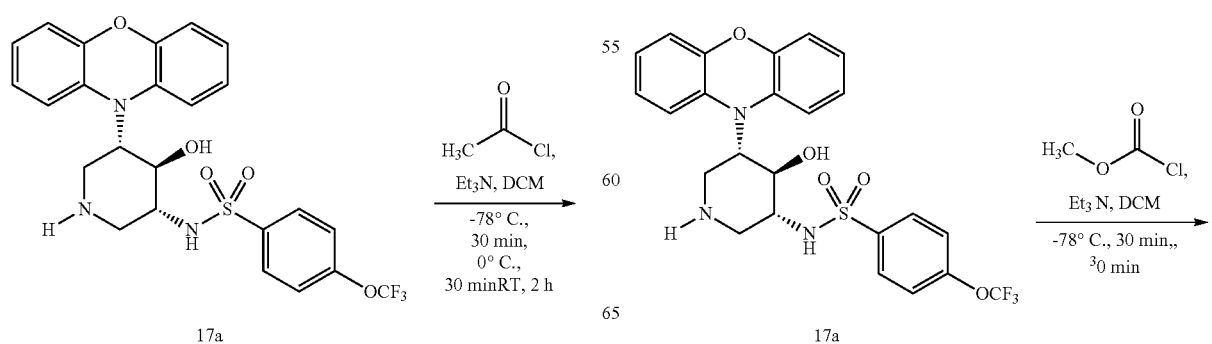

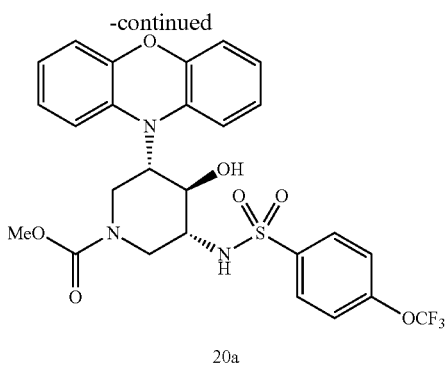

20a (3S,4R,5R)-methyl 4-hydroxy-3-(10H-phenoxazin-10-yl)-5-(4-(trifluoromethoxy)phenylsulfonamido)piperidine-1-carboxylate (Example 20a)

A solution of N-((3R,4R,5S)-4-hydroxy-5-(10H-phenoxazin-10-yl)piperidin-3-yl)-4-(trifluoromethoxy)benzenesulfonamide Example 17a (0.200 g, 0.384 mmol) and triethylamine (0.080 mL, 0.576 mmol) in dichloromethane (3.60 mL) was cooled to −78° C. Methyl chloroformate (0.027 mL, 0.345 mmol) was added slowly. The reaction mixture was stirred at −78° C. for 30 min, 0° C. for 30 min, RT for 30 min, concentrated on rotavapor. The residue obtained was purified by flash chromatography (SiO$_2$, 0%-66% ethyl acetate-hexanes), triturated with 9:1 ether-hexanes to afford title compound Example 20a (0.124 g, 56%) as a white powder. $^1$H NMR (600 MHz, MeOD) δ 7.99 (2H, d, J=9.0 Hz), 7.41 (2H, br s), 6.90-6.72 (8H, m), 4.30-4.22 (1H, m), 4.05-4.02 (2H, m), 3.69 (3H, s), 3.48 (1H, td, J=11.4, 4.8 Hz), 3.18-3.13 (2H, m), 2.71 (1H, br s); $^{13}$C NMR (150 MHz, MeOD) δ 156.1, 151.8, 149.3, 140.2, 134.9, 129.4, 123.5, 122.8, 120.9, 117.9, 115.7, 70.3, 65.7, 56.8, 52.4, 45.6; LCMS m/z 580.4 ([M+H$^+$], C$_{26}$H$_{25}$F$_3$N$_3$O$_7$S requires 580.1). Material produced in this fashion exhibited [α]D=+23.0° (c=1.0, CH$_3$OH).

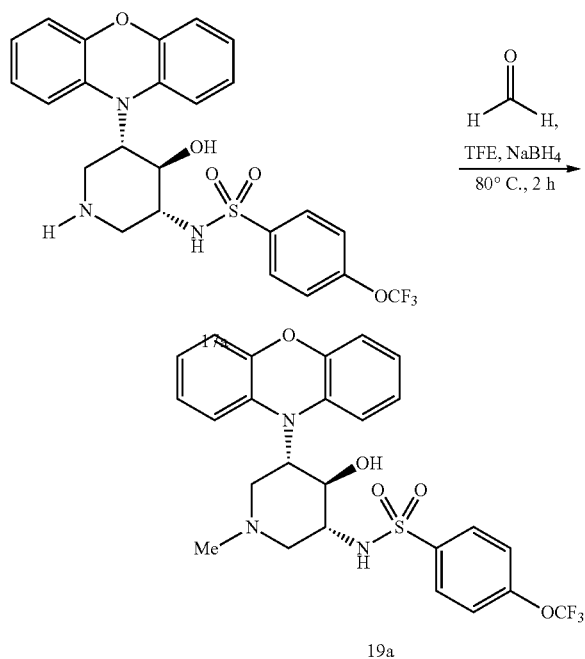

19a

N-((3R,4R,5S)-4-hydroxy-1-methyl-5-(10H-phenoxazin-10-yl)piperidin-3-yl)-4-(trifluoromethoxy)benzenesulfonamide (Example 19a)

A solution of formaldehyde (0.032 mL, 0.384 mmol, 37% by weight) in trifluoroethanol (2.50 ml) was stirred at 40° C. for 5 min. After this, N-((3R,4R,5S)-4-hydroxy-5-(10H-phenoxazin-10-yl)piperidin-3-yl)-4-(trifluoromethoxy)benzenesulfonamide Example 17a (0.200 g, 0.384 mmol) was added, and the mixture was stirred for 5 min more at 40° C. Following this sodium borohydride (0.017 g, 0.461 mmol) was added and the reaction was stirred in a sealed vessel at 80° C. for 2 h. Reaction mixture was concentrated and purified by flash chromatography (SiO$_2$, 0%-66% ethyl acetate-hexanes) to afford title compound Example 19a (0.141 g, 69%). $^1$H NMR (600 MHz, MeOD) δ 8.00 (2H, d, J=8.4 Hz), 7.40 (2H, d, J=7.8 Hz), 6.97 (2H, d, J=7.8 Hz), 6.87 (2H, t, J=7.2 Hz), 6.81 (2H, t, J=7.2 Hz), 6.74 (2H, t, J=7.2 Hz), 3.86 (1H, t, J=10.2 Hz), 3.60 (1H, td, J=11.4, 4.2 Hz), 3.25 (1H, td, J=10.8, 4.8 Hz), 3.02 (1H, d, J=9.6 Hz), 2.89 (1H, d, J=11.4 Hz), 2.43 (1H, t, J=11.4 Hz), 2.23 (3H, s), 2.00 (1H, t, J=10.8 Hz); $^{13}$C NMR (150 MHz, MeOD) δ 151.8, 149.6, 140.3, 135.0, 129.4, 123.5, 122.9, 120.9, 118.6, 115.7, 70.3, 66.6, 60.0, 57.1, 56.8, 44.3; LCMS m/z 536.4 ([M+H$^+$], C$_{25}$H$_{25}$F$_3$N$_3$O$_5$S requires 536.1). Material produced in this fashion exhibited [α]$_D$=−11.0° (c=1.0, CH$_3$OH).

Procedure A: Typical procedure for synthesis of 3-(Nitrogen bearing nucleophile)cycloalkane-1,2-diol:

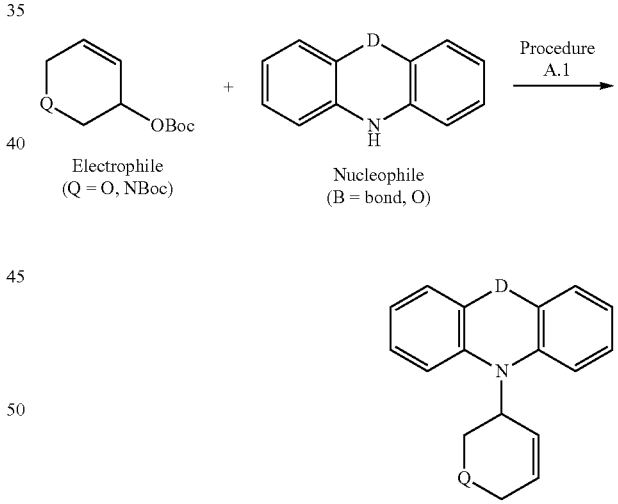

Procedure A.1: To an oven-dried microwave vial equipped with a magnetic stir bar was added Pd$_2$.dba$_3$.CHCl$_3$ (5 mol %), and Ligand (15 mol %). The system was evacuated and filled with argon (3×), and dry, degassed DCM (0.40 M) was added. This vial was stirred at RT for 60 min. Electrophile was added. The nitrogen containing nucleophile was added in dry, degassed DCM (0.33 M). The reaction mixture was stirred at room temperature for the specified time. After completion of reaction time, the mixture was evaporated onto silica gel and subjected to column chromatography (SiO$_2$; ethyl acetate in hexanes) to afford Cycloalkenyl-N-nucleophile.

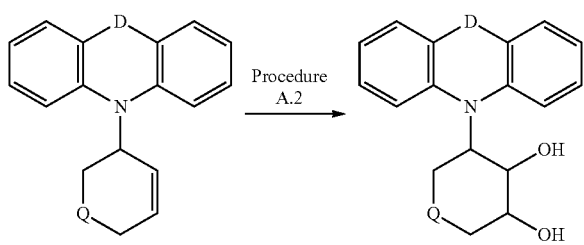

Procedure A.2: A solution of Cycloalkenyl-N-nucleophile (1.00 Eq), 4-methylmorpholine N-oxide monohydrate (2.20 Eq), and osmium tetroxide (0.02 Eq, 2.5% in tert-butanol) in tert-butanol (0.50 M) and water (2.5 M), was stirred at RT for 36 h. The reaction mixture was treated with solid sodium bisulfite solution, stirred for 1 h, evaporated on to silica gel and subjected to column chromatography ($SiO_2$, 0%-70% ethyl acetate in hexanes) to afford 3-(Nitrogen bearing nucleophile)cycloalkane-1,2-diol.

Trost ligands used in synthesis:

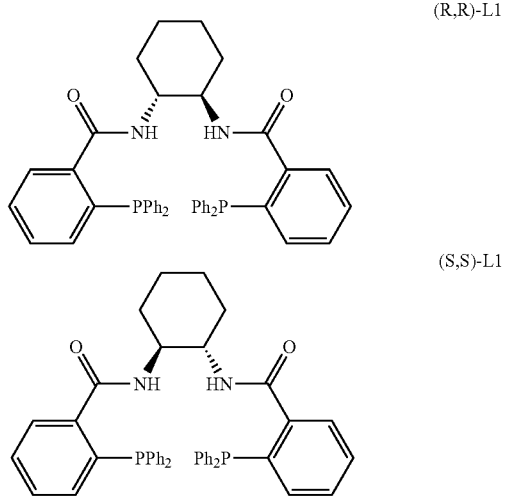

Procedure B: Typical procedure for synthesis of 3-azido-5-(Nitrogen bearing nucleophile)tetrahydro-cycloalkane-4-ol:

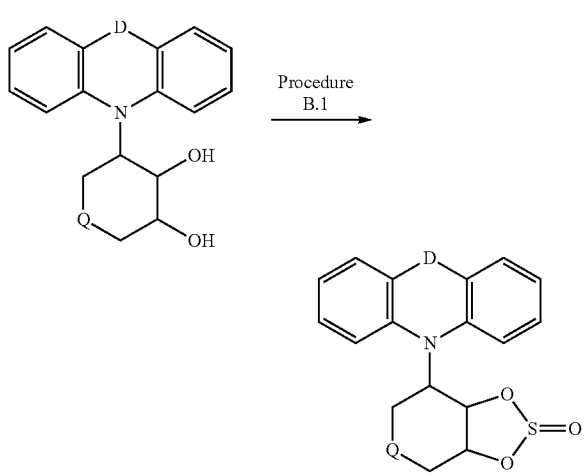

Procedure B.1: A solution of 3-(Nitrogen bearing nucleophile)cycloalkane-1,2-diol in dichloromethane under argon was cooled to −78° C., and treated with triethylamine. Following this thionyl chloride was added very slowly over 5 min. The reaction mixture was warmed to 0° C./RT, and stirred for 30 min/1 h/2 h. The reaction mixture was partitioned between dichloromethane and water, concentrated to obtain a residue which was purified by flash chromatography ($SiO_2$; ethyl acetate in hexanes) to afford 7-(Nitrogen bearing nucleophile)tetrahydro-3aH-[1,3,2]dioxathiolo[4,5-c]cycloalkane 2-oxide.

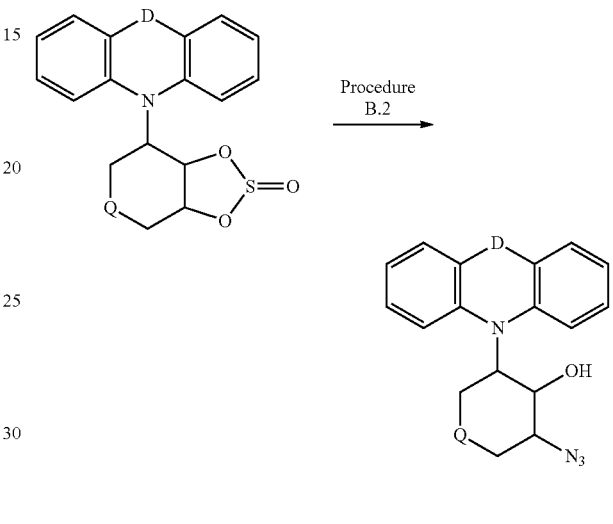

Procedure B.2: A solution of 7-(Nitrogen bearing nucleophile)tetrahydro-3aH-[1,3,2]dioxathiolo[4,5-c]cycloalkane 2-oxide in DMF was treated with sodium azide and heated to 100° C./110° C. in a Biotage Initiator® microwave reactor for the specified time. Sat. aq. $NH_4Cl$ was added, and the mixture was extracted with ethylacetate, washed with brine (100 mL×4), concentrated, and purified by flash chromatography ($SiO_2$; ethyl acetate in hexanes) to afford 3-azido-5-(Nitrogen bearing nucleophile)tetrahydro-cycloalkane-4-ol.

Procedure C: Typical procedure for synthesis of N-(4-hydroxy-5-(Nitrogen bearing nucleophile)tetrahydro-cycloalkane-3-yl)-aryl sulfonamide:

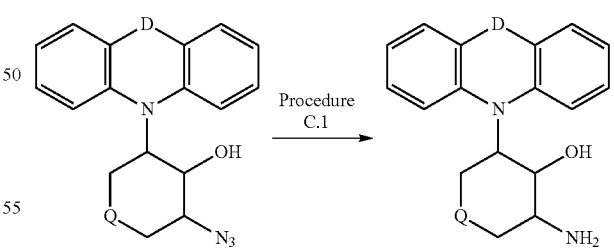

Procedure C.1: A solution of 3-azido-5-(Nitrogen bearing nucleophile)tetrahydro-cycloalkane-4-ol in THF was cooled to 0° C., treated with triphenylphosphine, water, and stirred for 14 h at RT. The solution was concentrated to dryness, dissolved in a minimal amount of $CH_2Cl_2$ and purified by flash chromatography ($SiO_2$, ethyl acetate in hexanes, dichloromethane:methanol:35% ammonium hydroxide) to afford 3-amino-5-(Nitrogen bearing nucleophile)tetrahydro-cycloalkane-4-ol.

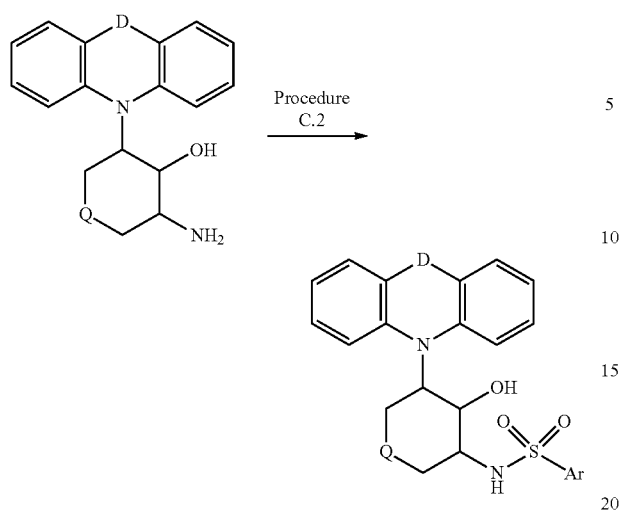

Procedure C.2

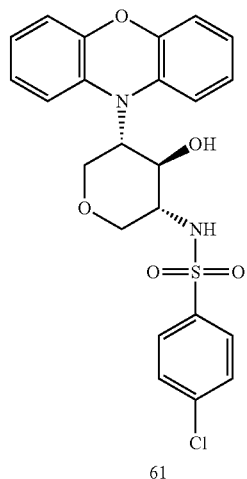

61

Procedure C.2: A solution of 3-amino-5-(Nitrogen bearing nucleophile)tetrahydro-cycloalkane-4-ol in DMF was cooled to 0° C., treated with triethylamine, and aryl sulfonyl chloride. The mixture was warmed to RT, and stirred for 16 h. The mixture was partitioned between water (10 mL) and $CH_2Cl_2$ (10 mL). The organic layer was washed with saturated aqueous NaCl (30 mL×5), and concentrated in vacuo. The residue was dissolved in a minimal amount of $CH_2Cl_2$ and purified by chromatography ($SiO_2$, ethylacetate-hexanes/$SiO_2$, acetone-hexanes/HPLC) to afford N-(4-hydroxy-5-(Nitrogen bearing nucleophile)tetrahydro-cycloalkane-3-yl)-aryl sulfonamide.

Procedure D: Typical procedure for synthesis of N-(4-hydroxy-5-(Nitrogen bearing nucleophile)piperidin-3-yl)-4aryl sulfonamide: A solution of tert-butyl 4-hydroxy-3-(Nitrogen bearing nucleophile)-5-(arylsulfonamido)piperidine-1-carboxylate in dichloromethane was cooled to 0° C., treated with trifluoroacetic acid, and stirred at RT for the specified time. Mixture was quenched with sat. aq. $NaHCO_3$ solution and extracted with dichloromethane. The dichloromethane layer along with silica was concentrated to make a dry plug which was purified by flash chromatography ($SiO_2$, ethyl acetate-hexanes, dichloromethane:methanol:35% ammonium hydroxide) to afford N-4-hydroxy-5-(Nitrogen bearing nucleophile)piperidin-3-yl)-4aryl sulfonamide.

Group I (Sulfonamide Variants):

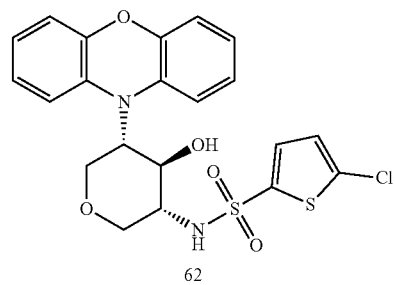

62

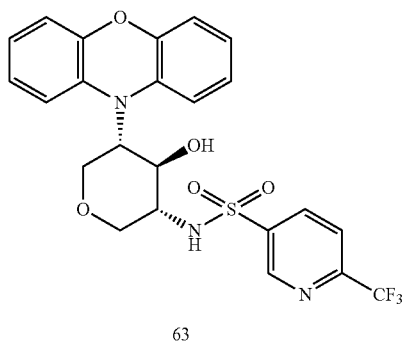

63

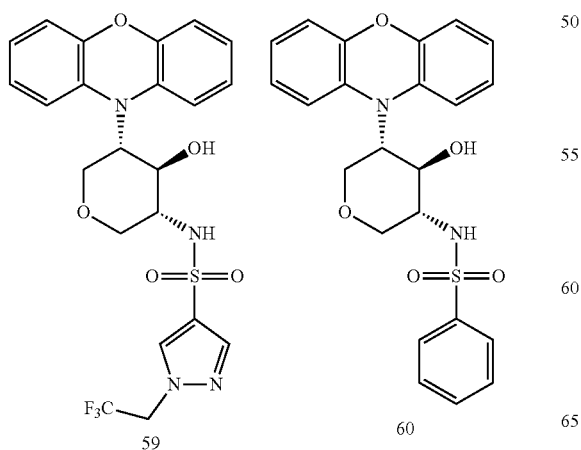

59

60

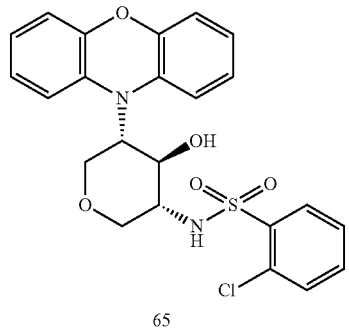

65

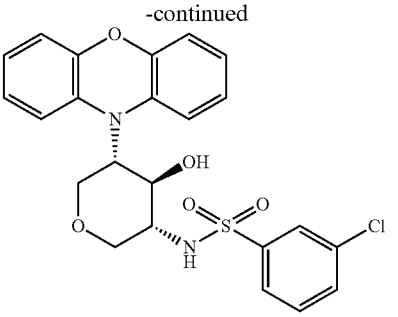

64

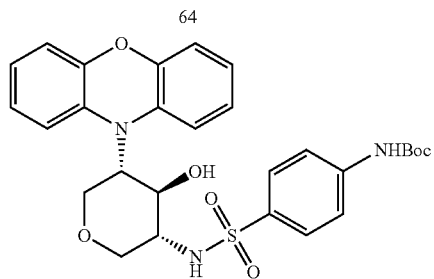

66

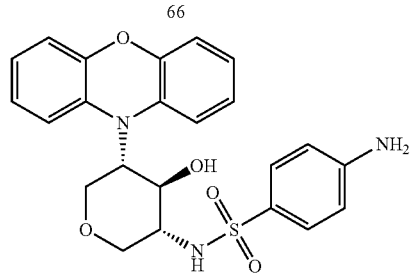

67

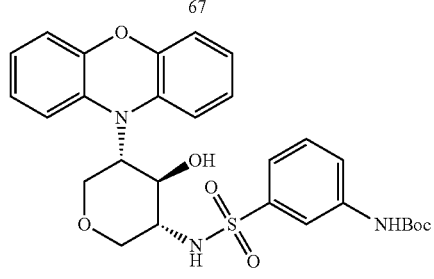

68

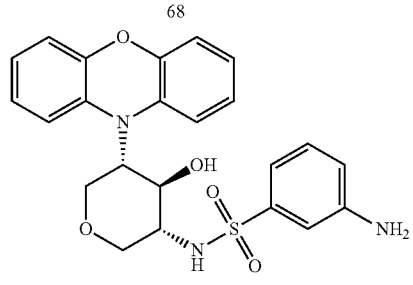

69

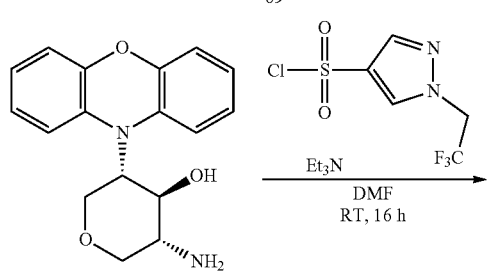

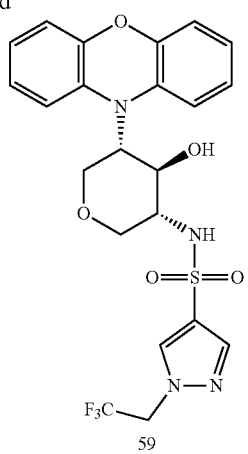

59

N-(4-hydroxy-5-(10H-phenoxazin-10-yl)tetrahydro-2H-pyran-3-yl)-1-(2,2,2-trifluoroethyl)-1H-pyrazole-4-sulfonamide (59): Using the typical procedure C.2 (3R,4S,5S)-3-amino-5-(10H-phenoxazin-10-yl)tetrahydro-2H-pyran-4-ol (0.060 g, 0.201 mmol) in DMF (1.0 mL) was reacted with triethylamine (0.111 mL, 0.805 mmol), and 1-(2,2,2-trifluoroethyl)-1H-pyrazole-4-sulfonyl chloride (0.050 g, 0.201 mmol). Purification by flash chromatography (SiO$_2$, 10%-50% ethylacetate-hexanes) afforded N-((3R,4R,5S)-4-hydroxy-5-(10H-phenoxazin-10-yl)tetrahydro-2H-pyran-3-yl)-1-(2,2,2-trifluoroethyl)-1H-pyrazole-4-sulfonamide 59 (0.080 g, 78%). $^1$H NMR (600 MHz, MeOD) δ 8.27 (1H, s), 7.87 (1H, s), 6.93-6.88 (4H, m), 6.83 (2H, t, J=7.2 Hz), 6.74 (2H, d, J=7.8 Hz), 4.11-4.06 (2H, m), 4.02 (1H, t, J=9.6 Hz), 3.93-3.91 (1H, m), 3.76 (1H, t, J=12.0 Hz), 3.60 (1H, td, J=12.0, 5.4 Hz), 3.25-3.18 (3H, m); $^{13}$C NMR (150 MHz, MeOD) δ 149.5, 139.4, 135.1, 133.8, 123.5, 122.8, 118.4, 115.7, 70.3, 69.9, 68.6, 67.2, 57.3, 52.5, 52.3, 52.0, 51.8; Material produced in this fashion exhibited [α]$^{25}$D=−14.0° (c=1.0, CH$_2$Cl$_2$). LCMS m/z 511.3 ([M+H$^+$], C$_{22}$H$_{22}$F$_3$N$_4$O$_5$S requires 511.1).

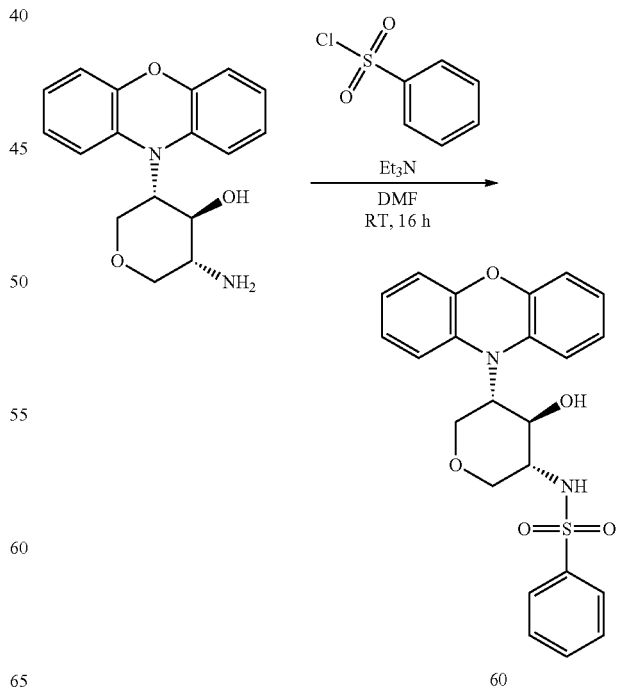

60

N-((3R,4R,5S)-4-hydroxy-5-(10H-phenoxazin-10-yl)tetrahydro-2H-pyran-3-yl)benzenesulfonamide (60): Using the typical procedure C.2 (3R,4S,5S)-3-amino-5-(10H-phenoxazin-10-yl)tetrahydro-2H-pyran-4-ol (0.060 g, 0.201 mmol) in DMF (1.0 mL) was reacted with triethylamine (0.111 mL, 0.805 mmol), and benzenesulfonyl chloride (0.025 mL, 0.201 mmol). Purification by flash chromatography (SiO$_2$, 10%-50% ethylacetate-hexanes) afforded N-((3R,4R,5S)-4-hydroxy-5-(10H-phenoxazin-10-yl)tetrahydro-2H-pyran-3-yl)benzenesulfonamide 60 (0.031 g, 35%). $^1$H NMR (600 MHz, MeOD) δ 7.89 (2H, d, J=7.8 Hz), 7.60-7.58 (1H, m), 7.54-7.52 (2H, m), 6.92-6.88 (4H, m), 6.83 (2H, t, J=8.4 Hz), 6.74 (2H, d, J=7.8 Hz), 4.05 (1H, dd, J=10.8, 4.2 Hz), 4.00 (1H, t. J=9.6 Hz), 3.75-3.69 (2H, m), 3.57 (1H, td, J=11.4, 4.8 Hz), 3.21-3.17 (1H, m), 3.12 (1H, t, J=11.4 Hz); $^{13}$C NMR (150 MHz, MeOD) δ 132.4, 128.9, 126.8, 123.5, 122.9, 118.7, 115.8, 70.0, 68.7, 67.1, 65.4, 57.1; Material produced in this fashion exhibited [α]$^{25}$D=+26.0° (c=1.0, CH$_2$Cl$_2$). LCMS m/z 439.4 ([M+H$^+$], C$_{23}$H$_{23}$N$_2$O$_5$S requires 439.1).

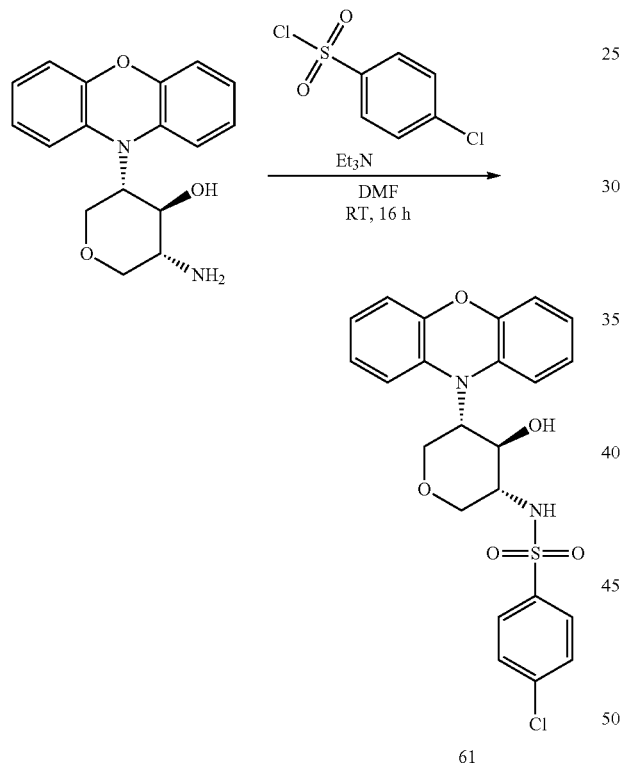

4-chloro-N-((3R,4R,5S)-4-hydroxy-5-(10H-phenoxazin-10-yl)tetrahydro-2H-pyran-3-yl)benzenesulfonamide (61)

Using the typical procedure C.2 (3R,4S,5S)-3-amino-5-(10H-phenoxazin-10-yl)tetrahydro-2H-pyran-4-ol (0.060 g, 0.201 mmol) in DMF (1.0 mL) was reacted with triethylamine (0.111 mL, 0.805 mmol), and 4-chlorobenzene-1-sulfonyl chloride (0.042 g, 0.201 mmol). Purification by flash chromatography (SiO$_2$, 10%-50% ethylacetate-hexanes) afforded 4-chloro-N-((3R,4R,5S)-4-hydroxy-5-(10H-phenoxazin-10-yl)tetrahydro-2H-pyran-3-yl)benzenesulfonamide 61 (0.056 g, 59%). $^1$H NMR (600 MHz, MeOD) δ 7.85 (2H, d, J=7.8 Hz), 7.52 (1H, d, J=7.8 Hz), 6.92-6.88 (4H, m), 6.82 (2H, t, J=7.8 Hz), 6.74 (2H, d, J=7.8 Hz), 4.06 (1H, dd, J=11.4, 4.8 Hz), 3.99 (1H, t, J=9.0 Hz), 3.83 (1H, d, J=7.2 Hz), 3.73 (1H, t, J=11.4 Hz), 3.57 (1H, dd, J=10.2, 7.2 Hz), 3.20-3.14 (2H, m); $^{13}$C NMR (150 MHz, MeOD) δ 149.6, 140.2, 138.4, 135.1, 129.0, 128.6, 123.5, 122.9, 118.5, 115.6, 70.3, 69.9, 68.6, 67.2, 57.3; Material produced in this fashion exhibited [α]$^{25}$D=+24.0° (c=1.0, CH$_2$Cl$_2$). LCMS m/z 473.0 ([M+H$^+$], C$_{23}$H$_{22}$C$_1$N$_2$O5S requires 473.0).

Example 66 and Example 67

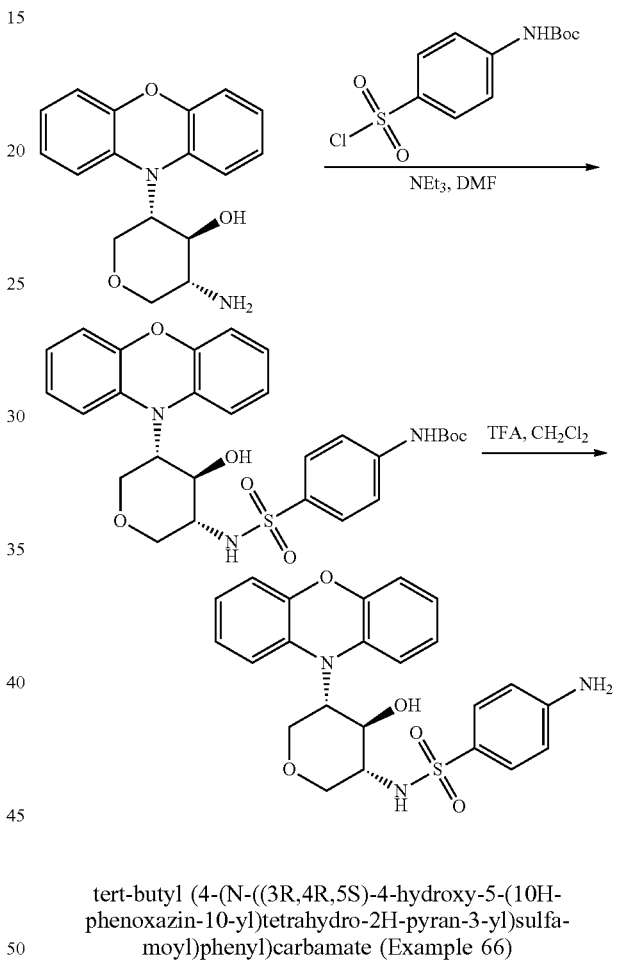

tert-butyl (4-(N-((3R,4R,5S)-4-hydroxy-5-(10H-phenoxazin-10-yl)tetrahydro-2H-pyran-3-yl)sulfamoyl)phenyl)carbamate (Example 66)

Using the typical procedure C.2 (3R,4S,5S)-3-amino-5-(10H-phenoxazin-10-yl)tetrahydro-2H-pyran-4-ol (0.160 g, 0.536 mmol) in DMF (1.75) was reacted with Et$_3$N (0.298 mL, 2.14 mmol), and tert-butyl (4-(chlorosulfonyl)phenyl) carbamate (0.172 g, 0.589 mmol). Purification by flash chromatography (SiO$_2$, 17%-50% ethylacetate-hexanes) afforded tert-butyl (4-(N-(4-hydroxy-5-(10H-phenoxazin-10-yl)tetrahydro-2H-pyran-3-yl)sulfamoyl)phenyl)carbamate Example 66 (0.249 g, 84%) as a white powder. $^1$H NMR (600 MHz, MeOD) δ 7.76 (2H, d, J=9.0 Hz), 7.56 (2H, d, J=9.0 Hz), 6.92-6.88 (4H, m), 6.82 (2H, td, J=7.8, 1.8 Hz), 6.74-6.73 (2H, m), 4.05 (1H, dd, J=11.4, 5.4 Hz), 3.98 (1H, t, J=9.6 Hz), 3.76-3.75 (1H, m), 3.70 (1H, t, J=12.0 Hz), 3.57 (1H, td, J=11.4, 5.4 Hz), 3.17-3.10 (2H, m), 1.52 (9H, br s); ESI-HRMS calcd for C$_{28}$H$_{32}$N$_3$O$_2$S [M+H$^+$] 554.1956, found 554.1950.

4-amino-N-((3R,4R,5S)-4-hydroxy-5-(10H-phenoxazin-10-yl)tetrahydro-2H-pyran-3-yl)benzenesulfonamide (Example 67): A solution of tert-butyl (4-(N-((3R,4R,5S)-4-hydroxy-5-(10H-phenoxazin-10-yl)tetrahydro-2H-pyran-3-yl)sulfamoyl)phenyl)carbamate (0.201 g, 0.363 mmol), and trifluoroacetic acid (0.172 mL, 2.25 mmol) in DCM (1.0 mL) were stirred at RT for 20 h. About 5 mL DCM was added, and mixture was washed with sat. aq. sodium bicarbonate solution. To the organic layer silica was added and mixture was concentrated to make a dry plug which was purified by flash chromatography (SiO$_2$, 50 g, 33%-75% ethylacetate-hexanes) to afford 4-amino-N-(4-hydroxy-5-(10H-phenoxazin-10-yl)tetrahydro-2H-pyran-3-yl) Example 67 (0.081 g, 49%) as a white powder. $^1$H NMR (600 MHz, MeOD) δ 7.55 (2H, d, J=8.4 Hz), 6.93-6.88 (4H, m), 6.83 (2H, td, J=9.6, 1.8 Hz), 6.74 (2H, dd, J=7.8, 1.2 Hz), 6.67 (2H, d, J=8.4 Hz), 4.04 (1H, dd, J=11.4, 4.8 Hz), 3.97 (1H, t, J=9.0 Hz), 3.75-3.68 (2H, m), 3.56 (1H, td, J=10.8, 4.8 Hz), 3.11-3.07 (2H, m); ESI-HRMS calcd for C$_{23}$H$_{24}$H$_3$O$_5$S [M+H$^+$]454.1432, found 454.1432.

Example 68 and Example 69

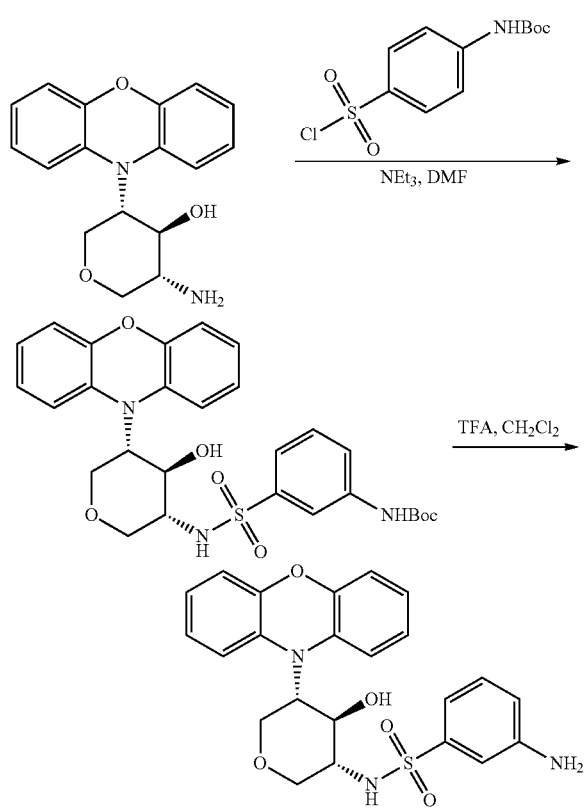

tert-butyl (3-(N-((3R,4R,5S)-4-hydroxy-5-(10H-phenoxazin-10-yl)tetrahydro-2H-pyran-3-yl)sulfamoyl)phenyl)carbamate (Example 68): Using the typical procedure C.2 (3R,4S,5S)-3-amino-5-(10H-phenoxazin-10-yl)tetrahydro-2H-pyran-4-ol (0.160 g, 0.536 mmol) in DMF (1.75) was reacted with Et$_3$N (0.298 mL, 2.14 mmol), and tert-butyl (3-(chlorosulfonyl)phenyl)carbamate (0.172 g, 0.589 mmol). Purification by flash chromatography (SiO$_2$, 25%-75% ethylacetate-hexanes) afforded tert-butyl (3-(N-(4-hydroxy-5-(10H-phenoxazin-10-yl)tetrahydro-2H-pyran-3-yl)sulfamoyl)phenyl)carbamate Example 68 (0.230 g, 78%) as a white powder. $^1$H NMR (600 MHz, MeOD) δ 8.02 (1H, s), 7.53 (1H, d, J=7.8 Hz), 7.49 (1H, d, J=7.8 Hz), 7.40 (1H, t, J=8.4 Hz), 6.92-6.87 (4H, m), 6.81 (2H, td, J=7.8, 1.8 Hz), 6.74-6.73 (2H, m), 4.05 (1H, dd, J=11.4, 4.8 Hz), 4.00 (1H, t, J=9.6 Hz), 3.76 (1H, dd, J=11.4, 4.8 Hz), 3.71 (1H, t, J=11.4 Hz), 3.58 (1H, td, J=10.8, 4.8 Hz), 3.24-3.20 (1H, m), 3.13 (1H, t, J=11.4 Hz), 1.51 (9H, br s); ESI-HRMS calcd for C$_{28}$H$_{32}$N$_3$O$_7$S [M+H$^+$] 554.1956, found 554.1952.

3-amino-N-((3R,4R,5S)-4-hydroxy-5-(10H-phenoxazin-10-yl)tetrahydro-2H-pyran-3-yl)benzenesulfonamide (Example 69)

A solution of tert-butyl (3-(N-((3R,4R,5S)-4-hydroxy-5-(10H-phenoxazin-10-yl)tetrahydro-2H-pyran-3-yl)sulfamoyl)phenyl)carbamate (0.200 g, 0.361 mmol), and trifluoroacetic acid (0.200 mL, 2.60 mmol) in DCM (1.0 mL) were stirred at RT for 3 h. About 5 mL DCM was added, and mixture was washed with sat. aq. sodium bicarbonate solution. To the organic layer silica was added and mixture was concentrated to make a dry plug which was purified by flash chromatography (SiO$_2$, 50 g, 33%-75% ethylacetate-hexanes) to afford 3-amino-N-(4-hydroxy-5-(10H-phenoxazin-10-yl)tetrahydro-2H-pyran-3-yl)benzenesulfonamide Example 69 (0.160 g, 98%) as a white powder. $^1$H NMR (600 MHz, MeOD) δ 7.21 (1H, t, J=7.8 Hz), 7.16 (1H, br s), 7.11 (1H, d, J=7.8 Hz), 6.93-6.88 (4H, m), 6.86-6.81 (3H, m), 6.75-6.74 (2H, m), 4.05 (1H, dd, J=11.4, 4.8 Hz), 3.99 (1H, t, J=9.6 Hz), 3.72-3.69 (2H, m), 3.58 (1H, td, J=11.4, 4.8 Hz), 3.20-3.16 (1H, m), 3.09 (1H, t, J=11.4 Hz); ESI-HRMS calcd for C$_{23}$H$_{24}$N$_3$O$_5$S [M+H$^+$]454.1432, found 454.1430.

Examples 65 and 64

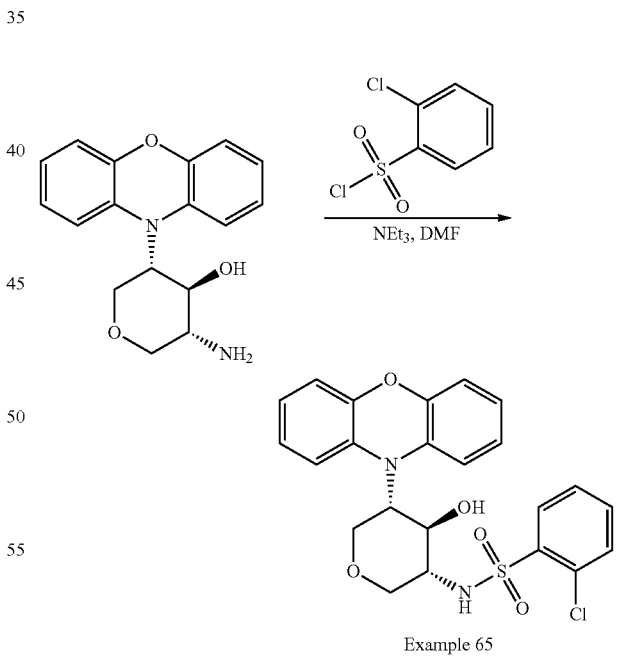

Example 65

2-chloro-N-((3R,4R,5S)-4-hydroxy-5-(10H-phenoxazin-10-yl)tetrahydro-2H-pyran-3-yl)benzenesulfonamide (Example 65)

Using the typical procedure C.2 (3R,4S,5S)-3-amino-5-(10H-phenoxazin-10-yl)tetrahydro-2H-pyran-4-ol (0.075 g, 0.251 mmol) in DMF (1.0 mL) was reacted with triethylamine (0.140 mL, 1.00 mmol), and 2-chlorobenzene-1-sulfonyl chloride (0.037 mL, 0.276 mmol). Purification by flash chromatography (SiO$_2$, 17%-25% acetone-hexanes) afforded 2-chloro-N-((3R,4R,5S)-4-hydroxy-5-(10H-phenoxazin-10-yl)tetrahydro-2H-pyran-3-yl)benzenesulfonamide Example 65 (0.049 g, 42%). $^1$H NMR (600 MHz, MeOD) δ 8.05 (1H, br s), 7.55-7.54 (2H, m), 7.448-7.443 (1H, m), 6.91-6.83 (5H, m), 6.723-6.721 (2H, m), 5.51 (1H, br s), 4.09 (1H, br s), 3.79-3.75 (3H, m), 3.52 (1H, sr s), 3.33-3.31 (2H, m); Material produced in this fashion exhibited [α]$^{25}$D=+14.0° (c=1.0, CH$_3$OH). FIRMS m/z 473.0934 ([M+H$^+$], C$_{23}$H$_{22}$ClN$_2$O$_5$S requires 473.0933).

Examples 62 and 63

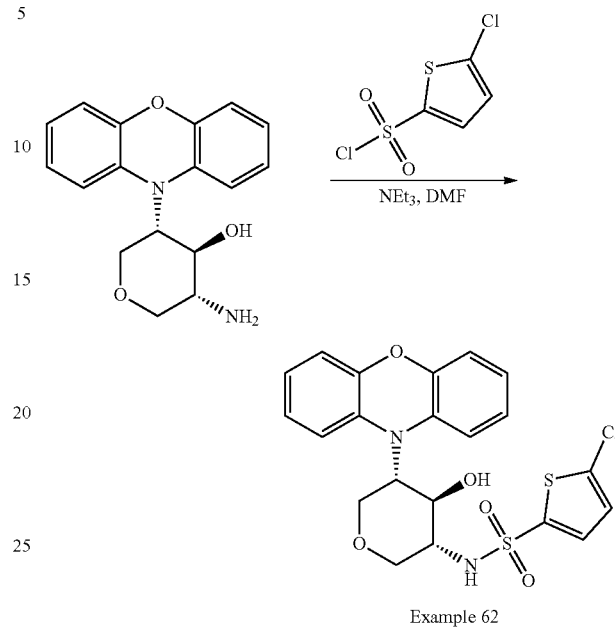

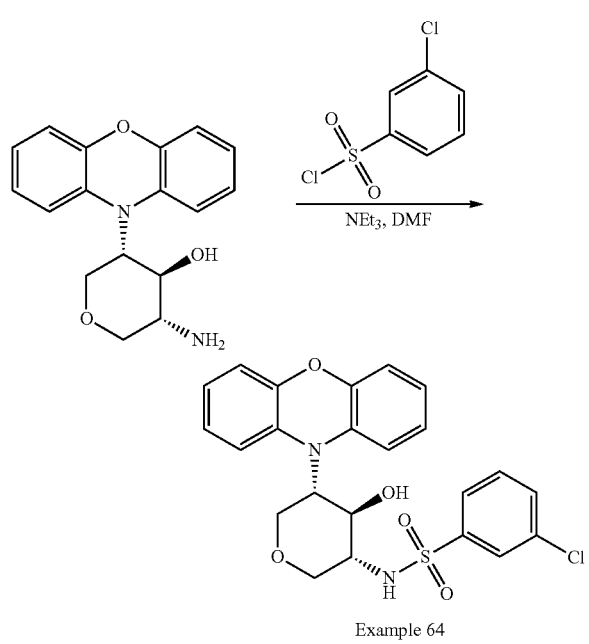

Example 64

3-chloro-N-((3R,4R,5S)-4-hydroxy-5-(10H-phenoxazin-10-yl)tetrahydro-2H-pyran-3-yl)benzenesulfonamide (Example 64)

Using the typical procedure C.2 (3R,4S,5S)-3-amino-5-(10H-phenoxazin-10-yl)tetrahydro-2H-pyran-4-ol (0.075 g, 0.251 mmol) in DMF (1.0 mL) was reacted with triethylamine (0.140 mL, 1.00 mmol), and 3-chlorobenzene-1-sulfonyl chloride (0.058 g, 0.276 mmol). Purification by flash chromatography (SiO$_2$, 17%-25% acetone-hexanes) afforded 3-chloro-N-((3R,4R,5S)-4-hydroxy-5-(10H-phenoxazin-10-yl)tetrahydro-2H-pyran-3-yl)benzenesulfonamide Example 64 (0.057 g, 48%). $^1$H NMR (600 MHz, MeOD) δ 7.89 (1H, br s), 7.80 (1H, d, J=7.8 Hz), 7.59 (1H, d, J=7.8 Hz), 7.51 (1H, t, J=7.8 Hz), 6.92-6.88 (4H, m), 6.82 (2H, t, J=7.2 Hz), 6.74 (2H, d, J=7.8 Hz), 4.06 (1H, dd, J=11.4, 4.8 Hz), 3.99 (1H, t, J=9.6 Hz), 3.81 (1H, dd, J=10.2, 4.2 Hz), 3.72 (1H, t, J=11.4 Hz), 3.58 (1H, td, J=10.8, 4.8 Hz), 3.23-3.14 (2H, m); Material produced in this fashion exhibited [α]$^{25}$D=+20.0° (c=1.0, CH$_3$OH). LCMS m/z 473.1022 ([M+H$^+$], C$_{23}$H$_{22}$ClN$_2$O$_5$S requires 473.0933).

5-chloro-N-((3R,4R,5S)-4-hydroxy-5-(10H-phenoxazin-10-yl)tetrahydro-2H-pyran-3-yl)thiophene-2-sulfonamide (Example 62)

Using the typical procedure C.2 (3R,4S,5S)-3-amino-5-(10H-phenoxazin-10-yl)tetrahydro-2H-pyran-4-ol (0.075 g, 0.251 mmol) in DMF (1.0 mL) was reacted with triethylamine (0.140 mL, 1.00 mmol), and 5-chlorothiophene-2-sulfonyl chloride (0.036 mL, 0.278 mmol). Purification by flash chromatography (SiO$_2$, 17%-25% acetone-hexanes) afforded 5-chloro-N-((3R,4R,5S)-4-hydroxy-5-(10H-phenoxazin-10-yl)tetrahydro-2H-pyran-3-yl)thiophene-2-sulfonamide Example 62 (0.038 g, 32%). $^1$H NMR (600 MHz, MeOD) δ 7.47 (1H, br s), 7.02 (1H, br s), 6.93-6.91 (4H, m), 6.84 (2H, br s), 6.75 (2H, d, J=7.2 Hz), 4.07 (1H, br s), 4.01-4.00 (1H, m), 3.87-3.85 (1H, m), 3.74 (1H, t, J=11.4 Hz), 3.61 (1H, br s), 3.26-3.17 (2H, m); Material produced in this fashion exhibited [α]$^{25}$D=+8.0° (c=0.5, CH$_3$OH). LCMS m/z 479.0615 ([M+H$^+$], C$_{21}$H$_{20}$ClN$_2$O$_5$S2 requires 479.0497).

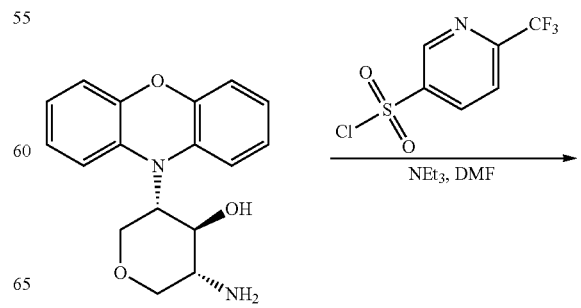

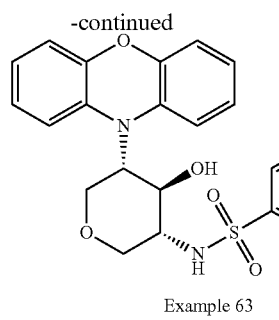

Example 63

Example 63

N-((3R,4R,5S)-4-hydroxy-5-(10H-phenoxazin-10-yl)tetrahydro-2H-pyran-3-yl)-6-(trifluoromethyl)pyridine-3-sulfonamide (Example 63): Using the typical procedure C.2 (3R,4S,5S)-3-amino-5-(10H-phenoxazin-10-yl)tetrahydro-2H-pyran-4-ol (0.075 g, 0.251 mmol) in DMF (1.0 mL) was reacted with triethylamine (0.140 mL, 1.00 mmol), and 6-(trifluoromethyl)pyridine-3-sulfonyl chloride (0.067 g, 0.276 mmol). Purification by flash chromatography (SiO$_2$, 17%-33% acetone-hexanes, 17:1:1 dichloromethane:methanol:35% ammonium hydroxide) afforded N-((3R,4R,5S)-4-hydroxy-5-(10H-phenoxazin-10-yl)tetrahydro-2H-pyran-3-yl)-6-(trifluoromethyl)pyridine-3-sulfonamide Example 63 (0.052 g, 41%). $^1$HNMR (600 MHz, MeOD) δ 9.12 (1H, br s), 8.46 (1H, br s), 7.93 (1H, d, J=6.6 Hz0, 6.89-6.74 (8H, m), 4.14 (1H, br s), 3.98-3.96 (2H, m), 3.74-3.72 (1H, m), 3.57 (1H, br s), 3.34 (1H, br s), 3.26 91H, br s); Material produced in this fashion exhibited [α]$^{25}$D=-2.0° (c=0.5, CH$_3$OH). LCMS m/z 508.1671 ([M+H$^+$], C$_{23}$H$_{21}$F$_3$N$_3$O$_5$S requires 508.1149).

Scheme A.1

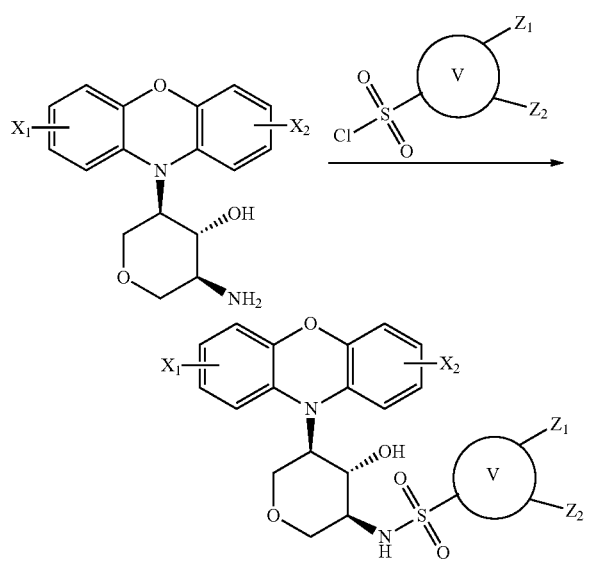

Related pyrans (Q=0) in the opposite enantiomeric series may be obtained by the use of (3S,4R,5R)-3-amino-5-(10H-phenoxazin-10-yl)tetrahydro-2H-pyran-4-ol and the appropriately substituted heterocyclyl sulfonyl chloride, as shown in Scheme A.1.

Scheme A.2

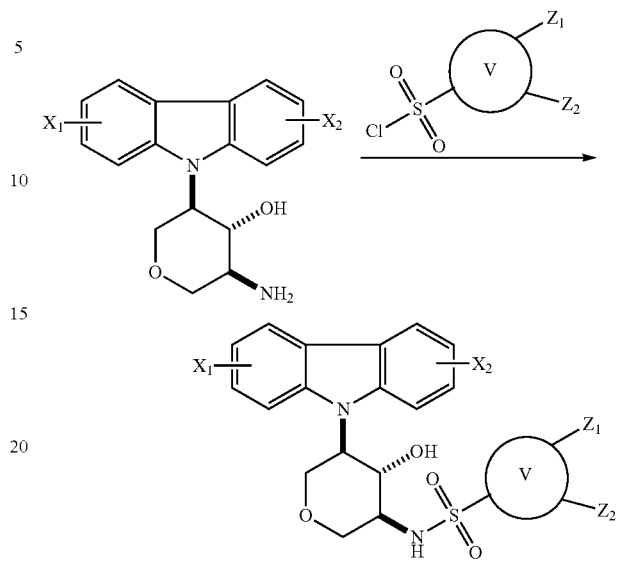

Synthesis of compounds in which the tricyclyl moiety is an appropriately substituted carbazole is carried out using either enantiomeric series of rel-(3S,4R,5R)-3-amino-5-(9H-carbazol-9-yl)tetrahydro-2H-pyran-4-ol as shown in Scheme A.2.

Scheme A.3

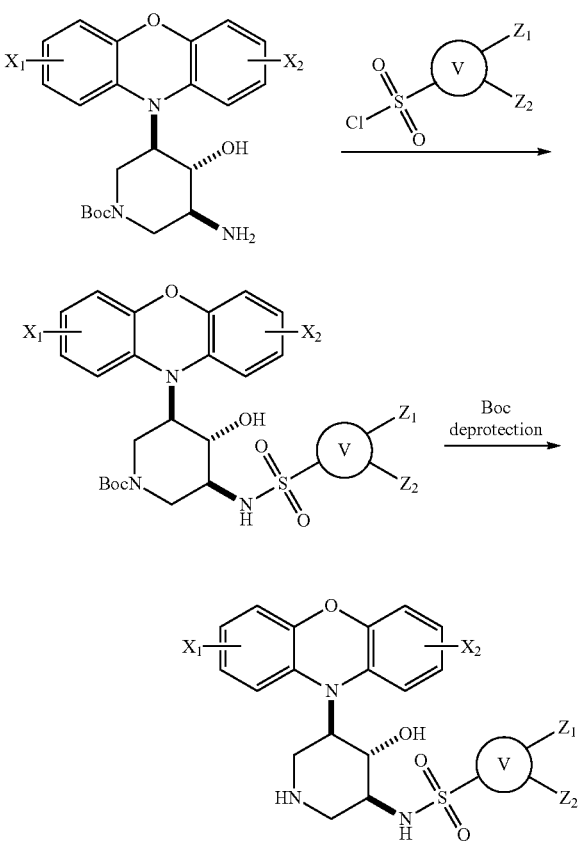

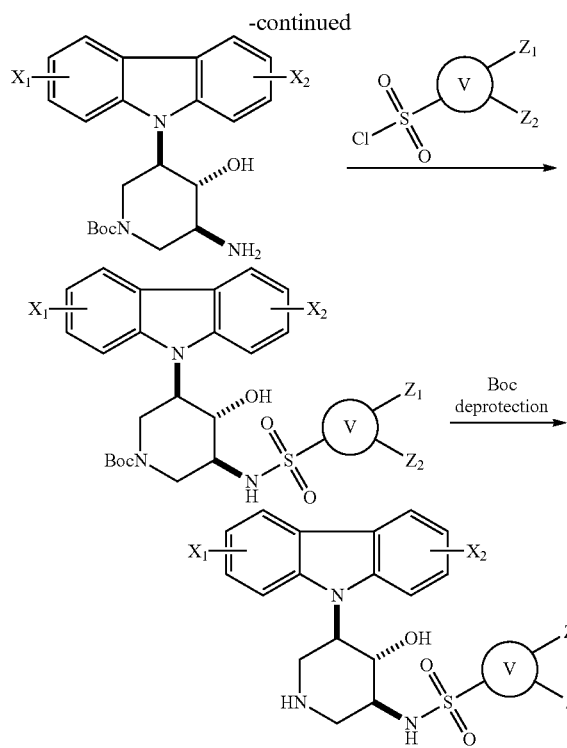

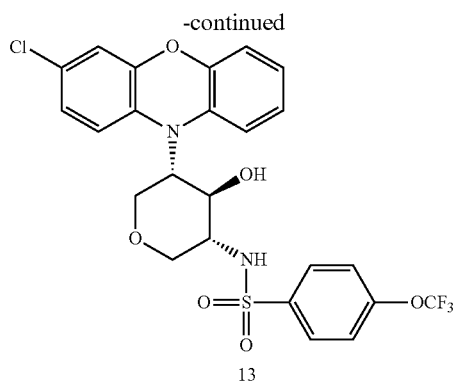

13

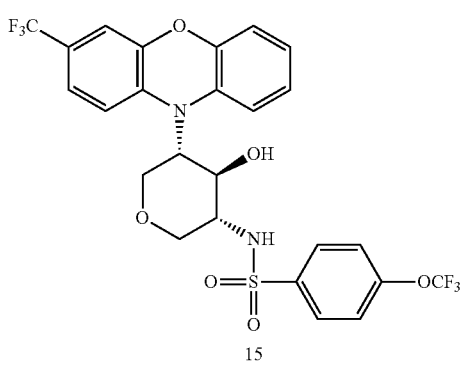

15

Compounds with a piperidine constraint (Q=NH) follow from the use of either enantiomeric series of tert-butyl rel-(3S,4R,5R)-3-amino-4-hydroxy-5-(1   OH-phenoxazin-10-yl)piperidine-1-carboxylate or tert-butyl rel-(3S,4R,5R)-3-amino-5-(9H-carbazol-9-yl)-4-hydroxypiperidine-1-carboxylate and the appropriately substituted heterocyclyl sulfonyl chloride shown in Scheme A.3

Group II (Substituted Phenoxazine):

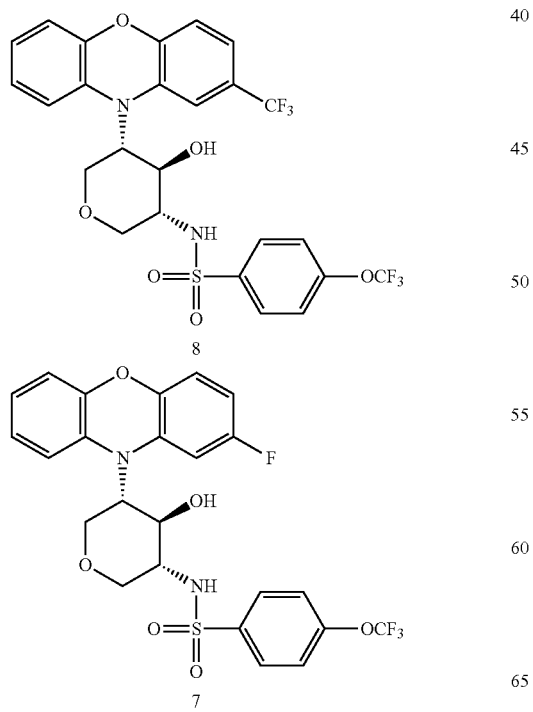

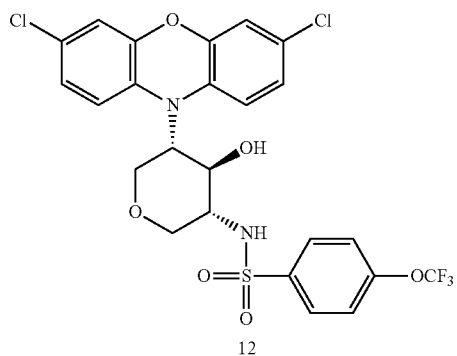

12

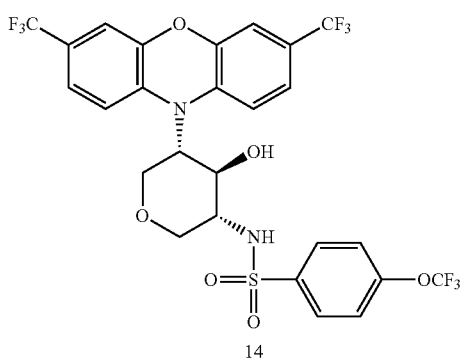

14

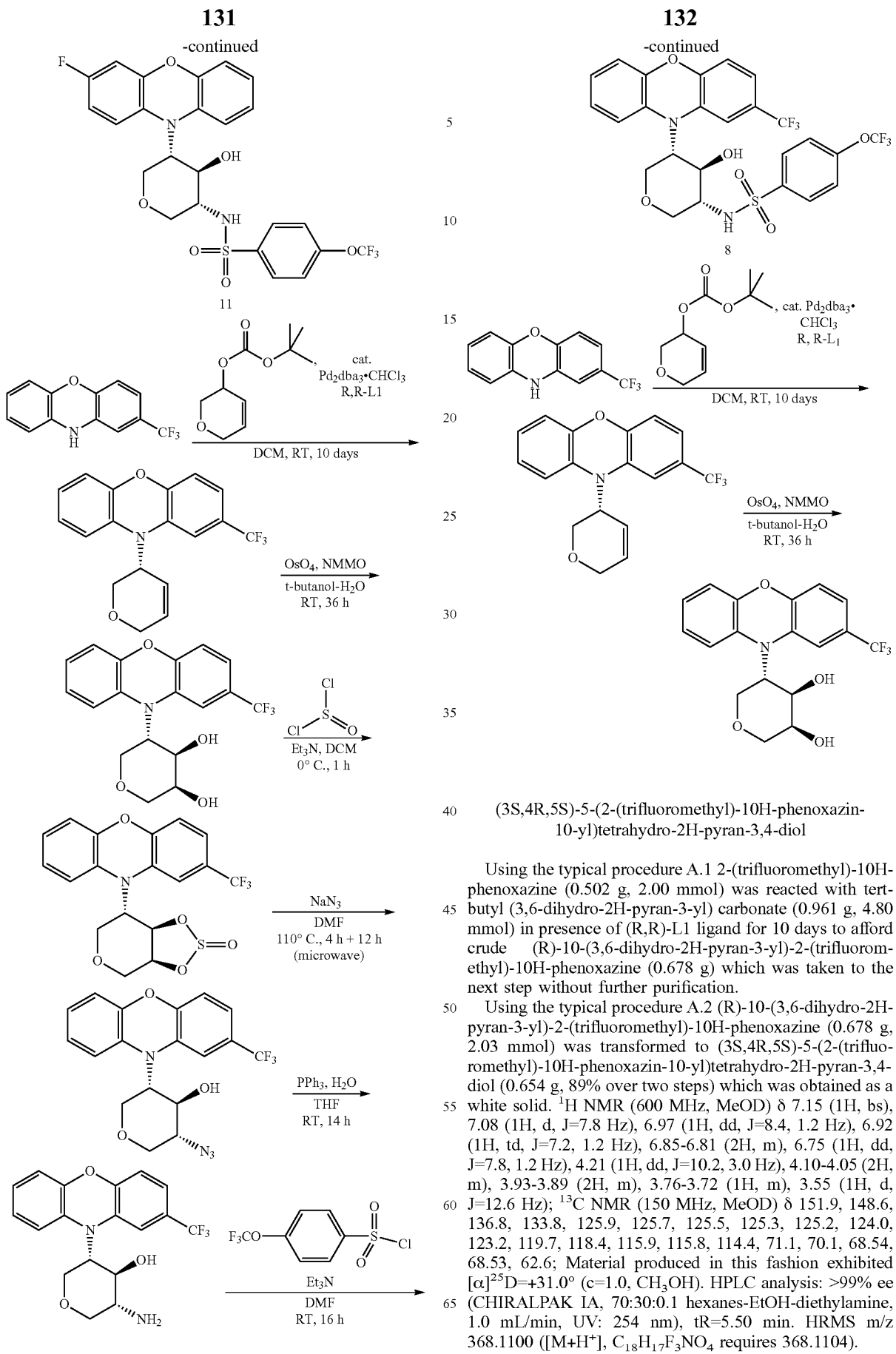

(3S,4R,5S)-5-(2-(trifluoromethyl)-10H-phenoxazin-10-yl)tetrahydro-2H-pyran-3,4-diol Using the typical procedure A.1 2-(trifluoromethyl)-10H-phenoxazine (0.502 g, 2.00 mmol) was reacted with tert-butyl (3,6-dihydro-2H-pyran-3-yl) carbonate (0.961 g, 4.80 mmol) in presence of (R,R)-L1 ligand for 10 days to afford crude (R)-10-(3,6-dihydro-2H-pyran-3-yl)-2-(trifluoromethyl)-10H-phenoxazine (0.678 g) which was taken to the next step without further purification.

Using the typical procedure A.2 (R)-10-(3,6-dihydro-2H-pyran-3-yl)-2-(trifluoromethyl)-10H-phenoxazine (0.678 g, 2.03 mmol) was transformed to (3S,4R,5S)-5-(2-(trifluoromethyl)-10H-phenoxazin-10-yl)tetrahydro-2H-pyran-3,4-diol (0.654 g, 89% over two steps) which was obtained as a white solid. $^1$H NMR (600 MHz, MeOD) δ 7.15 (1H, bs), 7.08 (1H, d, J=7.8 Hz), 6.97 (1H, dd, J=8.4, 1.2 Hz), 6.92 (1H, td, J=7.2, 1.2 Hz), 6.85-6.81 (2H, m), 6.75 (1H, dd, J=7.8, 1.2 Hz), 4.21 (1H, dd, J=10.2, 3.0 Hz), 4.10-4.05 (2H, m), 3.93-3.89 (2H, m), 3.76-3.72 (1H, m), 3.55 (1H, d, J=12.6 Hz); $^{13}$C NMR (150 MHz, MeOD) δ 151.9, 148.6, 136.8, 133.8, 125.9, 125.7, 125.5, 125.3, 125.2, 124.0, 123.2, 119.7, 118.4, 115.9, 115.8, 114.4, 71.1, 70.1, 68.54, 68.53, 62.6; Material produced in this fashion exhibited $[α]^{25}$D=+31.0° (c=1.0, CH$_3$OH). HPLC analysis: >99% ee (CHIRALPAK IA, 70:30:0.1 hexanes-EtOH-diethylamine, 1.0 mL/min, UV: 254 nm), tR=5.50 min. HRMS m/z 368.1100 ([M+H]$^+$), C$_{18}$H$_{17}$F$_3$NO$_4$ requires 368.1104).

133

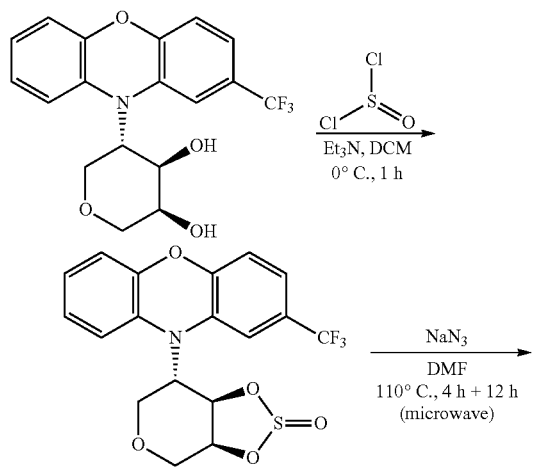

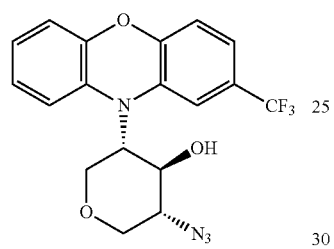

(3R,4R,5S)-3-azido-5-(2-(trifluoromethyl)-10H-phenoxazin-10-yl)tetrahydro-2H-pyran-4-ol Using the typical procedure B.1 (3S,4R,5S)-5-(2-(trifluoromethyl)-10H-phenoxazin-10-yl)tetrahydro-2H-pyran-3,4-diol (0.517 g, 1.40 mmol) in dichloromethane (10.0 mL) was reacted with triethylamine (1.55 mL, 11.2 mmol), and thionyl chloride (0.306 mL, 4.22 mmol). The mixture was stirred at 0° C. for 1 h. Flash chromatography (SiO$_2$, 10%-50% ethylacetate-hexanes) afforded crude (3aS,7S,7aR)-7-(2-(trifluoromethyl)-10H-phenoxazin-10-yl)tetrahydro-3aH-[1,3,2]dioxathiolo[4,5-c]pyran 2-oxide (0.555 g) which was taken to the next step without further purification.

Using the typical procedure B.2 (3aS,7S,7aR)-7-(2-(trifluoromethyl)-10H-phenoxazin-10-yl)tetrahydro-3aH-[1,3,2]dioxathiolo[4,5-c]pyran 2-oxide (0.555 g, 1.34 mmol) in DMF (3.0 mL) was reacted with sodium azide (0.262 g, 4.03 mmol) at 110° C. for 4 h, (pressure was released from the vial), then 110° C. for 12 h. Purification by flash chromatography (SiO$_2$, 6%-13% ethylacetate-hexanes) afforded (3R,4R,5S)-3-azido-5-(2-(trifluoromethyl)-10H-phenoxazin-10-yl)tetrahydro-2H-pyran-4-ol (0.370 g, 67% over two steps). $^1$H NMR (600 MHz, MeOD) δ 7.13-7.10 (2H, m), 6.97-6.93 (2H, m), 6.88-6.84 (2H, m), 6.78 (1H, d, J=8.4 Hz), 4.10-4.05 (2H, m), 3.94 (1H, dd, J=11.4, 4.8 Hz), 3.77 (1H, t, J=11.4 Hz), 3.66 (1H, td, J=11.4, 4.8 Hz), 3.55-3.50 (1H, m), 3.13 (1H, t, J=11.4 Hz); $^{13}$C NMR (150 MHz, MeOD) δ 152.0, 148.7, 136.6, 133.5, 126.0, 125.8, 125.6, 125.4, 125.2, 124.1, 123.5, 120.0, 118.6, 116.1, 115.9, 114.7, 72.1, 68.6, 66.7, 64.2; LCMS m/z 393.1 ([M+H$^+$], C$_{18}$H$_{16}$F$_3$N$_4$O$_3$ requires 393.1).

134

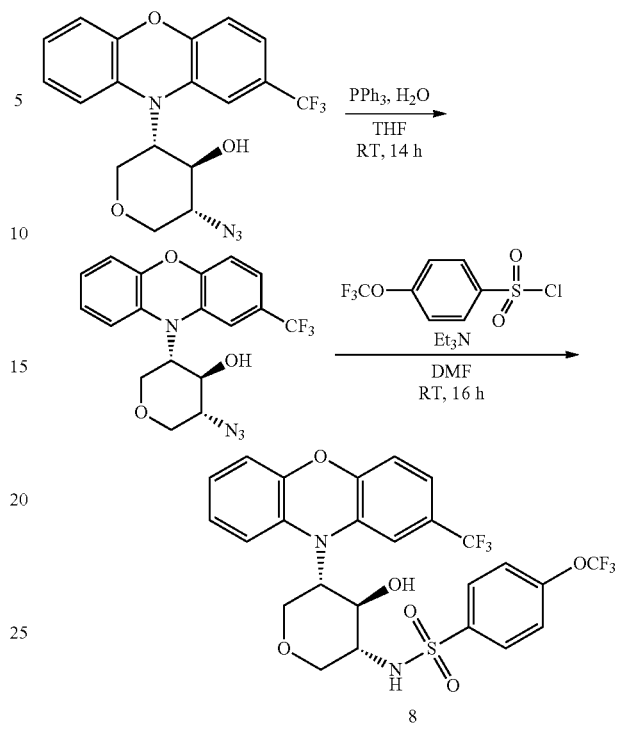

N-((3R,4R,5S)-4-hydroxy-5-(2-(trifluoromethyl)-10H-phenoxazin-10-yl)tetrahydro-2H-pyran-3-yl)-4-(trifluoromethoxy)benzenesulfonamide (8)

Using the typical procedure C.1 (3R,4R,5S)-3-azido-5-(2-(trifluoromethyl)-10H-phenoxazin-10-yl)tetrahydro-2H-pyran-4-ol (0.370 g, 0.943 mmol) in THF (4.0 mL) was reacted with triphenylphosphine (0.272 g, 1.04 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-3-amino-5-(2-(trifluoromethyl)-10H-phenoxazin-10-yl)tetrahydro-2H-pyran-4-ol (0.336 g) which was taken to the next step without further purification.

Using the typical procedure C.2 (3R,4S,5S)-3-amino-5-(2-(trifluoromethyl)-10H-phenoxazin-10-yl)tetrahydro-2H-pyran-4-ol (0.336 g, 0.917 mmol) in DMF (3.0 mL) was reacted with triethylamine (0.510 mL, 3.66 mmol), and 4-(trifluoromethoxy)benzene-1-sulfonyl chloride (0.171 mL, 1.01 mmol). Purification by flash chromatography (SiO$_2$, 17%-20% ethylacetate-hexanes) afforded N-((3R,4R,5S)-4-hydroxy-5-(2-(trifluoromethyl)-10H-phenoxazin-10-yl)tetrahydro-2H-pyran-3-yl)-4-(trifluoromethoxy)benzenesulfonamide 8 (0.082 g, 15% over two steps). $^1$H NMR (600 MHz, MeOD) δ 7.98 (2H, d, J=9.0 Hz), 7.40 (2H, d, J=8.4 Hz), 7.11-7.10 (2H, m), 6.94-6.93 (2H, m), 6.87-6.84 (2H, m), 6.77 (1H, d, J=7.8 Hz), 4.09 (1H, dd, J=10.8, 4.2 Hz), 3.96 (1H, t, J=10.2 Hz), 3.86 (1H, dd, J=10.2, 4.2 Hz), 3.76 (1H, t, J=11.4 Hz), 3.59 (1H, td, J=10.8, 4.8 Hz), 3.26-3.22 (1H, m), 3.18 (1H, t, J=11.4 Hz); $^{13}$C NMR (150 MHz, MeOD) δ 152.1, 151.8, 148.7, 140.3, 136.5, 133.6, 129.3, 125.8, 125.6, 124.0, 123.4, 120.8, 120.0, 118.6, 116.0, 115.9, 114.8, 70.3, 70.0, 68.6, 67.3, 57.2; Material produced in this fashion exhibited [α]$^{25}$D=+6.0° (c=1.0, CH$_3$OH). HPLC analysis: >99% ee (CHIRALPAK OZ-H, 70:30 hexanes- EtOH, 1.0 mL/min, UV: 230 nm), tR=4.85 min. LCMS m/z 591.1 ([M+H$^+$], $C_{25}H_{21}F_6N_2O_6S$ requires 591.1).

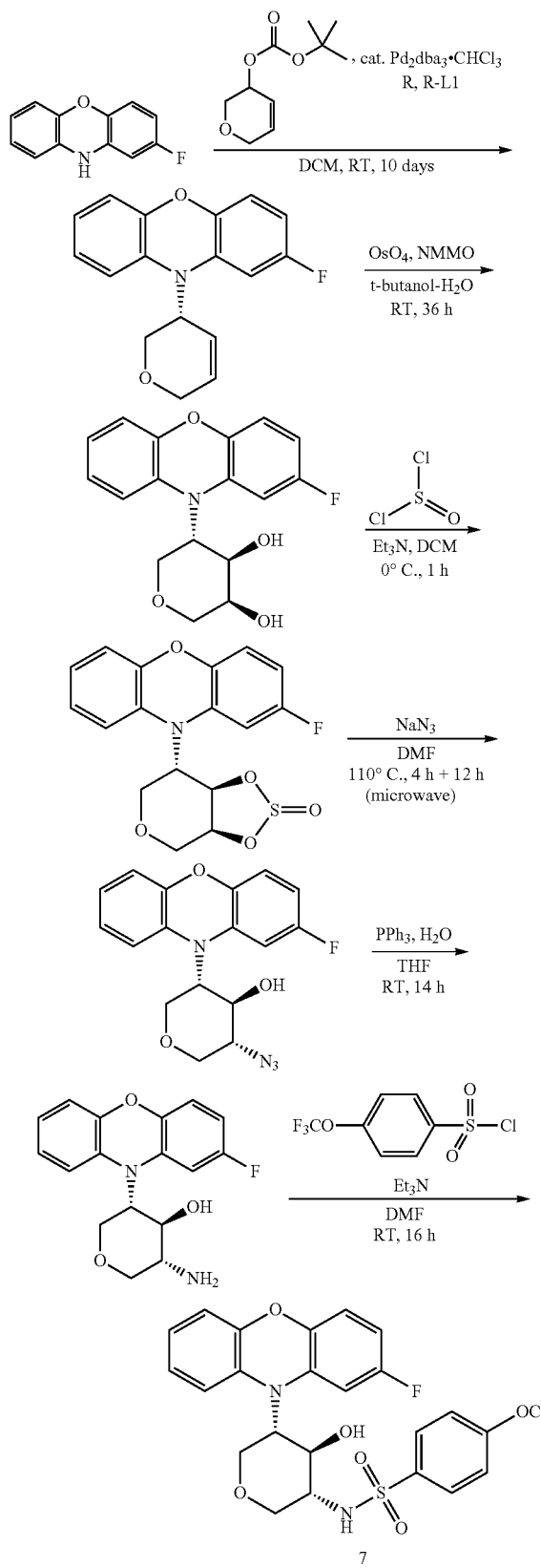

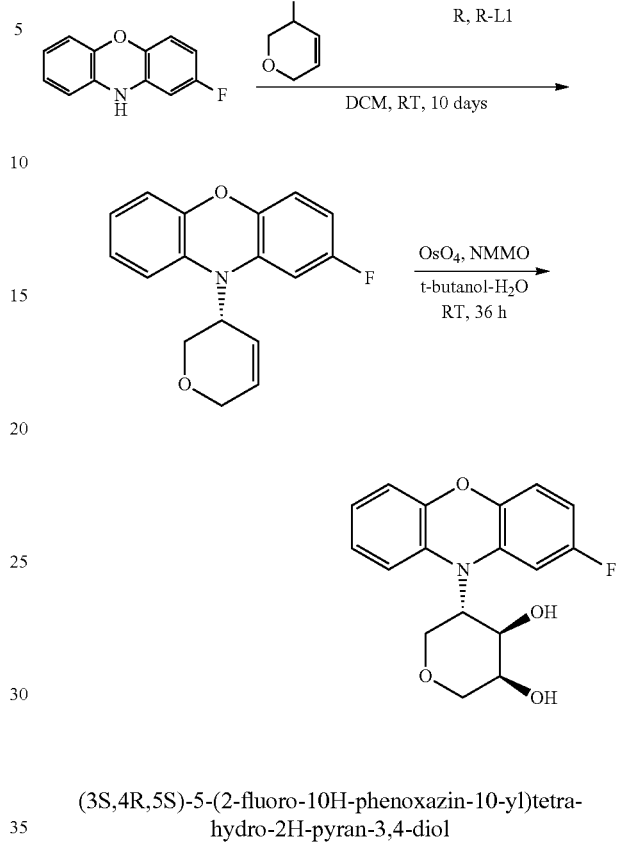

(3S,4R,5S)-5-(2-fluoro-10H-phenoxazin-10-yl)tetrahydro-2H-pyran-3,4-diol

Using the typical procedure A.1 2-fluoro-10H-phenoxazine (0.402 g, 2.00 mmol) was reacted with tert-butyl (3,6-dihydro-2H-pyran-3-yl) carbonate (0.961 g, 4.80 mmol) in presence of (R,R)-L1 ligand for 10 days to afford crude (R)-10-(3,6-dihydro-2H-pyran-3-yl)-2-fluoro-10H-phenoxazine (0.650 g) which was taken to the next step without further purification.

Using the typical procedure A.2 (R)-10-(3,6-dihydro-2H-pyran-3-yl)-2-fluoro-10H-phenoxazine (0.650 g, 2.29 mmol) was transformed to (3S,4R,5S)-5-(2-fluoro-10H-phenoxazin-10-yl)tetrahydro-2H-pyran-3,4-diol (0.556 g, 89% over two steps) which was obtained as a white solid. $^1$H NMR (600 MHz, MeOD) δ 6.99 (1H, dd, J=7.8, 0.6 Hz), 6.92-6.89 (1H, m), 6.83 (1H, td, J=7.8, 1.2 Hz), 6.77 (1H, dd, J=10.2, 3.0 Hz), 6.74 (1H, dd, J=7.8, 1.2 Hz), 6.71 (1H, dd, J=8.4, 5.4 Hz), 6.52 (1H, td, J=8.4, 2.4 Hz), 4.29 (1H, dd, J=10.2, 3.0 Hz), 4.10-4.06 (2H, m), 3.95 (1H, bs), 3.90 (1H, d, J=14.4 Hz), 3.81-3.77 (1H, m), 3.61 (1H, d, J=12.6 Hz); $^{13}$C NMR (150 MHz, MeOD) δ 160.0, 158.4, 149.1, 145.2, 137.0, 134.1, 132.6, 129.4, 128.2, 123.5, 122.9, 117.9, 115.8, 115.7, 107.8, 107.6, 105.0, 104.8, 71.0, 70.2, 68.5, 68.1, 61.9; Material produced in this fashion exhibited $[\alpha]^{25}$D=+38.0° (c=1.0, CH$_3$OH). HPLC analysis: 89% ee (CHIRALPAK IA, 70:30:0.1 hexanes-EtOH-diethylamine, 1.0 mL/min, UV: 230 nm), tR=8.43 min (minor), 7.02 min (major); HRMS m/z 318.1135 ([M+H$^+$], $C_{17}H_{17}FNO_4$ requires 318.1136).

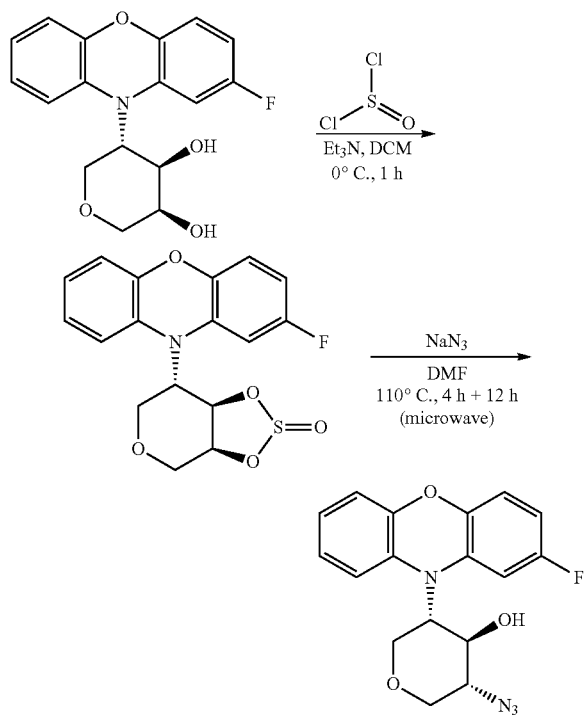

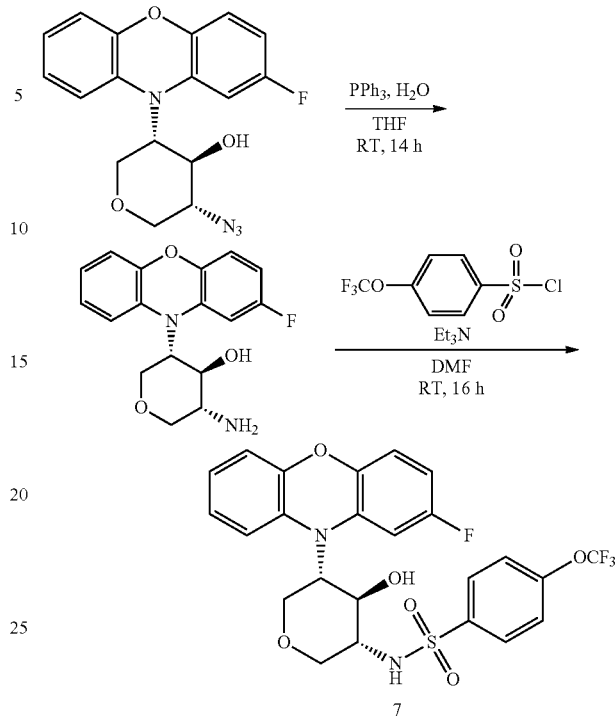

(3R,4R,5S)-3-azido-5-(2-fluoro-10H-phenoxazin-10-yl)tetrahydro-2H-pyran-4-ol

Using the typical procedure B.1 (3S,4R,5S)-5-(2-fluoro-10H-phenoxazin-10-yl)tetrahydro-2H-pyran-3,4-diol (0.535 g, 1.68 mmol) in dichloromethane (10.0 mL) was reacted with triethylamine (1.86 mL, 13.4 mmol), and thionyl chloride (0.182 mL, 2.52 mmol). The mixture was stirred at 0° C. for 1 h. Flash chromatography (SiO$_2$, 10%-50% ethylacetate-hexanes) afforded crude (3aS,7S,7aR)-7-(2-fluoro-10H-phenoxazin-10-yl)tetrahydro-3aH-[1,3,2]dioxathiolo[4,5-c]pyran 2-oxide (0.580 g) which was taken to the next step without further purification.

Using the typical procedure B.2 (3aS,7S,7aR)-7-(2-fluoro-10H-phenoxazin-10-yl)tetrahydro-3aH-[1,3,2]dioxathiolo[4,5-c]pyran 2-oxide (0.556 g, 1.53 mmol) in DMF (2.0 mL) was reacted with sodium azide (0.262 g, 4.03 mmol) at 110° C. for 4 h, (pressure was released from the vial), then 110° C. for 12 h. Purification by flash chromatography (SiO$_2$, 6%-13% ethylacetate-hexanes) afforded (3R,4R,5S)-3-azido-5-(2-fluoro-10H-phenoxazin-10-yl)tetrahydro-2H-pyran-4-ol (0.321 g, 58% over two steps). $^1$H NMR (600 MHz, MeOD) δ 6.97 (1H, dd, J=7.8, 1.2 Hz), 6.93 (1H, td, J=7.8, 1.8 Hz), 6.87 (1H, td, J=7.8, 1.8 Hz), 6.77-6.71 (3H, m), 6.55 (1H, td, J=8.4, 3.0 Hz), 4.16-4.12 (1H, m), 4.08 (I H, dd, J=11.4, 4.8 Hz), 3.95 (1H, dd, J=11.4, 4.8 Hz), 3.83 (1H, t, J=11.4 Hz), 3.69 (1H, td, J=10.8, 4.8 Hz), 3.56-3.52 (1H, m), 3.20 (1H, t, J=11.4 Hz); $^{13}$C NMR NMR (150 MHz, MeOD) δ 160.0, 158.4, 149.2, 145.3, 133.8, 123.5, 123.2, 118.0, 116.0, 115.9, 115.8, 108.1, 108.0, 105.2, 105.0, 71.9, 68.5, 68.2, 66.1, 64.2; HRMS m/z 343.1205 ([M+H$^+$], C$_{17}$H$_{16}$FN4O3 requires 343.1201).

N-((3R,4R,5S)-4-hydroxy-5-(2-(trifluoromethyl)-10H-phenoxazin-10-yl)tetrahydro-2H-pyran-3-yl)-4-(trifluoromethoxy)benzenesulfonamide (7)

Using the typical procedure C.1 (3R,4R,5S)-3-azido-5-(2-(trifluoromethyl)-10H-phenoxazin-10-yl)tetrahydro-2H-pyran-4-ol (0.020 g, 0.058 mmol) in THF (0.50 mL) was reacted with triphenylphosphine (0.017 g, 0.064 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-3-amino-5-(2-fluoro-10H-phenoxazin-10-yl)tetrahydro-2H-pyran-4-ol (0.016 g) which was taken to the next step without further purification.

Using the typical procedure C.2 (3R,4S,5S)-3-amino-5-(2-fluoro-10H-phenoxazin-10-yl)tetrahydro-2H-pyran-4-ol (0.037 g, 0.116 mmol) in DMF (3.0 mL) was reacted with triethylamine (0.030 mL, 0.464 mmol), and 4-(trifluoromethoxy)benzene-1-sulfonyl chloride (0.022 mL, 0.128 mmol). Purification by flash chromatography (SiO$_2$, 17%-20% ethylacetate-hexanes) afforded N-((3R,4R,5S)-5-(2-fluoro-10H-phenoxazin-10-yl)-4-hydroxytetrahydro-2H-pyran-3-yl)-4-(trifluoromethoxy)benzenesulfonamide 7 (0.026 g, 36% over two steps). $^1$H NMR (600 MHz, MeOD) δ 7.99 (2H, d, J=8.4 Hz), 7.41 (2H, d, J=8.4 Hz), 6.92-6.88 (2H, m), 6.84-6.81 (1H, m), 6.73 (1H, d, J=8.4 Hz), 6.70-6.67 (2H, m), 6.52 (1H, td, J=8.4, 3.0 Hz), 4.06-4.01 (2H, m), 3.85 (1H, dd, J=10.2, 4.2 Hz), 3.76 (1H, t, J=12.0 Hz), 3.62-3.58 (1H, m), 3.26-3.18 (2H, m); $^{13}$C NMR (150 MHz, MeOD) δ 159.9, 158.4, 151.8, 149.2, 145.3, 140.4, 136.5, 133.9, 129.3, 123.5, 123.1, 120.8, 118.0, 116.0, 115.9, 115.7, 108.1, 108.0, 105.2, 105.1, 70.3, 69.8, 68.2, 66.6, 57.3; Material produced in this fashion exhibited $[\alpha]^{25}$D=+5.0° (c=1.0, CH$_3$OH). HPLC analysis: >99% ee (CHIRALPAK OZ-H, 70:30 hexanes-EtOH, 1.0 mL/min, UV: 230 nm), tR=6.04 min. LCMS m/z 541.1101 ([M+H⁺], C₂₄H₂₁F₄N₂O₆S requires 541.1051).

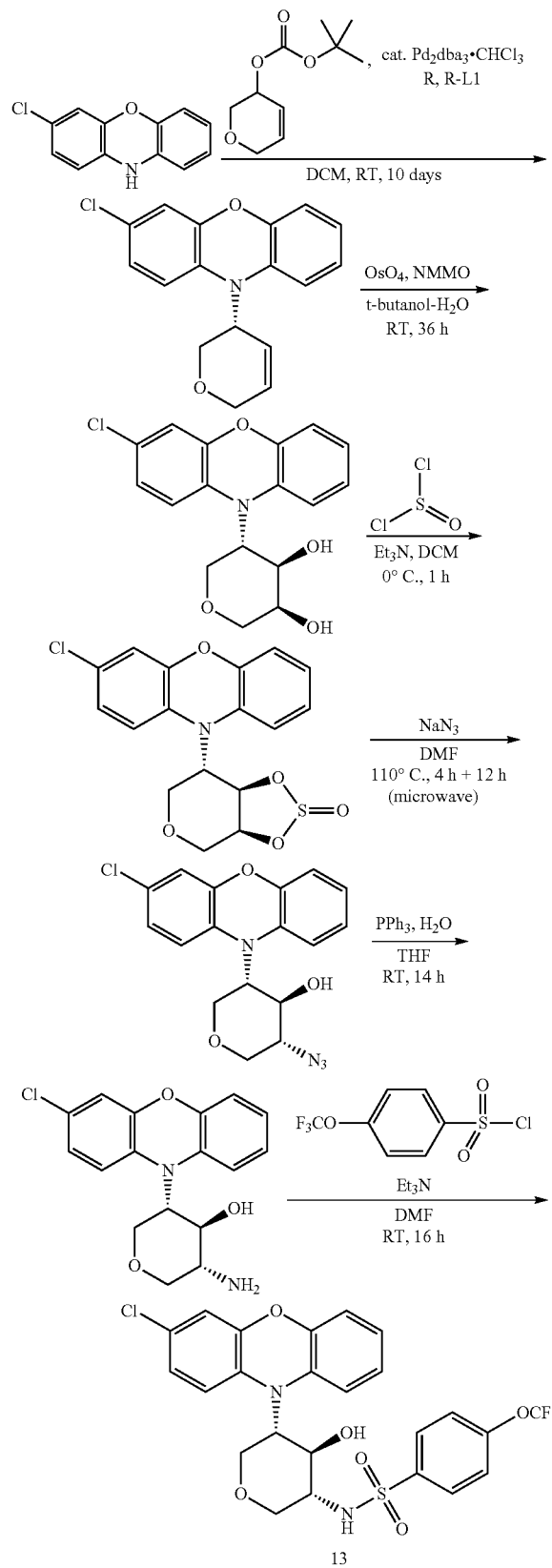

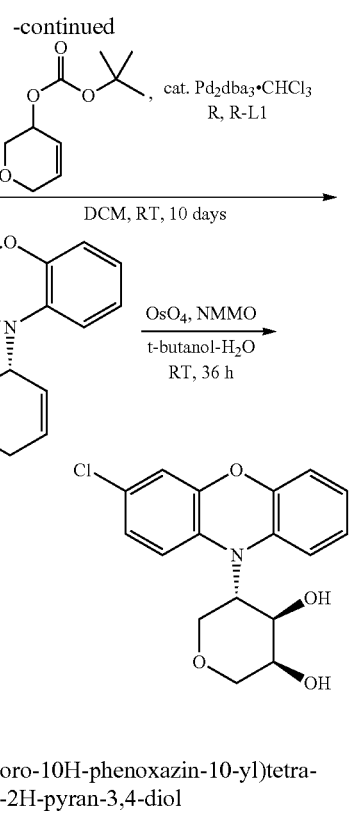

(3S,4R,5S)-5-(3-chloro-10H-phenoxazin-10-yl)tetrahydro-2H-pyran-3,4-diol

Using the typical procedure A.1 3-chloro-10H-phenoxazine (0.435 g, 2.00 mmol) was reacted with tert-butyl (3,6-dihydro-2H-pyran-3-yl) carbonate (0.961 g, 4.80 mmol) in presence of (R,R)-L1 ligand for 10 days to afford crude (R)-3-chloro-10-(3,6-dihydro-2H-pyran-3-yl)-10H-phenoxazine (0.357 g) which was taken to the next step without further purification.

Using the typical procedure A.2 (R)-3-chloro-10-(3,6-dihydro-2H-pyran-3-yl)-10H-phenoxazine (0.357 g, 1.19 mmol) was transformed to (3S,4R,5S)-5-(3-chloro-10H-phenoxazin-10-yl)tetrahydro-2H-pyran-3,4-diol (0.336 g, 85% over two steps) which was obtained as a white solid. ¹H NMR (600 MHz, MeOD) δ 6.98-6.97 (1H, m), 6.94-6.90 (2H, m), 6.88 (1H, dd, J=8.4, 2.4 Hz), 6.84-6.81 (1H, m), 6.75-6.74 (2H, m), 4.23 (1H, dd, J=10.8, 3.6 Hz), 4.09-4.01 (2H, m), 3.92-3.88 (2H, m), 3.76 (1H, t, J=10.8 Hz), 3.58 (1H, d, J=12.0 Hz); ¹³C NMR (150 MHz, MeOD) δ 149.9, 148.7, 134.9, 134.4, 126.9, 123.8, 123.1, 122.7, 118.8, 118.1, 115.6, 71.0, 70.2, 68.5, 68.4, 62.5; Material produced in this fashion exhibited [α]²⁵D=+28.0° (c=1.0, CH₃OH). HPLC analysis: >99% ee (CHIRALPAK IA, 70:30:0.1 hexanes-EtOH-diethylamine, 1.0 mL/min, UV: 254 nm), tR=8.82 min; HRMS m/z 334.0838 ([M+H⁺], C₁₇H₁₇Cl₁NO₄ requires 334.0841).

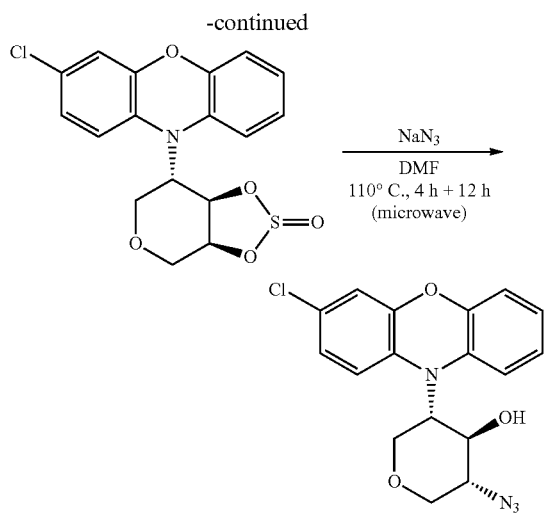

(3R,4R,5S)-3-azido-5-(3-chloro-10H-phenoxazin-10-yl)tetrahydro-2H-pyran-4-ol

Using the typical procedure B.1 (3S,4R,5S)-5-(3-chloro-10H-phenoxazin-10-yl)tetrahydro-2H-pyran-3,4-diol (0.316 g, 0.946 mmol) in dichloromethane (12.0 mL) was reacted with triethylamine (1.05 mL, 7.57 mmol), and thionyl chloride (0.103 mL, 1.42 mmol). The mixture was stirred at 0° C. for 2 h. Flash chromatography (SiO$_2$, 0%-50% ethylacetate-hexanes) afforded crude (3aS,7S,7aR)-7-(3-chloro-10H-phenoxazin-10-yl)tetrahydro-3aH-[1,3,2]dioxathiolo[4,5-c]pyran 2-oxide (0.343 g) which was taken to the next step without further purification.

Using the typical procedure B.2 (3aS,7S,7aR)-7-(3-chloro-10H-phenoxazin-10-yl)tetrahydro-3aH-[1,3,2]dioxathiolo[4,5-c]pyran 2-oxide (0.343 g, 0.903 mmol) in DMF (2.0 mL) was reacted with sodium azide (0.176 g, 2.71 mmol) at 110° C. for 4 h, (pressure was released from the vial), then 110° C. for 12 h. Purification by flash chromatography (SiO$_2$, 6%-13% ethylacetate-hexanes) afforded (3R,4R,5S)-3-azido-5-(3-chloro-10H-phenoxazin-10-yl)tetrahydro-2H-pyran-4-ol (0.124 g, 37% over two steps). $^1$H NMR (600 MHz, MeOD) δ 6.96-6.91 (2H, m), 6.89 (2H, br s), 6.84 (1H, td, J=8.4, 2.4 Hz), 6.76-6.75 (2H, m), 4.09-4.06 (2H, m), 3.93 (1H, dd, J=11.4, 5.4 Hz), 3.78 (1H, t, J=12.0 Hz), 3.64 (1H, td, J=10.8, 4.8 Hz), 3.53-3.48 (1H, m), 3.16 (1H, t, J=10.8 Hz); $^{13}$C NMR (150 MHz, MeOD) δ 149.9, 148.7, 134.7, 134.1, 127.2, 123.9, 123.2, 123.0, 119.0, 118.3, 115.8, 71.9, 68.6, 68.5, 66.5, 64.3; LCMS m/z 359.0 ([M+H$^+$], $C_{17}H_{16}C_1N_4O_3$ requires 359.0).

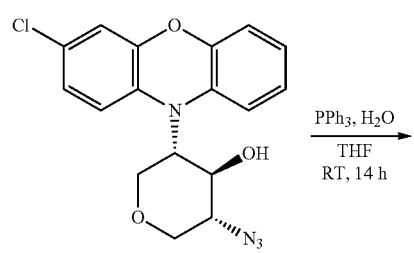

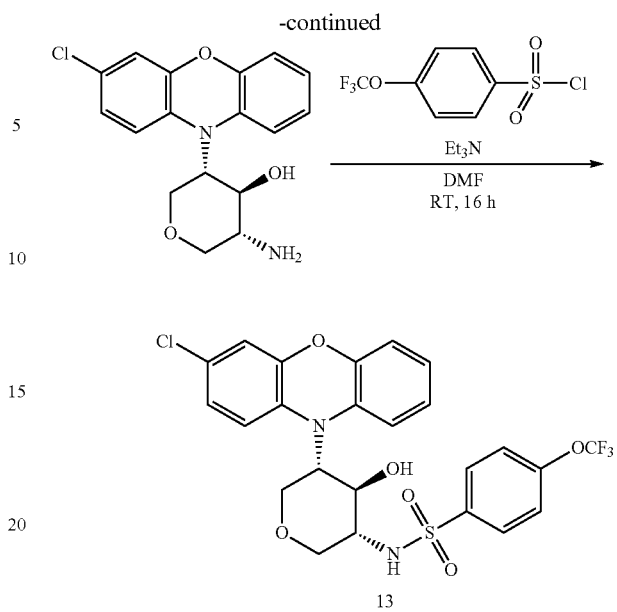

N-((3R,4R,5S)-5-(3-chloro-10H-phenoxazin-10-yl)-4-hydroxytetrahydro-2H-pyran-3-yl)-4-(trifluoromethoxy)benzenesulfonamide (13)

Using the typical procedure C.1 (3R,4R,5S)-3-azido-5-(3-chloro-10H-phenoxazin-10-yl)tetrahydro-2H-pyran-4-ol (0.116 g, 0.323 mmol) in THF (3.50 mL) was reacted with triphenylphosphine (0.093 g, 0.356 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-3-amino-5-(3-chloro-10H-phenoxazin-10-yl)tetrahydro-2H-pyran-4-ol (0.186 g) which was taken to the next step without further purification.

Using the typical procedure C.2 (3R,4S,5S)-3-amino-5-(3-chloro-10H-phenoxazin-10-yl)tetrahydro-2H-pyran-4-ol (0.186 g, 0.560 mmol) in DMF (1.80 mL) was reacted with triethylamine (0.312 g, 2.24 mmol), and 4-(trifluoromethoxy)benzene-1-sulfonyl chloride (0.160 mL, 0.616 mmol). Purification by flash chromatography (SiO$_2$, 17%-33% ethylacetate-hexanes) afforded N-((3R,4R,5S)-5-(3-chloro-10H-phenoxazin-10-yl)-4-hydroxytetrahydro-2H-pyran-3-yl)-4-(trifluoromethoxy)benzenesulfonamide 13 (0.045 g, 13% over two steps). $^1$H NMR (600 MHz, MeOD) δ 7.98 (2H, d, J=9.0 Hz), 7.40 (2H, d, J=8.4 Hz), 6.90-6.81 (5H, m), 6.75-6.73 (2H, m), 4.06 (1H, dd, J=11.4, 4.8 Hz), 3.96 (1H, t, J=9.6 Hz), 3.85 (1H, dd, J=10.2, 3.0 Hz), 3.74 (1H, t, J=11.4 Hz), 3.56 (1H, td, J=10.8, 4.8 Hz), 3.23-3.16 (2H, m); $^{13}$C NMR (150 MHz, MeOD) δ 151.8, 150.0, 148.8, 140.3, 134.6, 134.1, 129.3, 127.2, 123.9, 123.1, 123.0, 121.3, 120.8, 119.0, 118.3, 115.8, 70.3, 69.7, 68.6, 67.1, 57.3; Material produced in this fashion exhibited $[α]^{25}$D=−8.0° (c=1.0, CH$_3$OH). HPLC analysis: 98% ee (CHIRALPAK OZ-H, 70:30 hexanes-EtOH, 1.0 mL/min, UV: 230 nm), tR=7.18 min (minor), 5.79 min (major). HRMS m/z 557.0758 ([M+H$^+$], $C_{24}H_{21}ClF_3N_2O_6S$ requires 557.0756).

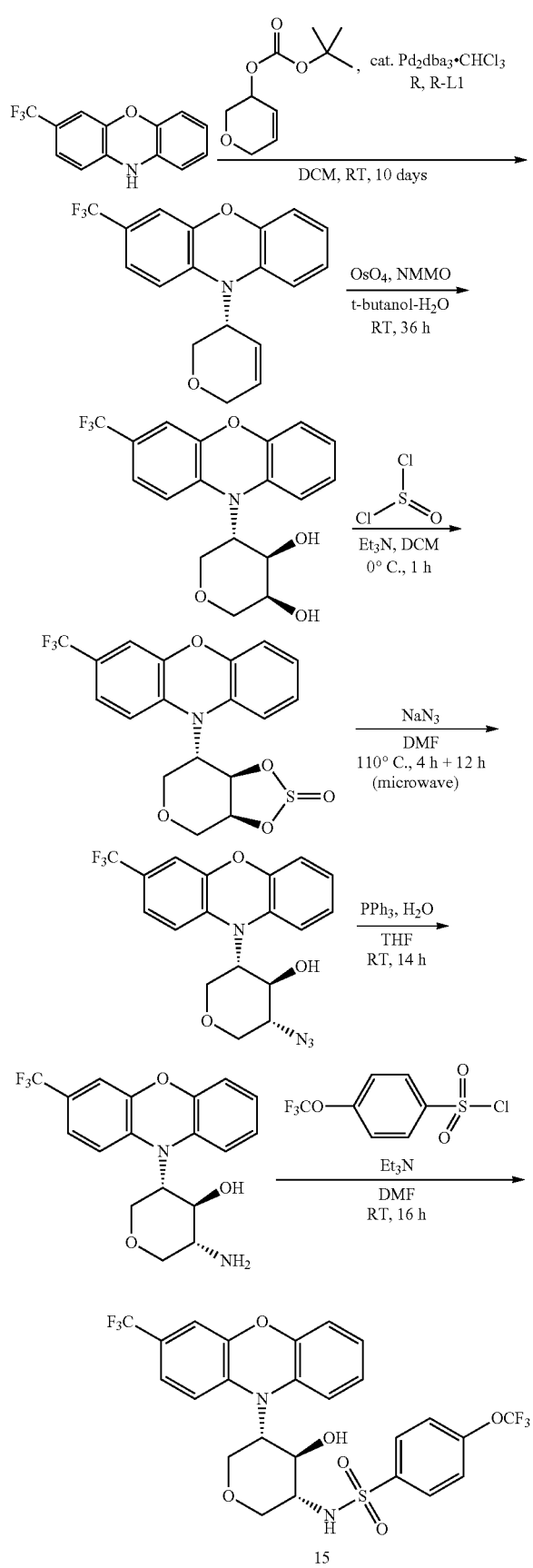

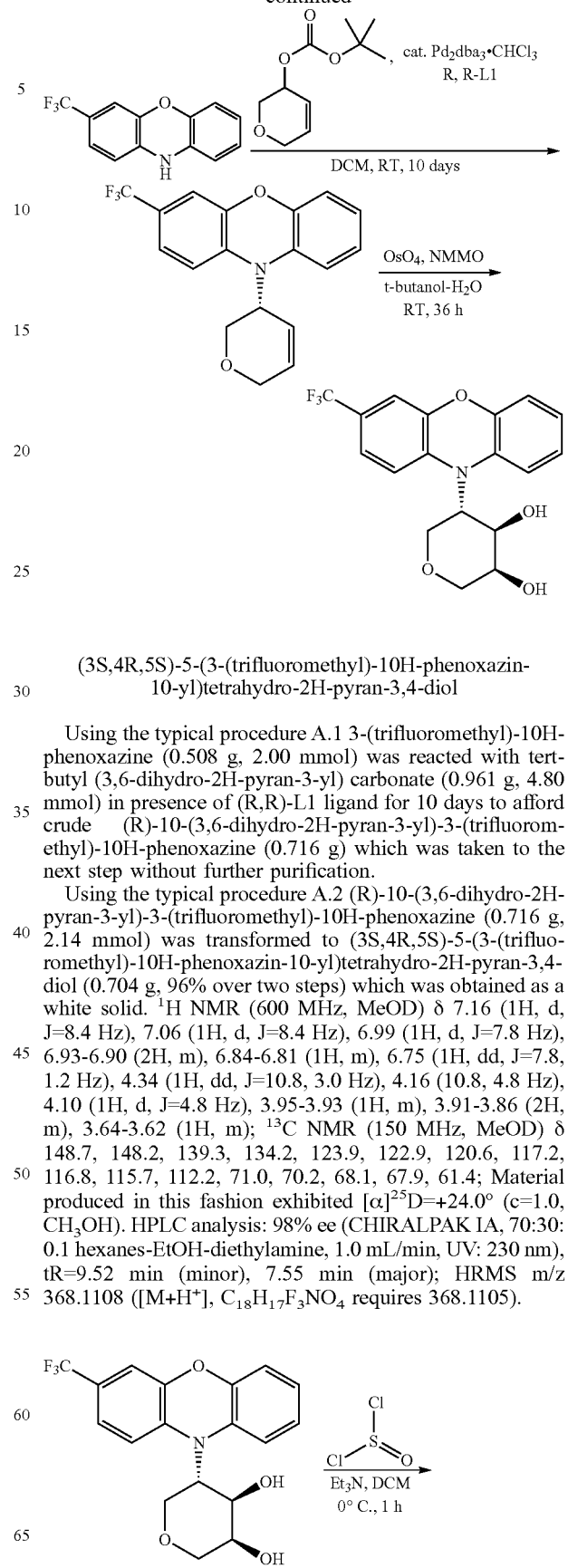

(3S,4R,5S)-5-(3-(trifluoromethyl)-10H-phenoxazin-10-yl)tetrahydro-2H-pyran-3,4-diol Using the typical procedure A.1 3-(trifluoromethyl)-10H-phenoxazine (0.508 g, 2.00 mmol) was reacted with tert-butyl (3,6-dihydro-2H-pyran-3-yl) carbonate (0.961 g, 4.80 mmol) in presence of (R,R)-L1 ligand for 10 days to afford crude (R)-10-(3,6-dihydro-2H-pyran-3-yl)-3-(trifluoromethyl)-10H-phenoxazine (0.716 g) which was taken to the next step without further purification.

Using the typical procedure A.2 (R)-10-(3,6-dihydro-2H-pyran-3-yl)-3-(trifluoromethyl)-10H-phenoxazine (0.716 g, 2.14 mmol) was transformed to (3S,4R,5S)-5-(3-(trifluoromethyl)-10H-phenoxazin-10-yl)tetrahydro-2H-pyran-3,4-diol (0.704 g, 96% over two steps) which was obtained as a white solid. $^1$H NMR (600 MHz, MeOD) δ 7.16 (1H, d, J=8.4 Hz), 7.06 (1H, d, J=8.4 Hz), 6.99 (1H, d, J=7.8 Hz), 6.93-6.90 (2H, m), 6.84-6.81 (1H, m), 6.75 (1H, dd, J=7.8, 1.2 Hz), 4.34 (1H, dd, J=10.8, 3.0 Hz), 4.16 (10.8, 4.8 Hz), 4.10 (1H, d, J=4.8 Hz), 3.95-3.93 (1H, m), 3.91-3.86 (2H, m), 3.64-3.62 (1H, m); $^{13}$C NMR (150 MHz, MeOD) δ 148.7, 148.2, 139.3, 134.2, 123.9, 122.9, 120.6, 117.2, 116.8, 115.7, 112.2, 71.0, 70.2, 68.1, 67.9, 61.4; Material produced in this fashion exhibited $[α]^{25}D$=+24.0° (c=1.0, CH$_3$OH). HPLC analysis: 98% ee (CHIRALPAK IA, 70:30:0.1 hexanes-EtOH-diethylamine, 1.0 mL/min, UV: 230 nm), tR=9.52 min (minor), 7.55 min (major); HRMS m/z 368.1108 ([M+H$^+$], C$_{18}$H$_{17}$F$_3$NO$_4$ requires 368.1105).

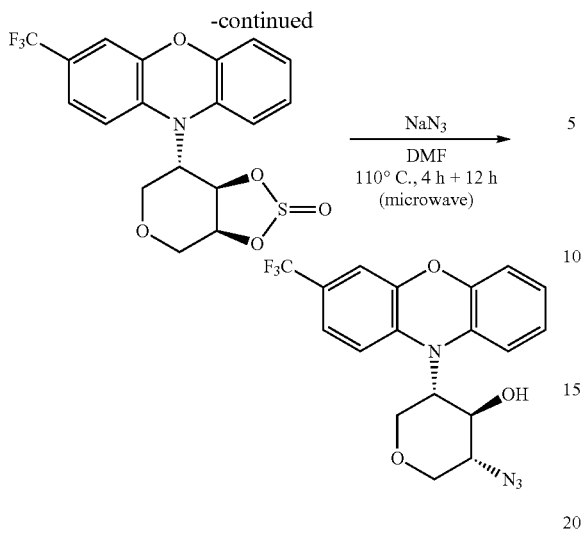

((3R,4R,5S)-3-azido-5-(3-(trifluoromethyl)-10H-phenoxazin-10-yl)tetrahydro-2H-pyran-4-ol Using the typical procedure B.1 (3S,4R,5S)-5-(3-(trifluoromethyl)-10H-phenoxazin-10-yl)tetrahydro-2H-pyran-3,4-diol (0.684 g, 1.86 mmol) in dichloromethane (24.0 mL) was reacted with triethylamine (2.06 mL, 14.9 mmol), and thionyl chloride (0.202 mL, 2.79 mmol). The mixture was stirred at 0° C. for 1 h. Flash chromatography (SiO$_2$, 10%-50% ethylacetate-hexanes) afforded crude (3aS,7S,7aR)-7-(3-(trifluoromethyl)-10H-phenoxazin-10-yl)tetrahydro-3aH-[1,3,2]dioxathiolo[4,5-c]pyran 2-oxide (0.686 g) which was taken to the next step without further purification.

Using the typical procedure B.2 (3aS,7S,7aR)-7-(3-(trifluoromethyl)-10H-phenoxazin-10-yl)tetrahydro-3aH-[1,3,2]dioxathiolo[4,5-c]pyran 2-oxide (0.686 g, 1.66 mmol) in DMF (2.0 mL) was reacted with sodium azide (0.324 g, 4.98 mmol) at 110° C. for 4 h, (pressure was released from the vial), then 110° C. for 12 h. Purification by flash chromatography (SiO$_2$, 6%-13% ethylacetate-hexanes) afforded (3R,4R,5S)-3-azido-5-(3-(trifluoromethyl)-10H-phenoxazin-10-yl)tetrahydro-2H-pyran-4-ol (0.434 g, 59% over two steps). $^1$H NMR (600 MHz, MeOD) δ 7.18 (1H, d, J=8.4 Hz), 7.03 (1H, d, J=8.4 Hz), 6.96-6.92 (3H, m), 6.86-6.83 (1H, m), 6.76 (1H, d, J=7.2 Hz), 4.20 (1H, t, J=10.2 Hz), 4.10 (1H, dd, J=11.4, 4.8 Hz), 3.96 (1H, dd, J=11.4, 4.8 Hz), 3.90 (1H, t, J=11.4 Hz), 3.77 (1H, td, J=10.8, 4.8 Hz), 3.56-3.51 (1H, m), 3.22 (1H, t, J=11.4 Hz); $^{13}$C NMR (150 MHz, MeOD) δ 148.7, 148.2, 139.0, 133.9, 124.0, 123.2, 120.7, 117.4, 117.0, 115.9, 112.4, 71.4, 68.5, 68.2, 65.4, 64.3; LCMS m/z 392.1224 ([M+H$^+$], C$_{18}$H$_{16}$F$_3$N$_4$O$_3$ requires 393.1170).

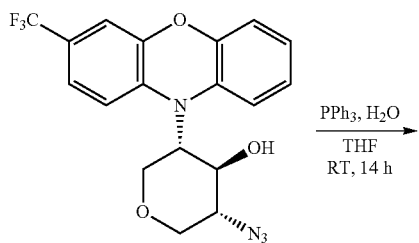

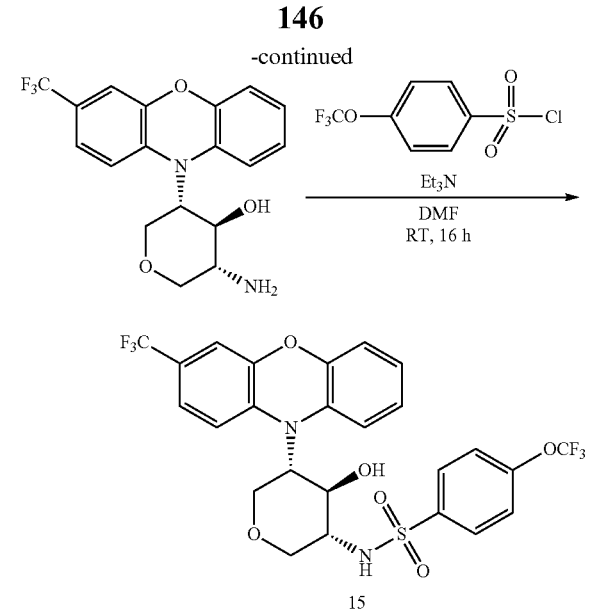

N-((3R,4R,5S)-4-hydroxy-5-(3-(trifluoromethyl)-10H-phenoxazin-10-yl)tetrahydro-2H-pyran-3-yl)-4-(trifluoromethoxy)benzenesulfonamide (15)

Using the typical procedure C.1 (3R,4R,5S)-3-azido-5-(3-(trifluoromethyl)-10H-phenoxazin-10-yl)tetrahydro-2H-pyran-4-ol (0.430 g, 1.09 mmol) in THF (12.0 mL) was reacted with triphenylphosphine (0.314 g, 1.19 mmol), and water (0.002 mL, 0.110 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-3-amino-5-(3-(trifluoromethyl)-10H-phenoxazin-10-yl)tetrahydro-2H-pyran-4-ol (0.632 g) which was taken to the next step without further purification.

Using the typical procedure C.2 (3R,4S,5S)-3-amino-5-(3-(trifluoromethyl)-10H-phenoxazin-10-yl)tetrahydro-2H-pyran-4-ol (0.316 g, 0.862 mmol) in DMF (2.79 mL) was reacted with triethylamine (0.480 mL, 3.45 mmol), and 4-(trifluoromethoxy)benzene-1-sulfonyl chloride (0.161 mL, 0.948 mmol). Purification by flash chromatography (SiO$_2$, 17%-20% ethylacetate-hexanes) afforded N-((3R,4R,5S)-4-hydroxy-5-(3-(trifluoromethyl)-10H-phenoxazin-10-yl)tetrahydro-2H-pyran-3-yl)-4-(trifluoromethoxy)benzenesulfonamide 15 (0.203 g, 63% over two steps). $^1$H NMR (600 MHz, MeOD) δ 7.98 (2H, d, J=9.0 Hz), 7.40 (2H, d, J=8.4 Hz), 7.16 (1H, d, J=7.8 Hz), 6.99 (1H, d, J=7.8 Hz), 6.94-6.91 (3H, m), 6.85-6.82 (1H, m), 6.75 (1H, d, J=7.8 Hz), 4.11-4.06 (2H, m), 3.90-3.86 (2H, m), 3.69 (1H, td, J=11.4, 4.8 Hz), 3.24 (2H, d, J=7.2 Hz); $^{13}$C NMR (150 MHz, MeOD) δ 151.8, 148.8, 148.3, 140.3, 139.0, 133.9, 129.3, 124.1, 123.9, 123.2, 120.8, 120.6, 117.4, 117.1, 115.9, 112.4, 70.3, 69.2, 68.2, 60.2, 57.3; Material produced in this fashion exhibited [α]$^{25}$D=+13.0° (c=1.0, CH$_3$OH). HPLC analysis: >99% ee (CHIRALPAK OZ-H, 70:30 hexanes-EtOH, 1.0 mL/min, UV: 230 nm), tR=4.85 min. LCMS m/z 591.1098 ([M+H$^+$], C$_{25}$H$_{21}$F$_6$N$_2$O$_6$S requires 591.1020).

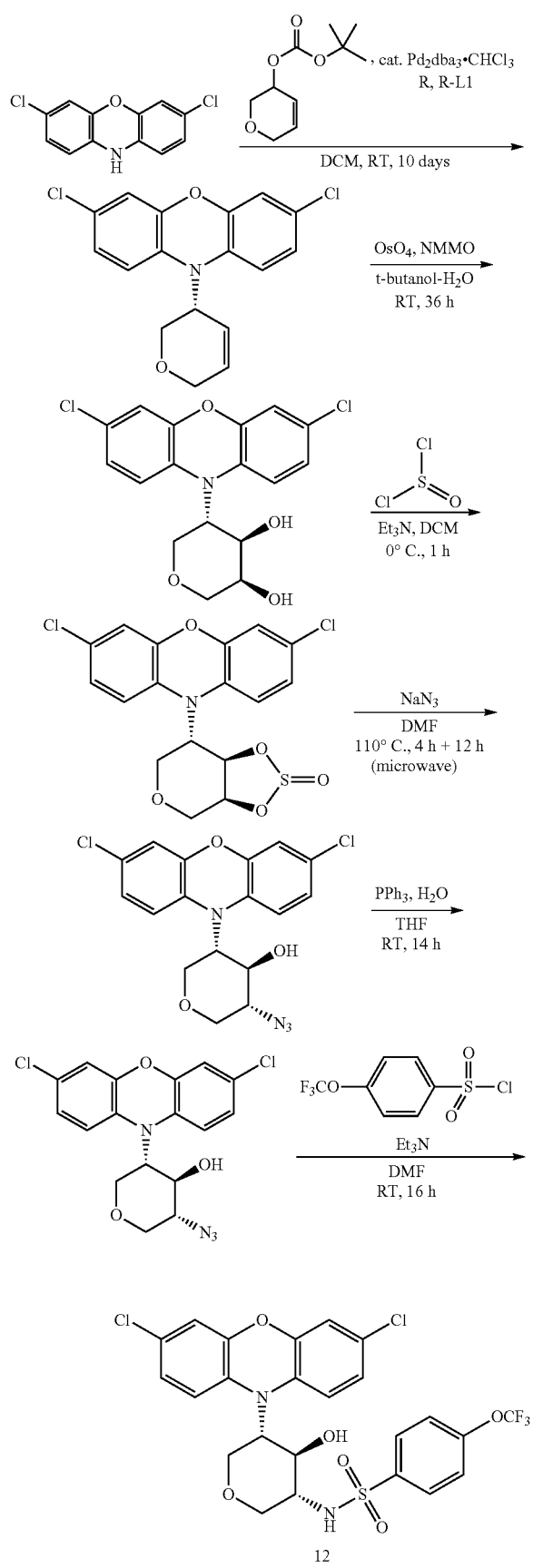

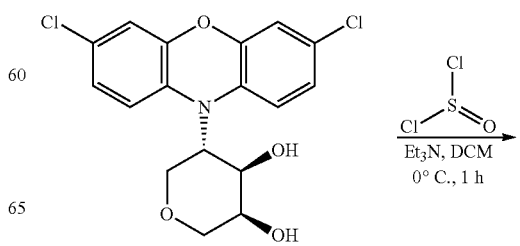

(3S,4R,5S)-5-(3,7-dichloro-10H-phenoxazin-10-yl)tetrahydro-2H-pyran-3,4-diol

Using the typical procedure A.1 3,7-dichloro-10H-phenoxazine (0.504 g, 2.00 mmol) was reacted with tert-butyl (3,6-dihydro-2H-pyran-3-yl) carbonate (0.961 g, 4.80 mmol) in presence of (R,R)-L1 ligand for 10 days to afford crude (R)-3,7-dichloro-10-(3,6-dihydro-2H-pyran-3-yl)-10H-phenoxazine (0.785 g) which was taken to the next step without further purification.

Using the typical procedure A.2 (R)-3,7-dichloro-10-(3,6-dihydro-2H-pyran-3-yl)-1OH-phenoxazine (0.785 g, 2.34 mmol) was transformed to (3S,4R,5S)-5-(3,7-dichloro-10H-phenoxazin-10-yl)tetrahydro-2H-pyran-3,4-diol (0.685 g, 93% over two steps) which was obtained as a white solid. $^1$H NMR (600 MHz, MeOD) δ 6.95-6.89 (4H, m), 6.779-6.775 (2H, m), 4.20 (1H, dd, J=10.8, 3.0 Hz), 4.08 (1H, dd, J=10.8, 4.2 Hz), 4.02 (1H, td, J=10.8, 4.8 Hz), 3.92-3.88 (2H, m), 3.77 (1H, t, J=11.4 Hz), 3.59 (1H, d, J=12.0 Hz); $^{13}$C NMR (150 MHz, MeOD) δ 149.1, 134.0, 127.1, 123.5, 118.8, 115.8, 71.0, 70.2, 68.4, 68.3, 62.5; Material produced in this fashion exhibited [α]$^{25}$D=+28.0° (c=1.0, CH$_3$OH). HPLC analysis: >99% ee (CHIRALPAK IA, 70:30:0.1 hexanes-EtOH-diethylamine, 1.0 mL/min, UV: 230 nm), tR=12.05 min; HRMS m/z 368.0448 ([M+H$^+$], C$_{17}$H$_{16}$Cl$_2$NO$_4$ requires 368.0451).

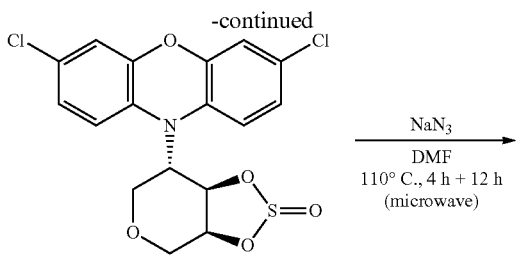

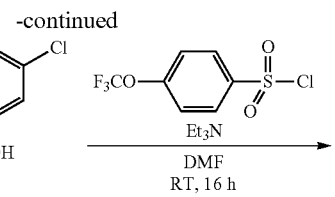

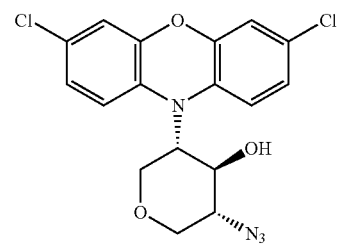

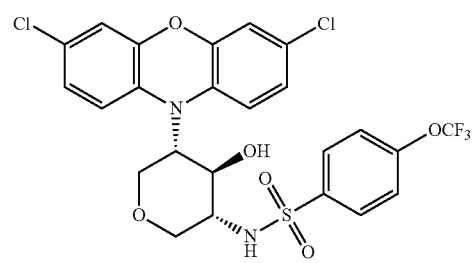

(3R,4R,5S)-3-azido-5-(3,7-dichloro-10H-phenoxazin-10-yl)tetrahydro-2H-pyran-4-ol Using the typical procedure B.1 (3S,4R,5S)-5-(3,7-dichloro-10H-phenoxazin-10-yl)tetrahydro-2H-pyran-3,4-diol (0.660 g, 1.79 mmol) in dichloromethane (10.0 mL) was reacted with triethylamine (1.98 mL, 14.3 mmol), and thionyl chloride (0.195 mL, 2.69 mmol). The mixture was stirred at 0° C. for 1 h. Flash chromatography (SiO$_2$, 10%-50% ethylacetate-hexanes) afforded crude (3aS,7S,7aR)-7-(3,7-dichloro-10H-phenoxazin-10-yl)tetrahydro-3aH-[1,3,2]dioxathiolo[4,5-c]pyran 2-oxide (0.734 g) which was taken to the next step without further purification.

Using the typical procedure B.2 (3aS,7S,7aR)-7-(3,7-dichloro-10H-phenoxazin-10-yl)tetrahydro-3aH-[1,3,2]dioxathiolo[4,5-c]pyran 2-oxide (0.734 g, 1.77 mmol) in DMF (4.0 mL) was reacted with sodium azide (0.345 g, 5.31 mmol) at 110° C. for 4 h, (pressure was released from the vial), then 110° C. for 12 h. Purification by flash chromatography (SiO$_2$, 6%-13% ethylacetate-hexanes) afforded (3R,4R,5S)-3-azido-5-(3,7-dichloro-10H-phenoxazin-10-yl)tetrahydro-2H-pyran-4-ol (0.374 g, 53% over two steps). $^1$H NMR (600 MHz, MeOD) δ 6.92 (4H, br s), 6.78 (2H, br s), 4.10-4.03 (2H, m), 3.94 (1H, dd, J=11.4, 5.4 Hz), 3.80 (1H, t, J=11.4 Hz), 3.63 (1H, td, J=10.8, 4.8 Hz), 3.53-3.49 (1H, m), 3.18 (1H, t, J=11.4 Hz); $^{13}$C NMR (150 MHz, MeOD) δ 149.2, 133.7, 127.4, 123.6, 119.0, 115.9, 71.7, 68.55, 68.53, 66.5, 64.2; LCMS m/z 393.1724 ([M+H$^+$], C$_{17}$H$_{15}$Cl$_2$N$_4$O$_3$ requires 393.0516).

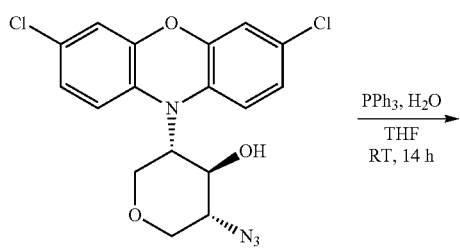

N-((3R,4R,5S)-5-(3,7-dichloro-10H-phenoxazin-10-yl)-4-hydroxytetrahydro-2H-pyran-3-yl)-4-(trifluoromethoxy)benzenesulfonamide (12)

Using the typical procedure C.1 (3R,4R,5S)-3-azido-5-(3,7-dichloro-10H-phenoxazin-10-yl)tetrahydro-2H-pyran-4-ol (0.374 g, 0.951 mmol) in THF (4.0 mL) was reacted with triphenylphosphine (0.274 g, 1.05 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-3-amino-5-(3,7-dichloro-10H-phenoxazin-10-yl)tetrahydro-2H-pyran-4-ol (0.357 g) which was taken to the next step without further purification.

Using the typical procedure C.2 (3R,4S,5S)-3-amino-5-(3,7-dichloro-10H-phenoxazin-10-yl)tetrahydro-2H-pyran-4-ol (0.238 g, 0.648 mmol) in DMF (2.10 mL) was reacted with triethylamine (0.361 mL, 2.59 mmol), and 4-(trifluoromethoxy)benzene-1-sulfonyl chloride (0.121 mL, 0.713 mmol). Purification by flash chromatography (SiO$_2$, 17%-20% ethylacetate-hexanes) afforded N-((3R,4R,5S)-5-(3,7-dichloro-10H-phenoxazin-10-yl)-4-hydroxytetrahydro-2H-pyran-3-yl)-4-(trifluoromethoxy)benzenesulfonamide 12 (0.122 g, 33% over two steps). $^1$H NMR (600 MHz, MeOD) δ 7.98 (2H, d, J=8.4 Hz), 7.41 (2H, d, J=8.4 Hz), 6.90-6.85 (4H, m), 6.77 (2H, br s), 4.06 (1H, dd, J=10.2, 3.0 Hz), 3.91 (1H, t, J=9.6 Hz), 3.85-3.84 (1H, m), 3.75 (1H, t, J=11.4 Hz), 3.55 (1H, td, J=11.4, 4.8 Hz), 3.24-3.16 (2H, m); $^{13}$C NMR (150 MHz, MeOD) δ 151.8, 149.2, 140.3, 133.6, 129.3, 127.4, 123.5, 120.8, 119.0, 115.9, 70.2, 69.6, 68.5, 67.1, 57.3; Material produced in this fashion exhibited [α]$^{25}$D=+13.0° (c=1.0, CH$_3$OH). HPLC analysis: >99% ee (CHIRALPAK OZ-H, 70:30 hexanes-EtOH, 1.0 mL/min, UV: 230 nm), tR=6.10 min. LCMS m/z 591.0248 ([M+H$^+$], C$_{24}$H$_{20}$Cl$_2$F$_3$N$_2$O$_6$S requires 591.0366).

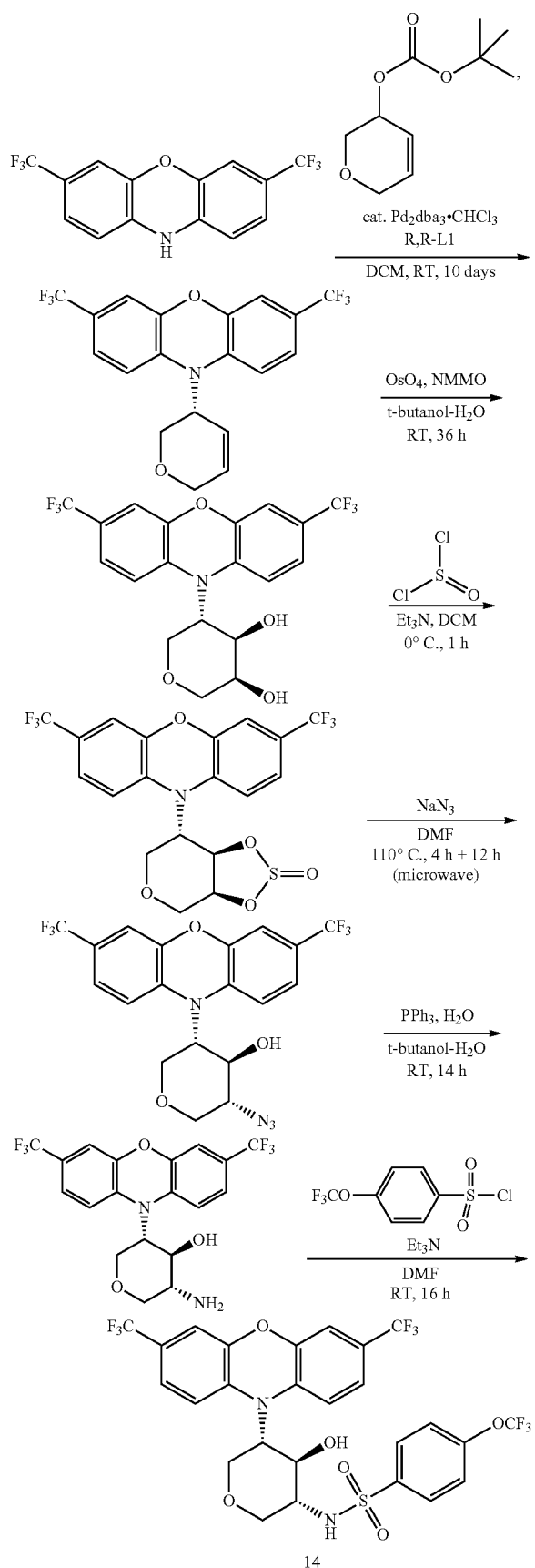

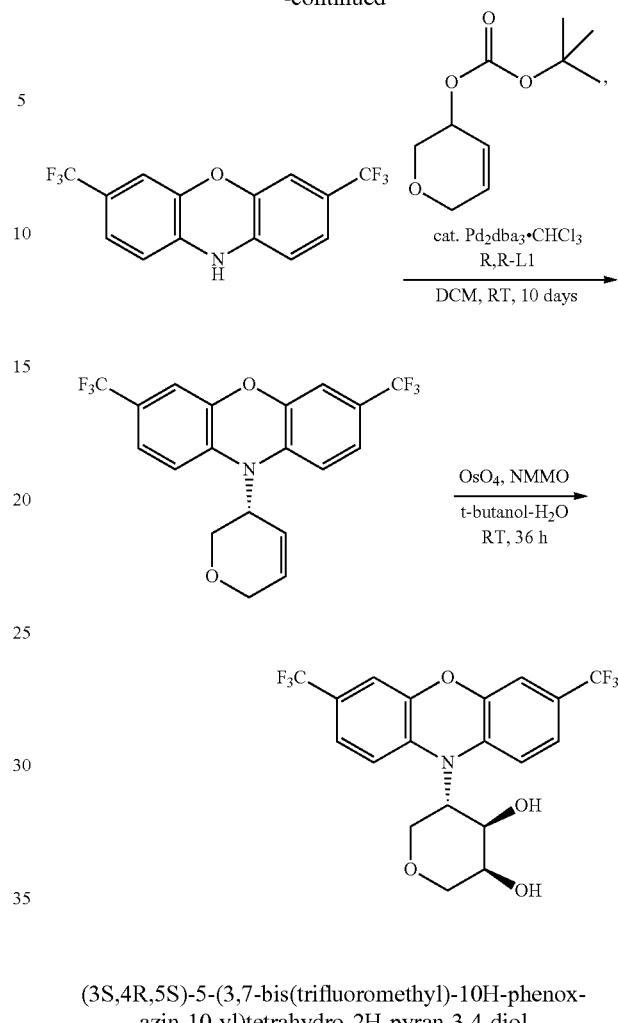

(3S,4R,5S)-5-(3,7-bis(trifluoromethyl)-10H-phenox-azin-10-yl)tetrahydro-2H-pyran-3,4-diol Using the typical procedure A.1 3,7-bis(trifluoromethyl)-10H-phenoxazine (0.638 g, 2.00 mmol) was reacted with tert-butyl (3,6-dihydro-2H-pyran-3-yl) carbonate (0.961 g, 4.80 mmol) in presence of (R,R)-L1 ligand for 10 days to afford crude (R)-10-(3,6-dihydro-2H-pyran-3-yl)-3,7-bis(trifluoromethyl)-10H-phenoxazine (0.733 g) which was taken to the next step without further purification.

Using the typical procedure A.2 (R)-10-(3,6-dihydro-2H-pyran-3-yl)-3,7-bis(trifluoromethyl)-10H-phenoxazine (0.733 g, 1.82 mmol) was transformed to (3S,4R,5S)-5-(3,7-bis(trifluoromethyl)-10H-phenoxazin-10-yl)tetrahydro-2H-pyran-3,4-diol (0.712 g, 82% over two steps) which was obtained as a white solid. $^1$H NMR (600 MHz, MeOD) δ 7.21 (2H, d, J=7.8 Hz), 7.13 (2H, d, J=8.4 Hz), 7.00 (2H, s), 4.40 (1H, dd, J=10.8, 3.0 Hz), 4.24 (1H, td, J=11.4, 4.8 Hz), 4.13 (1H, dd, J=11.4, 4.8 Hz), 3.98-3.93 (3H, m), 3.69 (2H, d, J=12.0 Hz); $^{13}$C NMR (150 MHz, MeOD) δ 147.8, 138.1, 124.3, 121.1, 116.7, 112.5, 71.0, 70.2, 67.6, 67.5, 60.9; Material produced in this fashion exhibited $[\alpha]^{25}$D=+30.0° (c=1.0, CH$_3$OH). HPLC analysis: >99% ee (CHIRALPAK IA, 70:30:0.1 hexanes-EtOH-diethylamine, 1.0 mL/min, UV: 230 nm), tR=7.99 min; HRMS m/z 436.0978 ([M+H$^+$], $C_{19}H_{16}F_6NO_4$ requires 436.0979).

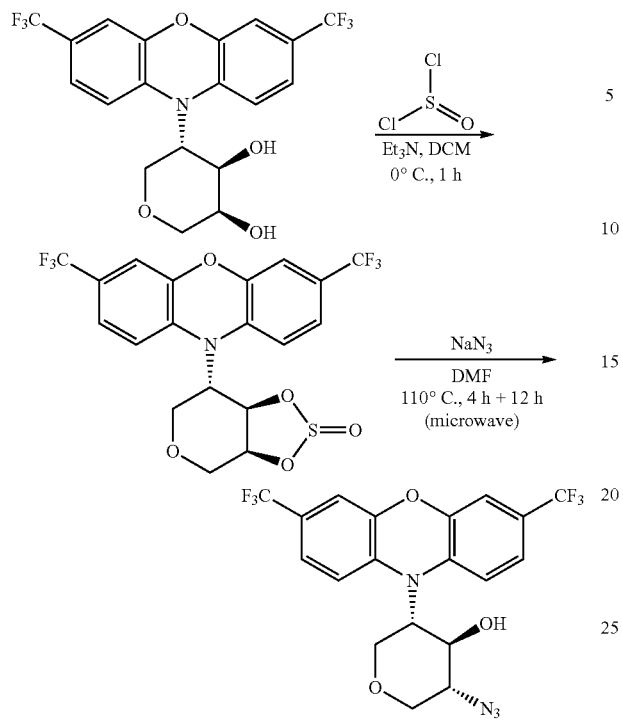
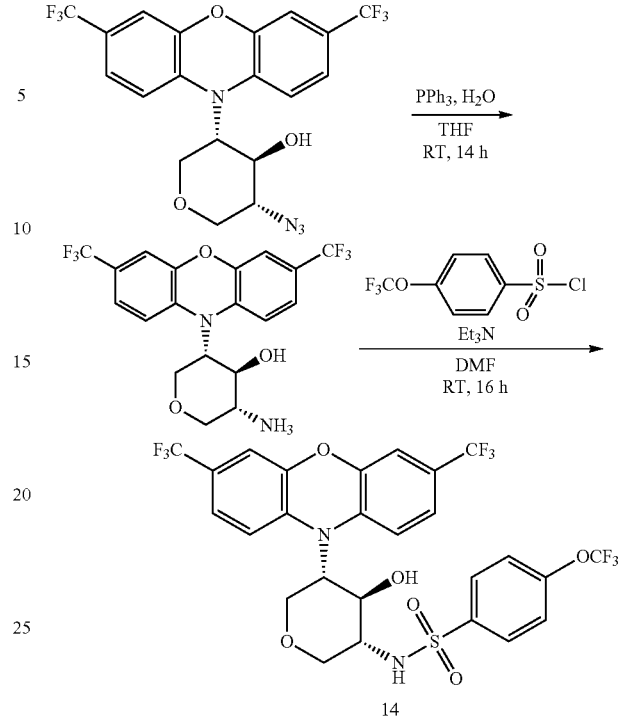

(3R,4R,5S)-3-azido-5-(3,7-bis(trifluoromethyl)-10H-phenoxazin-10-yl)tetrahydro-2H-pyran-4-ol Using the typical procedure B.1 (3S,4R,5S)-5-(3,7-bis(trifluoromethyl)-10H-phenoxazin-10-yl)tetrahydro-2H-pyran-3,4-diol (0.680 g, 1.56 mmol) in dichloromethane (20.0 mL) was reacted with triethylamine (1.73 mL, 12.5 mmol), and thionyl chloride (0.169 mL, 2.34 mmol). The mixture was stirred at 0° C. for 1 h. Flash chromatography (SiO$_2$, 0%-50% ethylacetate-hexanes) afforded crude (3aS, 7S,7aR)-7-(3,7-bis(trifluoromethyl)-10H-phenoxazin-10-yl)tetrahydro-3aH-[1,3,2]dioxathiolo[4,5-c]pyran 2-oxide (0.719 g) which was taken to the next step without further purification.

Using the typical procedure B.2 (3aS,7S,7aR)-7-(3,7-bis(trifluoromethyl)-10H-phenoxazin-10-yl)tetrahydro-3aH-[1,3,2]dioxathiolo[4,5-c]pyran 2-oxide (0.719 g, 1.49 mmol) in DMF (4.0 mL) was reacted with sodium azide (0.291 g, 4.48 mmol) at 110° C. for 4 h, (pressure was released from the vial), then 110° C. for 12 h. Purification by flash chromatography (SiO$_2$, 6%-13% ethylacetate-hexanes) afforded (3R,4R,5S)-3-azido-5-(3,7-bis(trifluoromethyl)-10H-phenoxazin-10-yl)tetrahydro-2H-pyran-4-ol (0.487 g, 68% over two steps). $^1$H NMR (600 MHz, MeOD) δ 7.25-7.23 (2H, m), 7.13-7.12 (2H, m), 7.05-7.03 (2H, m), 4.26 (1H, t, J=9.0 Hz), 4.14 (1H, dd, J=10.8, 4.2 Hz), 4.02-3.98 (2H, m), 3.88 (1H, dd, J=10.8, 4.8 Hz), 3.60-3.56 (1H, m), 3.33-3.27 (1H, m); $^{13}$C NMR (150 MHz, MeOD) δ 147.9, 124.8, 124.6, 121.2, 116.9, 112.7, 71.0, 68.5, 67.6, 64.7, 64.3; LCMS m/z 461.0223 ([M+H$^+$], C$_{19}$H$_{15}$F$_6$N$_4$O$_3$ requires 461.1043).

N-((3R,4R,5S)-5-(3,7-bis(trifluoromethyl)-10H-phenoxazin-10-yl)-4-hydroxytetrahydro-2H-pyran-3-yl)-4-(trifluoromethoxy)benzenesulfonamide (14)

Using the typical procedure C.1 (3R,4R,5S)-3-azido-5-(3,7-bis(trifluoromethyl)-10H-phenoxazin-10-yl)tetrahydro-2H-pyran-4-ol (0.486 g, 1.06 mmol) in THF (5.30 mL) was reacted with triphenylphosphine (0.305 g, 1.16 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane: methanol:35% ammonium hydroxide) afforded crude (3R, 4S,5S)-3-amino-5-(3,7-bis(trifluoromethyl)-10H-phenoxazin-10-yl)tetrahydro-2H-pyran-4-ol (0.669 g) which was taken to the next step without further purification.

Using the typical procedure C.2 (3R,4S,5S)-3-amino-5-(3,7-bis(trifluoromethyl)-10H-phenoxazin-10-yl)tetrahydro-2H-pyran-4-ol (0.334 g, 0.769 mmol) in DMF (2.50 mL) was reacted with triethylamine (0.428 mL, 3.08 mmol), and 4-(trifluoromethoxy)benzene-1-sulfonyl chloride (0.143 mL, 0.846 mmol). Purification by flash chromatography (SiO$_2$, 17%-20% ethylacetate-hexanes) afforded N-((3R,4R,5S)-5-(3,7-bis(trifluoromethyl)-10H-phenoxazin-10-yl)-4-hydroxytetrahydro-2H-pyran-3-yl)-4-(trifluoromethoxy) benzenesulfonamide 14 (0.118 g, 34% over two steps). $^1$H NMR (600 MHz, MeOD) δ 7.98 (2H, d, J=7.8 Hz), 7.39 (2H, d, J=9.4 Hz), 7.19 (2H, d, J=7.8 Hz), 7.03 (2H, d, J=8.4 Hz), 6.99 (2H, br s), 4.13-4.10 (2H, m), 3.96-3.88 (2H, m), 3.76 (1H, td, J=10.8, 4.8 Hz), 3.28-3.27 (2H, m); $^{13}$C NMR (150 MHz, MeOD) δ 151.8, 147.9, 140.3, 129.3, 126.7, 125.0, 124.9, 124.8, 124.6, 124.3, 123.1, 121.1, 120.8, 116.9, 112.7, 70.3, 68.8, 67.8, 65.4, 57.3; Material produced in this fashion exhibited [α]$^{25}$D=+21.0° (c=1.0, CH$_3$OH). HPLC analysis: >99% ee (CHIRALPAK OZ-H, 70:30 hexanes-EtOH, 1.0 mL/min, UV: 230 nm), tR=4.40 min. LCMS m/z 659.1741 ([M+H$^+$], C$_{26}$H$_{20}$F$_9$N$_2$O$_6$S requires 659.0893).

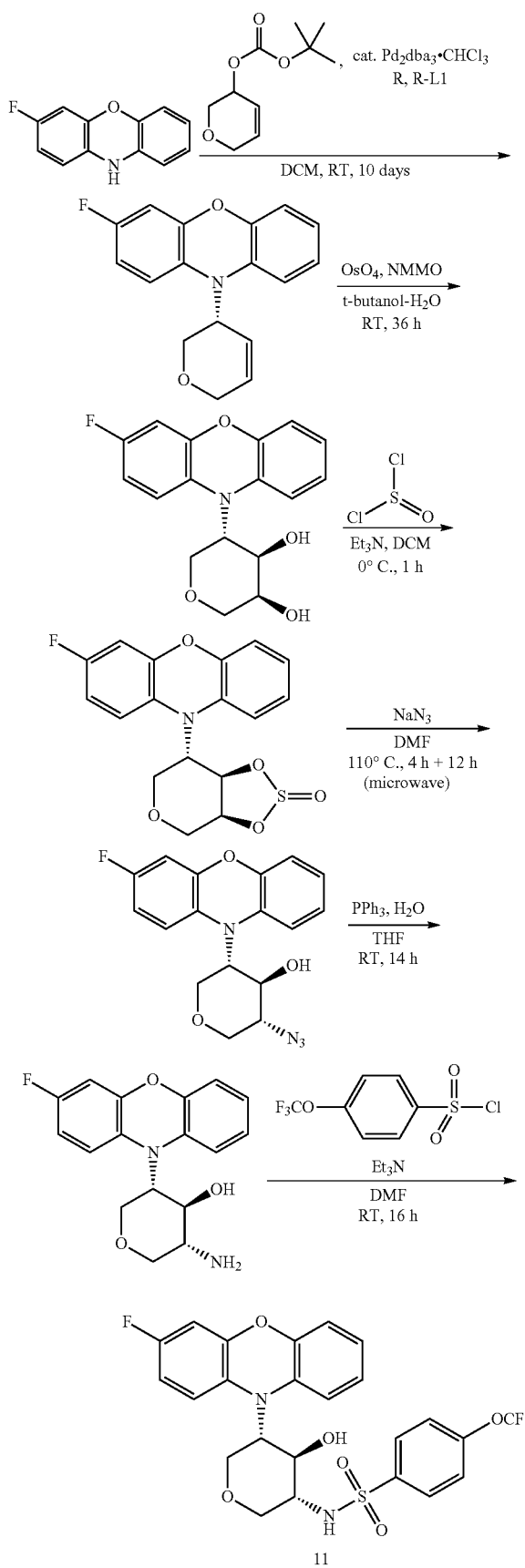
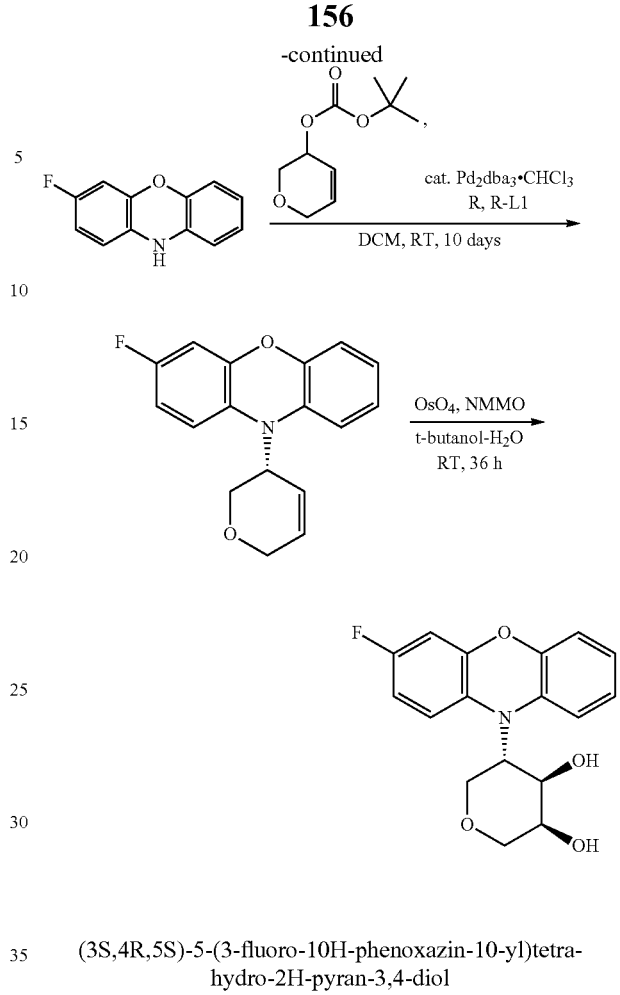

(3S,4R,5S)-5-(3-fluoro-10H-phenoxazin-10-yl)tetrahydro-2H-pyran-3,4-diol

Using the typical procedure 3-fluoro-10H-phenoxazine (0.402 g, 2.00 mmol) was reacted with tert-butyl (3,6-dihydro-2H-pyran-3-yl) carbonate (0.961 g, 4.80 mmol) in presence of (R,R)-L1 ligand for 10 days to afford crude (R)-10-(3,6-dihydro-2H-pyran-3-yl)-3-fluoro-10H-phenoxazine (0.570 g) which was taken to the next step without further purification.

Using the typical procedure (R)-10-(3,6-dihydro-2H-pyran-3-yl)-3-fluoro-10H-phenoxazine (0.570 g, 2.01 mmol) was transformed to (3S,4R,5S)-5-(3-fluoro-10H-phenoxazin-10-yl)tetrahydro-2H-pyran-3,4-diol (0.583 g, 92% over two steps) which was obtained as a white solid. $^1$H NMR (600 MHz, MeOD) δ 6.99-6.98 (1H, m), 6.90 (1H, td, J=7.8, 1.2 Hz), 6.82 (1H, td, J=7.8, 0.6 Hz), 6.77 (1H, dd, J=10.2, 2.4 Hz), 6.72 (1H, dd, J=8.4, 1.2 Hz), 6.70-6.68 (1H, m), 6.51 (1H, td, J=8.4, 3.0 Hz), 4.28 (1H, dd, J=10.2, 3.0 Hz), 4.10-4.05 (2H, m), 3.94-3.89 (2H, m), 3.80-3.77 (1H, m), 3.60 (1H, d, J=12.0 Hz); $^{13}$C NMR (150 MHz, MeOD) δ 160.0, 158.4, 149.1, 145.2, 136.9, 134.1, 123.5, 122.9, 117.8, 115.8, 115.7, 115.6, 107.8, 107.6, 105.0, 104.8, 71.0, 70.2, 68.5, 68.1, 61.9; Material produced in this fashion exhibited $[α]^{25}$D=+39.0° (c=1.0, CH$_3$OH). HPLC analysis: 96% ee (CHIRALPAK IA, 70:30:0.1 hexanes-EtOH-diethylamine, 1.0 mL/min, UV: 230 nm), tR=8.17 min (minor), 6.85 min (major); HRMS m/z 318.1137 ([M+H]$^+$, C$_{17}$H$_{17}$FNO$_4$ requires 318.1137).

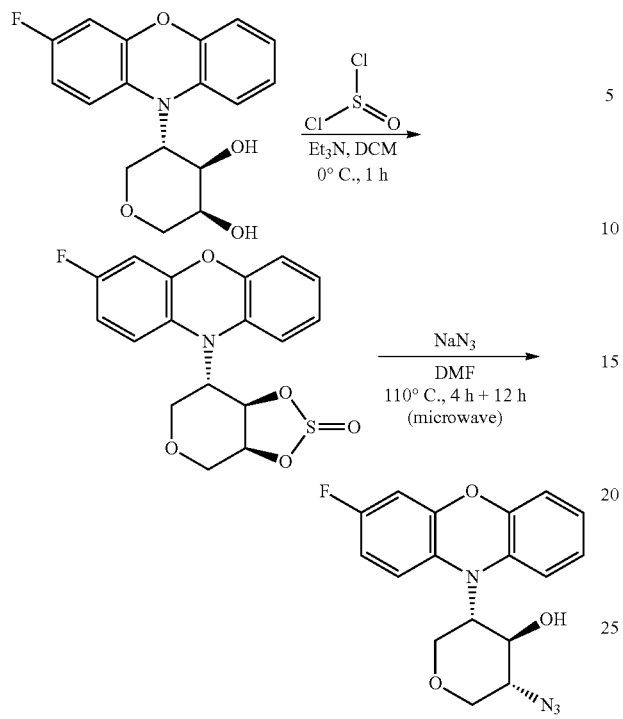

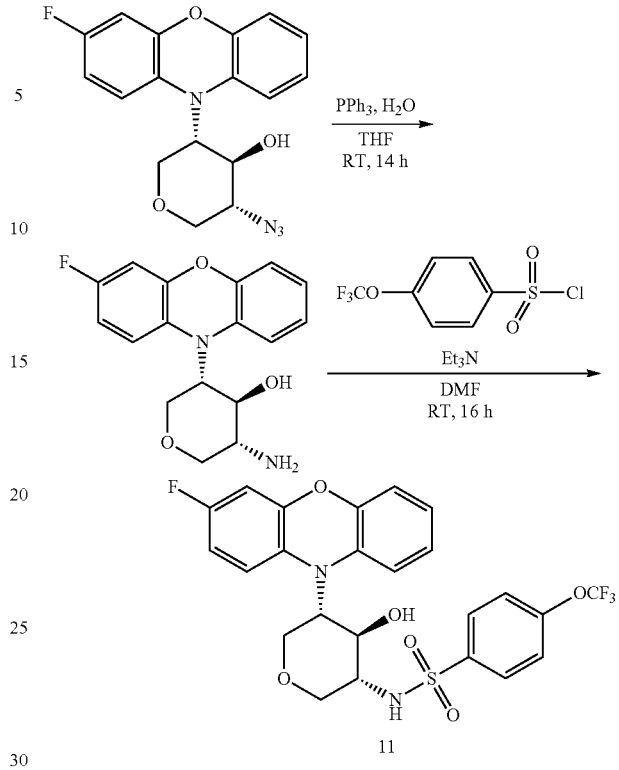

(3R,4R,5S)-3-azido-5-(3-fluoro-10H-phenoxazin-10-yl)tetrahydro-2H-pyran-4-ol

Using the typical procedure B.1 (3S,4R,5S)-5-(3-fluoro-10H-phenoxazin-10-yl)tetrahydro-2H-pyran-3,4-diol (0.558 g, 1.76 mmol) in dichloromethane (23.0 mL) was reacted with triethylamine (1.95 mL, 14.1 mmol), and thionyl chloride (0.191 mL, 2.64 mmol). The mixture was stirred at 0° C. for 2 h. Flash chromatography (SiO$_2$, 0%-50% ethylacetate-hexanes) afforded crude (3aS,7S,7aR)-7-(3-fluoro-10H-phenoxazin-10-yl)tetrahydro-3aH-[1,3,2]dioxathiolo[4,5-c]pyran 2-oxide (0.610 g) which was taken to the next step without further purification.

Using the typical procedure B.2 (3aS,7S,7aR)-7-(3-fluoro-10H-phenoxazin-10-yl)tetrahydro-3aH-[1,3,2]dioxathiolo[4,5-c]pyran 2-oxide (0.610 g, 1.68 mmol) in DMF (4.0 mL) was reacted with sodium azide (0.327 g, 5.04 mmol) at 110° C. for 4 h, (pressure was released from the vial), then 110° C. for 12 h. Purification by flash chromatography (SiO$_2$, 6%-13% ethylacetate-hexanes) afforded (3R,4R,5S)-3-azido-5-(3-fluoro-10H-phenoxazin-10-yl)tetrahydro-2H-pyran-4-ol (0.388 g, 65% over two steps). $^1$H NMR (600 MHz, MeOD) δ 6.97 (1H, dd, J=7.8, 1.2 Hz), 6.93 (1H, td, J=7.8, 1.2 Hz), 6.86 (1H, td, J=7.8, 1.2 Hz), 6.77-6.71 (3H, m), 6.55 (1H, td, J=10.8, 2.4 Hz), 4.14 (1H, t, J=10.2 Hz), 4.09 (1H, dd, J=11.4, 4.8 Hz), 3.95 (1H, dd, J=11.4, 4.8 Hz), 3.83 (1H, t, J=11.4 Hz), 3.69 (1H, td, J=10.8, 5.4 Hz), 3.56-3.52 (1H, m), 3.20 (1H, t, J=10.8 Hz); $^{13}$C NMR (150 MHz, MeOD) δ 160.0, 158.4, 149.2, 145.3, 136.7, 133.8, 123.5, 123.2, 118.1, 116.0, 115.9, 115.8, 108.1, 108.0, 105.2, 105.0, 71.9, 68.5, 68.2, 66.1, 64.3; LCMS m/z 343.0754 ([M+H$^+$], C$_{17}$H$_{16}$FH$_4$O$_3$ requires 343.120).

N-((3R,4R,5S)-5-(3-fluoro-10H-phenoxazin-10-yl)-4-hydroxytetrahydro-2H-pyran-3-yl)-4-(trifluoromethoxy)benzenesulfonamide (11)

Using the typical procedure C.1 (3R,4R,5S)-3-azido-5-(3-fluoro-10H-phenoxazin-10-yl)tetrahydro-2H-pyran-4-ol (0.374 g, 1.09 mmol) in THF (4.0 mL) was reacted with triphenylphosphine (0.315 g, 1.20 mmol), and water (0.002 mL, 0.110 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-3-amino-5-(3-fluoro-10H-phenoxazin-10-yl)tetrahydro-2H-pyran-4-ol (0.331 g) which was taken to the next step without further purification.

Using the typical procedure C.2 (3R,4S,5S)-3-amino-5-(3-fluoro-10H-phenoxazin-10-yl)tetrahydro-2H-pyran-4-ol (0.165 g, 0.522 mmol) in DMF (1.70 mL) was reacted with triethylamine (0.291 mL, 2.91 mmol), and 4-(trifluoromethoxy)benzene-1-sulfonyl chloride (0.097 mL, 0.574 mmol). Purification by flash chromatography (SiO$_2$, 17%-20% ethylacetate-hexanes) afforded N-((3R,4R,5S)-5-(3-fluoro-10H-phenoxazin-10-yl)-4-hydroxytetrahydro-2H-pyran-3-yl)-4-(trifluoromethoxy)benzenesulfonamide 11 (0.119 g, 40% over two steps). $^1$H NMR (600 MHz, MeOD) δ 7.99 (2H, d, J=9.0 Hz), 7.41 (2H, d, J=9.0 Hz), 7.41 (2H, d, J=8.4 Hz), 6.92-6.88 (2H, m), 6.85-6.82 (1H, m), 6.74-6.68 (3H, m), 6.53 (1H, td, J=8.4, 1.8 Hz), 4.07-4.01 (2H, m), 3.86-3.84 (1H, m), 3.77 (1H, t, J=11.4 Hz), 3.60 (1H, td, J=10.8, 5.4 Hz), 3.26-3.18 (2H, m); $^{13}$C NMR (150 MHz, MeOD) δ 159.9, 158.4, 151.8, 149.2, 145.3, 140.4, 136.5, 133.9, 129.3, 123.5, 123.1, 120.8, 118.0, 116.0, 115.9, 115.7, 108.1, 108.0, 105.3, 105.1, 70.3, 69.8, 68.2, 66.6, 57.3; Material produced in this fashion exhibited [α]$^{25}$D=+13.0° (c=1.0, CH$_3$OH). HPLC analysis: >99% ee (CHIRALPAK OZ-H, 70:30 hexanes-EtOH, 1.0 mL/min, UV: 230 nm), tR=6.04 min. LCMS m/z 541.0242 ([M+H$^+$], $C_{24}H_{21}F_4N_2O_6S$ requires 541.1051).

Group III (Pyran-Carbazole):

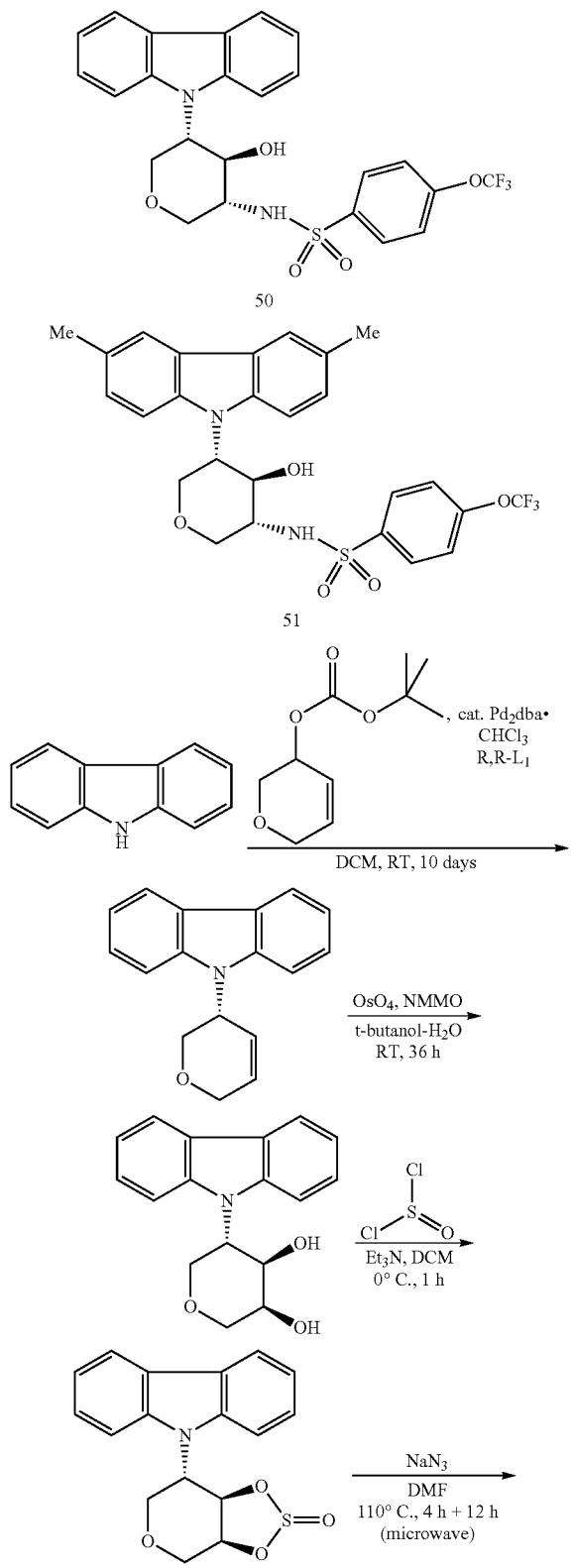

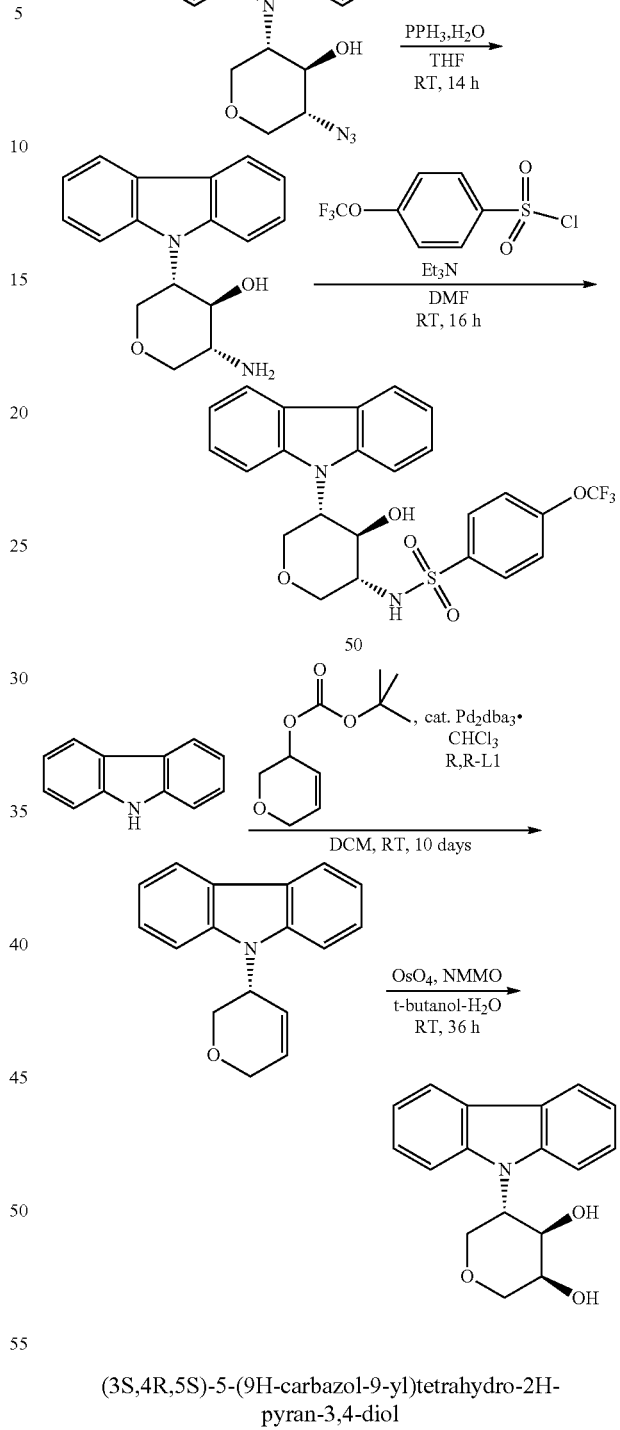

(3S,4R,5S)-5-(9H-carbazol-9-yl)tetrahydro-2H-pyran-3,4-diol

Using the typical procedure A.1 9H-carbazole (0.334 g, 2.00 mmol) was reacted with tert-butyl (3,6-dihydro-2H-pyran-3-yl) carbonate (0.961 g, 4.80 mmol) in presence of (R,R)-L1 ligand for 10 days to afford crude (R)-9-(3,6-dihydro-2H-pyran-3-yl)-9H-carbazole (0.234 g) which was taken to the next step without further purification.

Using the typical procedure A.2 (R)-9-(3,6-dihydro-2H-pyran-3-yl)-9H-carbazole (0.234 g, 0.939 mmol) was transformed to (3S,4R,5S)-5-(9H-carbazol-9-yl)tetrahydro-2H-pyran-3,4-diol (0.129 g, 23% over two steps) which was obtained as a white solid. NMR (600 MHz, MeOD) δ 8.06 (2H, d, J=7.8 Hz), 7.66 (2H, bs), 7.41 (2H, t, J=7.8 Hz), 7.18 (2H, t, J=7.8 Hz), 5.06 (1H, td, J=11.4, 5.4 Hz), 4.76 (1H, dd, J=10.8, 3.0 Hz), 4.23 (1H, t, J=11.4 Hz), 4.04-4.02 (2H, m), 3.90 (1H, dd, J=10.8, 4.8 Hz), 3.81 (1H, d, J=11.4 Hz); $^{13}$C NMR (150 MHz, MeOD) δ 125.4, 123.3, 119.8, 118.8, 111.2, 109.3, 71.1, 69.7, 68.4, 66.8, 54.1; Material produced in this fashion exhibited [α]$^{25}$D=+9.0° (c=1.0, CH$_3$OH). HPLC analysis: >99% ee (CHIRALPAK IA, 70:30:0.1 hexanes-EtOH-diethylamine, 1.0 mL/min), tR=7.16 min. HRMS m/z 284.1283 ([M+H$^+$], C$_{17}$H$_{18}$NO$_3$ requires 284.1282).

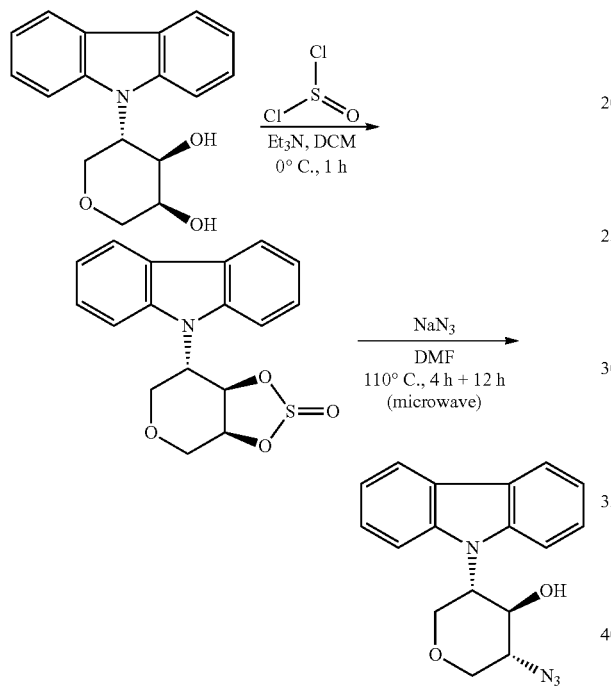

(3R,4R,5S)-3-azido-5-(9H-carbazol-9-yl)tetrahydro-2H-pyran-4-ol

Using the typical procedure B.1 (3S,4R,5S)-5-(9H-carbazol-9-yl)tetrahydro-2H-pyran-3,4-diol (0.109 g, 0.385 mmol) in dichloromethane (10.0 mL) was reacted with triethylamine (0.426 mL, 3.08 mmol), and thionyl chloride (0.042 mL, 0.577 mmol). The mixture was stirred at 0° C. for 1 h. Flash chromatography (SiO$_2$, 20%-33% ethylacetate-hexanes) afforded crude (3aS,7S,7aR)-7-(9H-carbazol-9-yl)tetrahydro-3aH-[1,3,2]dioxathiolo[4,5-c]pyran 2-oxide (0.123 g) which was taken to the next step without further purification.

Using the typical procedure B.2 (3aS,7S,7aR)-7-(9H-carbazol-9-yl)tetrahydro-3aH-[1,3,2]dioxathiolo[4,5-c]pyran 2-oxide (0.123 g, 0.373 mmol) in DMF (2.0 mL) was reacted with sodium azide (0.327 g, 5.04 mmol) at 110° C. for 4 h, (pressure was released from the vial), then 110° C. for 12 h. Purification by flash chromatography (SiO$_2$, 6%-20% ethylacetate-hexanes) afforded (3R,4R,5S)-3-azido-5-(9H-carbazol-9-yl)tetrahydro-2H-pyran-4-ol (0.079 g, 67% over two steps). $^1$H NMR (600 MHz, MeOD) δ 8.08 (2H, dd, J=21.6, 7.2 Hz), 7.73 (1H, d, J=8.4 Hz), 7.58 (1H, d, J=8.4 Hz), 7.46-7.40 (2H, m), 7.21-7.20 (2H, m), 4.73-4.71 (1H, m), 4.65 (1H, t, J=9.6 Hz), 4.33 (1H, t, J=11.4 Hz), 4.09 (1H, dd, J=10.8, 4.2 Hz), 3.93 (1H, dd, J=10.8, 4.2 Hz), 3.75-3.71 (1H, m), 3.47 (1H, t, J=11.4 Hz); $^{13}$C NMR (150 MHz, MeOD) δ 141.9, 138.7, 125.7, 125.3, 124.3, 122.9, 120.1, 119.5, 119.1, 119.0, 111.3, 109.0, 71.9, 68.7, 66.8, 63.7, 57.8; LCMS m/z 309.0 ([M+H$^+$], C$_{17}$H$_{17}$N$_4$O$_2$ requires 309.1).

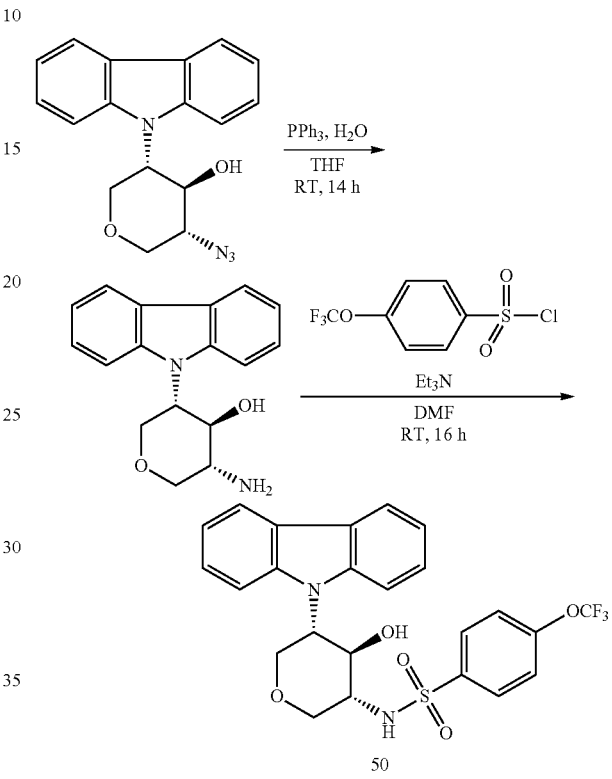

N-((3R,4R,5S)-5-(9H-carbazol-9-yl)-4-hydroxytetrahydro-2H-pyran-3-yl)-4-(trifluoromethoxy)benzenesulfonamide (50)

Using the typical procedure C.1 (3R,4R,5S)-3-azido-5-(9H-carbazol-9-yl)tetrahydro-2H-pyran-4-ol (0.079 g, 0.256 mmol) in THF (2.0 mL) was reacted with triphenylphosphine (0.074 g, 0.282 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-3-amino-5-(9H-carbazol-9-yl)tetrahydro-2H-pyran-4-ol (0.068 g) which was taken to the next step without further purification.

Using the typical procedure C.2 (3R,4S,5S)-3-amino-5-(9H-carbazol-9-yl)tetrahydro-2H-pyran-4-ol (0.068 g, 0.240 mmol) in DMF (1.0 mL) was reacted with triethylamine (0.134 mL, 0.963 mmol), and 4-(trifluoromethoxy)benzene-1-sulfonyl chloride (0.044 mL, 0.264 mmol). Purification by flash chromatography (SiO$_2$, 17%-20% ethylacetate-hexanes) afforded N-((3R,4R,5S)-5-(9H-carbazol-9-yl)-4-hydroxytetrahydro-2H-pyran-3-yl)-4-(trifluoromethoxy)benzenesulfonamide 50 (0.018 g, 14% over two steps). $^1$H NMR (600 MHz, MeOD) δ 8.08 (1H, d, J=7.8 Hz), 8.03-8.02 (3H, m), 7.68 (1H, d, J=8.4 Hz), 7.53 (1H, d, J=7.8 Hz), 7.41-7.38 (4H, m), 7.20-7.16 (2H, m), 4.67-4.63 (1H, m), 4.55 (1H, t, J=9.0 Hz), 4.28 (1H, t, J=11.4 Hz), 4.05-4.03 (1H, m), 3.90 (1H, dd, J=10.8, 4.8 Hz), 3.51-3.43 (2H, m); $^{13}$C NMR (150 MHz, MeOD) δ 151.8, 141.8, 140.5, 138.6, 129.3, 125.7, 125.2, 124.3, 122.8, 120.8, 120.2, 119.5, 119.0, 118.9, 111.2, 109.0, 70.5, 69.9, 66.8, 58.3, 56.9; Material produced in this fashion exhibited [α]$^{25}$D=−22.2° (c=1.0, CH$_3$OH). HPLC analysis: >99% ee (CHIRALPAK OZ-H, 70:30 hexanes-EtOH, 1.0 mL/min, UV: 254 nm), tR=5.75 min. LCMS m/z 507.1 ([M+H$^+$], C$_{24}$H$_{22}$F$_3$N$_2$O$_5$S requires 507.1).

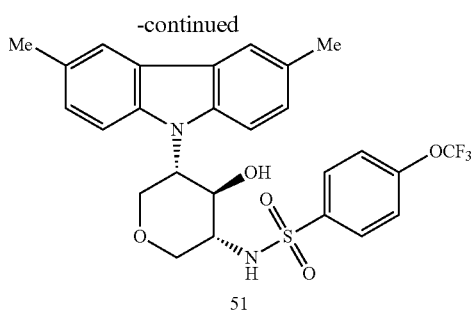

51

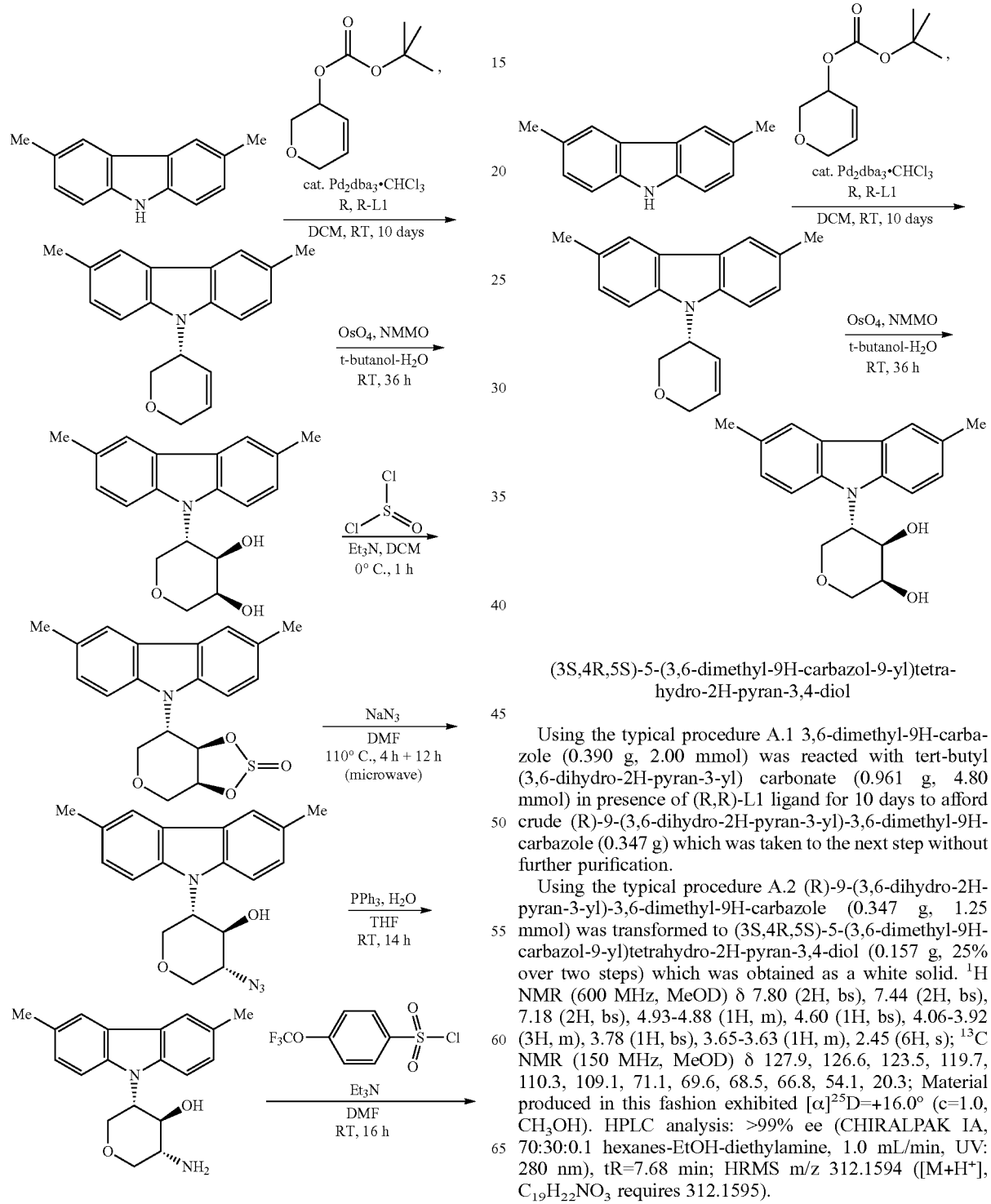

(3S,4R,5S)-5-(3,6-dimethyl-9H-carbazol-9-yl)tetrahydro-2H-pyran-3,4-diol

Using the typical procedure A.1 3,6-dimethyl-9H-carbazole (0.390 g, 2.00 mmol) was reacted with tert-butyl (3,6-dihydro-2H-pyran-3-yl) carbonate (0.961 g, 4.80 mmol) in presence of (R,R)-L1 ligand for 10 days to afford crude (R)-9-(3,6-dihydro-2H-pyran-3-yl)-3,6-dimethyl-9H-carbazole (0.347 g) which was taken to the next step without further purification.

Using the typical procedure A.2 (R)-9-(3,6-dihydro-2H-pyran-3-yl)-3,6-dimethyl-9H-carbazole (0.347 g, 1.25 mmol) was transformed to (3S,4R,5S)-5-(3,6-dimethyl-9H-carbazol-9-yl)tetrahydro-2H-pyran-3,4-diol (0.157 g, 25% over two steps) which was obtained as a white solid. $^1$H NMR (600 MHz, MeOD) δ 7.80 (2H, bs), 7.44 (2H, bs), 7.18 (2H, bs), 4.93-4.88 (1H, m), 4.60 (1H, bs), 4.06-3.92 (3H, m), 3.78 (1H, bs), 3.65-3.63 (1H, m), 2.45 (6H, s); $^{13}$C NMR (150 MHz, MeOD) δ 127.9, 126.6, 123.5, 119.7, 110.3, 109.1, 71.1, 69.6, 68.5, 66.8, 54.1, 20.3; Material produced in this fashion exhibited [α]$^{25}$D=+16.0° (c=1.0, CH$_3$OH). HPLC analysis: >99% ee (CHIRALPAK IA, 70:30:0.1 hexanes-EtOH-diethylamine, 1.0 mL/min, UV: 280 nm), tR=7.68 min; HRMS m/z 312.1594 ([M+H$^+$], C$_{19}$H$_{22}$NO$_3$ requires 312.1595).

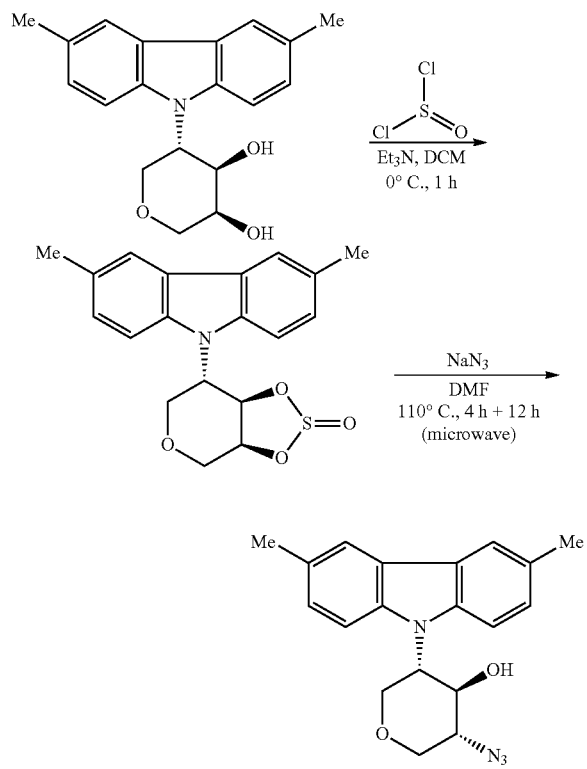
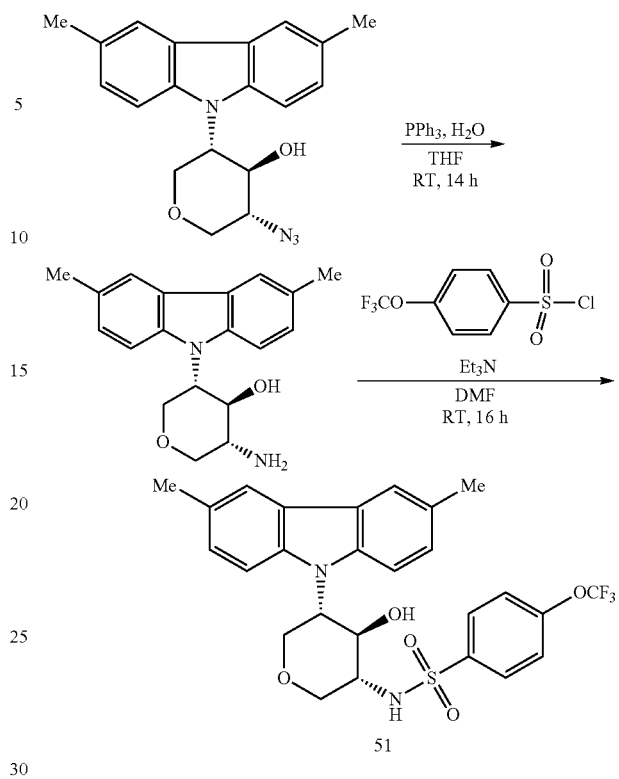

(3R,4R,5S)-3-azido-5-(3,6-dimethyl-9H-carbazol-9-yl)tetrahydro-2H-pyran-4-ol Using the typical procedure B.1 (3S,4R,5S)-5-(3,6-dimethyl-9H-carbazol-9-yl)tetrahydro-2H-pyran-3,4-diol (0.141 g, 0.453 mmol) in dichloromethane (10.0 mL) was reacted with triethylamine (0.502 mL, 3.62 mmol), and thionyl chloride (0.042 mL, 0.675 mmol). The mixture was stirred at 0° C. for 1 h. Flash chromatography (SiO$_2$, 17% ethylacetate-hexanes) afforded crude (3aS,7S,7aR)-7-(3,6-dimethyl-9H-carbazol-9-yl)tetrahydro-3aH-[1,3,2]dioxathiolo[4,5-c]pyran 2-oxide (0.120 g) which was taken to the next step without further purification.

Using the typical procedure B.2 (3aS,7S,7aR)-7-(3,6-dimethyl-9H-carbazol-9-yl)tetrahydro-3aH-[1,3,2]dioxathiolo[4,5-c]pyran 2-oxide (0.120 g, 0.335 mmol) in DMF (2.0 mL) was reacted with sodium azide (0.065 g, 1.01 mmol) at 110° C. for 4 h, (pressure was released from the vial), then 110° C. for 12 h. Purification by flash chromatography (SiO$_2$, 6%-20% ethylacetate-hexanes) afforded (3R,4R,5S)-3-azido-5-(3,6-dimethyl-9H-carbazol-9-yl)tetrahydro-2H-pyran-4-ol (0.079 g, 52% over two steps). $^1$H NMR (600 MHz, MeOD) δ 7.83 (2H, d, J=22.8 Hz), 7.55 (1H, d, J=7.2 Hz), 7.40 (1H, d, J=7.2 Hz), 7.22 (2H, dd, J=16.8, 7.2 Hz), 4.60 (2H, br s), 4.25 (1H, t, J=10.8 Hz), 4.07-4.06 (1H, m), 3.88-3.86 (1H, m), 3.70 (1H, br s), 3.43 (1H, t, J=11.4 Hz), 2.48 (6H, br s); $^{13}$C NMR (150 MHz, MeOD) δ 140.5, 137.2, 128.17, 128.11, 126.8, 126.4, 124.3, 122.8, 120.0, 119.4, 110.9, 108.6, 72.0, 68.7, 66.9, 63.7, 57.8, 20.15, 20.10; LCMS m/z 337.0 ([M+H$^+$], C$_{19}$H$_{21}$N$_4$O$_2$ requires 337.1).

N-((3R,4R,5S)-5-(3,6-dimethyl-9H-carbazol-9-yl)-4-hydroxytetrahydro-2H-pyran-3-yl)-4-(trifluoromethoxy)benzenesulfonamide (51)

Using the typical procedure C.1 (3R,4R,5S)-3-azido-5-(3,6-dimethyl-9H-carbazol-9-yl)tetrahydro-2H-pyran-4-ol (0.079 g, 0.234 mmol) in THF (2.0 mL) was reacted with triphenylphosphine (0.068 g, 0.258 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-3-amino-5-(3,6-dimethyl-9H-carbazol-9-yl)tetrahydro-2H-pyran-4-ol (0.060 g) which was taken to the next step without further purification.

Using the typical procedure C.2 (3R,4S,5S)-3-amino-5-(3,6-dimethyl-9H-carbazol-9-yl)tetrahydro-2H-pyran-4-ol (0.060 g, 0.193 mmol) in DMF (1.0 mL) was reacted with triethylamine (0.107 mL, 0.773 mmol), and 4-(trifluoromethoxy)benzene-1-sulfonyl chloride (0.036 mL, 0.212 mmol). Purification by flash chromatography (SiO$_2$, 17%-20% ethylacetate-hexanes) afforded N-((3R,4R,5S)-5-(3,6-dimethyl-9H-carbazol-9-yl)-4-hydroxytetrahydro-2H-pyran-3-yl)-4-(trifluoromethoxy)benzenesulfonamide 51 (0.017 g, 14% over two steps). NMR (600 MHz, MeOD) δ 8.02 (2H, d, J=8.4 Hz), 7.84 (1H, br s), 7.79 (1H, br s), 7.52 (1H, d, J=8.4 Hz), 7.40 (2H, d, J=8.4 Hz), 7.36 (1H, d, J=8.4 Hz), 7.20 (2H, t, J=6.6 Hz), 4.57-4.48 (2H, m), 4.21 (1H, t, J=10.8 Hz), 4.03-4.02 (1H, m), 3.85 (1H, dd, J=10.8, 4.8 Hz), 3.47-3.42 (2H, m), 2.46 (6H, br s); $^{13}$C NMR (150 MHz, MeOD) δ 151.8, 140.5, 140.4, 137.1, 129.3, 128.1, 128.0, 126.8, 126.3, 124.3, 122.7, 120.8, 120.0, 119.3, 110.8, 108.6, 70.5, 70.0, 66.8, 58.3, 56.9, 20.11, 20.0; Material produced in this fashion exhibited [α]$^{25}$D=−8.8° (c=0.34, CH$_3$OH). HPLC analysis: >99% ee (CHIRALPAK OZ-H, 70:30 hexanes-EtOH, 1.0 mL/min, UV: 254 nm), tR=5.80 min. LCMS m/z 535.0 ([M+H$^+$], C$_{26}$H$_{26}$F$_3$N$_2$O$_5$S requires 535.1).
Group IV (Piperidine-Carbazole):
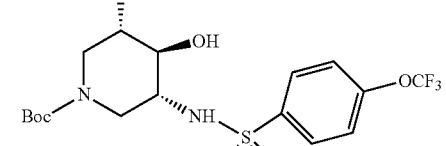
52a
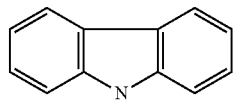
41a
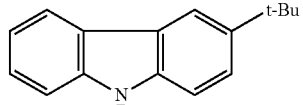
53a
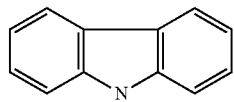
52b
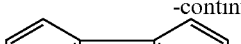
-continued
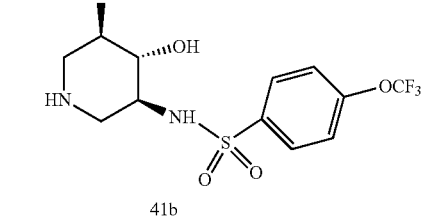
41b
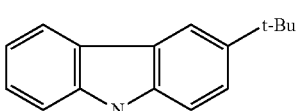
53b
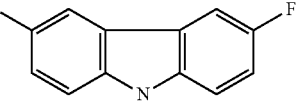
54
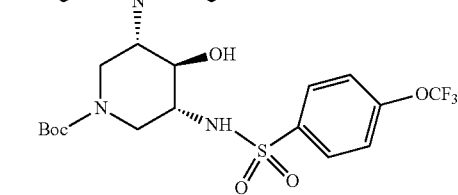
56
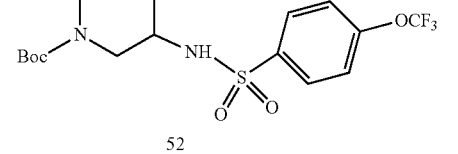
52

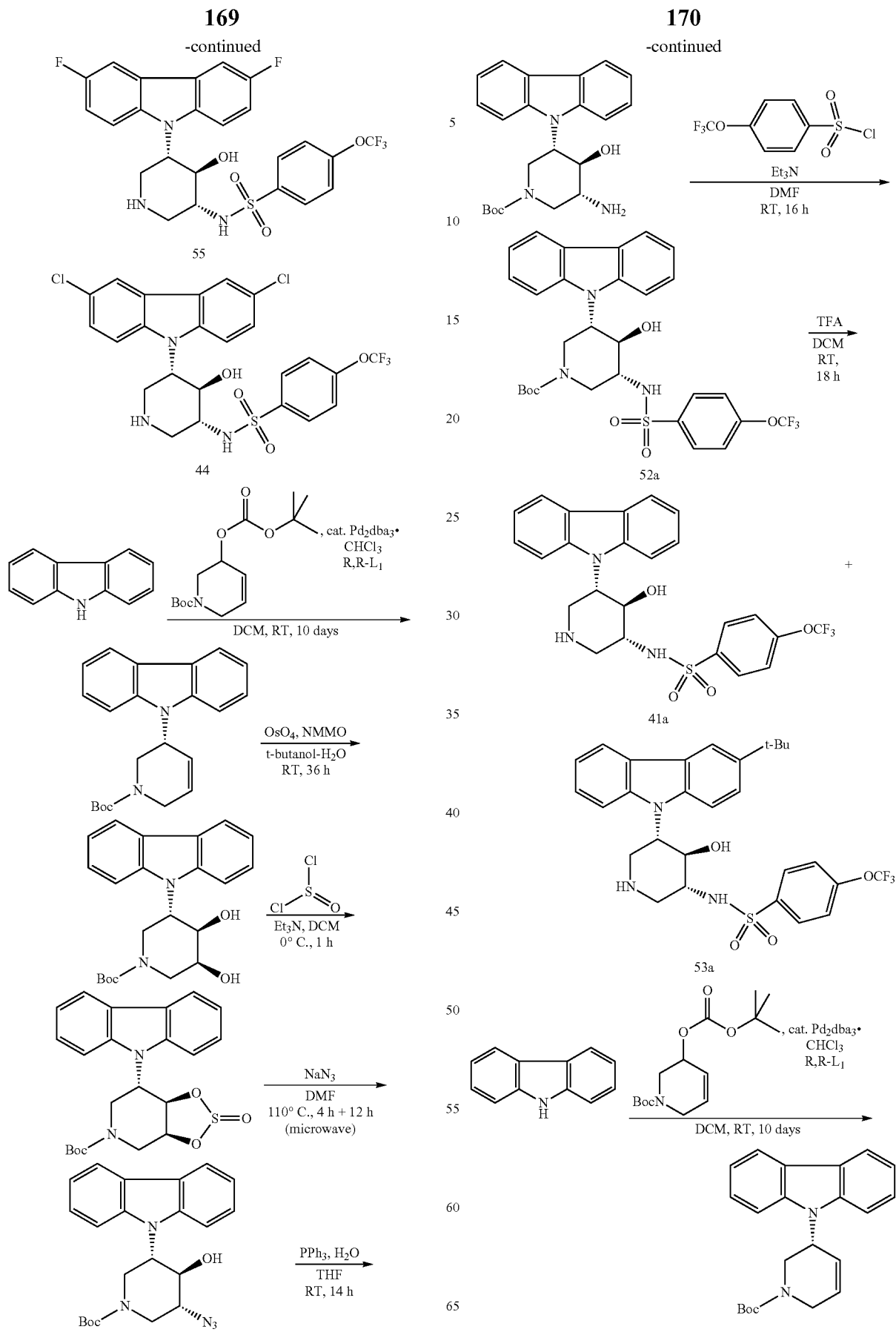

(R)-tert-butyl 5-(9H-carbazol-9-yl)-5,6-dihydropyridine-1(2H)-carboxylate

Using the typical procedure A.1 9H-carbazole (0.334 g, 2.00 mmol) was reacted with tert-butyl (3,6-dihydro-2H-pyran-3-yl) carbonate (1.44 g, 4.80 mmol) in presence of (R,R)-L1 ligand for 10 days to afford tert-butyl 5-((tert-butoxycarbonyl)oxy)-5,6-dihydropyridine-1(2H)-carboxylate (0.448 g, 64%) as a white solid. $^1$H NMR (600 MHz, MeOD) δ (mixture of rotamers) 8.07 (2H, d, J=7.8 Hz), 7.58 (2H, d, J=8.4 Hz), 7.37 (2H, br s), 7.18 (2H, t, J=7.2 Hz), 6.24-6.13 (2H, m), 5.44-5.40 (1H, m), 4.32-4.02 (3H, m), [1H, 3.83 (br s), 3.52 (br s)], [9H, 1.46 (br s), 1.08 (br s)]; $^{13}$C NMR (150 MHz, MeOD) δ 140.5, 129.0, 127.4, 126.3, 125.4, 123.4, 119.8, 119.0, 109.8, 49.8, 49.5, 44.7, 43.4, 42.8, 42.4, 27.4, 26.9; HRMS m/z 249.1385 ([M+H$^+$−100], $C_{17}H_{18}NO_3$ requires 249.1387).

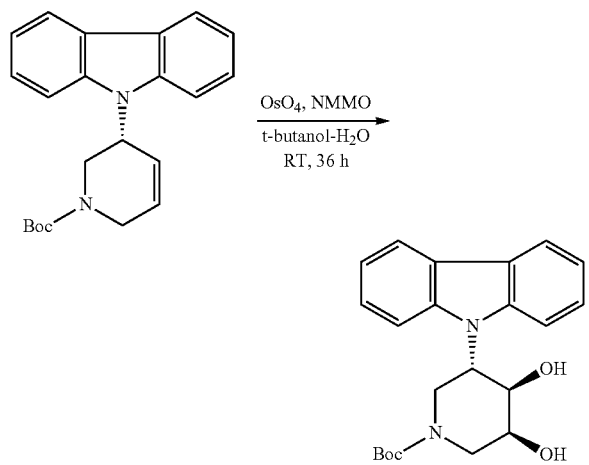

(3S,4R,5S)-tert-butyl 3-(9H-carbazol-9-yl)-4,5-dihydroxypiperidine-1-carboxylate Using the typical procedure A.2 tert-butyl 5-((tert-butoxycarbonyl)oxy)-5,6-dihydropyridine-1(2H)-carboxylate (0.430 g, 1.23 mmol) was transformed to (3S,4R,5S)-tert-butyl 3-(9H-carbazol-9-yl)-4,5-dihydroxypiperidine-1-carboxylate (0.401 g, 85%) which was obtained as a white solid. $^1$H NMR (600 MHz, MeOD) δ (mixture of rotamers) 8.08-8.07 (2H, m), 7.72-7.59 (2H, m), 7.41-7.38 (2H, m), 7.20-7.18 (2H, m), 4.96-4.95 (1H, m), 4.74-4.72 (1H, m), 4.37-4.30 (1H, m), 4.18-4.10 (2H, m), [1H, 3.68-3.66 (m), 3.19 (br s)], [9H, 1.50 (br s), 1.44 (br s)]; Material produced in this fashion exhibited $[\alpha]^{25}_D$=+19.0° (c=1.0, CH$_3$OH). HPLC analysis: >99% ee (CHIRALPAK IA-3, 80:20:0.1 hexanes-EtOH-diethylamine, 1.0 mL/min), tR=1.60 min; HRMS m/z 283.1442 ([M+H$^f$], $C_{17}H_{19}N_2O_2$ requires 283.1442).

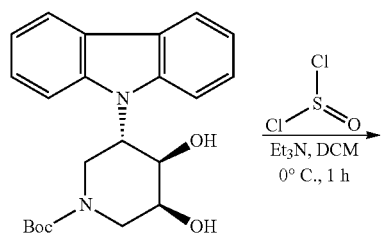

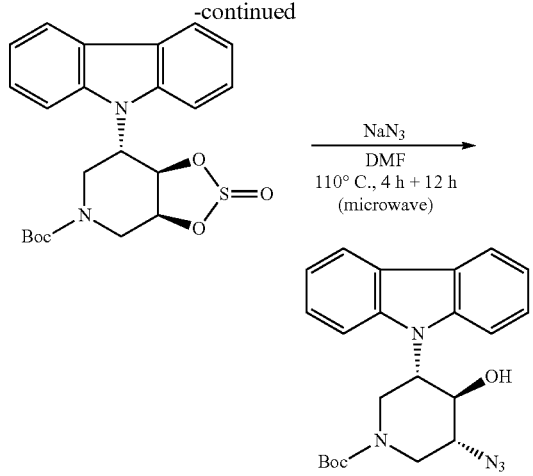

(3R,4R,5S)-tert-butyl 3-azido-5-(9H-carbazol-9-yl)-4-hydroxypiperidine-1-carboxylate Using the typical procedure B.1 (3S,4R,5S)-tert-butyl 3-(9H-carbazol-9-yl)-4,5-dihydroxypiperidine-1-carboxylate (0.404 g, 1.06 mmol) in dichloromethane (13.5 mL) was reacted with triethylamine (1.17 mL, 8.48 mmol), and thionyl chloride (0.115 mL, 1.58 mmol). The mixture was stirred at 0° C. for 2 h. Flash chromatography (SiO$_2$, 0%-50% ethylacetate-hexanes) afforded crude (3aS,7S,7aR)-tert-butyl 7-(9H-carbazol-9-yl)tetrahydro-[1,3,2]dioxathiolo[4,5-c]pyridine-5(6H)-carboxylate 2-oxide (0.305 g) which was taken to the next step without further purification.

Using the typical procedure B.2 (3aS,7S,7aR)-tert-butyl 7-(9H-carbazol-9-yl)tetrahydro-[1,3,2]dioxathiolo[4,5-c]pyridine-5(6H)-carboxylate 2-oxide (0.305 g, 0.712 mmol) in DMF (3.0 mL) was reacted with sodium azide (0.138 g, 2.14 mmol) at 110° C. for 4 h, (pressure was released from the vial), then 110° C. for 12 h. Purification by flash chromatography (SiO$_2$, 6%-13% ethylacetate-hexanes) afforded (3R,4R,5S)-tert-butyl 3-azido-5-(9H-carbazol-9-yl)-4-hydroxypiperidine-1-carboxylate (0.200 g, 47% over two steps). $^1$H NMR (600 MHz, MeOD) δ 8.09 (2H, dd, J=21.6, 7.8 Hz), 7.73 (1H, d, J=8.4 Hz), 7.53 (1H, d, J=7.8 Hz), 7.43-7.40 (2H, m), 7.21 (2H, t, J=7.2 Hz), 4.62 (1H, t, J=10.2 Hz), 4.57 (1H, td, J=15.0, 10.2 Hz), 4.30 (1H, br s), 4.15-4.07 (1H, m), 3.80 (1H, br s), 3.61-3.57 (1H, m), 2.93 (1H, br s), 1.46 (9H, br s); $^{13}$C NMR (150 MHz, MeOD) δ 154.9, 141.8, 138.6, 125.7, 125.4, 124.3, 122.9, 120.2, 119.6, 119.1, 111.3, 108.8, 81.0, 72.7, 63.2, 57.3, 27.3; LCMS m/z 308.0300 ([M−Boc+H$^+$], $C_{17}H_{18}N_5O$ requires 308.1506).

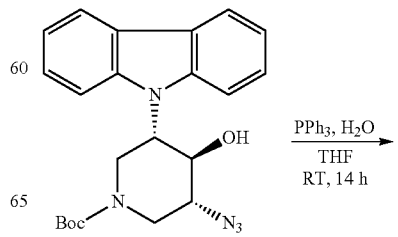

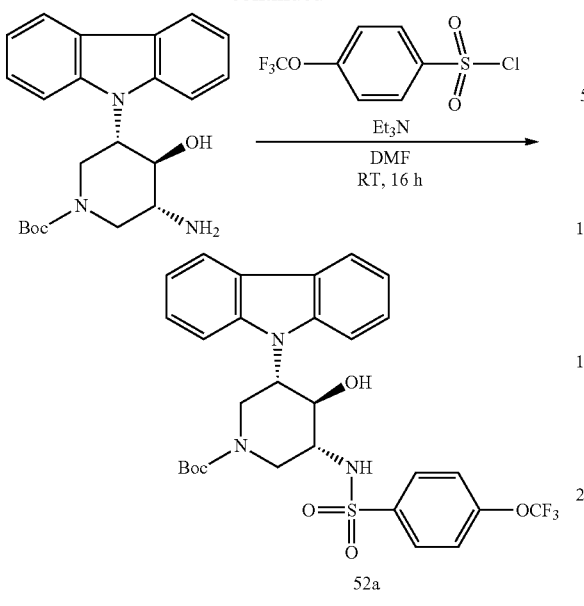

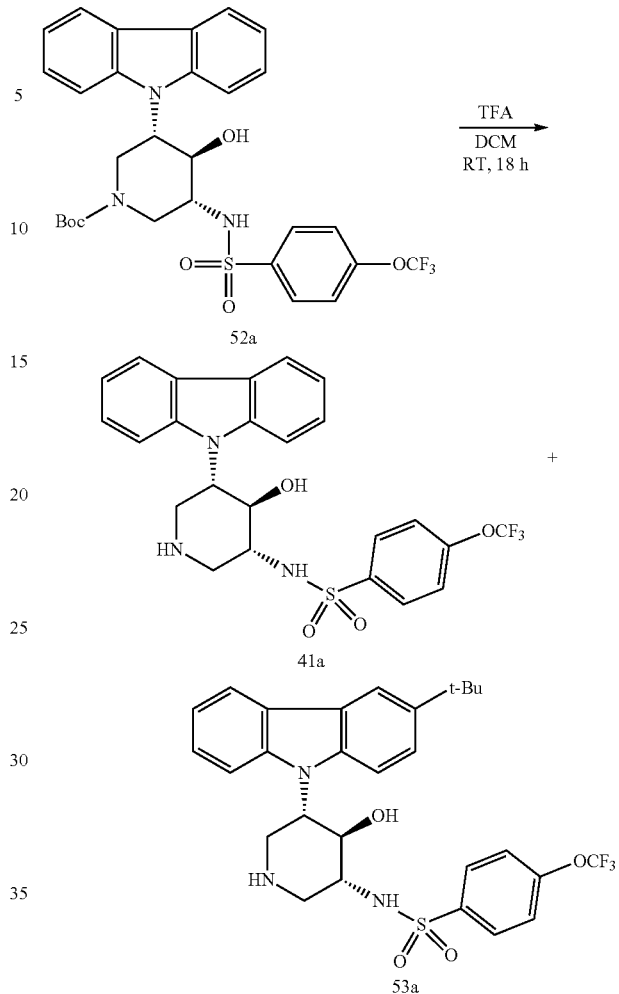

(3S,4R,5R)-tert-butyl 3-(9H-carbazol-9-yl)-4-hydroxy-5-(4-(trifluoromethoxy)phenylsulfonamido)piperidine-1-carboxylate (52a)

Using the typical procedure C.1 (3R,4R,5S)-tert-butyl 3-azido-5-(9H-carbazol-9-yl)-4-hydroxypiperidine-1-carboxylate (0.190 g, 0.466 mmol) in THF (2.05 mL) was reacted with triphenylphosphine (0.135 g, 0.512 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-tert-butyl 3-amino-5-(9H-carbazol-9-yl)-4-hydroxypiperidine-1-carboxylate (0.195 g) which was taken to the next step without further purification.

Using the typical procedure C.2 (3R,4S,5S)-tert-butyl 3-amino-5-(9H-carbazol-9-yl)-4-hydroxypiperidine-1-carboxylate (0.195 g, 0.511 mmol) in DMF (1.65 mL) was reacted with triethylamine (0.285 mL, 2.04 mmol), and 4-(trifluoromethoxy)benzene-1-sulfonyl chloride (0.095 mL, 0.562 mmol). Purification by flash chromatography (SiO$_2$, 17%-25% acetone-hexanes) afforded (3S,4R,5R)-tert-butyl 3-(9H-carbazol-9-yl)-4-hydroxy-5-(4-(trifluoromethoxy)phenylsulfonamido)piperidine-1-carboxylate 52a (0.117 g, 41% over two steps). $^1$H NMR (600 MHz, MeOD) δ 8.10 (1H, d, J=7.8 Hz), 8.06-8.03 (3H, m), 7.68 (1H, d, J=7.8 Hz), 7.49 (1H, d, J=8.4 Hz), 7.44-7.38 (4H, m), 7.21-7.17 (2H, m), 4.54-4.47 (2H, m), 4.33 (1H, br s), 4.10 (1H, br s), 3.72 (1H, br s), 2.99-2.91 (1H, m), 1.47 (9H, br s); $^{13}$C NMR (150 MHz, MeOD) δ 154.9, 151.8, 150.0, 141.7, 140.5, 138.5, 129.3, 128.1, 125.7, 125.3, 124.3, 122.8, 121.3, 121.0, 120.9, 120.2, 119.6, 119.0, 111.2, 109.5, 89.5, 80.8, 70.6, 57.5, 56.6, 27.3; Material produced in this fashion exhibited [α]$^{25}$D=+18.0° (c=1.0, CH$_3$OH). HPLC analysis: 98% ee (CHIRALPAK IA, 70:30 hexanes-EtOH, 1.0 mL/min, UV: 230 nm), tR=4.49 min (minor), 5.34 (major). LCMS m/z 506.1358 ([M−Boc+H$^+$], C$_{24}$H$_{23}$F$_3$N$_3$O$_4$S requires 506.1356).

N-((3R,4R,5S)-5-(9H-carbazol-9-yl)-4-hydroxypiperidin-3-yl)-4-(trifluoromethoxy)benzenesulfonamide (41a) & N-((3R,4R,5S)-5-(3-(tert-butyl)-9H-carbazol-9-yl)-4-hydroxypiperidin-3-yl)-4-(trifluoromethoxy)benzenesulfonamide (53a)

Using the typical procedure D (3S,4R,5R)-tert-butyl 3-(9H-carbazol-9-yl)-4-hydroxy-5-(4-(trifluoromethoxy)phenylsulfonamido)piperidine-1-carboxylate 52a (0.090 g, 0.148 mmol), in dichloromethane (0.20 mL) was reacted with trifluoroacetic acid (0.070 mL, 0.921 mmol) for 18 h. Purification by flash chromatography (SiO$_2$, 50% ethyl acetate-hexanes, 17:2:1 dichloromethane:methanol:35% ammonium hydroxide) followed by semi-prep HPLC (XDB-C$_{18}$, ACN-H$_2$O) afforded N-((3R,4R,5S)-5-(9H-carbazol-9-yl)-4-hydroxypiperidin-3-yl)-4-(trifluoromethoxy)benzenesulfonamide 41a (0.045 g, 60%) and N-((3R,4R,5S)-5-(3-(tert-butyl)-9H-carbazol-9-yl)-4-hydroxypiperidin-3-yl)-4-(trifluoromethoxy)benzenesulfonamide 53a (0.011 g, 13%). 41a: $^1$H NMR (600 MHz, MeOD) δ 8.33 (1H, br s), 8.10 (1H, d, J=7.2 Hz), 8.05-8.02 (3H, m), 7.69 (1H, d, J=7.8 Hz), 7.51 (1H, d, J=7.8 Hz), 7.42-7.41 (4H, m), 7.22-7.17 (2H, m), 4.68 (1H, br s), 4.52 (1H, t, J=9.6 Hz), 3.73 (1H, br s), 3.49-3.44 (2H, m), 3.24 (1H, br s), 3.00 (1H, br s); $^{13}$C NMR (150 MHz, MeOD) δ 151.8, 141.7, 140.3, 138.4, 129.3, 125.7, 125.3, 124.4, 122.8, 120.8, 120.3, 119.6, 119.1, 111.0, 109.0, 69.8, 57.5, 56.5, 49.0, 45.2; HRMS m/z 506.1356 ([M+H⁺], C$_{24}$H$_{23}$F$_3$N$_3$O$_4$S requires 506.1356). 53a: $^1$H NMR (600 MHz, MeOD) δ 8.36 (1H, br s), 8.11-8.02 (4H, m), 7.66-7.60 (1H, m), 7.51-7.47 (2H, m), 7.42-7.39 (4H, m), 7.20-7.15 (1H, m), 4.62 (I H, br s), 4.49 (1H, br s), 3.68 (1H, br s), 3.46-3.43 (2H, m), 3.19 (1H, br s), 2.96 (1H, br s), 1.42 (9H, br s); FIRMS m/z 562.1982 ([M+H⁺], C$_{28}$H$_{31}$F$_{13}$N$_3$O$_4$S requires 562.1982).

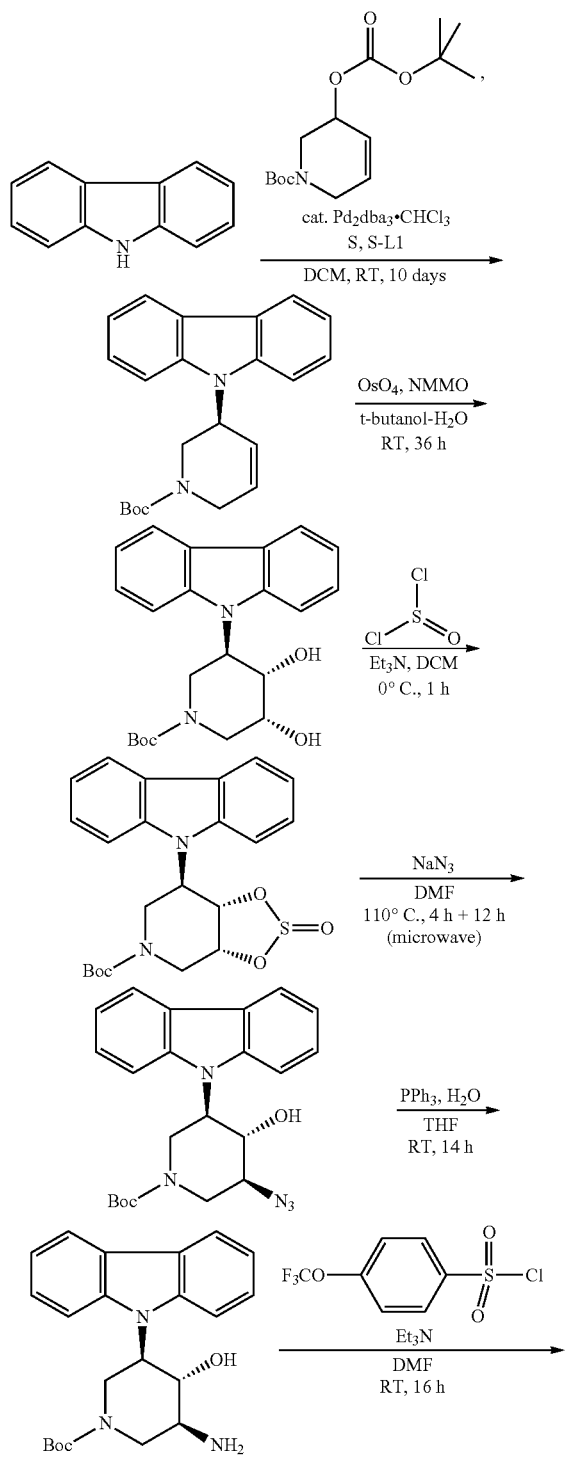

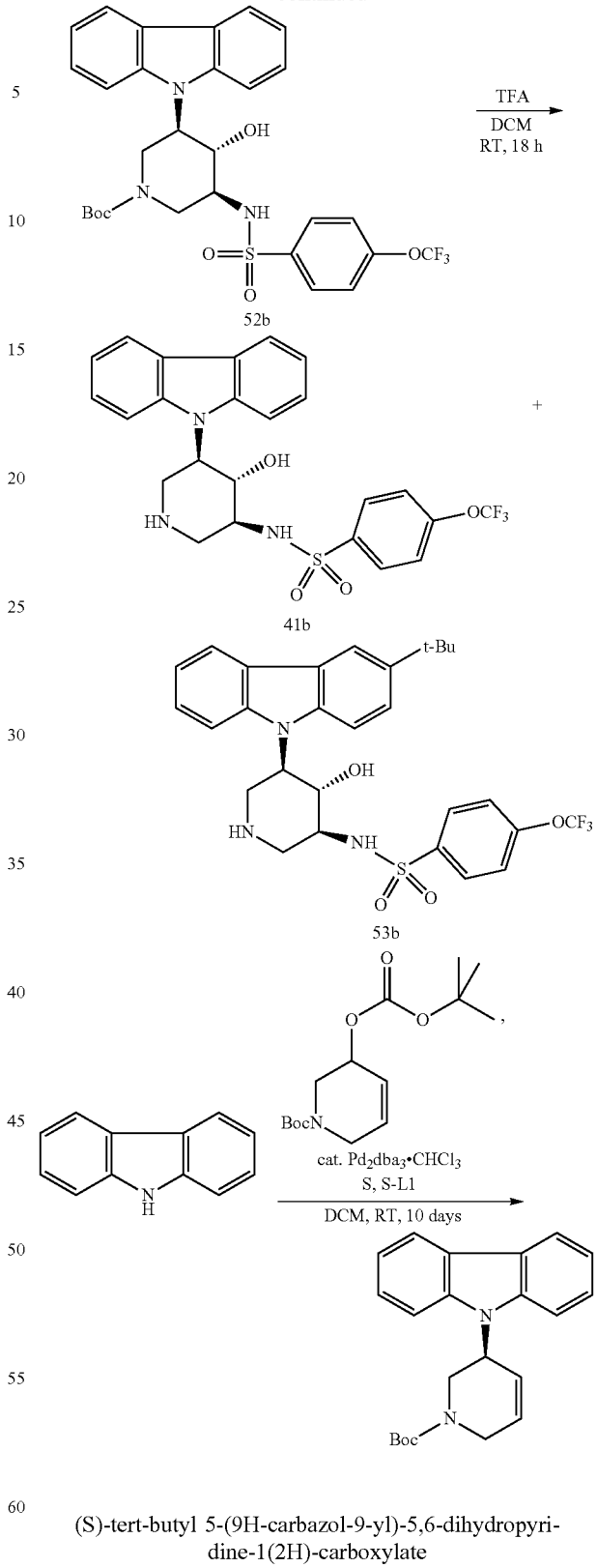

(S)-tert-butyl 5-(9H-carbazol-9-yl)-5,6-dihydropyridine-1(2H)-carboxylate

Using the typical procedure 9H-carbazole (0.334 g, 2.00 mmol) was reacted with tert-butyl 5-((tert-butoxycarbonyl)oxy)-5,6-dihydropyridine-1(2H)-carboxylate (1.44 g, 4.80 mmol) in presence of (S,S)-L1 for 10 days to afford (S)- tert-butyl 5-(9H-carbazol-9-yl)-5,6-dihydropyridine-1(2H)-carboxylate (0.450 g, 65%). ¹H NMR (600 MHz, MeOD) δ reported as a mixture of rotamers δ 8.07 (2H, d, J=7.8 Hz), 7.58 (2H, d, J=7.8 Hz), 7.37 (2H, br s), 7.18 (2H, t, J=7.2 Hz), 2H [6.24 (br s); 6.13 (br s)], 5.44-5.39 (1H, m), 4.32-4.01 (3H, m), 1H [3.52 (br s); 3.30 (br s)], 9H [1.46 (br s); 1.07 (br s)]; LCMS m/z 249.1408 ([M+H⁺-Boc], $C_{17}H_{17}N_2$ requires 249.1387).

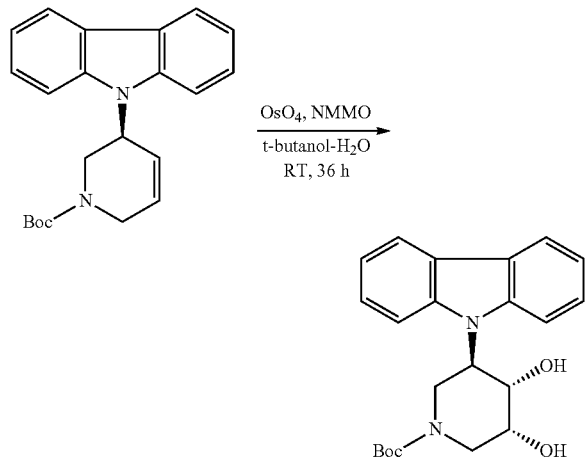

(1S,2R,3S)-3-(10H-phenoxazin-10-yl)cyclopentane-1,2-diol

Using the typical procedure A.2 (S)-tert-butyl 5-(9H-carbazol-9-yl)-5,6-dihydropyridine-1(2H)-carboxylate (0.430 g, 1.23 mmol) was transformed to (3R,4S,5R)-tert-butyl 3-(9H-carbazol-9-yl)-4,5-dihydroxypiperidine-1-carboxylate (0.421 g, 89%). ¹H NMR (600 MHz, MeOD) δ reported as a mixture of rotamers δ 8.08-8.07 (2H, m), 7.71-7.59 (2H, m), 7.41-7.37 (2H, m), 7.20-7.18 (2H, m), 4.96-4.95 (1H, m), 4.71 (1H, d, J=9.6 Hz), 4.36-4.08 (3H, m), 3.71-3.65 (1H, m), 3.28-3.18 (1H, m), 9H [1.50 (br s); 1.43 (br s)]; Material produced in this fashion exhibited $[\alpha]^{25}D=-3.0°$ (c=1.0, $CH_3OH$). HPLC analysis: >99% ee (CHIRALPAK IA-3, 80:20:0.1 hexanes-EtOH-diethylamine, 1.0 mL/min, UV: 254 nm), tR=2.36 min; LCMS m/z 283.1349 ([M+H⁺-Boc], $C_{17}H_{19}N_2O_2$ requires 283.1442).

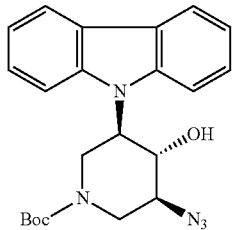

(3S,4S,5R)-tert-butyl 3-azido-5-(9H-carbazol-9-yl)-4-hydroxypiperidine-1-carboxylate Using the typical procedure B.1 (3R,4S,5R)-tert-butyl 3-(9H-carbazol-9-yl)-4,5-dihydroxypiperidine-1-carboxylate (0.455 g, 1.18 mmol) in dichloromethane (15.0 mL) was reacted with triethylamine (1.31 mL, 9.44 mmol), and thionyl chloride (0.129 mL, 1.78 mmol). The mixture was stirred at 0° C. for 1 h. Flash chromatography (SiO₂, 0%-75% ethylacetate-hexanes) afforded crude (3aR,7R,7aS)-tert-butyl 7-(9H-carbazol-9-yl)tetrahydro-[1,3,2]dioxathiolo[4,5-c]pyridine-5(6H)-carboxylate 2-oxide (0.295 g) which was taken to the next step without further purification.

Using the typical procedure B.2 (3aR,7R,7aS)-tert-butyl 7-(9H-carbazol-9-yl)tetrahydro-[1,3,2]dioxathiolo[4,5-c]pyridine-5(6H)-carboxylate 2-oxide (0.295 g, 0.688 mmol) in DMF (3.0 mL) was reacted with sodium azide (0.134 g, 2.07 mmol) at 110° C. for 4 h, (pressure was released from the vial), then 110° C. for 12 h. Purification by flash chromatography (SiO₂, 0%-50% ethylacetate-hexanes) afforded (3S,4S,5R)-tert-butyl 3-azido-5-(9H-carbazol-9-yl)-4-hydroxypiperidine-1-carboxylate (0.175 g, 36% over two steps). ¹H NMR (600 MHz, MeOD) δ 8.09 (2H, dd, J=21.6, 7.8 Hz), 7.73 (1H, d, J=8.4 Hz), 7.53 (1H, d, J=8.4 Hz), 7.43-7.40 (2H, m), 7.21 (2H, t, J=7.2 Hz), 4.62 (1H, t, J=10.2 Hz), 4.57 (1H, td, J=15.0, 10.2 Hz), 4.30 (1H, br s), 4.14-4.07 (1H, m), 3.79 (1H, br s), 3.61-3.57 (1H, m), 2.93 (1H, br s), 1.46 (9H, br s); ¹³C NMR (150 MHz, MeOD) δ 154.9, 141.8, 138.6, 125.7, 125.4, 124.3, 122.9, 120.2, 119.6, 119.1, 111.3, 108.8, 81.0, 72.7, 63.2, 57.3, 27.3; LCMS m/z 308.1300 ([M–Boc+H⁺], $C_{17}H_{18}N_5O$ requires 308.1506).

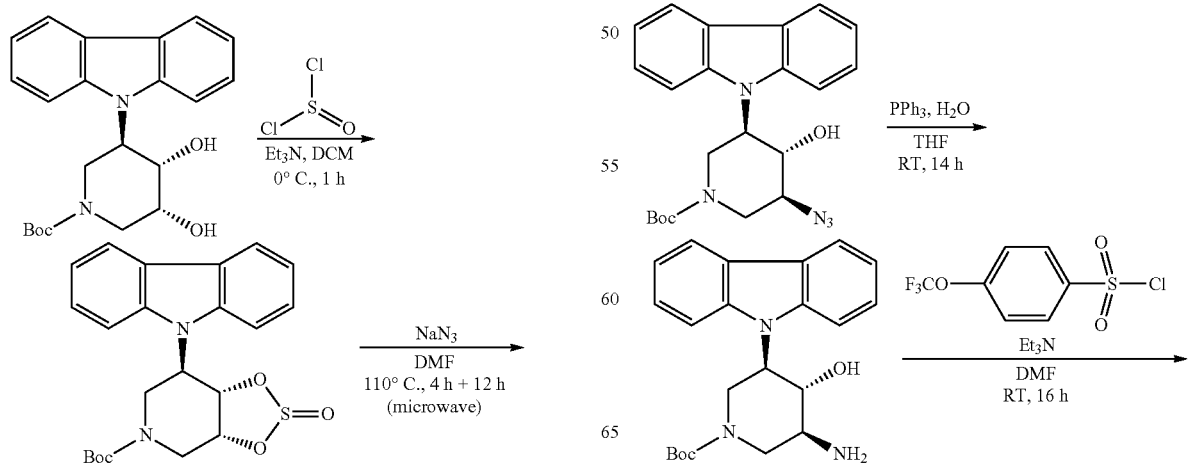

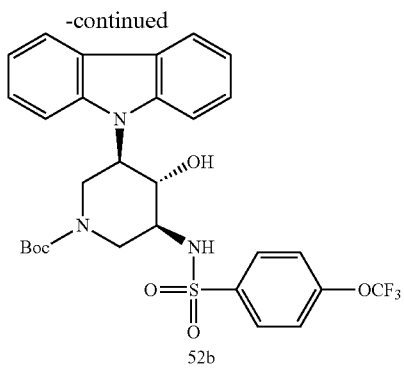

(3R,4S,5S)-tert-butyl 3-(9H-carbazol-9-yl)-4-hydroxy-5-(4-(trifluoromethoxy)phenylsulfonamido)piperidine-1-carboxylate (52b)

Using the typical procedure C.1 (3S,4S,5R)-tert-butyl 3-azido-5-(9H-carbazol-9-yl)-4-hydroxypiperidine-1-carboxylate (0.175 g, 0.429 mmol) in THF (1.90 mL) was reacted with triphenylphosphine (0.124 g, 0.472 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3S,4R,5R)-tert-butyl 3-amino-5-(9H-carbazol-9-yl)-4-hydroxypiperidine-1-carboxylate (0.140 g) which was taken to the next step without further purification.

Using the typical procedure C.2 (3S,4R,5R)-tert-butyl 3-amino-5-(9H-carbazol-9-yl)-4-hydroxypiperidine-1-carboxylate (0.140 g, 0.367 mmol) in DMF (1.20 mL) was reacted with triethylamine (0.203 mL, 1.46 mmol), and 4-(trifluoromethoxy)benzene-1-sulfonyl chloride (0.068 mL, 0.403 mmol). Purification by flash chromatography (SiO$_2$, 17% acetone-hexanes) afforded (3R,4S,5S)-tert-butyl 3-(9H-carbazol-9-yl)-4-hydroxy-5-(4-(trifluoromethoxy)phenylsulfonamido)piperidine-1-carboxylate 52b (0.166 g, 64% over two steps). $^1$H NMR (600 MHz, MeOD) δ 8.10 (1H, d, J=7.8 Hz), 8.06-8.03 (3H, m), 7.68 (1H, d, J=8.4 Hz), 7.49 (1H, d, J=8.4 Hz), 7.44-7.38 (4H, m), 7.21-7.17 (2H, m), 4.54-4.47 (2H, m), 4.33 (1H, br s), 4.10 (1H, br s), 3.72 (1H, br s), 2.99-2.90 (1H, m), 1.47 (9H, br s); $^{13}$C NMR (150 MHz, MeOD) δ 154.9, 151.8, 141.7, 140.6, 138.5, 129.2, 125.7, 125.2, 124.3, 122.8, 121.3, 120.9, 120.2, 119.5, 119.1, 119.0, 111.2, 109.0, 80.8, 70.6, 57.5, 56.6, 43.8, 27.3; Material produced in this fashion exhibited [α]$^{25}$D=−13.0° (c=1.0, CH$_3$OH). HPLC analysis: 96% ee (CHIRALPAK IA, 70:30 hexanes-EtOH, 1.0 mL/min, UV: 230 nm), tR=5.34 min (minor), 4.48 (major). LCMS m/z 506.1359 ([M−Boc+H$^+$], C$_{24}$H$_{23}$F$_3$N$_3$O$_4$S requires 506.1356).

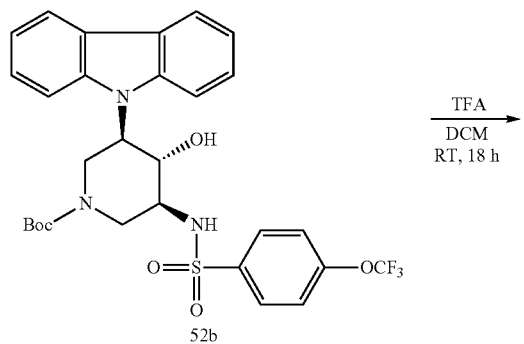

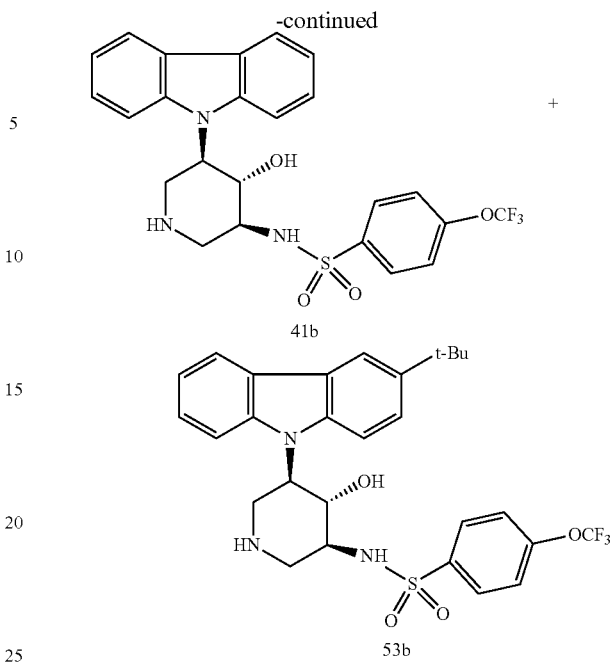

N-((3S,4S,5R)-5-(9H-carbazol-9-yl)-4-hydroxypiperidin-3-yl)-4-(trifluoromethoxy)benzenesulfonamide (41b) & N-((3S,4S,5R)-5-(3-(tert-butyl)-9H-carbazol-9-yl)-4-hydroxypiperidin-3-yl)-4-(trifluoromethoxy)benzenesulfonamide (53b)

Using the typical procedure D (3R,4S,5S)-tert-butyl 3-(9H-carbazol-9-yl)-4-hydroxy-5-(4-(trifluoromethoxy)phenylsulfonamido)piperidine-1-carboxylate 52b (1.31 g, 0.216 mmol), in dichloromethane (0.20 mL) was reacted with trifluoroacetic acid (1.02 mL, 1.34 mmol) for 18 h. Purification by flash chromatography (SiO$_2$, 50% ethyl acetate-hexanes, 17:2:1 dichloromethane:methanol:35% ammonium hydroxide) followed by semi-prep HPLC (XDB-C$_{18}$, ACN-H$_2$O) afforded N-((3S,4S,5R)-5-(9H-carbazol-9-yl)-4-hydroxypiperidin-3-yl)-4-(trifluoromethoxy)benzenesulfonamide 41b (0.042 g, 38%) and N-((3S,4S,5R)-5-(3-(tert-butyl)-9H-carbazol-9-yl)-4-hydroxypiperidin-3-yl)-4-(trifluoromethoxy)benzenesulfonamide 53b (0.027, 22%). 41b: $^1$H NMR (600 MHz, MeOD) δ 8.31 (1H, br s), 8.10 (1H, d, J=7.8 Hz), 8.05-8.02 (3H, m), 7.69 (1H, d, J=8.4 Hz), 7.51 (1H, d, J=8.4 Hz), 7.42-7.40 (4H, m), 7.22-7.17 (2H, m), 4.69-4.66 (1H, m), 4.52 (1H, t, J=9.6 Hz), 3.73 (1H, t, J=12.0 Hz), 3.51-3.44 (2H, m), 3.23 (1H, d, J=9.6 Hz), 3.00 (1H, t, J=11.4 Hz); $^{13}$C NMR (150 MHz, MeOD) δ 151.8, 141.7, 140.3, 138.4, 129.3, 125.7, 125.3, 124.4, 122.8, 120.8, 120.3, 119.6, 119.2, 111.0, 109.0, 69.8, 57.5, 56.5, 49.0, 45.2; LCMS m/z 506.1365 ([M+H$^+$], C$_{24}$H$_{23}$F$_3$N$_3$O$_4$S requires 506.1356). 53b: $^{13}$H NMR (600 MHz, MeOD) δ 8.36 (1H, br s), 8.11-8.09 (1H, m), 8.06-8.02 (3H, m), 7.66-7.60 (1H, m), 7.52-7.47 (2H, m), 7.42-7.36 (4H, m), 7.19-7.15 (1H, m), 4.60 (1H, br s), 4.497-4.490 (1H, m), 3.68-3.64 (1H, m), 3.45-3.41 (2H, m), 3.19 (1H, br s), 2.94 (1H, br s), 1.42 (9H, br s); HRMS m/z 562.1979 ([M+H$^+$], C$_{281}$H$_{31}$F$_3$N$_3$O$_4$S requires 562.1982).

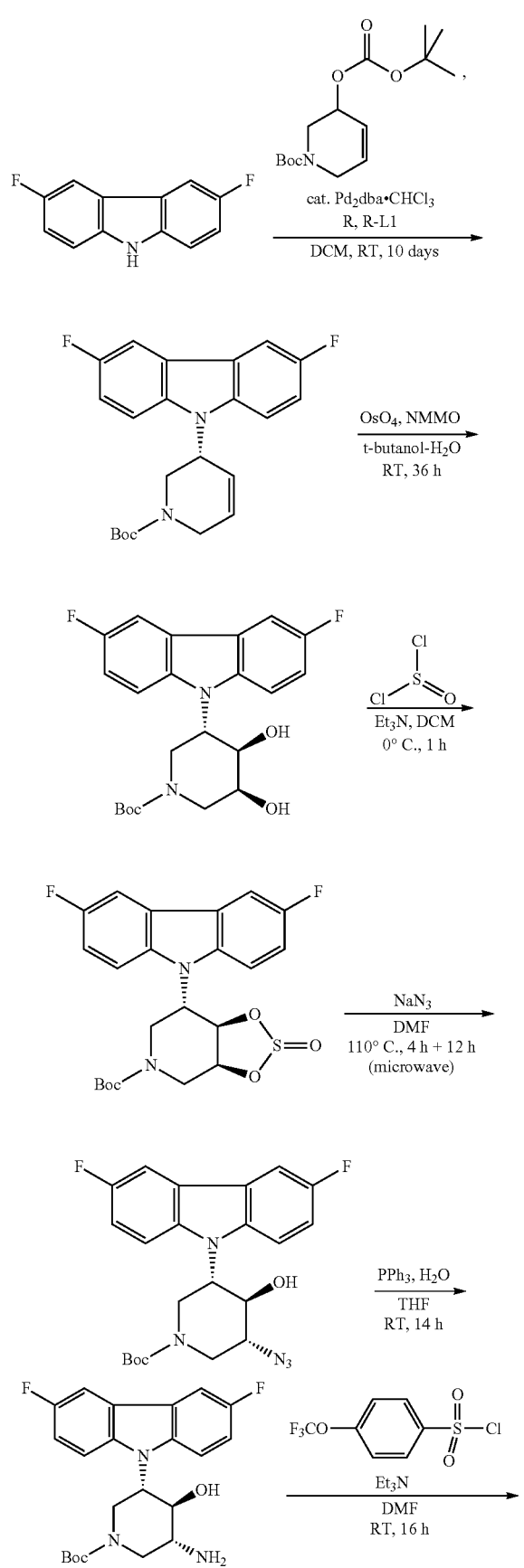
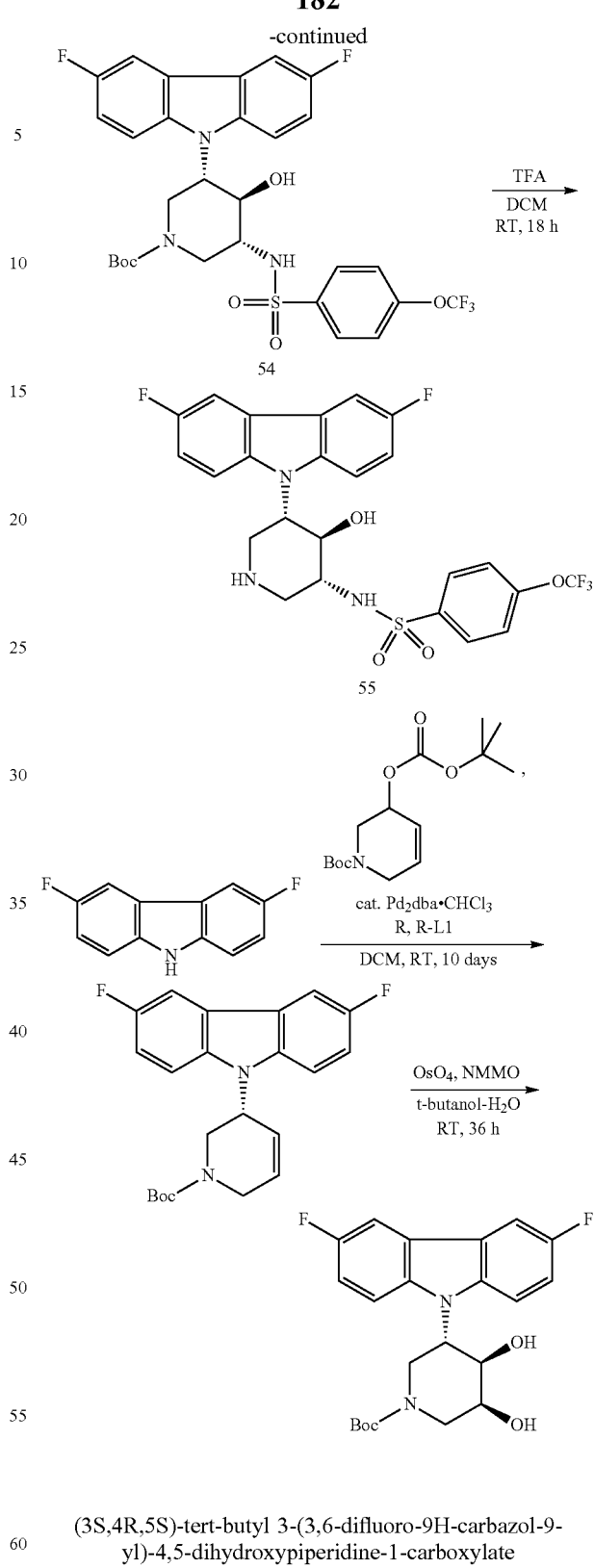
(3S,4R,5S)-tert-butyl 3-(3,6-difluoro-9H-carbazol-9-yl)-4,5-dihydroxypiperidine-1-carboxylate
Using the typical procedure A.1 3,6-difluoro-9H-carbazole (0.609 g, 3.00 mmol) was reacted with tert-butyl 5-((tert-butoxycarbonyl)oxy)-5,6-dihydropyridine-1(2H)-carboxylate (2.15 g, 7.20 mmol) in presence of (R,R)-L1 for 10 days to afford crude (R)-tert-butyl 5-(3,6-difluoro-9H- carbazol-9-yl)-5,6-dihydropyridine-1(2H)-carboxylate (1.33 g) which was taken to the next step without further purification.

Using the typical procedure A.2 (R)-tert-butyl 5-(3,6-difluoro-9H-carbazol-9-yl)-5,6-dihydropyridine-1(2H)-carboxylate (0.666 g, 1.73 mmol) was transformed to (3S,4R,5S)-tert-butyl 3-(3,6-difluoro-9H-carbazol-9-yl)-4,5-dihydroxypiperidine-1-carboxylate (0.409 g, 65% over two steps). $^1$H NMR (600 MHz, MeOD) δ reported as a mixture of rotamers δ 7.78-7.72 (3H, m), 7.57 (1H, br s), 7.20 (2H, br s), 4.65-4.61 (1H, m), 4.28 (1H, br s), 4.17-4.09 (2H, m), 3.78-3.50 (2H, m), 3.30-3.20 (2H, m), 9H [1.49 (br s); 1.45 (br s)]; Material produced in this fashion exhibited [α]$^{25}$D=+17.0° (c=1.0, CH$_3$OH). HPLC analysis: >99% ee (CHIRALPAK IA-3, 80:20:0.1 hexanes-EtOH-diethylamine, 1.0 mL/min, UV: 254 nm), tR=1.64 min; HRMS m/z 363.1157 ([M+H$^+$-t-Bu], C$^{18}$H$_{17}$F$_2$N$_2$O$_4$ requires 363.1151).

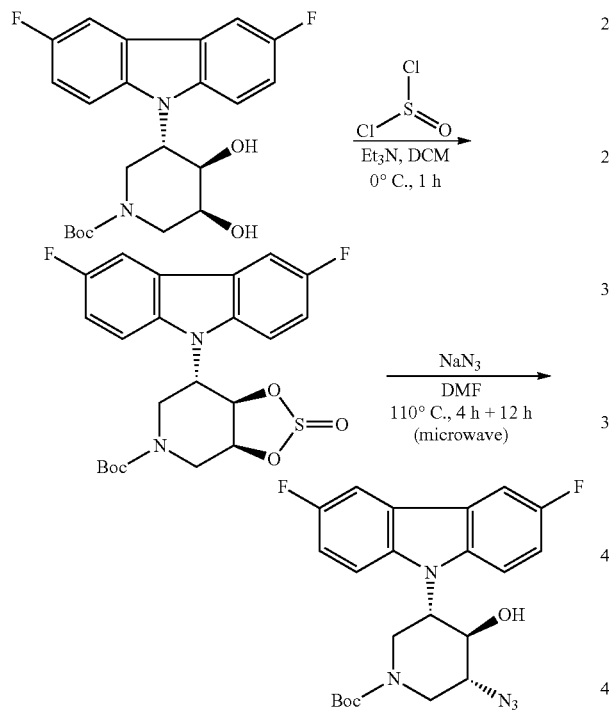

(3R,4R,5S)-tert-butyl 3-azido-5-(3,6-difluoro-9H-carbazol-9-yl)-4-hydroxypiperidine-1-carboxylate Using the typical procedure B.1 (3S,4R,5S)-tert-butyl 3-(3,6-difluoro-9H-carbazol-9-yl)-4,5-dihydroxypiperidine-1-carboxylate (0.382 g, 0.912 mmol) in dichloromethane (11.6 mL) was reacted with triethylamine (1.01 mL, 7.29 mmol), and thionyl chloride (0.098 mL, 1.37 mmol). The mixture was stirred at 0° C. for 30 min. Flash chromatography (SiO$_2$, 0%-50% ethylacetate-hexanes) afforded crude (3aS,7S,7aR)-tert-butyl 7-(3,6-difluoro-9H-carbazol-9-yl) tetrahydro[1,3,2]dioxathiolo[4,5-c]pyridine-5(6H)-carboxylate 2-oxide (0.420 g) which was taken to the next step without further purification.

Using the typical procedure B.2 (3aS,7S,7aR)-tert-butyl 7-(3,6-difluoro-9H-carbazol-9-yl)tetrahydro-[1,3,2]dioxathiolo[4,5-c]pyridine-5(6H)-carboxylate 2-oxide (0.420 g, 0.904 mmol) in DMF (2.0 mL) was reacted with sodium azide (0.176 g, 2.71 mmol) at 100° C. for 12 h. Purification by flash chromatography (SiO$_2$, 0%-50% ethylacetate-hexanes) afforded (3R,4R,5S)-tert-butyl 3-azido-5-(3,6-difluoro-9H-carbazol-9-yl)-4-hydroxypiperidine-1-carboxylate (0.245 g, 61% over two steps). $^1$H NMR (600 MHz, MeOD) δ 7.82-7.73 (3H, m), 7.54-7.53 (1H, m), 7.23-7.20 (2H, m), 4.54-4.53 (2H, m), 4.30 (1H, br s), 4.15-4.08 (1H, m), 3.78-3.71 (1H, m), 3.59 (1H, br s), 3.00-2.93 (1H, m); $^{13}$C NMR (150 MHz, MeOD) δ 158.2, 158.1, 156.6, 156.5, 154.9, 139.2, 135.8, 124.4, 122.9, 114.0, 113.8, 113.6, 113.4, 112.48, 112.43, 110.2, 106.1, 105.9, 105.5, 105.3, 81.1, 72.8, 63.1, 57.5, 48.2, 27.3; HRMS m/z 388.1220 ([M−t-Bu+H$^+$], C$_{18}$H$_{16}$F$_2$N$_5$O$_3$ requires 388.1216).

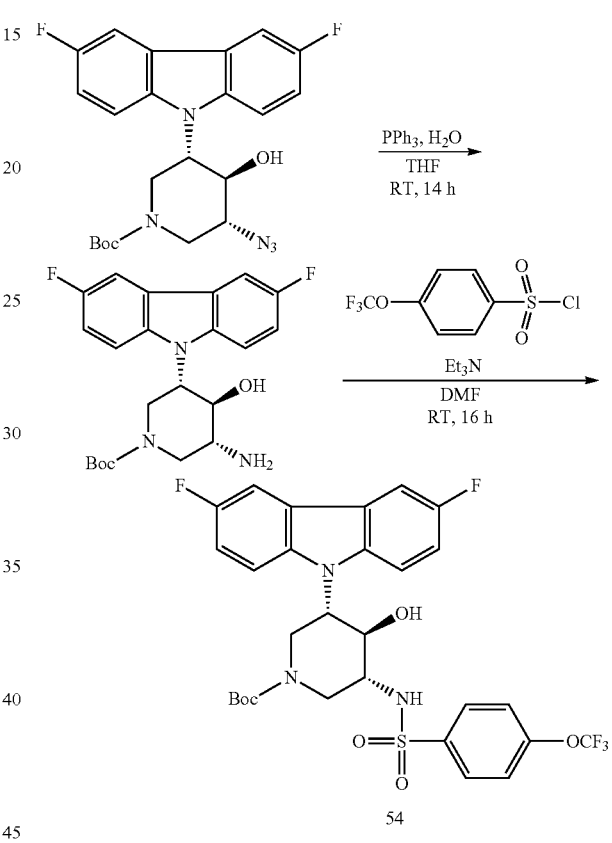

(3S,4R,5R)-tert-butyl 3-(3,6-difluoro-9H-carbazol-9-yl)-4-hydroxy-5-(4-(trifluoromethoxy)phenylsulfonamido)piperidine-1-carboxylate (54)

Using the typical procedure C.1 (3R,4R,5S)-tert-butyl 3-azido-5-(3,6-difluoro-9H-carbazol-9-yl)-4-hydroxypiperidine-1-carboxylate (0.227 g, 0.512 mmol) in THF (2.45 mL) was reacted with triphenylphosphine (0.148 g, 0.563 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-tert-butyl 3-amino-5-(3,6-difluoro-9H-carbazol-9-yl)-4-hydroxypiperidine-1-carboxylate (0.216 g) which was taken to the next step without further purification.

Using the typical procedure C.2 (3R,4S,5S)-tert-butyl 3-amino-5-(3,6-difluoro-9H-carbazol-9-yl)-4-hydroxypiperidine-1-carboxylate (0.216 g, 0.517 mmol) in DMF (1.67 mL) was reacted with triethylamine (0.288 mL, 2.07 mmol), and 4-(trifluoromethoxy)benzene-1-sulfonyl chloride (0.096 mL, 0.568 mmol). Purification by flash chromatography (SiO$_2$, 17%-25% acetone-hexanes) afforded (3S,4R,5R)-tert-butyl 3-(3,6-difluoro-9H-carbazol-9-yl)-4-hydroxy-5-(4-(trifluoromethoxy)phenylsulfonamido)piperidine-1-carboxylate 54 (0.174 g, 53% over two steps). $^1$H NMR (600 MHz, MeOD) Reported as rotamers δ 8.04 (2H, d, J=9.0 Hz), 7.80 (1H, d, J=7.2 Hz), 7.75 (1H, d, J=7.8 Hz), 7.67 (1H, d, J=6.0 Hz), 7.49-7.48 (1H, m), 7.43 (2H, d, J=8.4 Hz), 7.20 (2H, t, J=7.8 Hz), 3H [4.60 (br s), 4.48-4.41 (m)], 4.32 (1H, br s), 4.09 (1H, br s), 3.67 (1H, br s), 2.98 (1H, br s), 1.46 (9H, br s); $^{13}$C NMR (150 MHz, MeOD) δ 158.2, 158.0, 156.6, 156.5, 154.9, 151.8, 140.5, 139.1, 135.7, 129.2, 124.5, 122.8, 120.9, 124.5, 122.8, 120.9, 119.6, 114.0, 113.8, 113.5, 113.3, 112.3, 110.4, 106.1, 105.9, 105.4, 105.2, 80.9, 70.7, 57.8, 56.5, 27.3; Material produced in this fashion exhibited [α]$^{25}$D=+15.0° (c=1.0, CH$_3$OH). HPLC analysis: 94% ee (CHIRALPAK IA, 70:30 hexanes-EtOH, 1.0 mL/min, UV: 230 nm), tR=4.45 min (minor), 5.24 (major). HRMS m/z 586.1073 ([M+H$^+$], C$_{25}$H$_{21}$F$_5$N$_3$O$_6$S requires 586.1066).

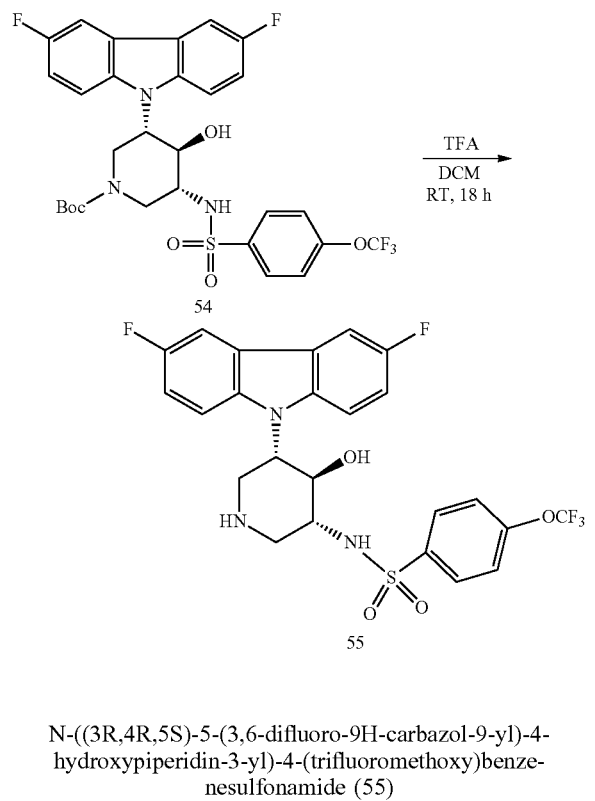

N-((3R,4R,5S)-5-(3,6-difluoro-9H-carbazol-9-yl)-4-hydroxypiperidin-3-yl)-4-(trifluoromethoxy)benzenesulfonamide (55)

Using the typical procedure D (3S,4R,5R)-tert-butyl 3-(3,6-difluoro-9H-carbazol-9-yl)-4-hydroxy-5-(4-(trifluoromethoxy)phenylsulfonamido)piperidine-1-carboxylate 54 (0.080 g, 0.124 mmol), in dichloromethane (0.30 mL) was reacted with trifluoroacetic acid (0.058 mL, 0.768 mmol) for 18 h. Purification by flash chromatography (SiO$_2$, 50% ethyl acetate-hexanes, 17:2:1 dichloromethane:methanol:35% ammonium hydroxide) afforded N-((3R,4R,5S)-5-(3,6-difluoro-9H-carbazol-9-yl)-4-hydroxypiperidin-3-yl)-4-(trifluoromethoxy)benzenesulfonamide 55 (0.056, 84%).

$^1$H NMR (600 MHz, MeOD) δ 8.02 (2H, d, J=9.0 Hz), 7.78 (1H, d, J=8.4 Hz), 7.73 (1H, d, J=8.4 Hz), 7.65 (1H, dd, J=9.0, 3.6 Hz), 7.49 (1H, dd, J=9.0, 3.6 Hz), 7.41 (2H, d, J=8.4 Hz), 7.19 (2H, t, J=9.0 Hz), 4.60 (1H, br s), 4.49 (1H, td, J=11.4, 4.8 Hz), 4.36 (1H, t, J=9.6 Hz), 3.45 (1H, J=12.6 Hz), 3.35 (1H, td, J=10.8, 4.8 Hz), 3.20-2.99 (1H, m), 2.69 (1H, J=12.0 Hz); $^{13}$C NMR (150 MHz, MeOD) δ 158.0, 157.9, 156.5, 156.4, 151.8, 140.7, 139.2, 135.8, 129.2, 124.4, 122.7, 120.8, 113.9, 113.7, 113.4, 113.2, 112.3, 112.2, 110.4, 110.3, 106.0, 105.8, 105.2, 105.1, 70.9, 59.7, 58.2, 50.4, 46.6; LCMS m/z 542.8352 ([M+H$^+$], C$_{24}$H$_{21}$F$_5$N$_3$O$_4$S requires 542.1168).

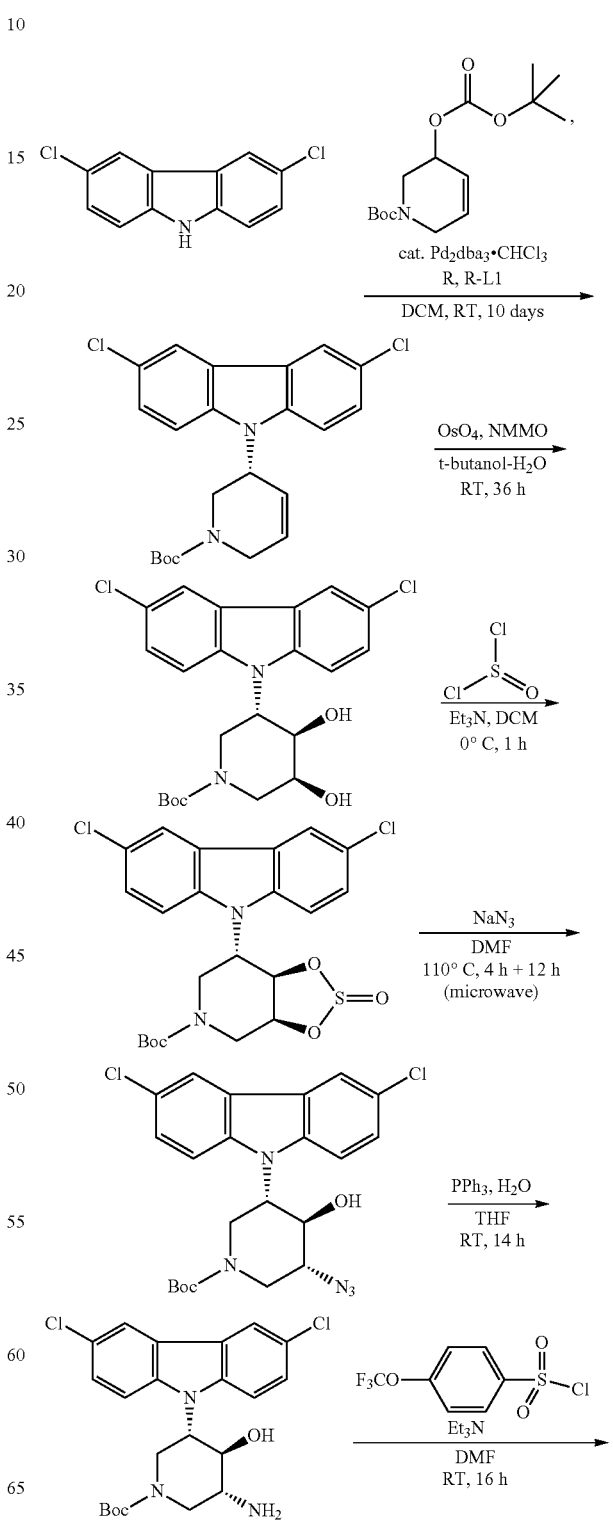

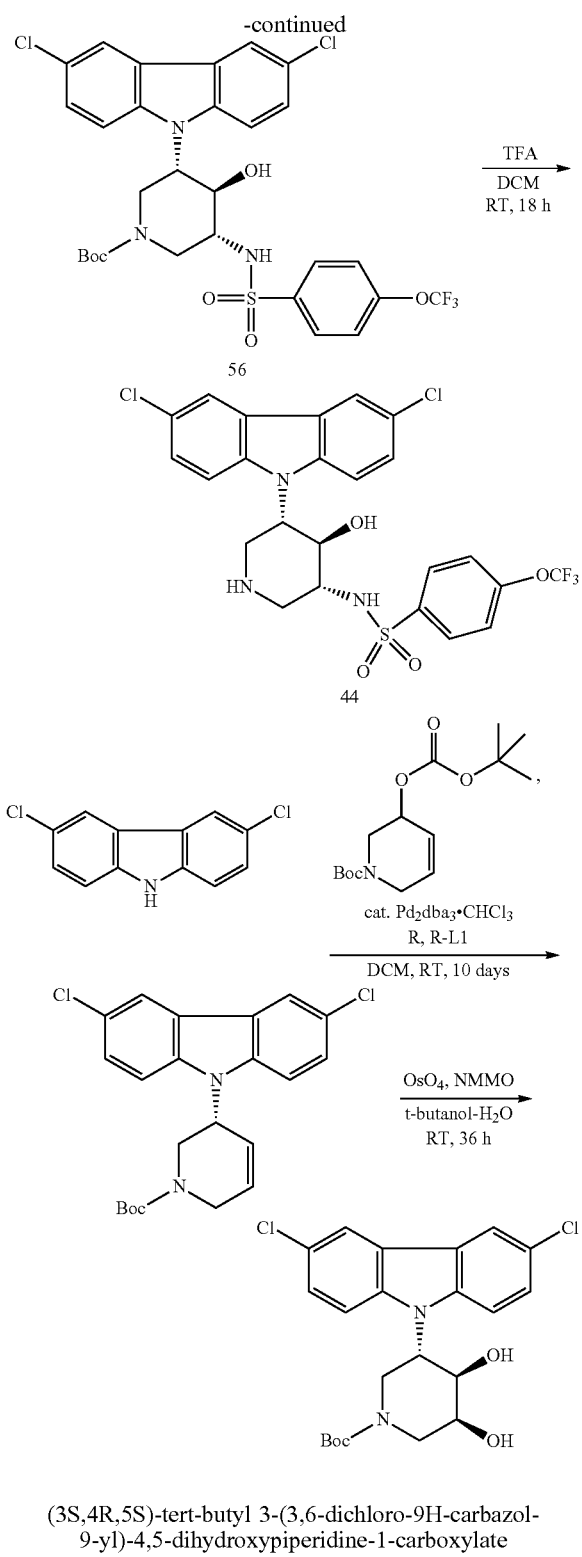

(3S,4R,5S)-tert-butyl 3-(3,6-dichloro-9H-carbazol-9-yl)-4,5-dihydroxypiperidine-1-carboxylate Using the typical procedure A.1 3,6-dichloro-9H-carbazole (0.708 g, 3.00 mmol) was reacted with tert-butyl 5-((tert-butoxycarbonyl)oxy)-5,6-dihydropyridine-1(2H)-carboxylate (2.15 g, 7.20 mmol) in presence of (R,R)-L1 for 10 days to afford crude (R)-tert-butyl 5-(3,6-dichloro-9H-carbazol-9-yl)-5,6-dihydropyridine-1(2H)-carboxylate (1.28 g) which was taken to the next step without further purification.

Using the typical procedure A.2 (R)-tert-butyl 5-(3,6-dichloro-9H-carbazol-9-yl)-5,6-dihydropyridine-1(2H)-carboxylate (0.644 g, 1.44 mmol) was transformed to (3S,4R,5S)-tert-butyl 3-(3,6-dichloro-9H-carbazol-9-yl)-4,5-dihydroxypiperidine-1-carboxylate (0.646 g, 95% over two steps). $^1$H NMR (600 MHz, MeOD) δ reported as a mixture of rotamers δ 8.10 (2H, br s), 7.74-7.58 (2H, br s), 7.41 (2H, br s), 4.64-4.63 (1H, m), 4.29 (1H, br s), 4.18-4.08 (3H, m), 3.77-3.52 (1H, m), 3.28-3.21 (1H, m), 9H [1.50 (br s); 1.45 (br s)]; Material produced in this fashion exhibited [α]$^{25}$D=+24.0° (c=1.0, CH$_3$OH). HPLC analysis: >99% ee (CHIRALPAK IA-3, 80:20:0.1 hexanes-EtOH-diethylamine, 1.0 mL/min, UV: 254 nm), tR=1.83 min; LCMS m/z 395.0596 ([M+H$^+$-t-Bu], C$_{18}$H$_{17}$Cl$_2$N$_2$O$_4$ requires 395.0560).

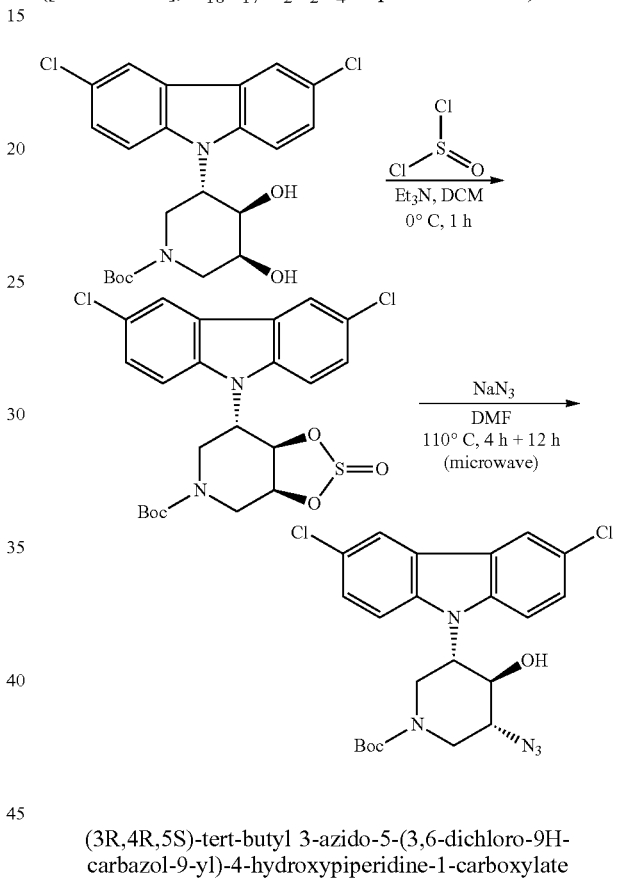

(3R,4R,5S)-tert-butyl 3-azido-5-(3,6-dichloro-9H-carbazol-9-yl)-4-hydroxypiperidine-1-carboxylate Using the typical procedure B.1 (3S,4R,5S)-tert-butyl 3-(3,6-dichloro-9H-carbazol-9-yl)-4,5-dihydroxypiperidine-1-carboxylate (0.646 g, 1.43 mmol) in dichloromethane (18.3 mL) was reacted with triethylamine (1.58 mL, 11.4 mmol), and thionyl chloride (0.212 mL, 2.14 mmol). The mixture was stirred at 0° C. for 30 min. Flash chromatography (SiO$_2$, 0%-50% ethylacetate-hexanes) afforded crude (3aS,7S,7aR)-tert-butyl 7-(3,6-dichloro-9H-carbazol-9-yl)tetrahydro-[1,3,2]dioxathiolo[4,5-c]pyridine-5(6H)-carboxylate 2-oxide (0.678 g) which was taken to the next step without further purification.

Using the typical procedure B.2 (3aS,7S,7aR)-tert-butyl 7-(3,6-dichloro-9H-carbazol-9-yl)tetrahydro-[1,3,2]dioxathiolo[4,5-c]pyridine-5(6H)-carboxylate 2-oxide (0.678 g, 1.36 mmol) in DMF (3.0 mL) was reacted with sodium azide (0.266 g, 4.09 mmol) at 100° C. for 12 h. Purification by flash chromatography (SiO$_2$, 0%-50% ethylacetate-hexanes) afforded (3R,4R,5S)-tert-butyl 3-azido-5-(3,6-dichloro-9H-carbazol-9-yl)-4-hydroxypiperidine-1-carboxylate (0.445 g, 65% over two steps). $^1$H NMR (600 MHz, MeOD) δ 8.13-8.09 (2H, m), 7.76 (1H, d, J=9.0 Hz), 7.56 (1H, d, J=9.0 Hz), 7.45-7.41 (2H, m), 4.60-4.50 (2H, m), 4.29 (1H, br s), 4.10-4.09 (1H, m), 3.72 (1H, br s), 3.61-3.57 (1H, m), 2.94 (1H, br s), 1.49 (9H, br s); $^{13}$C NMR (150 MHz, MeOD) δ 154.9, 140.8, 137.5, 126.4, 126.0, 125.1, 125.0, 124.6, 123.1, 120.2, 119.6, 112.8, 110.7, 81.1, 72.7, 63.1, 57.5, 27.3; HRMS m/z 420.0626 ([M−t-Bu+H$^+$], $C_{18}H_{16}Cl_2N_5O_3$ requires 420.0625).

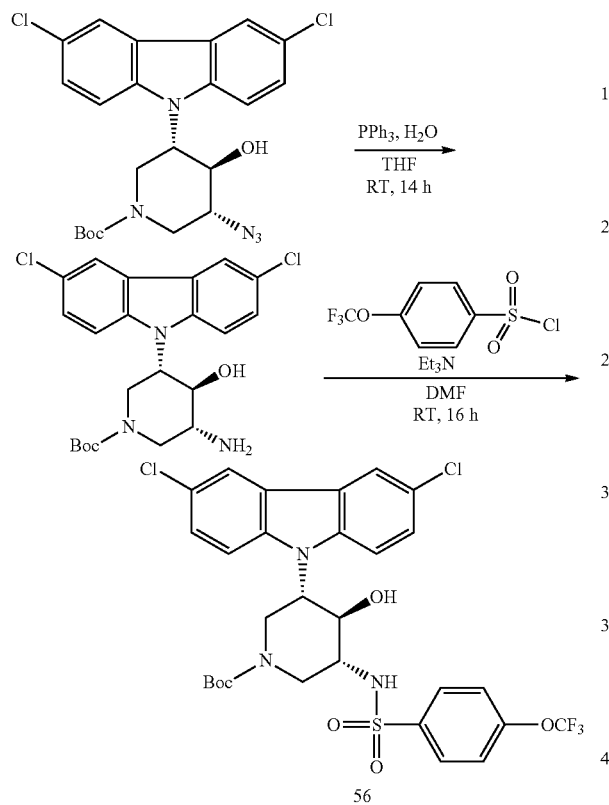

(3S,4R,5R)-tert-butyl 3-(3,6-dichloro-9H-carbazol-9-yl)-4-hydroxy-5-(4-(trifluoromethoxy)phenylsulfonamido)piperidine-1-carboxylate (56)

Using the typical procedure C.1 (3R,4R,5S)-tert-butyl 3-azido-5-(3,6-dichloro-9H-carbazol-9-yl)-4-hydroxypiperidine-1-carboxylate (0.425 g, 0.892 mmol) in THF (4.60 mL) was reacted with triphenylphosphine (0.257 g, 0.981 mmol), and water (0.002 mL, 0.110 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-tert-butyl 3-amino-5-(3,6-dichloro-9H-carbazol-9-yl)-4-hydroxypiperidine-1-carboxylate (0.389 g) which was taken to the next step without further purification.

Using the typical procedure C.2 (3R,4S,5S)-tert-butyl 3-amino-5-(3,6-dichloro-9H-carbazol-9-yl)-4-hydroxypiperidine-1-carboxylate (0.389 g, 0.859 mmol) in DMF (2.77 mL) was reacted with triethylamine (0.479 mL, 3.44 mmol), and 4-(trifluoromethoxy)benzene-1-sulfonyl chloride (0.160 mL, 0.945 mmol). Purification by flash chromatography (SiO$_2$, 10% acetone-hexanes) afforded (3S,4R,5R)-tert-butyl dichloro-9H-carbazol-9-yl)-4-hydroxy-5-(4-(trifluoromethoxy)phenylsulfonamido)piperidine-1-carboxylate 56 (0.315 g, 52% over two steps). $^1$H NMR (600 MHz, MeOD) δ 8.11-8.04 (4H, m), 7.68 (1H, br s), 7.49-7.41 (5H, m), 4.61 (1H, br s), 4.46-4.40 (2H, m), 4.31 (1H, br s), 4.09 (1H, br s), 3.66 (1H, br s), 2.98 (1H, br s)m 1.46 (9H, br s); $^{13}$C NMR (150 MHz, MeOD) δ 154.8, 151.8, 140.7, 140.5, 137.3, 129.2, 126.4, 125.9, 125.0, 124.7, 123.1, 120.9, 120.2, 119.5, 112.7, 110.8, 81.0, 70.6, 57.8, 56.5, 44.7, 43.7, 27.3; Material produced in this fashion exhibited [α]$^{25}$D=+ 21.0° (c=1.0, CH$_3$OH). HPLC analysis: >99% ee (CHIRAL-PAK IA, 70:30 hexanes-EtOH, 1.0 mL/min, UV: 230 nm), tR=5.66 min. LCMS m/z 618.0447 ([M−t-Bu+H$^+$], $C_{25}H_{21}Cl_2F_3N_3O_6S$ requires 618.0475).

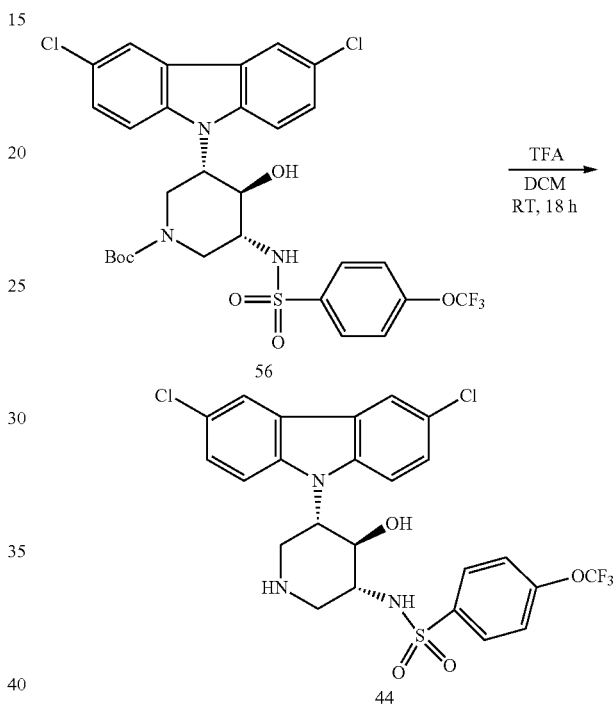

N-((3R,4R,5S)-5-(3,6-dichloro-9H-carbazol-9-yl)-4-hydroxypiperidin-3-yl)-4-(trifluoromethoxy)benzenesulfonamide (44)

Using the typical procedure D (3S,4R,5R)-tert-butyl 3-(3,6-dichloro-9H-carbazol-9-yl)-4-hydroxy-5-(4-(trifluoromethoxy)phenylsulfonamido)piperidine-1-carboxylate 56 (0.160 g, 0.237 mmol), in dichloromethane (0.50 mL) was reacted with trifluoroacetic acid (0.112 mL, 1.47 mmol) for 18 h. Purification by flash chromatography (SiO$_2$, 50% ethyl acetate-hexanes, 17:2:1 dichloromethane:methanol:35% ammonium hydroxide) afforded N-((3R,4R,5S)-5-(3,6-dichloro-9H-carbazol-9-yl)-4-hydroxypiperidin-3-yl)-4-(trifluoromethoxy)benzenesulfonamide 44 (0.107 g, 79%).

$^1$H NMR (600 MHz, MeOD) δ 8.09 (1H, br s), 8.04-8.01 (3H, m), 7.66 (1H, d, J=9.0 Hz), 7.50 (1H, d, J=9.0 Hz), 7.40 (4H, t, J=9.6 Hz), 4.60 (1H br s), 4.49 (1H, td, J=11.4, 4.8 Hz), 4.33 (1H, t, J=9.6 Hz), 3.44 (1H, t, J=12.6 Hz), 3.35 (1H, td, J=11.4, 4.8 Hz), 3.19-3.17 (1H, m), 3.00 (1H, dd, J=12.6, 3.6 Hz), 2.68 (1H, t, J=12.6 Hz); $^{13}$C NMR (150 MHz, MeOD) δ 151.8, 140.8, 140.7, 137.4, 129.2, 126.3, 125.8, 124.8, 124.7, 124.5, 123.0, 120.8, 120.1, 119.4, 112.7, 110.8, 70.8, 59.7, 58.2, 50.4, 46.5; LCMS m/z 575.0924 ([M+H$^+$], $C_{24}H_{21}Cl_2F_3N_3O_4S$ requires 575.0577).

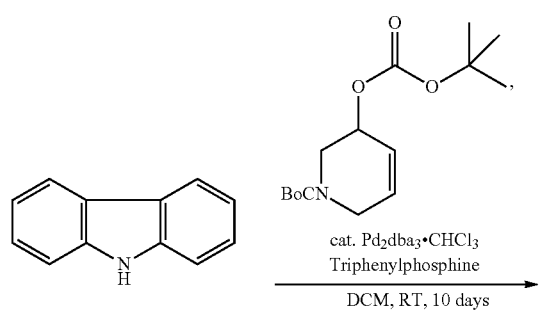
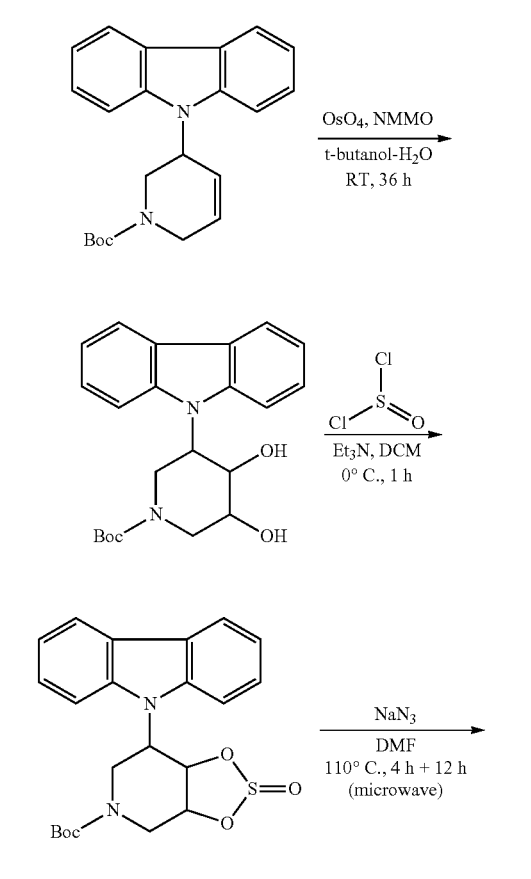
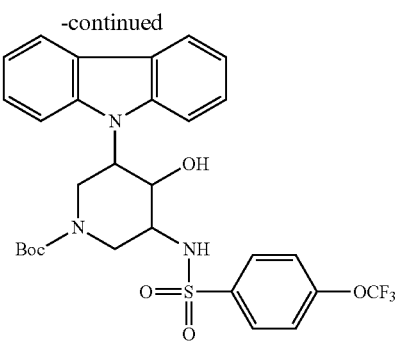

Tert-butyl 3-(9H-carbazol-9-yl)-4,5-dihydroxypiperidine-1-carboxylate

Using the typical procedure A.1 9H-carbazole (0.334 g, 2.00 mmol) was reacted with tert-butyl (3,6-dihydro-2H-pyran-3-yl) carbonate (1.44 g, 4.80 mmol) in presence of triphenylphosphine ligand for 10 days to afford crude tert-butyl 5-((tert-butoxycarbonyl)oxy)-5,6-dihydropyridine-1 (2H)-carboxylate (0.210 g), which was taken to the next step without further purification.

Using the typical procedure A.2 tert-butyl 5-((tert-butoxycarbonyl)oxy)-5,6-dihydropyridine-1(2H)-carboxylate (0.210 g, 0.602 mmol) was transformed to tert-butyl 3-(9H-carbazol-9-yl)-4,5-dihydroxypiperidine-1-carboxylate (0.140 g, 18% over two steps) which was obtained as a white solid. $^1$H NMR (600 MHz, MeOD) δ (mixture of rotamers) 8.08-8.07 (2H, m), 7.72-7.59 (2H, m), 7.41-7.37 (2H, m), 7.20-7.18 (2H, m), 4.97-4.95 (1H, m), 4.72-4.71 (1H, m), 4.36-4.29 (1H, m), 4.18-4.16 (2H, m), [1H, 3.72-3.64 (m), 3.18 (br s)], [9H, 1.50 (br s), 1.43 (br s)]; HPLC analysis: (CHIRALPAK IA-3, 80:20:0.1 hexanes-EtOH-diethylamine, 1.0 mL/min), tR=2.37 min (minor), 1.60 min (major); HRMS m/z 283.1441 ([M+H⁺], $C_{17}H_{19}N_2O_2$ requires 283.1442).

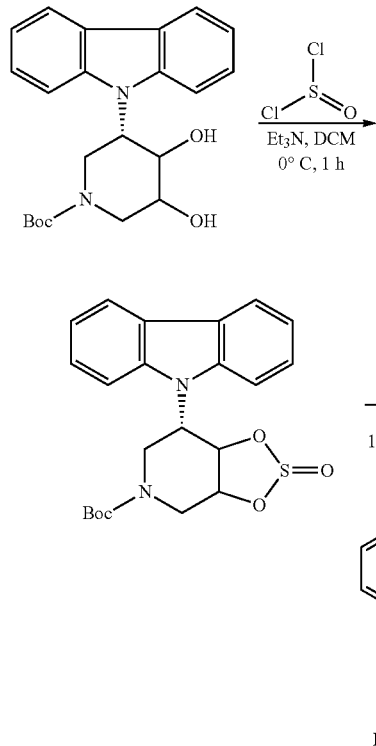

tert-butyl 3-azido-5-(9H-carbazol-9-yl)-4-hydroxypiperidine-1-carboxylate

Using the typical procedure B.1 tert-butyl 3-(9H-carbazol-9-yl)-4,5-dihydroxypiperidine-1-carboxylate (0.329 g, 0.860 mmol) in dichloromethane (11.0 mL) was reacted with triethylamine (0.953 mL, 6.88 mmol), and thionyl chloride (0.093 mL, 1.29 mmol). The mixture was stirred at 0° C. for 30 min. Flash chromatography (SiO₂, 0%-50% ethylacetate-hexanes) afforded crude tert-butyl 7-(9H-carbazol-9-yl)tetrahydro-[1,3,2]dioxathiolo[4,5-c]pyridine-5(6H)-carboxylate 2-oxide (0.307 g) which was taken to the next step without further purification.

Using the typical procedure B.2 tert-butyl 7-(9H-carbazol-9-yl)tetrahydro-[1,3,2]dioxathiolo[4,5-c]pyridine-5(6H)-carboxylate 2-oxide (0.307 g, 0.716 mmol) in DMF (2.0 mL) was reacted with sodium azide (0.139 g, 2.14 mmol) at 100° C. for 12 h. Purification by flash chromatography (SiO₂, 6%-13% ethylacetate-hexanes) afforded tert-butyl 3-azido-5-(9H-carbazol-9-yl)-4-hydroxypiperidine-1-carboxylate (0.185 g, 53% over two steps). ¹H NMR (600 MHz, MeOD) δ 8.09 (2H, dd, J=21.0, 7.2 Hz), 7.73 (1H, d, J=7.8 Hz), 7.53 (1H, d, J=7.8 Hz), 7.43-7.42 (2H, m), 7.21 (2H, br s), 4.64-4.30 (2H, m), 4.30 (1H, br s), 4.07 (1H, br s), 3.79 (1H, br s), 3.59 (1H, br s), 2.95 (1H, br s), 1.48 (9H, br s); ¹³C NMR (150 MHz, MeOD) δ 155.0, 141.8, 138.6, 125.7, 125.4, 124.3, 122.9, 120.2, 119.6, 119.1, 111.3, 108.8, 81.1, 72.7, 63.2, 57.3, 27.3; LCMS m/z 352.1497 ([M-t-Bu+H⁺], $C_{18}H_{18}N_5O_3$ requires 352.1405).

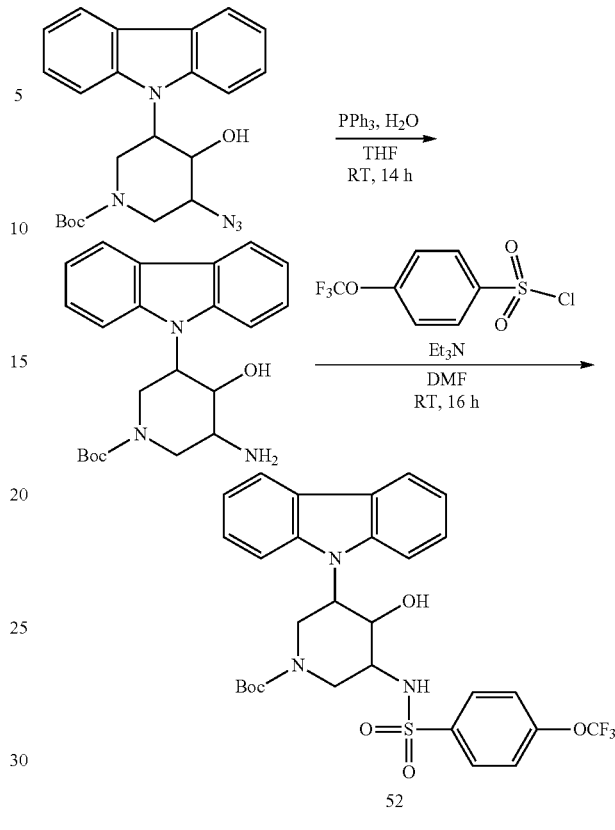

Tert-butyl 3-(9H-carbazol-9-yl)-4-hydroxy-5-(4-(trifluoromethoxy)phenylsulfonamido)piperidine-1-carboxylate (52)

Using the typical procedure C.1 tert-butyl 3-azido-5-(9H-carbazol-9-yl)-4-hydroxypiperidine-1-carboxylate (0.185 g, 0.454 mmol) in THF (2.0 mL) was reacted with triphenylphosphine (0.130 g, 0.499 mmol), and water (0.001 mL, 0.055 mmol). Flash chromatography (SiO₂, 100% hexanes, 50% ethyl acetate-hexanes, 5% methanol-dichloromethane, 17:1:1 dichloromethane:methanol:35% ammonium hydroxide, 17:2:1 dichloromethane:methanol:35% ammonium hydroxide) afforded crude tert-butyl 3-amino-5-(9H-carbazol-9-yl)-4-hydroxypiperidine-1-carboxylate (0.150 g) which was taken to the next step without further purification.

Using the typical procedure C.2 tert-butyl 3-amino-5-(9H-carbazol-9-yl)-4-hydroxypiperidine-1-carboxylate (0.075 g, 0.196 mmol) in DMF (0.63 mL) was reacted with triethylamine (0.109 mL, 0.786 mmol), and 4-(trifluoromethoxy)benzene-1-sulfonyl chloride (0.036 mL, 0.216 mmol). Purification by flash chromatography (SiO₂, 17%-25% acetone-hexanes) afforded tert-butyl 3-(9H-carbazol-9-yl)-4-hydroxy-5-(4-(trifluoromethoxy)phenylsulfonamido)piperidine-1-carboxylate 52 (0.097 g, 71% over two steps). ¹H NMR (600 MHz, MeOD) δ 8.09 (1H, d, J=7.8 Hz), 8.05-8.04 (3H, m), 7.67 (1H, d, J=7.8 Hz), 7.47 (1H, d, J=7.8 Hz), 7.42-7.37 (4H, m), 7.20-7.17 (2H, m), 4.55-4.47 (2H, m), 4.33 (1H, br s), 4.08 (1H, br s), 3.69 (1H, br s), 2.98 (1H, m), 1.45 (9H, br s); ¹³C NMR (150 MHz, MeOD) δ 154.9, 151.8, 141.7, 140.5, 138.5, 129.3, 125.7, 125.3, 124.4, 122.8, 120.9, 120.2, 119.6, 119.1, 119.0, 111.2, 109.0, 80.9, 70.6, 57.6, 56.6, 44.9, 43.8, 27.4; HRMS m/z 550.1262 ([M-t-Bu+H⁺], $C_{25}H_{23}F_3N_3O_6S$ requires 550.1255).

Group V (Substituted Phenoxazine-Piperidine):
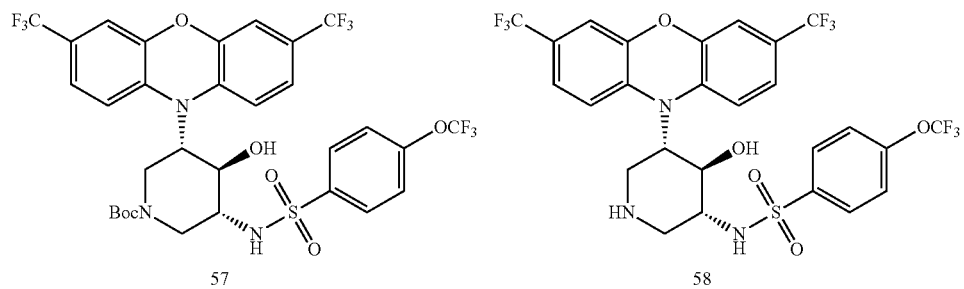
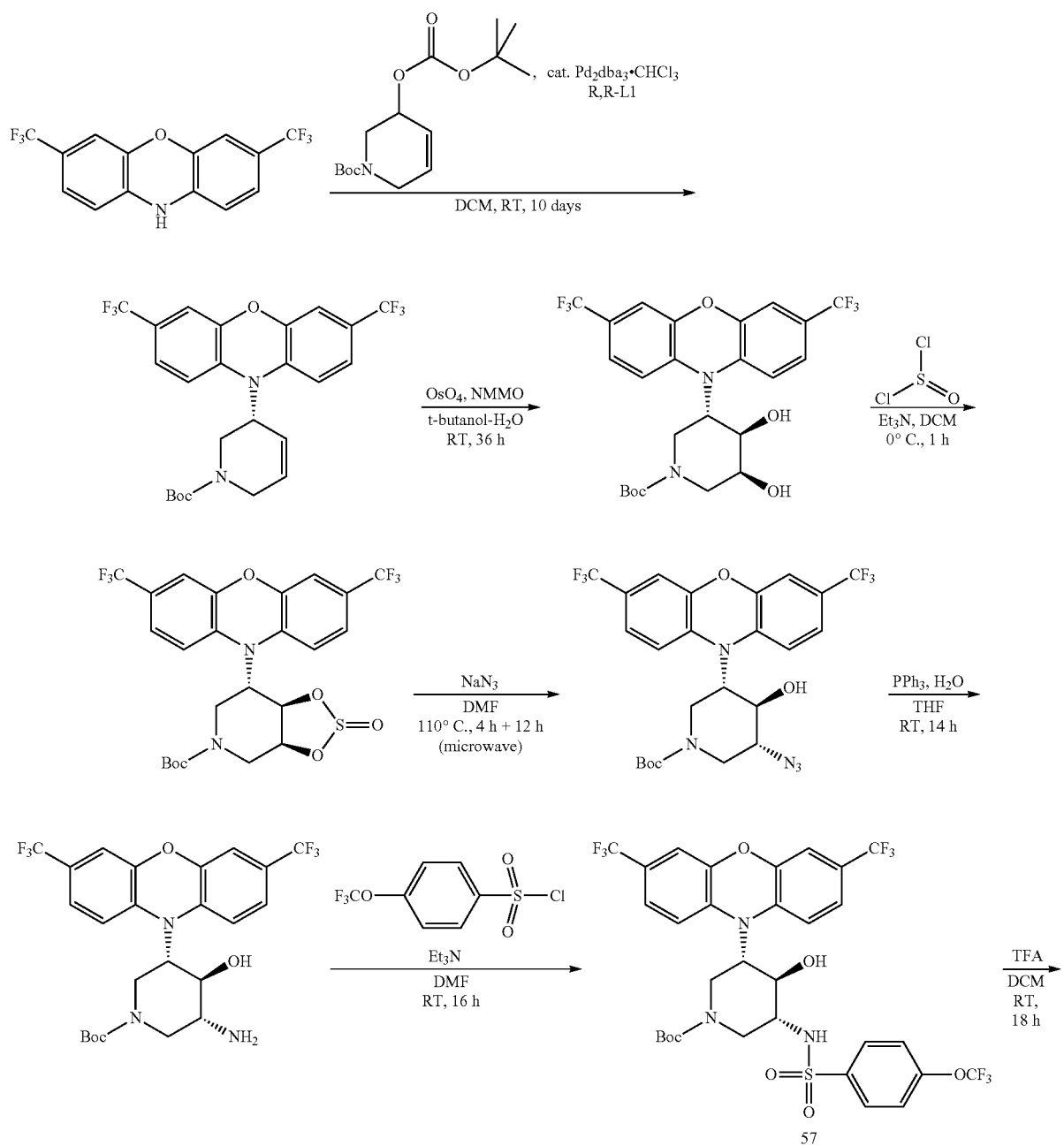

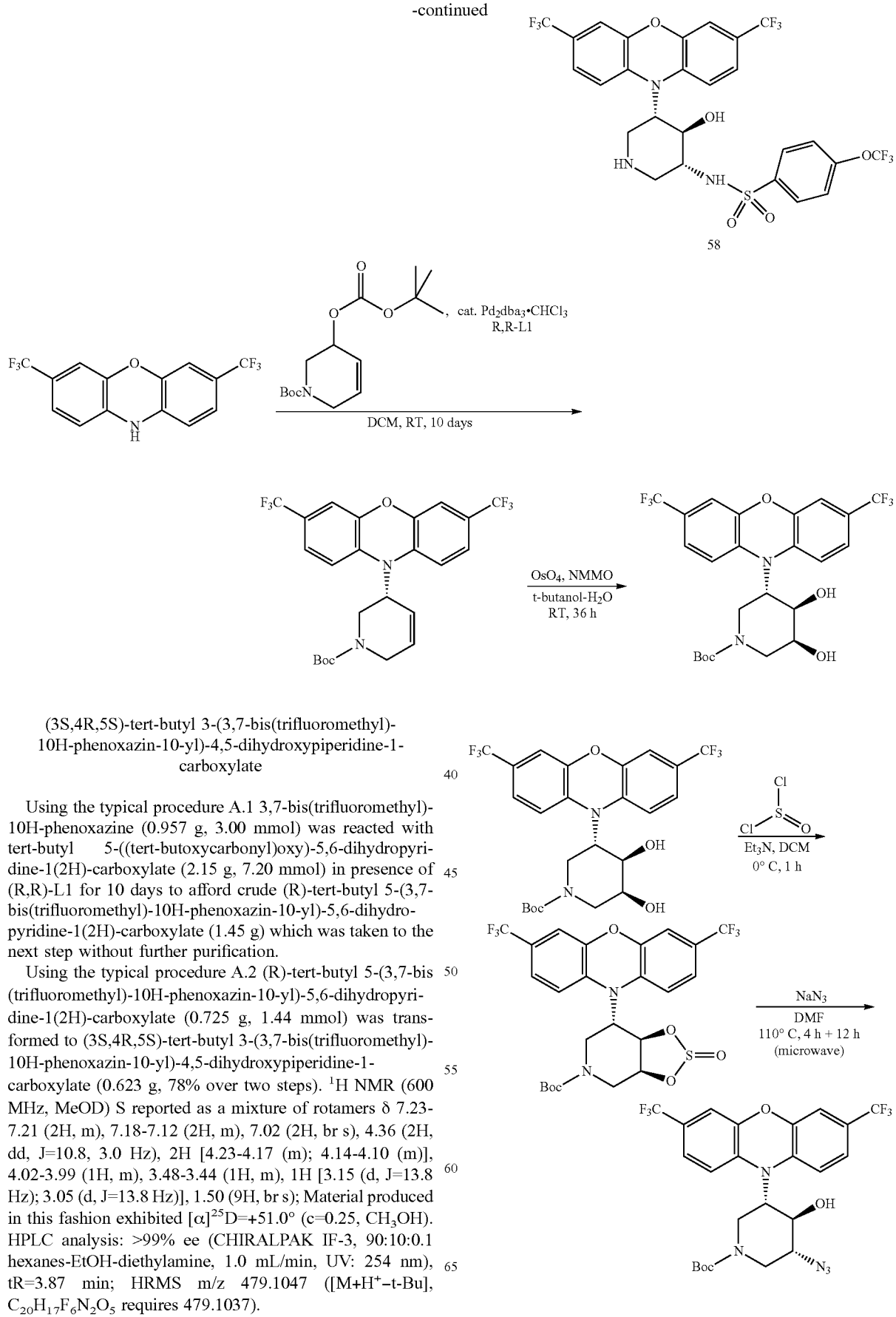

(3S,4R,5S)-tert-butyl 3-(3,7-bis(trifluoromethyl)-10H-phenoxazin-10-yl)-4,5-dihydroxypiperidine-1-carboxylate Using the typical procedure A.1 3,7-bis(trifluoromethyl)-10H-phenoxazine (0.957 g, 3.00 mmol) was reacted with tert-butyl 5-((tert-butoxycarbonyl)oxy)-5,6-dihydropyridine-1(2H)-carboxylate (2.15 g, 7.20 mmol) in presence of (R,R)-L1 for 10 days to afford crude (R)-tert-butyl 5-(3,7-bis(trifluoromethyl)-10H-phenoxazin-10-yl)-5,6-dihydropyridine-1(2H)-carboxylate (1.45 g) which was taken to the next step without further purification.

Using the typical procedure A.2 (R)-tert-butyl 5-(3,7-bis(trifluoromethyl)-10H-phenoxazin-10-yl)-5,6-dihydropyridine-1(2H)-carboxylate (0.725 g, 1.44 mmol) was transformed to (3S,4R,5S)-tert-butyl 3-(3,7-bis(trifluoromethyl)-10H-phenoxazin-10-yl)-4,5-dihydroxypiperidine-1-carboxylate (0.623 g, 78% over two steps). $^1$H NMR (600 MHz, MeOD) δ reported as a mixture of rotamers δ 7.23-7.21 (2H, m), 7.18-7.12 (2H, m), 7.02 (2H, br s), 4.36 (2H, dd, J=10.8, 3.0 Hz), 2H [4.23-4.17 (m); 4.14-4.10 (m)], 4.02-3.99 (1H, m), 3.48-3.44 (1H, m), 1H [3.15 (d, J=13.8 Hz); 3.05 (d, J=13.8 Hz)], 1.50 (9H, br s); Material produced in this fashion exhibited $[\alpha]^{25}{}_D$=+51.0° (c=0.25, CH$_3$OH). HPLC analysis: >99% ee (CHIRALPAK IF-3, 90:10:0.1 hexanes-EtOH-diethylamine, 1.0 mL/min, UV: 254 nm), tR=3.87 min; HRMS m/z 479.1047 ([M+H$^+$-t-Bu], C$_{20}$H$_{17}$F$_6$N$_2$O$_5$ requires 479.1037).

(3R,4R,5S)-tert-butyl 3-azido-5-(3,7-bis(trifluoromethyl)-10H-phenoxazin-10-yl)-4-hydroxypiperidine-1-carboxylate Using the typical procedure B.1 (3S,4R,5S)-tert-butyl bis(trifluoromethyl)-10H-phenoxazin-10-yl)-4,5-dihydroxypiperidine-1-carboxylate (0.605 g, 1.13 mmol) in dichloromethane (14.4 mL) was reacted with triethylamine (1.25 mL, 9.04 mmol), and thionyl chloride (0.122 mL, 1.69 mmol). The mixture was stirred at 0° C. for 30 min. Flash chromatography (SiO$_2$, 0%-75% ethylacetate-hexanes) afforded crude (3 aS,7S,7aR)-tert-butyl 7-(3,7-bis(trifluoromethyl)-10H-phenoxazin-10-yl)tetrahydro-[1,3,2]dioxathiolo[4,5-c]pyridine-5(6H)-carboxylate 2-oxide (0.559 g) which was taken to the next step without further purification.

Using the typical procedure B.2 (3aS,7S,7aR)-tert-butyl 7-(3,7-bis(trifluoromethyl)-10H-phenoxazin-10-yl)tetrahydro-[1,3,2]dioxathiolo[4,5-c]pyridine-5(6H)-carboxylate 2-oxide (0.559 g, 0.962 mmol) in DMF (3.0 mL) was reacted with sodium azide (0.187 g, 2.88 mmol) at 100° C. for 12 h. Purification by flash chromatography (SiO$_2$, 6%-13% ethylacetate-hexanes) afforded (3R,4R,5S)-tert-butyl 3-azido-5-(3,7-bis(trifluoromethyl)-10H-phenoxazin-10-yl)-4-hydroxypiperidine-1-carboxylate (0.264 g, 42% over two steps). $^1$H NMR (600 MHz, MeOD) δ 7.25-7.23 (2H, m), 7.13 (2H, br s), 7.05 (2H, br s), 4.34-4.17 (3H, m), 3.69 (1H, td, J=12.0, 4.2 Hz), 3.51-3.41 (2H, m), 2.88-2.77 (1H, m), 1.52 (9H, br s); $^{13}$C NMR (150 MHz, MeOD) δ 147.9, 124.9, 124.6, 123.1, 121.2, 116.5, 112.8, 81.2, 71.4, 63.7, 46.4, 45.3, 44.5, 27.3; LCMS m/z 504.1097 ([M−t-Bu+H$^+$], C$_{20}$H$_{16}$F$_6$N$_5$O$_4$ requires 504.1101).

(3S,4R,5R)-tert-butyl 3-(3,7-bis(trifluoromethyl)-10H-phenoxazin-10-yl)-4-hydroxy-5-(4-(trifluoromethoxy)phenylsulfonamido)piperidine-1-carboxylate (57)

Using the typical procedure C.1 (3R,4R,5S)-tert-butyl 3-azido-5-(3,7-bis(trifluoromethyl)-10H-phenoxazin-10-yl)-4-hydroxypiperidine-1-carboxylate (0.244 g, 0.436 mmol) in THF (2.63 mL) was reacted with triphenylphosphine (0.126 g, 0.478 mmol), and water (0.001 mL, 0.055 mmol). Flash chromatography (SiO$_2$, 100% hexanes, 50% ethyl acetate-hexanes, 5% methanol-dichloromethane, 17:2:1 dichloromethane:methanol:35% ammonium hydroxide) afforded crude (3R,4S,5S)-tert-butyl 3-amino-5-(3,7-bis(trifluoromethyl)-10H-phenoxazin-10-yl)-4-hydroxypiperidine-1-carboxylate (0.213 g) which was taken to the next step without further purification. Using the typical procedure C.2 (3R,4S,5S)-tert-butyl 3-amino-5-(3,7-bis(trifluoromethyl)-10H-phenoxazin-10-yl)-4-hydroxypiperidine-1-carboxylate (0.213 g, 0.399 mmol) in DMF (1.29 mL) was reacted with triethylamine (0.223 mL, 1.59 mmol), and 4-(trifluoromethoxy)benzene-1-sulfonyl chloride (0.074 mL, 0.439 mmol). Purification by flash chromatography (SiO$_2$, 10% acetone-hexanes) afforded (3S,4R,5R)-tert-butyl 3-(3,7-bis(trifluoromethyl)-10H-phenoxazin-10-yl)-4-hydroxy-5-(4-(trifluoromethoxy)phenylsulfonamido)piperidine-1-carboxylate 57 (0.179 g, 54% over two steps). $^1$H NMR (600 MHz, MeOD) δ 7.99 (2H, d, J=8.4 Hz), 7.42 (2H, d, J=8.4 Hz), 7.21 (2H, d, J=7.8 Hz), 7.07-7.02 (4H, m), 4.60 (1H, br s), 4.31 (1H, br s), 4.17 (1H, br s), 3.61-3.58 (1H, m), 3.38 (1H, m), 3.12 (1H, br s), 2.84 (1H, br s), 1.48 (9H, br s); $^{13}$C NMR (150 MHz, MeOD) δ 151.9, 147.8, 140.4, 129.2, 124.9, 124.6, 123.1, 121.2, 120.9, 116.5, 112.8, 81.0, 69.2, 64.3, 57.1, 48.3, 44.7, 27.3; Material produced in this fashion exhibited [α]$^{25}$D=+10.0° (c=1.0, CH$_3$OH). HPLC analysis: >99% ee (CHIRALPAK IA, 70:30 hexanes-EtOH, 1.0 mL/min, UV: 230 nm), tR=4.97 min. LCMS m/z 702.0925 ([M−t-Bu+H$^+$], C$_{27}$H$_{21}$F$_9$N$_3$O$_7$S requires 702.0591).

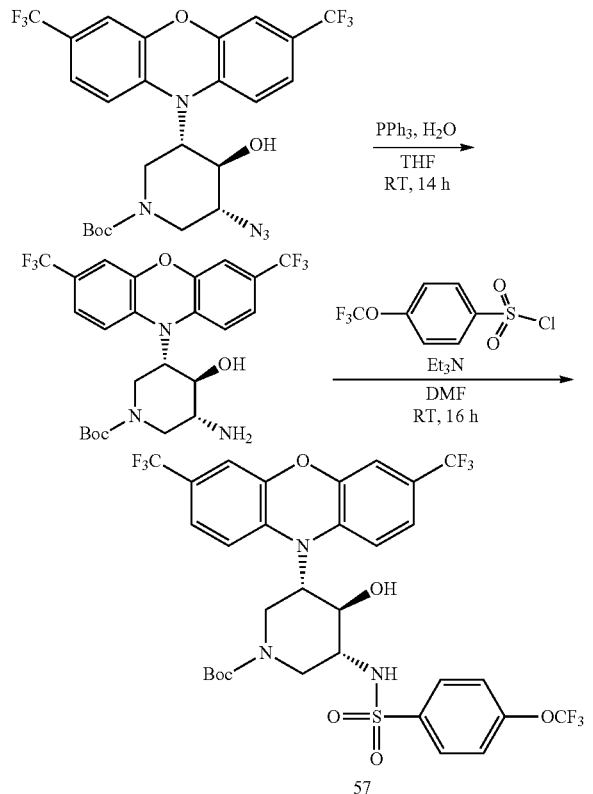

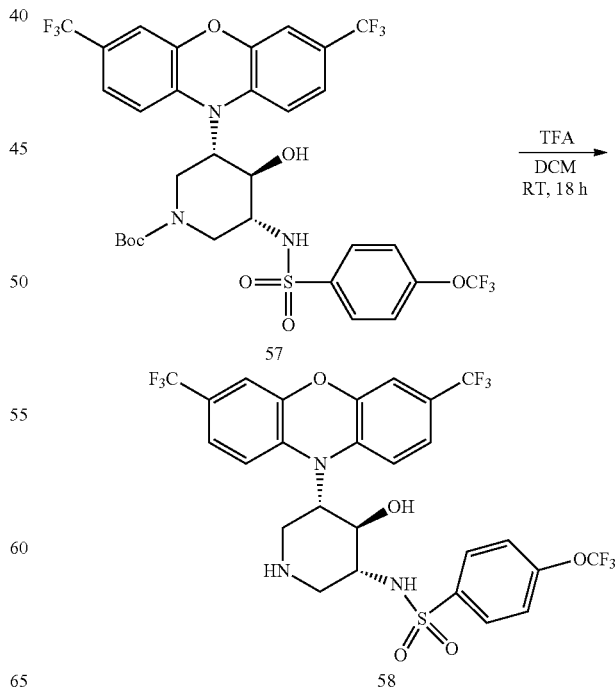

N-((3R,4R,5S)-5-(3,7-bis(trifluoromethyl)-10H-phenoxazin-10-yl)-4-hydroxypiperidin-3-yl)-4-(trifluoromethoxy)benzenesulfonamide (58)

Using the typical procedure D (3S,4R,5R)-tert-butyl bis(trifluoromethyl)-10H-phenoxazin-10-yl)-4-hydroxy-5-(4-(trifluoromethoxy)phenylsulfonamido)piperidine-1-carboxylate 57 (0.080 g, 0.105 mmol), in dichloromethane (0.30 mL) was reacted with trifluoroacetic acid (0.050 mL, 0.654 mmol) for 18 h. Purification by flash chromatography (SiO$_2$, 50% ethyl acetate-hexanes, 17:2:1 dichloromethane:methanol:35% ammonium hydroxide) afforded N-((3R,4R,5S)-5-(3,7-bis(trifluoromethyl)-10H-phenoxazin-10-yl)-4-hydroxypiperidin-3-yl)-4-(trifluoromethoxy)benzenesulfonamide 58 (0.039, 56%). $^1$H NMR (600 MHz, MeOD) δ 7.99 (2H, d, J=9.0 Hz), 7.42 (2H, d, J=8.4 Hz), 7.19 (2H, d, J=8.4 Hz), 7.05 (2H, d, J=8.4 Hz), 6.99 (2H, br s), 4.60 (1H, br s), 4.06 (1H, t, J=9.6 Hz), 3.68-3.67 (1H, m), 3.19 (3H br s), 3.06-3.04 (1H, m), 2.51 (1H, t, J=12.6 Hz); $^{13}$C NMR (150 MHz, MeOD) δ 151.8, 147.8, 140.6, 129.3, 124.9, 124.8, 124.5, 124.3, 123.1, 121.1, 120.8, 116.6, 112.6, 69.8, 66.2, 58.6, 50.2; LCMS m/z 658.7123 ([M+H$^+$], C$_{26}$H$_{21}$F$_9$N$_3$O$_5$S requires 658.1053).

Alternate Epoxidation Route

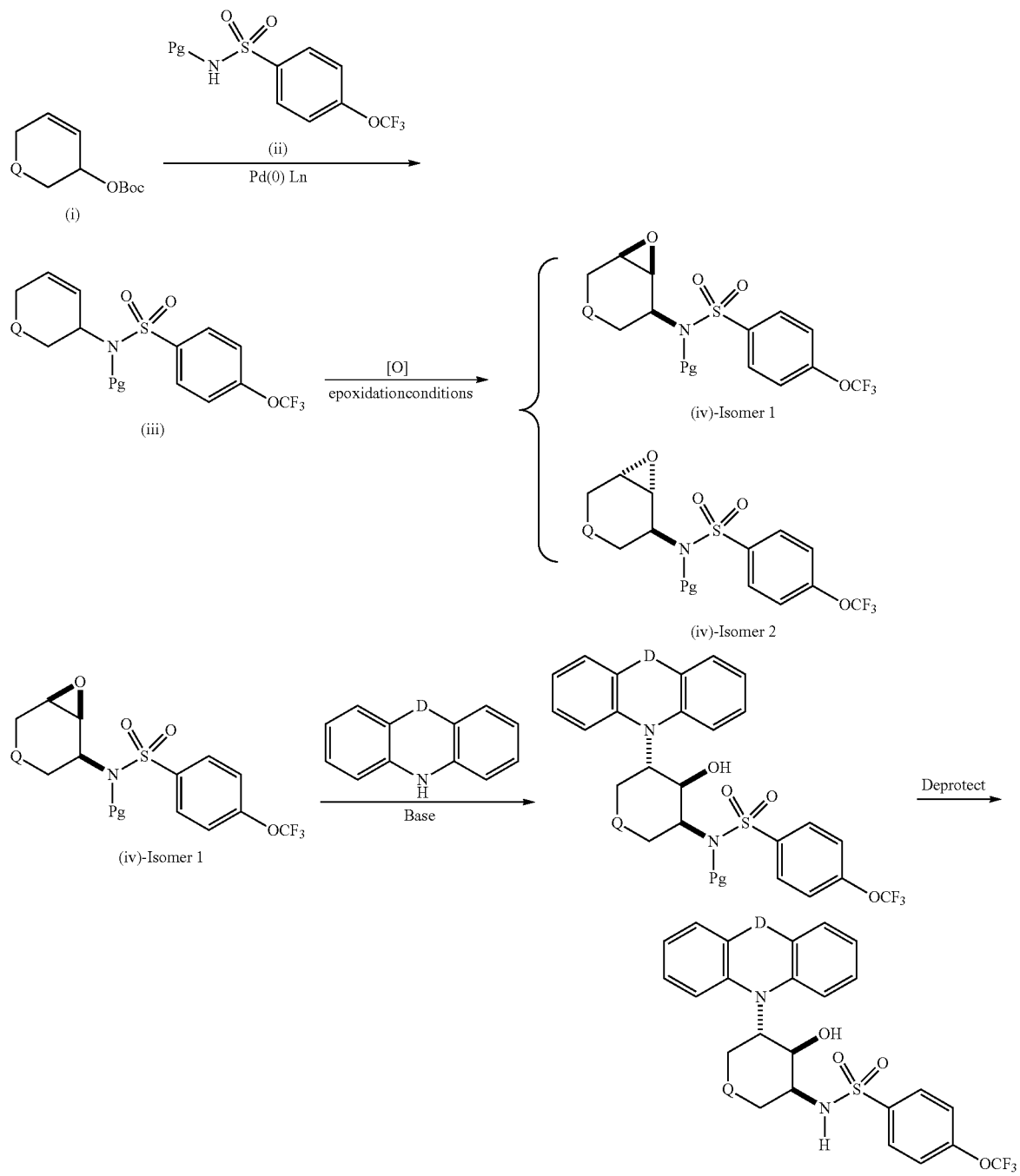

General Scheme 1

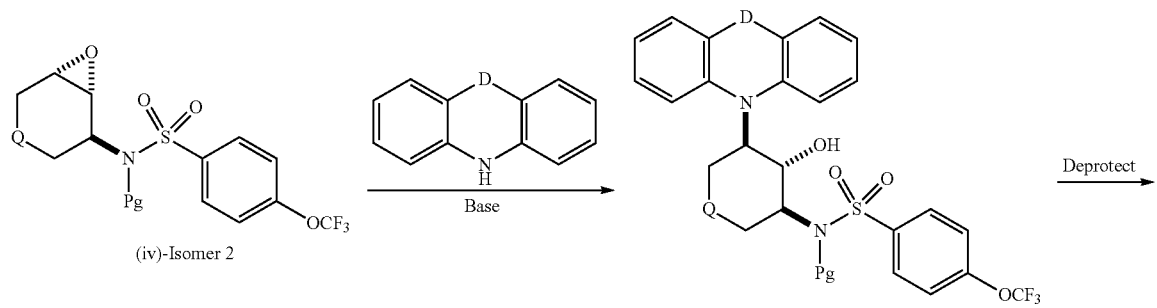

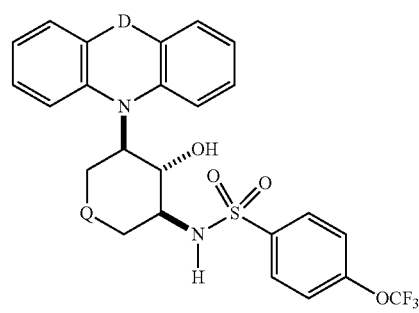

An alternative route to PP2A modulators described in the present application is outlined in Scheme 1 in which a heterocyclic allylic carbonate is first reacted with a protected aryl sulfonamide in the presence of a palladium catalyst. This may be carried out with control of the newly formed chiral center by using a chiral ligand such as the Trost-DACH bisphosphine. Thus reagents of type (i) are reacted with an optionally protected arylsulfonamide (ii), for example 4-trifluoromethoxybenzene sulfonamide in the presence of a chiral palladium catalyst to give enantiomerically enriched allylarylsulfonamides of type (iii). Protecting groups, Pg, include but are not limited to, benzyl and substituted benzyl groups or alkoxycarbonyl groups such as Boc or Cbz. The protected allylic sulfonamides (iii) may be epoxidized in a non-diastereoselective fashion to give a diastereomeric mixture of epoxides, (iv), which are separated by chromatographic techniques; or alternatively stereoselective epoxidation will give access to one diastereoisomer preferentially. Epoxidation reagents include peroxoic acids such as mCPBA, dioxiranes such as dimethyldioxirane, oxaziridines such as 3-phenyl-2-tosyl-1,2-oxaziridine or hydroperoxides such as t-butylhydroperoxide with transition metal ion catalysis. Either isomer of compound (iv) is converted to a PP2A activator by treatment with a tricyclic moiety such as an optionally substituted carbazole or phenoxazine in the presence of a base such as sodium amide, sodium hydride or potassium t-butoxide in an aprotic solvent, followed by deprotection under conditions appropriate for the original choice of Pg. Alternatively the diastereomeric mixture of (iv) may be carried forward and isomers separated at the penultimate benzyl protected stage or the final deprotected products. A specific example of this process is shown in Scheme 2.

Scheme 2

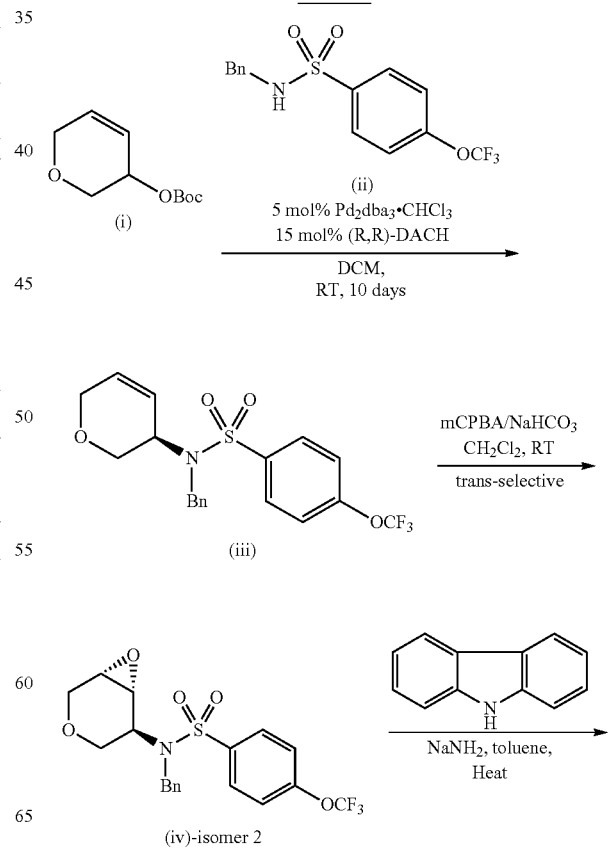

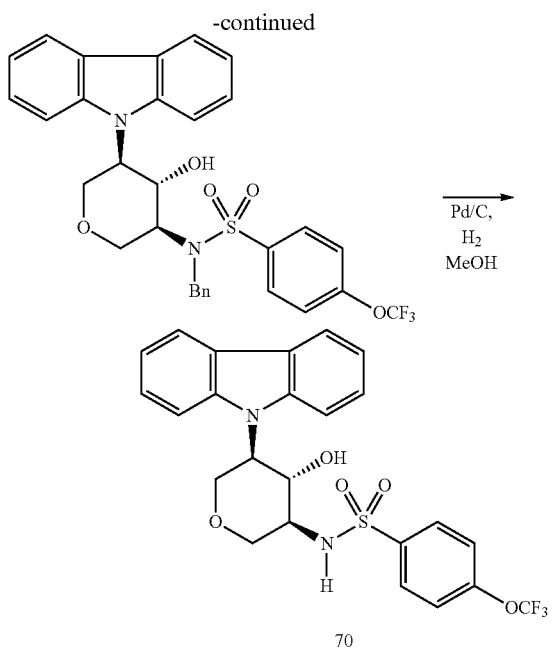

Synthesis of (R)—N-benzyl-N-(3,6-dihydro-2H-pyran-3-yl)-4-(trifluoromethoxy)benzenesulfonamide (iii)

Using the typical procedure N-benzyl-4-(trifluoromethoxy)benzenesulfonamide (0.200 g, 0.603 mmol) was reacted with tert-butyl (3,6-dihydro-2H-pyran-3-yl) carbonate (0.289 g, 1.45 mmol) in presence of (R,R)-L1 for 10 days to afford (R)—N-benzyl-N-(3,6-dihydro-2H-pyran-3-yl)-4-(trifluoromethoxy)benzenesulfonamide (0.228 g, 92%). $^1$H NMR (600 MHz, MeOD) δ 7.89 (2H, d, J=8.4 Hz), 7.43 (2H, d, J=8.4 Hz), 7.32 (2H, d, J=7.2 Hz), 7.26-7.20 (3H, m), 5.93 (1H, d, J=10.2 Hz), 5.41 (1H, d, J=10.2 Hz), 4.66-4.63 (1H, m), 4.48-4.44 (2H, m), 3.98-3.91 (2H, m), 3.70 (1H, dd, J=12.0, 4.2 Hz), 3.55 (1H, dd, J=12.0 3.6 Hz); $^{13}$C NMR (150 MHz, MeOD) δ 152.0, 140.0, 138.6, 132.0, 129.3, 127.9, 127.0, 123.0, 121.2, 119.6, 68.1, 64.5, 51.6, 48.3; HPLC analysis: (CHIRALPAK IA-3, 70:30 hexanes-EtOH-diethylamine, 1.0 mL/min, UV: 254 nm), tR=2.72 min (minor), 5.10 min (major); HPLC analysis: >94% ee Material produced in this fashion exhibited $[α]^{25}D=-93.0°$ (c=1.0, $CH_3OH$); HRMS m/z 414.0989 ([M+H$^+$], $C_{19}H_{19}F_3NO_4S$ requires 414.0988).

Trans-stereoselective epoxidation of intermediate (iii) is carried out using conditions reported in O'Brein et al, Organic Letters, vol. 5, Pages 4955-4957, 2003, to give epoxide intermediate, (iv)-isomer 2. Epoxide opening is carried out with carbazole in the presence of a base such as NaNH$_2$ in toluene with heating for 50-100° C. for between 1 and 24 hours. Deprotection of the benzyl group is carried out by hydrogenolysis with a catalyst such as palladium on carbon or palladium hydroxide, to give the PP2A modulator.

This synthetic approach may also be used for the synthesis other systems including those containing heteroaromatic tricyclic moieties as shown in Scheme 3.

Scheme 3

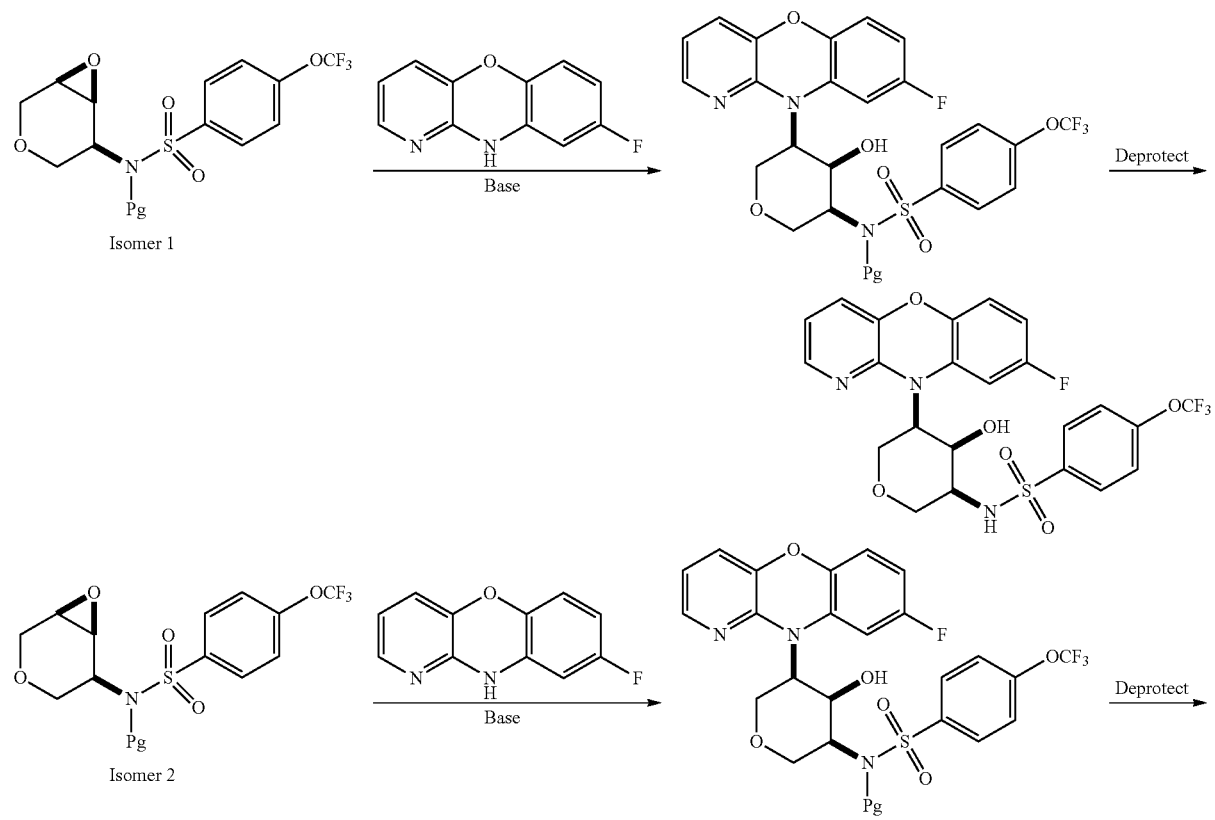

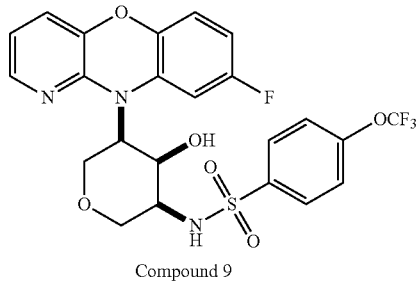

Compound 9

Cyclic Sulfone, Q=SO$_2$

Synthesis of 3,6-dihydro-2H-thiopyran-3-ol is described in Evans et al, J. Am. Chem. Soc. 2000, Vol. 122, Pages 7095-7920. This may be converted to tert-butyl (3,6-dihydro-2H-thiopyran-3-yl) carbonate as already described and used in the synthesis of PP2A modulators in two ways. First as shown in by the example in Scheme 4, where conditions are analogous to those described for the pyran, except that additional oxidant may be employed the dihydroxylation step to effect oxidation of the ring sulfur. Extended reaction times or heating may also be used in the dihydroxylation step.

Scheme 4

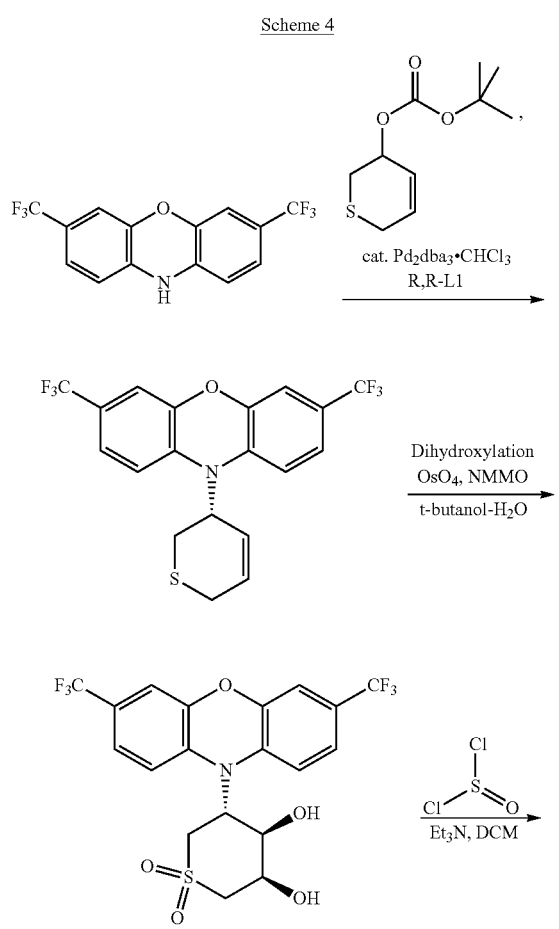

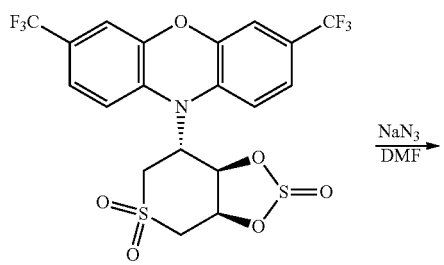

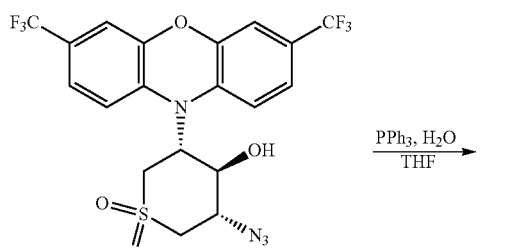

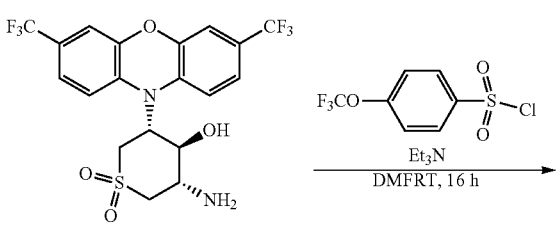

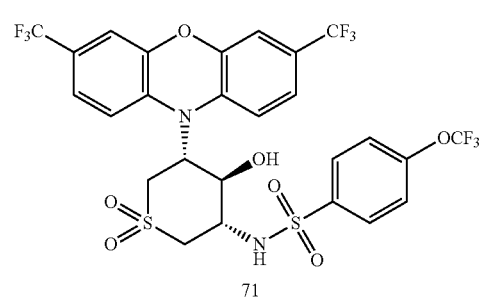

71

A second route to the cyclic sulfone is shown in Scheme 5; again, additional oxidant or extended reaction times may be used in the epoxidation step to effect oxidation of the ring sulfur.

Scheme 5

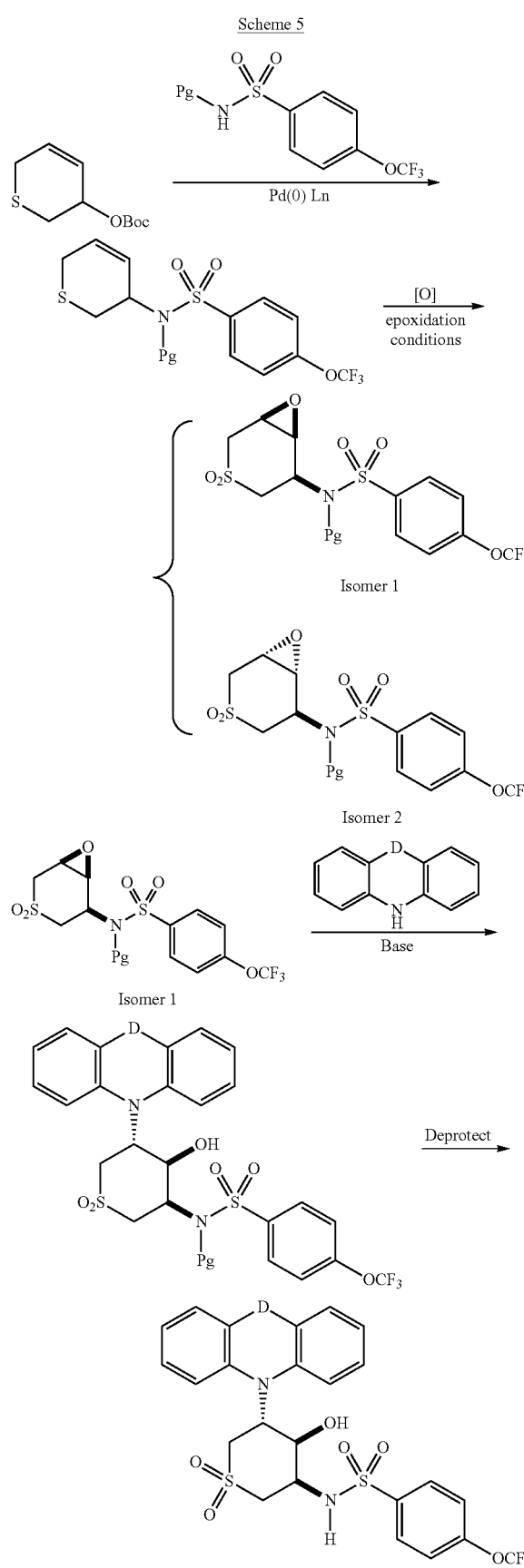

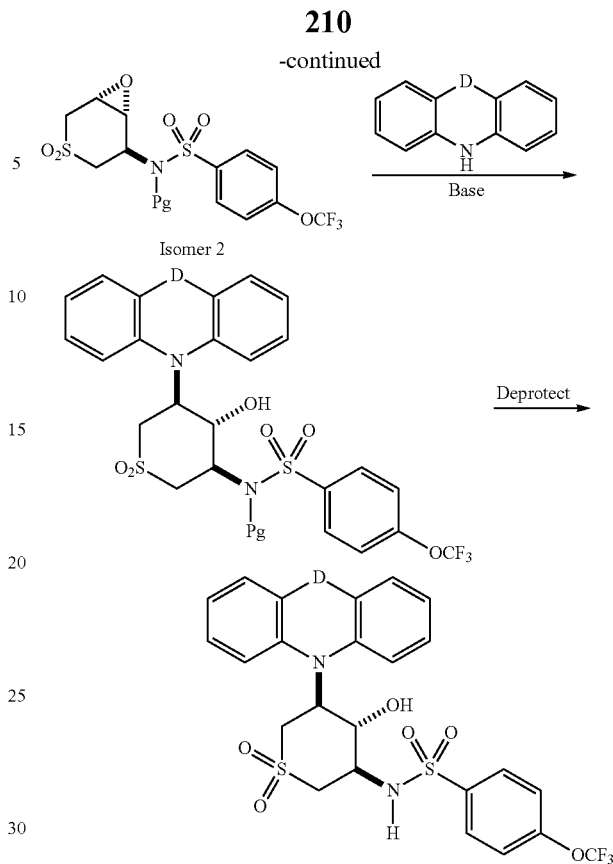

Cell Viability Assays (IC$_{50}$ Determination)

Cell viability assays were performed according to Denizot, F. and R. Lang, Journal of Immunological Methods, 1986. 89(22): p. 271-277. H1650 lung cancer cells were plated at 150,000 cells per well in a 12 well plate. Twenty-four hours after plating, cells were treated as described with increasing concentrations of drug and control. Forty-eight hours after drug treatment, cells were treated with 100 µL of 3-(4,5-Dimethylthiazol-2-yl)-2,5-diphenyltetrazolium bromide (MTT) and incubated for 2 hours at 37 C. The MTT solution was subsequently replaced with 300 µL of n-propyl alcohol and re-aliquoted to a 96 well plate. Spectrophotometric analysis of each solution was performed using a 96 well plate reader at 600 nm in triplicate. Results are shown in Table 1:

TABLE 1

Cell Viability Data

| Example No. | H1650 | Example No. | H1650 |
|---|---|---|---|
| 1 | 15 uM | 17b | 10 uM |
| 2 | 15 uM | 19a | 25 uM |
| 2a | 15 uM | 19b | 15 uM |
| 2b | 15 uM | 18a | 25 uM |
| 3 | 10 uM | 18b | 15 uM |
| 4 | 15 uM | 20a | 15 uM |
| 5 | 5 uM | 20b | 5 uM |
| 6 | 25 uM | 41a | 10 uM |
| 7 | 15 uM | 41b | 10 uM |
| 8 | 10 uM | 50 | 10 uM |
| 11 | 10 uM | 51 | 5 uM |
| 12 | 10 uM | 52a | 5 uM |
| 13 | 5 uM | 53a | 5 uM |
| 14 | 5 uM | 52b | 5 uM |
| 15 | 5 uM | 60 | 37% at 40 uM |

TABLE 1-continued

Cell Viability Data

| Example No. | H1650 | Example No. | H1650 |
|---|---|---|---|
| 16 | 10 uM | 61 | 5 uM |
| 17 | 5 uM | 66 | 5 uM |
| 18 | 20 uM | 67 | 56% at 40 uM |
| 16a | 10 uM | 68 | 5 uM |
| 16b | 10 uM | 69 | 54% at 40 uM |
| 17a | 15 uM | 44 | 10 uM |
| 54 | 5 uM | 62 | 15 uM |
| 55 | 5 uM | 63 | 20 uM |
| 56 | 5 uM | 64 | 15 uM |
| 57 | 5 uM | 65 | 20 uM |
| 58 | 5 uM | | |

Colony Formation Assay

Protocol for clonogenic assay follows Sangodkar et al., J Clin Invest 2012; 122:2637-51.

Cell culture and staining: For both A549luc and H1650 cells, 500 cells are seeded into each well of a 6-well plate and allowed to attach for 24 hours before drug treatment. The following day, cells are treated with either the appropriate dose of drug or an equivalent volume of DMSO (two replicates are treated for each condition). For each condition, depleted media is replaced with fresh media containing the equivalent drug dose four days after initial treatment. Cells are harvested either 7 (A549luc) or 8 (H1650) days after initial treatment. Briefly, medium is aspirated from each well and the cells are washed twice with ice-cold PBS, then plates are allowed to dry at room temperature for 4 hours. Cells are fixed for one hour in a fixing solution consisting of 10% methanol and 10% glacial acetic acid in distilled water, then stained overnight in 1% (w/v) crystal violet dissolved in methanol. The next day, staining solution is aspirated from the wells and plates are washed gently with distilled water to remove excess stain before colony counting. Colonies are imaged on a ChemiDoc XRS+(Bio-Rad) and images are exported as 8-bit TIFF files. Colonies are counted using the Colony Counter plugin in ImageJ, with colony size defined as between 4 and 400 square pixels, and minimum circularity set at 0.6. Duplicate wells are averaged to obtain a single value for each condition. Results (number of colonies) for A549luc cells and results (number of colonies) for H1650 cells may be analyzed separately.

In Vivo Cancer Model

To assess the in vivo effects of the compounds, subcutaneous xenograft of lung cancer cell line H358 was generated. Cells ($5 \times 10^6$) were injected into the right flank of 6- to 8-week-old male BALB/c nu/nu mice (Charles River, Wilmington, Mass.). Tumor volume was assessed twice a week by caliper measurement. Mice were randomized to treatment groups based on initial tumor volume average of 200 mm$^3$ per group. Mice were dosed by oral gavage with 5 mg/kg Example 2a BID. Mouse tumors were measured twice a week for the duration of the study. Mouse body weights were recorded weekly and percentage of mice body weights during treatment was calculated as: weight at each time point/initial weight×100. Animals were observed for signs of toxicity (mucous diarrhea, abdominal stiffness and weight loss) and no adverse signs were observed. Compound showed statistically significant inhibition of tumor (T) growth versus vehicle control (C) as shown in the Table A below at treatment day 17. No statistically significant toxicity was observed as judged from animal body weights of compound treated groups versus vehicle control group as shown in Table B below.

TABLE A

| Compound: dose; frequency | Mean Tumor Volume (T) | % T/C | Median Tumor Volume (T) | % T/C | Standard error | Student's ttest |
|---|---|---|---|---|---|---|
| Vehicle Control(C) DMA:solutol:water (10:10:80) | 775.03 | 100 | 742.55 | 100 | 82.82 | |
| Example 2a 5 mg/kg; BID | 208.64 | 28.82 | 191.78 | 25.82 | 15.80 | <0.01 |

TABLE B

| Compound: dose; frequency | Mean body weight/g | % T/C | Median body weight/g | % T/C | Standard error | Student's ttest |
|---|---|---|---|---|---|---|
| Vehicle Control (C) DMA:solutol:water (10:10:80) | 31.35 | 100 | 30.9 | 100 | 0.75 | |
| Example 2a 5 mg/kg; BID | 30.21 | 96.36 | 29.95 | 96.92 | 0.65 | 0.26 |

In Vivo Data for Example 17b

To evaluate the efficacy of Example 17b in vivo, xenograft model was utilized using the H358 cell line. H358 cells ($1 \times 10^7$) were injected into the right flank of 6- to 8-week-old male BALB/c nu/nu mice. Mice were randomized to treatment groups based on initial tumor volume. Tumor volume was assessed twice a week by caliper measurement, until volumes reached an average of 200 mm$^3$. Mice were treated by oral gavage with vehicle control or Example 17b (5 mg/kg) BID. The treatment schedules were initiated, and the mouse tumors were measured every other day for the duration of the study. Mice body weights were recorded weekly and percentage of mice body weights during treatment was calculated as: weight at each time point/initial weight×100. Animals were observed for signs of toxicity (mucous diarrhea, abdominal stiffness and weight loss) and no adverse signs were observed. Compound showed statistically significant inhibition of tumor (T) growth versus vehicle control (C) as shown in the Table C below at treatment day 32. No statistically significant toxicity was observed as judged from animal body weights of compound treated groups versus vehicle control group as shown in Table D below.

TABLE C

| Compound Dose, Frequency | Mean Tumor Volume (T)/mm$^3$ | % T/C | Median Tumor Volume (T)/mm$^3$ | % T/C | Standard error | Student's ttest |
|---|---|---|---|---|---|---|
| Vehicle Control (C) DMA:solutol:water (10:10:80) | 1014 | 100 | 968 | 100 | 128 | |
| Example 17b 5 mg/kg, BID | 562 | 55 | 520 | 54 | 94 | 0.015 |

TABLE D

| Compound Dose, Frequency | Mean body weight/g | % T/C | Median body weight/g | % T/C | Standard error | Student's ttest |
|---|---|---|---|---|---|---|
| Vehicle Control (C) DMA:solutol:water (10:10:80) | 34.23 | 100 | 34.3 | 100 | 1.001 | |
| Example 17b 5 mg/kg, BID | 34.41 | 100.5 | 34.1 | 99.4 | 1.256 | 0.91 |

Various embodiments of the invention can be described in the text below:

[1]. A compound of formula I:

wherein:

D is selected from a direct bond, —O—, —CH$_2$O—, —OCH$_2$—, —C(═O)NR$^D$—, and —N(R$^D$)C(═O)—;

R$^D$ is selected from hydrogen and (C$_1$-C$_6$)alkyl;

T is a benzene ring or a five- or six-membered heteroaromatic ring;

U is a benzene ring or a five- or six-membered heteroaromatic ring;

X$^1$, X$^2$, X$^3$, and X$^4$ are independently selected in each instance from hydrogen, halogen, nitro, cyano, (C$_1$-C$_6$)alkyl, (C$_1$-C$_6$)haloalkyl, (C$_1$-C$_6$)haloalkoxy, (C$_1$-C$_6$)haloalkylthio, —NR$^1$R$^2$, —OR$^1$, —C(O)R$^1$, —OC(O)R$^1$, —C(O)NR$^1$R$^2$, —C(O)OR$^1$, —SR$^1$, —SO$_2$R$^1$, and —SO$_2$NR$^1$R$^2$;

R$^1$ and R$^2$ are independently selected in each instance from the group consisting of hydrogen and (C$_1$-C$_6$)alkyl;

Q is selected from —O—, S(O)$_n$—, and —NR—;

n is zero, 1 or 2;

R is selected from hydrogen, optionally substituted (C$_1$-C$_6$)alkyl, (C$_3$-C$_7$)cycloalkyl, aryl, or heteroaryl; —SO$_2$R$^3$; —SO$_2$N(R$^3$R$^4$); —C(═O)R$^5$; —C(═O)OR$^5$; or —C(═O)N(R$^3$R$^4$); wherein said substituents on the (C$_1$-C$_6$)alkyl, (C$_3$-C$_7$)cycloalkyl, aryl, or heteroaryl are selected from the group consisting of hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_3$-C$_7$)cycloalkyl, (C$_1$-C$_4$)haloalkyl, (C$_1$-C$_4$)haloalkoxy, and (C$_1$-C$_4$)alkoxy;

R$^3$ and R$^4$ are independently selected in each instance from hydrogen, (C$_1$-C$_6$)alkyl, aryl, and arylalkyl, wherein said aryl or the aryl of the arylalkyl is optionally substituted with hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_1$-C$_4$)haloalkyl, (C$_1$-C$_4$)haloalkoxy, or (C$_1$-C$_4$)alkoxy;

R$^5$ is selected from hydrogen, optionally substituted (C$_1$-C$_4$)alkyl, or optionally substituted aryl, wherein said optional substituents are selected from the group consisting of (C$_1$-C$_3$)alkyl, OR$^1$, NH$_2$, NHMe, N(Me)$_2$, and heterocycle;

Y is selected from hydrogen or hydroxyl; and

Z$^1$ and Z$^2$ are independently selected in each instance from the group consisting of hydrogen, halogen, nitro, cyano, azide, (C$_1$-C$_6$)alkyl, (C$_1$-C$_6$)haloalkyl, (C$_1$-C$_6$)haloalkoxy, —NR$^1$R$^2$, —NR$^1$C(O)R$^2$, —OR$^1$, —C(O)R$^1$, —OC(O)R$^1$, —C(O)NR$^1$R$^2$, —C(O)OR$^1$, —SR$^1$, —SO$_2$R$^1$, and —SO$_2$NR$^1$R$^2$.

[2]. A compound of [1] above, or according to other embodiments of the invention, wherein D is a direct bond.

[3]. A compound of [1] above, or according to other embodiments of the invention, wherein D is —O—.

[4]. A compound of [1] above, or according to other embodiments of the invention, wherein D is —OCH$_2$—.

[5]. A compound of [1] above, or according to other embodiments of the invention, wherein D is —C(=O)NR$^D$—.

[6]. A compound of [1] above, or according to other embodiments of the invention, wherein D is —N(R$^D$)C(=O)—.

[7]. A compound of [1] above, or according to other embodiments of the invention, wherein T and U are each independently selected from the group consisting of a benzene ring and pyridine.

[8]. A compound of [7] above, or according to other embodiments of the invention, wherein at least one of T and U is a benzene ring.

[9]. A compound of [8] above, or according to other embodiments of the invention, wherein both T and U are benzene rings.

[10]. A compound of [1], [2], [3], [4], [5], [6], [7], [8], or [9] above, or according to other embodiments of the invention, wherein Y is hydroxyl.

[11]. A compound of [1], [2], [3], [4], [5], [6], [7], [8], or [9] above, or according to other embodiments of the invention, wherein Y is hydrogen.

[12]. A compound of [1], [2], [3], [4], [5], [6], [7], [8], or [9] above, or according to other embodiments of the invention, wherein Q is —O—.

[13]. A compound of [1], [2], [3], [4], [5], [6], [7], [8], or [9] above, or according to other embodiments of the invention, wherein Q is —NR—.

[14]. A compound of [13] above, or according to other embodiments of the invention, wherein R is selected from hydrogen; (C$_1$-C$_6$)alkyl optionally substituted with one or more of OR$^1$, (C$_3$-C$_7$)cycloalkyl, fluoro or phenyl; (C$_3$-C$_7$)cycloalkyl optionally substituted with one or more of hydroxy, methyl, or fluoro; aryl optionally substituted with one or more of hydroxy, methoxy, halogen, nitro, amino, or methyl; heteroaryl optionally substituted with one or more of hydroxy, methoxy, halogen, nitro, amino, or methyl; —SO$_2$R$^3$; —SO$_2$NR$^3$R$^4$; —C(=O)R$^5$; —C(=O)OR$^5$; or —C(=O)NR$^3$R$^4$;
R$^3$ is selected in each instance from hydrogen, (C$_1$-C$_6$)alkyl, (C$_1$-C$_6$)haloalkyl, aryl, and arylalkyl, wherein said aryl or the aryl of the arylalkyl is optionally substituted with one or more of hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_1$-C$_4$)haloalkyl, (C$_1$-C$_4$)haloalkoxy, and (C$_1$-C$_4$)alkoxy;
R$^4$ is selected in each instance from hydrogen and methyl;
R$^5$ is selected from optionally substituted (C$_1$-C$_4$)alkyl or optionally substituted aryl, wherein said optional substituents are selected from one or more of OH, OMe, NH$_2$, NHMe, N(Me)$_2$, or heterocycle.

[15]. A compound of [14] above, or according to other embodiments of the invention, wherein R is selected from hydrogen; (C$_1$-C$_3$)alkyl optionally substituted with one or more of hydroxy, methoxy, fluoro, or phenyl; phenyl optionally substituted with one or more of hydroxy, fluoro, methoxy, nitro, amino, or methyl; or a nitrogen-containing heteroaryl optionally substituted with one or two methyl groups.

[16]. A compound of [14] above, or according to other embodiments of the invention, wherein R is —C(=O)R$^5$.

[17]. A compound of [16] above, or according to other embodiments of the invention, wherein R$^5$ is selected from (C$_1$-C$_3$)alkyl and phenyl, each of which may be optionally substituted with OR$^1$, NH$_2$, NHMe, N(Me)$_2$, or heterocycle.

[18]. A compound of [14] above, or according to other embodiments of the invention, wherein R is —C(=O)OR$^5$.

[19]. A compound of [18] above, or according to other embodiments of the invention, wherein R$^5$ is selected from the group consisting of phenyl and (C$_1$-C$_4$)alkyl, each of which may be substituted with OR'.

[20]. A compound of [14] above, or according to other embodiments of the invention, wherein R is —SO$_2$R$^3$.

[21]. A compound of [20] above, or according to other embodiments of the invention, wherein wherein R$^3$ is selected from the group consisting of (C$_1$-C$_6$)alkyl, CF$_3$, and aryl; wherein said aryl is optionally substituted with hydroxy, halogen, cyano, amino, or (C$_1$-C$_4$)alkoxy.

[22]. A compound of [14] above, or according to other embodiments of the invention, wherein R is SO$_2$NR$^3$R$^4$.

[23]. A compound of [22] above, or according to other embodiments of the invention, wherein R$^3$ is selected from the group consisting of hydrogen, (C$_1$-C$_3$)alkyl, and aryl optionally substituted with hydroxy, halogen, cyano, amino, or methoxy; and R$^4$ is hydrogen or methyl.

[24]. A compound of [14] above, or according to other embodiments of the invention, wherein R is —C(=O)NR$^3$R$^4$.

[25]. A compound of [24] above, or according to other embodiments of the invention, wherein R$^3$ is selected from the group consisting of hydrogen, (C$_1$-C$_3$)alkyl, and aryl optionally substituted with hydroxy, halogen, cyano, amino, or methoxy; and R$^4$ is hydrogen or methyl.

[26]. A compound of [1], [2], [3], [4], [5], or [6] above, or according to other embodiments of the invention, wherein Q is —S(O)$_2$—.

[27]. A compound of [1], [2], [3], [4], [5], [6], [7], [8], or [9] above, or according to other embodiments of the invention, wherein zero, one or two of X$^1$, X$^2$, X$^3$, and X$^4$ are independently selected in each instance from halogen and halo(C$_1$-C$_6$)alkyl, and the remainder are hydrogen.

[28]. A compound of [27] above, or according to other embodiments of the invention, wherein one or two of X$^1$, X$^2$, X$^3$, and X$^4$ are independently selected in each instance from chloro, fluoro, and fluoro(C$_1$-C$_3$)alkyl, and the remainder are hydrogen.

[29]. A compound of [1], [2], [3], [4], [5], [6], [7], [8], or [9] above, or according to other embodiments of the invention, wherein Z$^1$ and Z$^2$ are independently selected in each instance from hydrogen, halogen, halo(C$_1$-C$_6$)alkyl, (C$_1$-C$_6$)alkoxy, and halo(C$_1$-C$_6$)alkoxy.

[30]. A compound of [29] above, or according to other embodiments of the invention, wherein Z$^1$ is hydrogen and Z$^2$ is selected from hydrogen, halogen, halo(C$_1$-C$_6$)alkyl, (C$_1$-C$_6$)alkoxy, and halo(C$_1$-C$_6$)alkoxy.

[31]. A compound of [30] above, or according to other embodiments of the invention, wherein Z$^2$ is hydrogen, fluoro, chloro, trifluoromethyl, methoxy, or trifluoromethoxy.

[32]. A compound of [31] above, or according to other embodiments of the invention, wherein Z$^2$ is para to the attachment of the phenyl ring to the sulfonyl.

[33]. A compound [1], [2], [3], [4], [5], [6], [7], [8], or [9] above, or according to other embodiments of the invention, wherein the relative stereochemistry is of formula II:

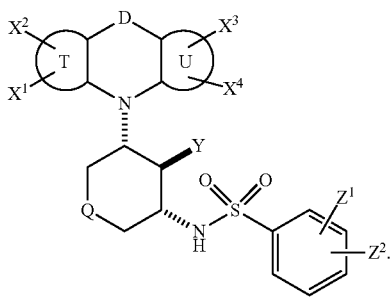

II

[34]. A compound of [33] above, or according to other embodiments of the invention, of formula IIIa:

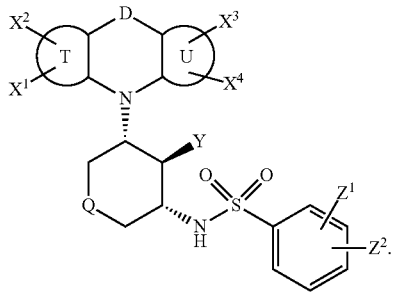

IIIa

[35]. A compound of [33] above, or according to other embodiments of the invention, of formula IIIb:

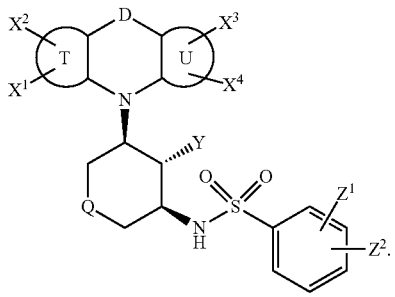

IIIb

[36]. A compound of [1] above, or according to other embodiments of the invention, of formula:

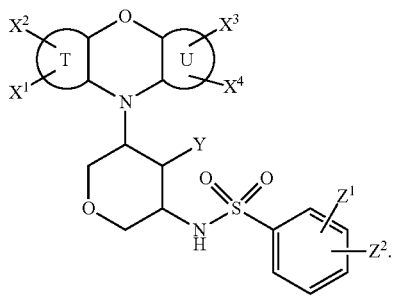

[37]. A compound of [1] above, or according to other embodiments of the invention, of formula:

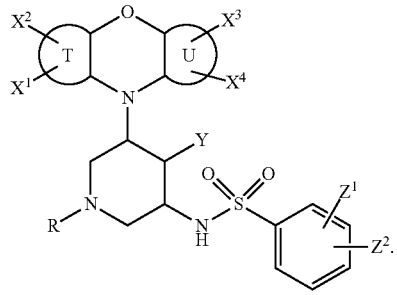

[38]. A compound of [1] above, or according to other embodiments of the invention, of formula:

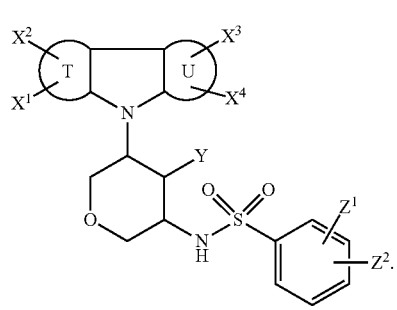

[39]. A compound of [1] above, or according to other embodiments of the invention, of formula:

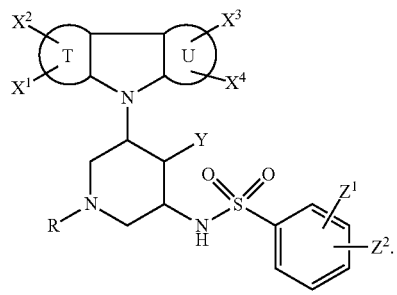

[40]. A compound of [36], [37], [38, or [39] above, or according to other embodiments of the invention, wherein $Z^1$ is hydrogen and $Z^2$ is selected from hydrogen, halogen, halo($C_1$-$C_6$)alkyl, ($C_1$-$C_6$)alkoxy, or halo($C_1$-$C_6$)alkoxy.

[41]. A compound of [40] above, or according to other embodiments of the invention, wherein $Z^2$ is hydrogen, fluoro, chloro, trifluoromethyl, methoxy, or trifluoromethoxy.

[42]. A compound of [41] above, or according to other embodiments of the invention, wherein $Z^2$ is trifluoromethoxy.

[43]. A method for treating a disease in a patient chosen from:
(a) cancer
(b) diabetes
(c) autoimmune disease
(d) age onset proteotoxic disease
(e) mood disorder (f) acne vulgaris
(g) solid organ transplant rejection
(h) graft vs. host disease
(i) cardiac hypertrophy
(j) viral infection and
(k) parasitic infection;
the method comprising administering to the patient a therapeutically effective amount of a compound of [1], [2], [3], [4], [5], [6], [7], [8], [9], [36], [37], [38], or [39] above, or according to other embodiments of the invention.

[44]. The method of [43] above, or according to other embodiments of the invention, wherein said cancer is selected from the group consisting of: ovarian, pancreatic, renal cell, breast, prostate, lung, hepatocellular carcinoma, glioma, leukemia, lymphoma, colorectal cancers, and sarcomas.

[45]. The method of [43] above, or according to other embodiments of the invention, for treating cancer, wherein said cancer is chemotherapy resistant cancer.

[46]. The method of [45] above, or according to other embodiments of the invention, wherein the method further comprises administering one or more additional cancer chemotherapeutic agents.

[47]. The method of [43] above, or according to other embodiments of the invention, for treating an age onset proteotoxic disease, wherein said disease is selected from the group consisting of: Alzheimer's disease, Parkinson's disease, Huntington's disease, and amyotrophic lateral sclerosis.

[48]. The method of [43] above, or according to other embodiments of the invention, for treating a viral infection.

[49]. The method of [48] above, or according to other embodiments of the invention, wherein said viral infection is caused by a virus selected from the group consisting of influenza, HIV-1, HPV, adenovirus, BKV, EBV, JCV, HCV, MCV, polyomavirus, SV40, HTLV-1, HSV-1, CMV, hepatitis B, BPV-1, human T-cell lymphotropic virus type 1, Japanese encephalitis virus, RSV, and West Nile virus.

[50]. The method of [43] above, or according to other embodiments of the invention, for treating a parasitic infection.

[51]. The method of [50] above, or according to other embodiments of the invention, wherein said parasitic infection is caused by a parasite selected from the group consisting of *Plasmodium* and *Theileria*.

[52]. A method for restoring sensitivity to one or more chemotherapeutic agents in the treatment of cancer, the method comprising administering an effective amount of a compound of [1], [2], [3], [4], [5], [6], [7], [8], [9], [36], [37], [38], or [39] above, or according to other embodiments of the invention.

[53]. A method for treating a disease or disorder in a patient where the disease or disorder involves the dysregulation of the PI3K-AKT-FOXO signaling pathway, the method comprising administering to the patient a therapeutically effective amount of a compound of [1], [2], [3], [4], [5], [6], [7], [8], [9], [36], [37], [38], or [39] above, or according to other embodiments of the invention.

[54]. A method for treating a disease or disorder in a patient where the disease or disorder involves the dysregulation of a Myc dependant signaling pathway, the method comprising administering to the patient a therapeutically effective amount of a compound of [1], [2], [3], [4], [5], [6], [7], [8], [9], [36], [37], [38], or [39] above, or according to other embodiments of the invention.

[55]. A pharmaceutical composition comprising a pharmaceutically acceptable carrier and a compound of [1], [2], [3], [4], [5], [6], [7], [8], [9], [36], [37], [38], or [39] above, or according to other embodiments of the invention.

Various embodiments of the invention can be described in the text below:

[101]. A compound of formula I:

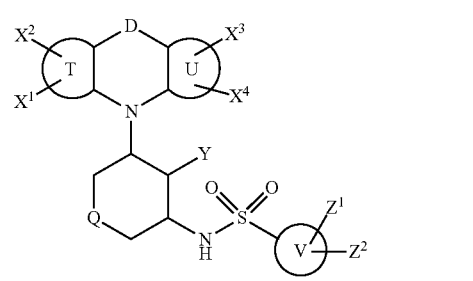

wherein:
D is selected from a direct bond, —O—, —CH$_2$O—, —OCH$_2$—, —C(=O)NR$^D$—, and —N(R$^D$)C(=O)—;
R$^D$ is selected from hydrogen and (C$_1$-C$_6$)alkyl;
T is a benzene ring or a five- or six-membered heteroaromatic ring;
U is a benzene ring or a five- or six-membered heteroaromatic ring;
X$^1$, X$^2$, X$^3$, and X$^4$ are independently selected in each instance from hydrogen, halogen, nitro, cyano, (C$_1$-C$_6$)alkyl, (C$_1$-C$_6$)haloalkyl, (C$_1$-C$_6$)haloalkoxy, (C$_1$-C$_6$)haloalkylthio, —NR$^1$R$^2$, —OR$^1$, —C(O)R', —OC(O)R$^1$, —C(O)NR$^1$R$^2$, —C(O)OR$^1$, —SR$^1$, —SO$_2$R$^1$, and —SO$_2$NR$^1$R$^2$;
R$^1$ and R$^2$ are independently selected in each instance from the group consisting of hydrogen and (C$_1$-C$_6$)alkyl;
Q is selected from —O—, S(O)$_n$—, and —NR—;
n is zero, 1 or 2;
R is selected from hydrogen, optionally substituted (C$_1$-C$_6$)alkyl, (C$_3$-C$_7$)cycloalkyl, aryl, or heteroaryl; —SO$_2$R$^3$; —SO$_2$N(R$^3$R$^4$); —C(=O)R$^5$; —C(=O)OR$^5$; or —C(=O)N(R$^3$R$^4$); wherein said substituents on the (C$_1$-C$_6$)alkyl, (C$_3$-C$_7$)cycloalkyl, aryl, or heteroaryl are selected from the group consisting of hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_3$-C$_7$)cycloalkyl, (C$_1$-C$_4$)haloalkyl, (C$_1$-C$_4$)haloalkoxy, and (C$_1$-C$_4$)alkoxy;
R$^3$ and R$^4$ are independently selected in each instance from hydrogen, (C$_1$-C$_6$)alkyl, aryl, and arylalkyl, wherein said aryl or the aryl of the arylalkyl is optionally substituted with hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_1$-C$_4$)haloalkyl, (C$_1$-C$_4$)haloalkoxy, or (C$_1$-C$_4$)alkoxy;
R$^5$ is selected from hydrogen, optionally substituted (C$_1$-C$_4$) alkyl, or optionally substituted aryl, wherein said optional substituents are selected from the group consisting of (C$_1$-C$_3$)alkyl, OR$^1$, NH$_2$, NHMe, N(Me)$_2$, and heterocycle;
Y is selected from hydrogen or hydroxyl;
V is selected from phenyl, a six-membered heteroaromatic ring, furan, and thiophene;

$Z^1$ and $Z^2$ are independently selected in each instance from the group consisting of hydrogen, halogen, nitro, cyano, azide, $(C_1$-$C_6)$alkyl, $(C_1$-$C_6)$haloalkyl, $(C_1$-$C_6)$haloalkoxy, —$(C_1$-$C_6)$haloalkylthio, —$NR^1R^2$, —$NR^1C(O)R^2$, —$NR^1C(O)OR^6$, —$OR^1$, —$C(O)R'$, —$OC(O)R^1$, —$C(O)NR^1R^2$, —$C(O)OR^1$, —$SR^1$, —$SO_2R^1$, and —$SO_2NR^1R^2$; and $R^6$ is $(C_1$-$C_8)$hydrocarbon.

[102]. A compound of [101] above, or according to other embodiments of the invention, wherein D is a direct bond.

[103]. A compound of [101] above, or according to other embodiments of the invention, wherein D is —O—.

[104]. A compound of [101] above, or according to other embodiments of the invention, wherein D is —$OCH_2$—.

[105]. A compound of [101] above, or according to other embodiments of the invention, wherein D is —$C(=O)NR^D$—.

[106]. A compound of [101] above, or according to other embodiments of the invention, wherein D is —$N(R^D)C(=O)$—.

[107]. A compound of [101] above, or according to other embodiments of the invention, wherein T and U are each independently selected from the group consisting of a benzene ring and pyridine.

[108]. A compound of [107] above, or according to other embodiments of the invention, wherein at least one of T and U is a benzene ring.

[109]. A compound of [108] above, or according to other embodiments of the invention, wherein both T and U are benzene rings.

[110]. A compound of [101], [102], [103, [104], [105], [106], [107], [109], or [109] above, or according to other embodiments of the invention, wherein Y is hydroxyl.

[111]. A compound of [101], [102], [103, [104], [105], [106], [107], [109], or [109] above, or according to other embodiments of the invention, wherein Y is hydrogen.

[112]. A compound of [101], [102], [103, [104], [105], [106], [107], [109], or [109] above, or according to other embodiments of the invention, wherein Q is —O—.

[113]. A compound of [101], [102], [103, [104], [105], [106], [107], [109], or [109] above, or according to other embodiments of the invention, wherein Q is —NR—.

[114]. A compound of [113] above, or according to other embodiments of the invention, wherein R is selected from hydrogen; $(C_1$-$C_6)$alkyl optionally substituted with one or more of $OR^1$, $(C_3$-$C_7)$cycloalkyl, fluoro or phenyl; $(C_3$-$C_7)$cycloalkyl optionally substituted with one or more of hydroxy, methyl, or fluoro; aryl optionally substituted with one or more of hydroxy, methoxy, halogen, nitro, amino, or methyl; heteroaryl optionally substituted with one or more of hydroxy, methoxy, halogen, nitro, amino, or methyl; —$SO_2R^3$; —$SO_2NR^3R^4$; —$C(=O)R^5$; —$C(=O)OR^5$; or —$C(=O)NR^3R^4$;

$R^3$ is selected in each instance from hydrogen, $(C_1$-$C_6)$alkyl, $(C_1$-$C_6)$haloalkyl, aryl, and arylalkyl, wherein said aryl or the aryl of the arylalkyl is optionally substituted with one or more of hydroxy, halogen, cyano, nitro, amino, $(C_1$-$C_4)$alkylamino, $(C_1$-$C_4)$dialkylamino, $(C_1$-$C_4)$acylamino, $(C_1$-$C_4)$alkylsulfonyl, $(C_1$-$C_4)$alkylthio, $(C_1$-$C_4)$alkyl, $(C_1$-$C_4)$haloalkyl, $(C_1$-$C_4)$haloalkoxy, and $(C_1$-$C_4)$alkoxy;

$R^4$ is selected in each instance from hydrogen and methyl;

$R^5$ is selected from optionally substituted $(C_1$-$C_4)$alkyl or optionally substituted aryl, wherein said optional substituents are selected from one or more of $OR^1$, $NH_2$, NHMe, $N(Me)_2$, or heterocycle.

[115]. A compound of [114] above, or according to other embodiments of the invention, wherein R is selected from hydrogen; $(C_1$-$C_3)$alkyl optionally substituted with one or more of hydroxy, methoxy, fluoro, or phenyl; phenyl optionally substituted with one or more of hydroxy, fluoro, methoxy, nitro, amino, or methyl; or a nitrogen-containing heteroaryl optionally substituted with one or two methyl groups.

[116]. A compound of [114] above, or according to other embodiments of the invention, wherein R is —$C(=O)R^5$.

[117]. A compound of [116] above, or according to other embodiments of the invention, wherein $R^5$ is selected from $(C_1$-$C_3)$alkyl and phenyl, each of which may be optionally substituted with $OR^1$, $NH_2$, NHMe, $N(Me)_2$, or heterocycle.

[118]. A compound of [114] above, or according to other embodiments of the invention, wherein R is —$C(=O)OR^5$.

[119]. A compound of [118] above, or according to other embodiments of the invention, wherein $R^5$ is selected from the group consisting of phenyl and $(C_1$-$C_4)$alkyl, each of which may be substituted with $OR^1$.

[120]. A compound of [114] above, or according to other embodiments of the invention, wherein R is —$SO_2R^3$.

[121]. A compound of [120] above, or according to other embodiments of the invention, wherein $R^3$ is selected from the group consisting of $(C_1$-$C_6)$alkyl, $CF_3$, and aryl; wherein said aryl is optionally substituted with hydroxy, halogen, cyano, amino, or $(C_1$-$C_4)$alkoxy.

[122]. A compound of [114] above, or according to other embodiments of the invention, wherein R is $SO_2NR^3R^4$.

[123]. A compound of [122] above, or according to other embodiments of the invention, wherein $R^3$ is selected from the group consisting of hydrogen, $(C_1$-$C_3)$alkyl, and aryl optionally substituted with hydroxy, halogen, cyano, amino, or methoxy; and $R^4$ is hydrogen or methyl.

[124]. A compound of [114] above, or according to other embodiments of the invention, wherein R is —$C(=O)NR^3R^4$.

[125]. A compound of [124] above, or according to other embodiments of the invention, wherein $R^3$ is selected from the group consisting of hydrogen, $(C_1$-$C_3)$alkyl, and aryl optionally substituted with hydroxy, halogen, cyano, amino, or methoxy; and $R^4$ is hydrogen or methyl.

[126]. A compound of [101], [102], [103, [104], [105], or [106] above, or according to other embodiments of the invention, wherein Q is —$S(O)_2$—.

[127]. A compound of [101], [102], [103, [104], [105], [106], [107], [109], or [109] above, or according to other embodiments of the invention, wherein zero, one or two of $X^1$, $X^2$, $X^3$, and $X^4$ are independently selected in each instance from halogen, $(C_1$-$C_6)$alkyl, and halo$(C_1$-$C_6)$alkyl, and the remainder are hydrogen.

[128]. A compound of [127] above, or according to other embodiments of the invention, wherein one or two of $X^1$, $X^2$, $X^3$, and $X^4$ are independently selected in each instance from chloro, fluoro, $(C_1$-$C_4)$alkyl, and fluoro$(C_1$-$C_3)$alkyl, and the remainder are hydrogen.

[129]. A compound of [101], [102], [103, [104], [105], [106], [107], [109], or [109] above, or according to other embodiments of the invention, wherein $Z^1$ and $Z^2$ are independently selected in each instance from hydrogen, halogen, halo$(C_1$-$C_6)$alkyl, —$NR^1C(O)OR^6$, $(C_1$-$C_6)$alkoxy, and halo$(C_1$-$C_6)$alkoxy.

[130]. A compound of [129] above, or according to other embodiments of the invention, wherein $Z^1$ is hydrogen and $Z^2$ is selected from hydrogen, halogen, halo$(C_1$-$C_6)$alkyl, —$NR^1C(O)OR^6$, $(C_1$-$C_6)$alkoxy, and halo$(C_1$-$C_6)$alkoxy.

[131]. A compound of [130] above, or according to other embodiments of the invention, wherein Z² is hydrogen, fluoro, chloro, trifluoromethyl, —NHBoc, methoxy, or trifluoromethoxy.

[132]. A compound of [131] above, or according to other embodiments of the invention, wherein Z² is para to the attachment of ring V to the sulfonyl.

[133]. A compound of [101], [102], [103, [104], [105], [106], [107], [109], or [109] above, or according to other embodiments of the invention, wherein the relative stereochemistry is of formula IIa or formula IIb:

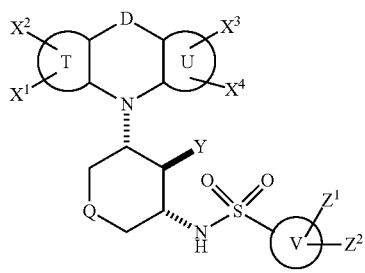

IIa

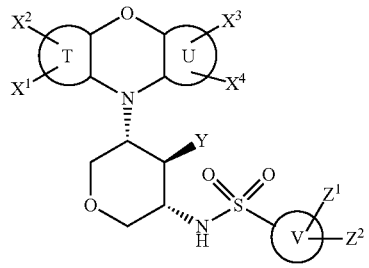

IIb

[134]. A compound of [133] above, or according to other embodiments of the invention, of formula IIIc or formula IIIb:

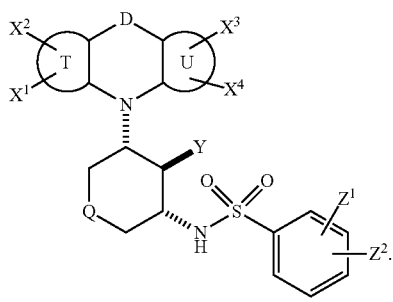

or

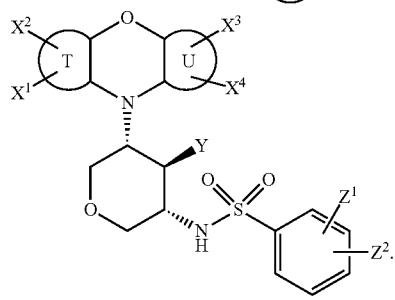

[135]. A compound of [133] above, or according to other embodiments of the invention, of formula IIIc or formula IIId:

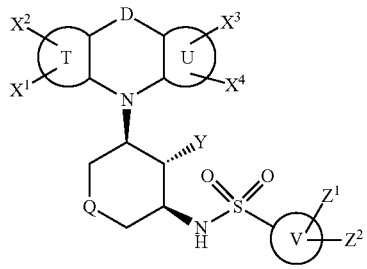

IIIc

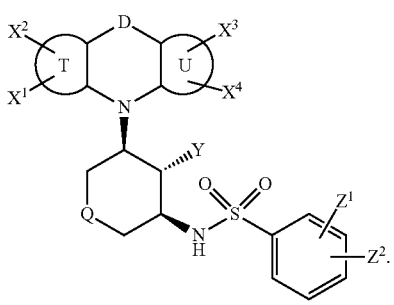

IIId

[136]. A compound of [101] above, or according to other embodiments of the invention, of formula:

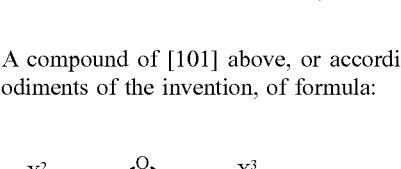

or

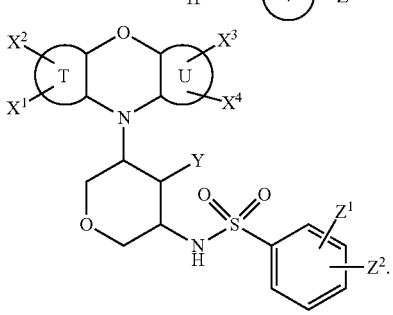

[137]. A compound of [101] above, or according to other embodiments of the invention, of formula:

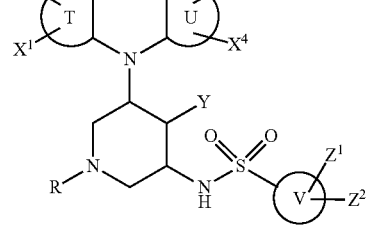

or

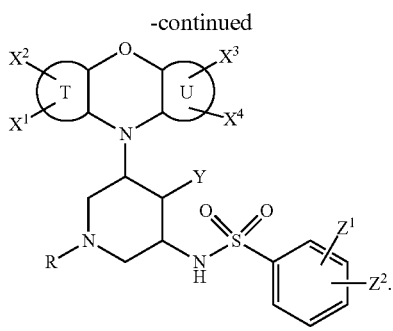

[138]. A compound of [101] above, or according to other embodiments of the invention, of formula:

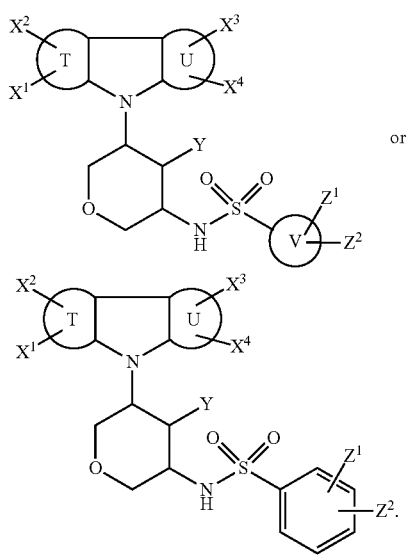

or

[139]. A compound of [101] above, or according to other embodiments of the invention, of formula:

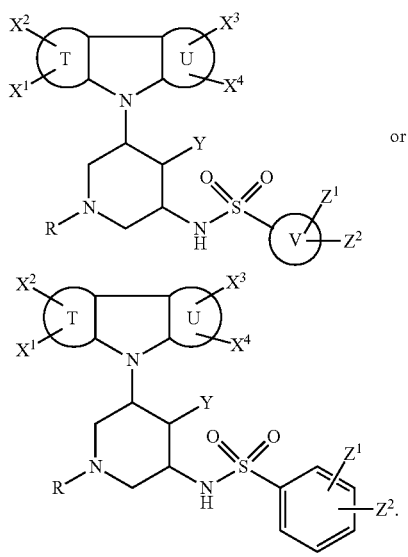

[140]. A compound of [136], [137], [138], or [139] above, or according to other embodiments of the invention, wherein $Z^1$ is hydrogen and $Z^2$ is selected from hydrogen, halogen, halo($C_1$-$C_6$)alkyl, —$NR^1C(O)OR^6$, ($C_1$-$C_6$)alkoxy, or halo($C_1$-$C_6$)alkoxy.

[141]. A compound of [140] above, or according to other embodiments of the invention, wherein $Z^2$ is hydrogen, fluoro, chloro, trifluoromethyl, —NHBoc, methoxy, or trifluoromethoxy.

[142]. A compound of [141] above, or according to other embodiments of the invention, wherein $Z^2$ is trifluoromethoxy.

[143]. A compound of any of [101] to [142] above, or according to other embodiments of the invention, wherein V is phenyl.

[144]. A method for treating a disease in a patient chosen from:
(a) cancer
(b) diabetes
(c) autoimmune disease
(d) age onset proteotoxic disease
(e) mood disorder
(f) acne vulgaris
(g) solid organ transplant rejection
(h) graft vs. host disease
(i) cardiac hypertrophy
(j) viral infection and
(k) parasitic infection;
the method comprising administering to the patient a therapeutically effective amount of a compound of any of [101] to [143] above, or according to other embodiments of the invention.

[145]. The method of [144] above, or according to other embodiments of the invention—wherein said cancer is selected from the group consisting of: ovarian, pancreatic, renal cell, breast, prostate, lung, hepatocellular carcinoma, glioma, leukemia, lymphoma, colorectal cancers, and sarcomas.

[146]. The method of [144] above, or according to other embodiments of the invention, for treating cancer, wherein said cancer is chemotherapy resistant cancer.

[147]. The method of [146] above, or according to other embodiments of the invention, wherein the method further comprises administering one or more additional cancer chemotherapeutic agents.

[148]. The method of [144] above, or according to other embodiments of the invention, for treating an age onset proteotoxic disease, wherein said disease is selected from the group consisting of: Alzheimer's disease, Parkinson's disease, Huntington's disease, and amyotrophic lateral sclerosis.

[149]. The method of [144] above, or according to other embodiments of the invention, for treating a viral infection.

[150]. The method of [149] above, or according to other embodiments of the invention, wherein said viral infection is caused by a virus selected from the group consisting of influenza, HIV-1, HPV, adenovirus, BKV, EBV, JCV, HCV, MCV, polyomavirus, SV40, HTLV-1, HSV-1, CMV, hepatitis B, BPV-1, human T-cell lymphotropic virus type 1, Japanese encephalitis virus, RSV, and West Nile virus.

[151]. The method of [144] above, or according to other embodiments of the invention, for treating a parasitic infection.

[152]. The method of [151] above, or according to other embodiments of the invention, wherein said parasitic infection is caused by a parasite selected from the group consisting of *Plasmodium* and *Theileria*.

[153]. A method for restoring sensitivity to one or more chemotherapeutic agents in the treatment of cancer, the method comprising administering an effective amount of a compound of any of [101] to [143] above, or according to other embodiments of the invention.

[154]. A method for treating a disease or disorder in a patient where the disease or disorder involves the dysregulation of the PI3K-AKT-FOXO signaling pathway, the method comprising administering to the patient a therapeutically effective amount of a compound of any of [101] to [143] above, or according to other embodiments of the invention.

[155]. A method for treating a disease or disorder in a patient where the disease or disorder involves the dysregulation of a Myc dependant signaling pathway, the method comprising administering to the patient a therapeutically effective amount of a compound of any of [101] to [143] above, or according to other embodiments of the invention.

[156]. A pharmaceutical composition comprising a pharmaceutically acceptable carrier and a compound of any of [101] to [143] above, or according to other embodiments of the invention.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

We claim:

1. A compound of formula I:

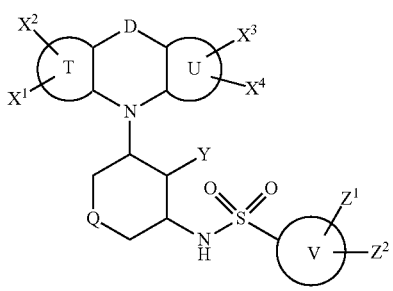

I wherein:
D is selected from a direct bond, —O—, —CH$_2$O—, —OCH$_2$—, —C(=O)NR$^D$—, and —N(R$^D$)C(=O)—;
R$^D$ is selected from hydrogen and (C$_1$-C$_6$)alkyl;
T is a benzene ring or a five- or six-membered heteroaromatic ring;
U is a benzene ring or a five- or six-membered heteroaromatic ring;
X$^1$, X$^2$, X$^3$, and X$^4$ are independently selected in each instance from hydrogen, halogen, nitro, cyano, (C$_1$-C$_6$)alkyl, (C$_1$-C$_6$)haloalkyl, (C$_1$-C$_6$)haloalkoxy, (C$_1$-C$_6$)haloalkylthio, —NR$^1$R$^2$, —C(O)R$^1$, —OC(O)R$^1$, —C(O)NR$^1$R$^2$, —C(O)OR$^1$, —SR$_1$, SO$^2$R$^1$, and —SO$_2$NR$^1$R$^2$;
R$^1$ and R$^2$ are independently selected in each instance from the group consisting of hydrogen and (C$_1$-C$_6$)alkyl;
Q is selected from —O—, S(O)$_n$—, and —NR—;
n is zero, 1 or 2;
R is selected from hydrogen, optionally substituted (C$_1$-C$_6$)alkyl, (C$_3$-C$_7$)cycloalkyl, aryl, or heteroaryl; —SO$_2$R$^3$; —SO$_2$N(R$^3$R$^4$); —C(=O)R$^5$; —C(=O)OR$^5$; or —C(=O)N(R$^3$R$^4$); wherein said substituents on the (C$_1$-C$_6$)alkyl, (C$_3$-C$_7$)cycloalkyl, aryl, or heteroaryl are selected from the group consisting of hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_3$-C$_7$)cycloalkyl, (C$_1$-C$_4$)haloalkyl, (C$_1$-C$_4$)haloalkoxy, and (C$_1$-C$_4$)alkoxy;
R$^3$ and R$^4$ are independently selected in each instance from hydrogen, (C$_1$-C$_6$)alkyl, aryl, and arylalkyl, wherein said aryl or the aryl of the arylalkyl is optionally substituted with hydroxy, halogen, cyano, nitro, amino, (C$_1$-C$_4$)alkylamino, (C$_1$-C$_4$)dialkylamino, (C$_1$-C$_4$)acylamino, (C$_1$-C$_4$)alkylsulfonyl, (C$_1$-C$_4$)alkylthio, (C$_1$-C$_4$)alkyl, (C$_1$-C$_4$)haloalkyl, (C$_1$-C$_4$)haloalkoxy, or (C$_1$-C$_4$)alkoxy;
R$^5$ is selected from hydrogen, optionally substituted (C$_1$-C$_4$)alkyl, or optionally substituted aryl, wherein said optional substituents are selected from the group consisting of (C$_1$-C$_3$)alkyl, OR$^1$, NH$_2$, NHMe, N(Me)$_2$, and heterocycle;
Y is selected from hydrogen or hydroxyl;
V is selected from phenyl, a six-membered heteroaromatic ring, furan, and thiophene;
Z$^1$ and Z$^2$ are independently selected in each instance from the group consisting of hydrogen, halogen, nitro, cyano, azide, (C$_1$-C$_6$)alkyl, (C$_1$-C$_6$)haloalkyl, (C$_1$-C$_6$)haloalkoxy, —(C$_1$-C$_6$)haloalkylthio, —NR$^1$R$^2$, —NR$^1$C(O)R$^2$, —NR$^1$C(O)OR$^6$, —C(O)R', —OC(O)R', —C(O)NR$^1$R$^2$, —C(O)OR$^1$, —SO$_2$R', and —SO$_2$NR$^1$R$^2$; and
R$^6$ is (C$_1$-C$_8$)hydrocarbon.

2. A compound according to claim 1 wherein D is a direct bond.

3. A compound according to claim 1 wherein D is —O—.

4. A compound according to claim 1 wherein D is chosen from —OCH$_2$—, —C(=O)NR$^D$— or —N(R$^D$)C(=O)—.

5. A compound according to claim 1 wherein T and U are each independently selected from the group consisting of a benzene ring and pyridine.

6. A compound according to claim 1 wherein Y is hydroxyl.

7. A compound according claim 1 wherein Q is —O—.

8. A compound according claim 1 wherein Q is —NR—.

9. A compound according to claim 1 wherein R is selected from hydrogen; (C$_1$-C$_3$)alkyl optionally substituted with one or more of hydroxy, methoxy, fluoro, or phenyl; phenyl optionally substituted with one or more of hydroxy, fluoro, methoxy, nitro, amino, or methyl; or a nitrogen-containing heteroaryl optionally substituted with one or two methyl groups.

10. A compound according to claim 1 wherein zero, one or two of X$^1$, X$^2$, X$^3$, and X$^4$ are independently selected in each instance from halogen, (C$_1$-C$_6$)alkyl, and halo(C$_1$-C$_6$)alkyl, and the remainder are hydrogen.

11. A compound according to claim 1 wherein the relative stereochemistry is of formula IIa or formula IIb:

12. A compound according to claim 1 of formula:
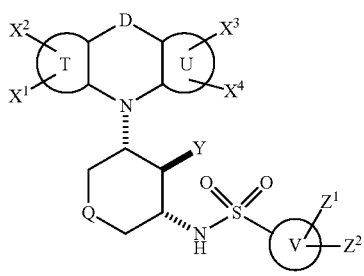
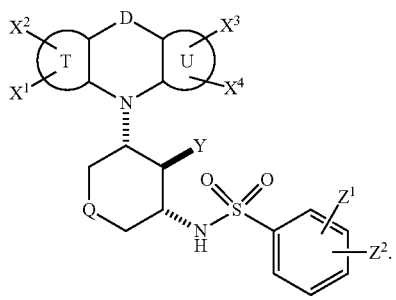
13. A compound according to claim 1 of formula:
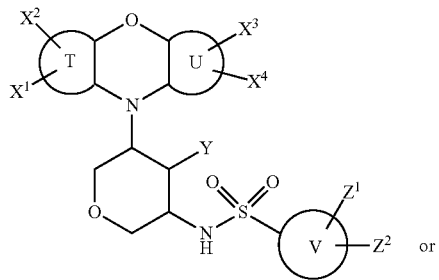
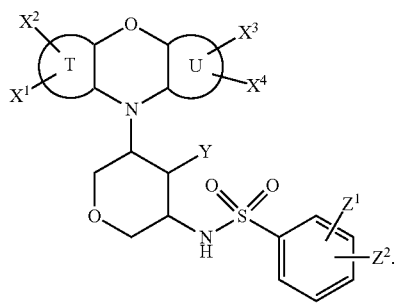
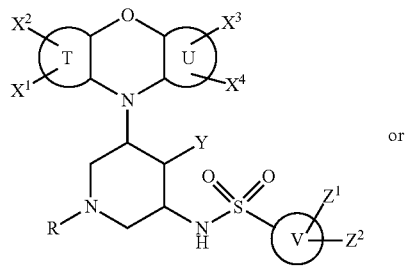
IIa
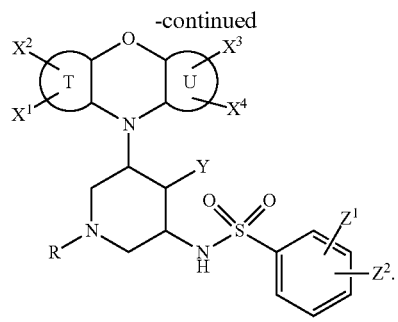
IIb
14. A compound according to claim 1 of formula:
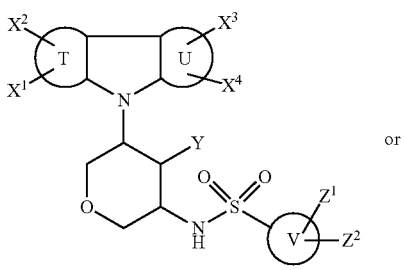
or
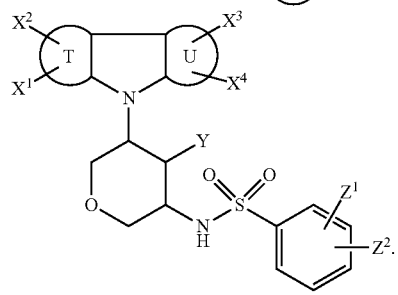
15. A compound according to claim 1 of formula:
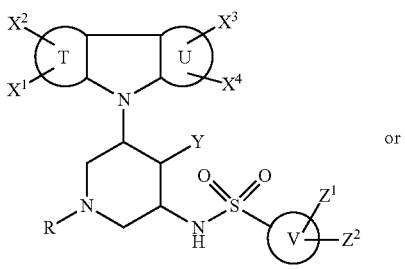
or
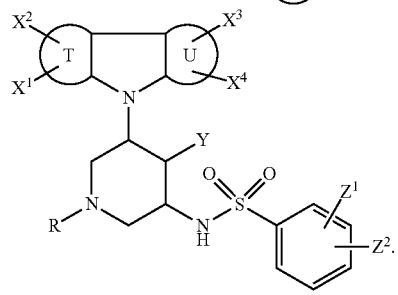
16. A compound according to claim 1, wherein $Z^1$ is hydrogen, and $Z^2$ is hydrogen, fluoro, chloro, trifluoromethyl, —NHBoc, methoxy, or trifluoromethoxy.

17. A compound according to claim 1, wherein V is phenyl.
18. A pharmaceutical composition comprising a pharmaceutically acceptable carrier and a compound according to claim 1.
19. A compound according to claim 1 selected from:
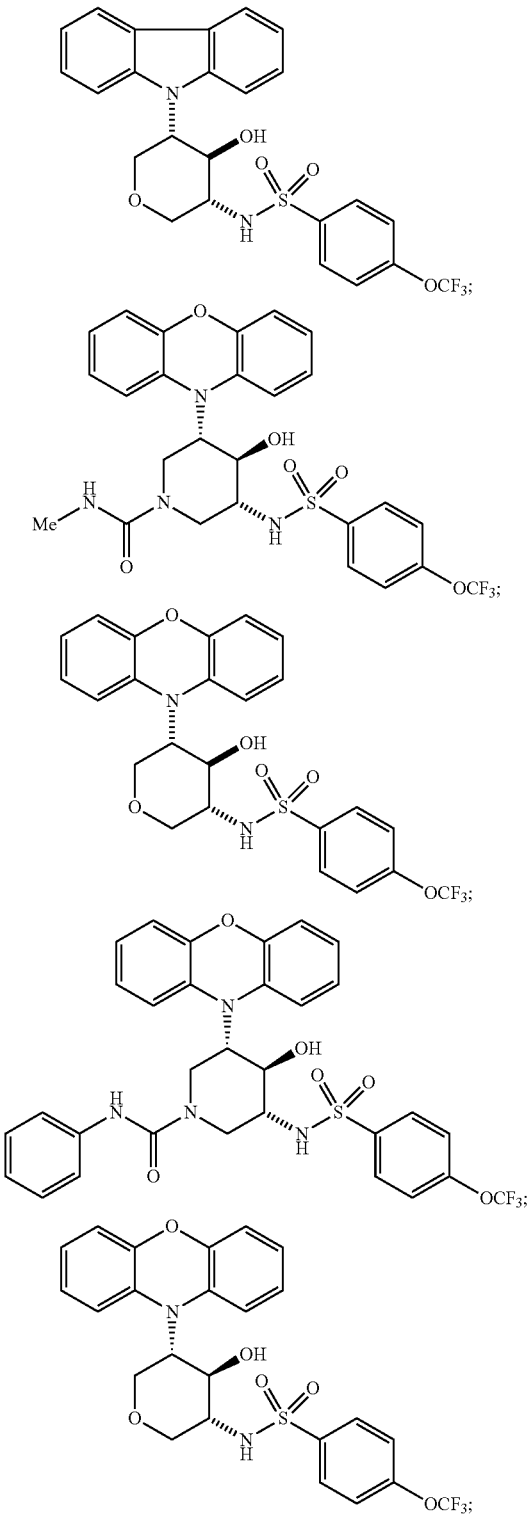
-continued
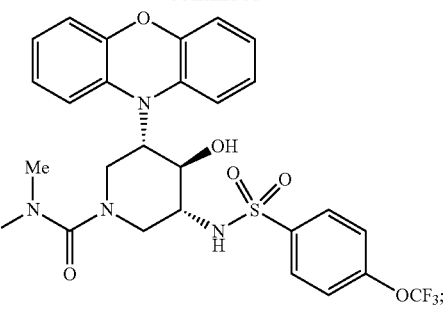
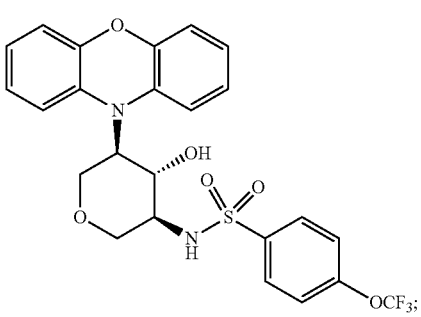
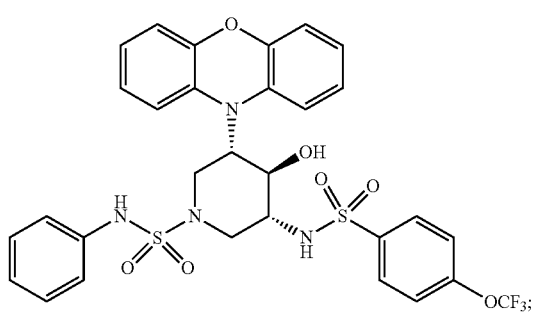
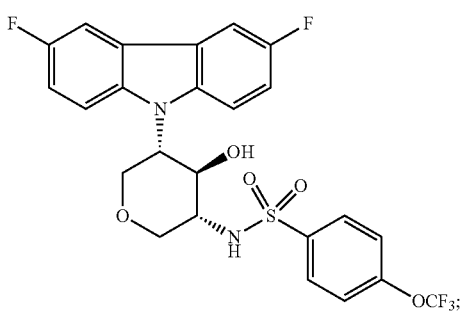
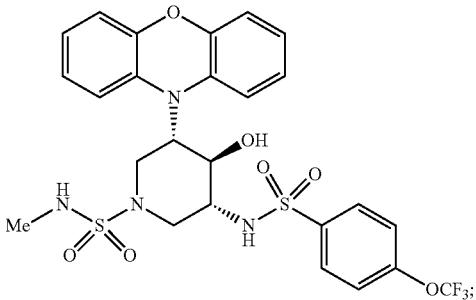

233
-continued
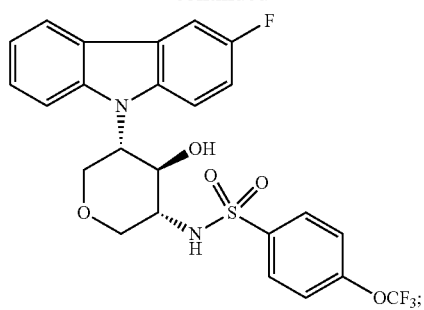
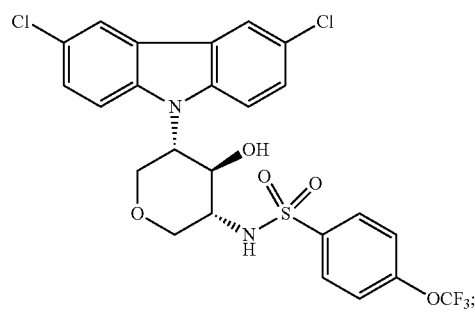
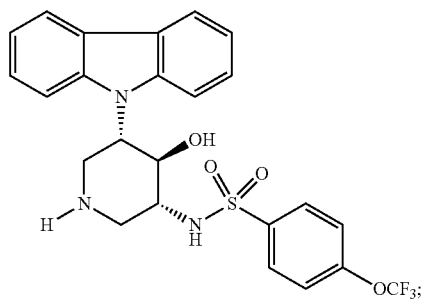
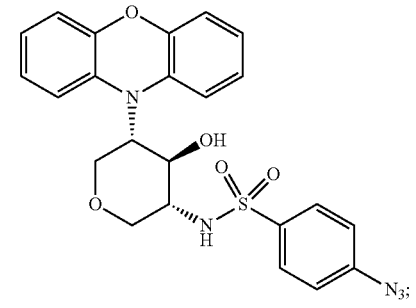
234
-continued
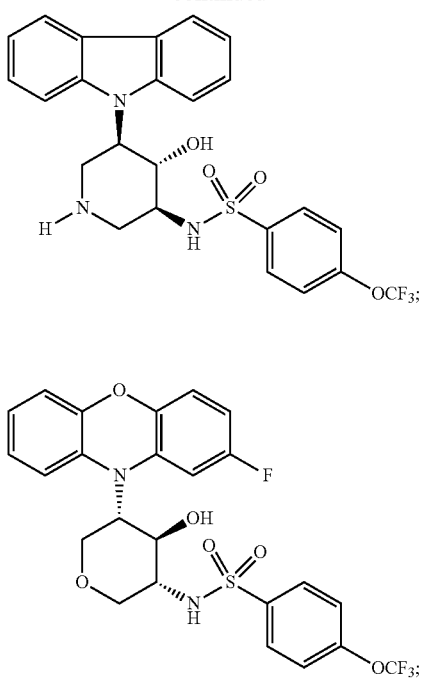
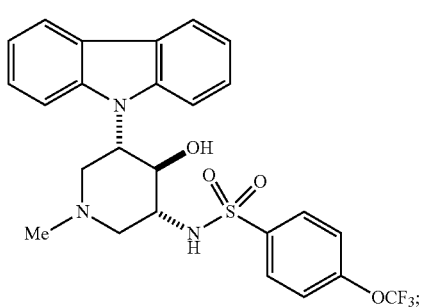
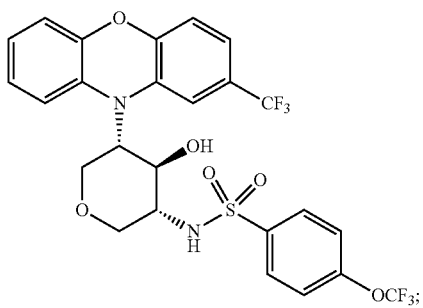
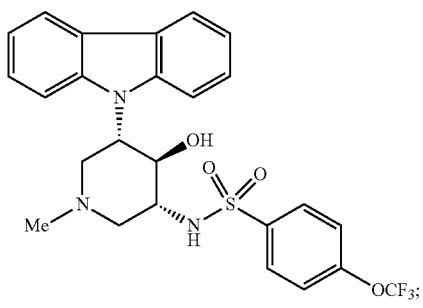

235
-continued
236
-continued
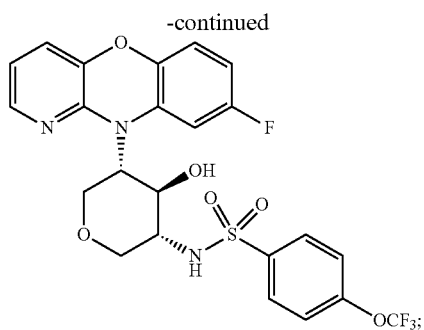
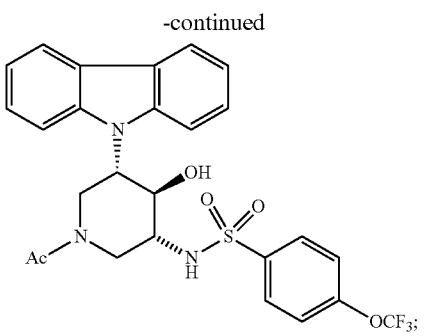

-continued
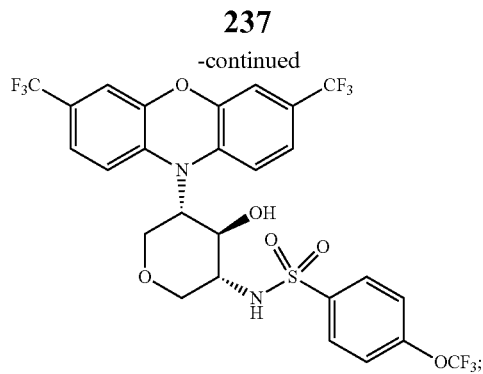
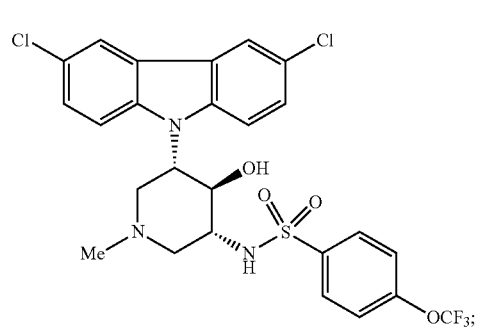
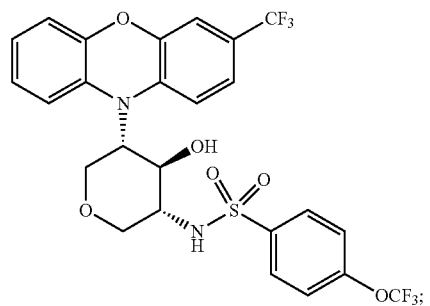
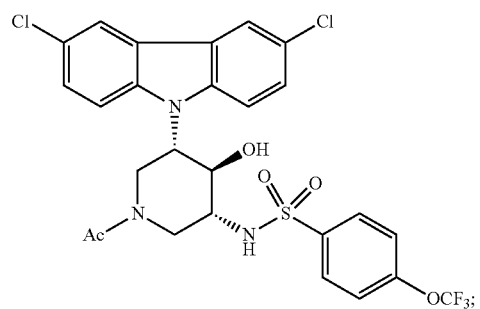
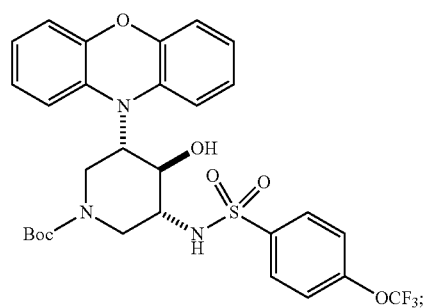
-continued
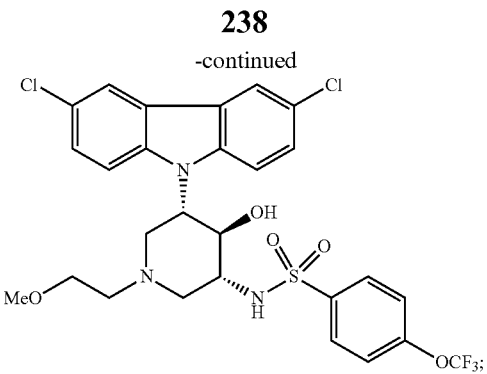
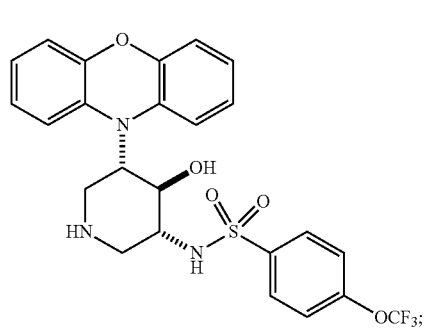
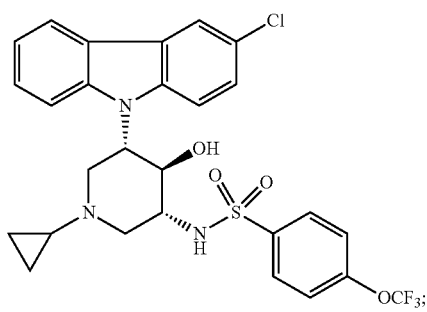
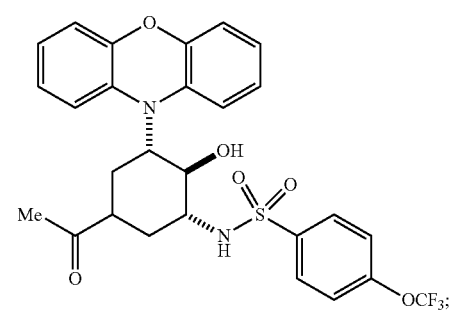
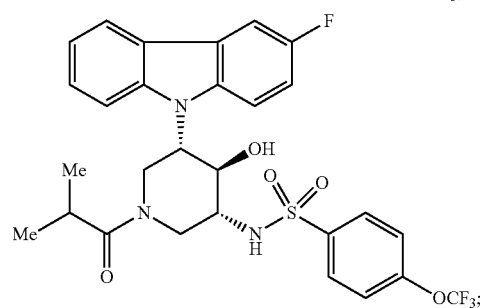

239
-continued
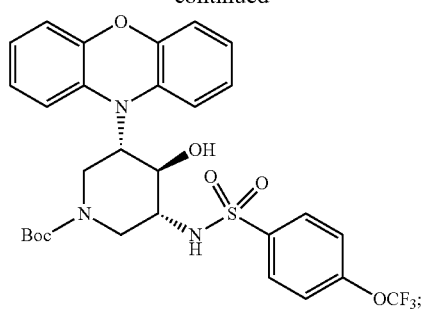
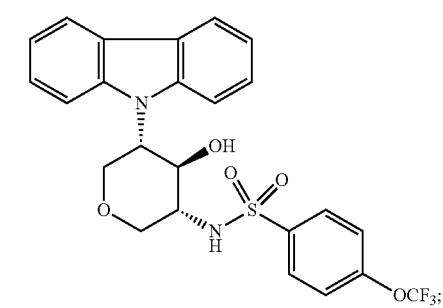
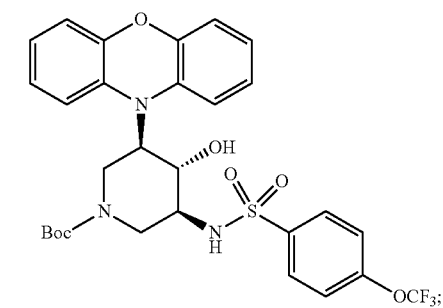
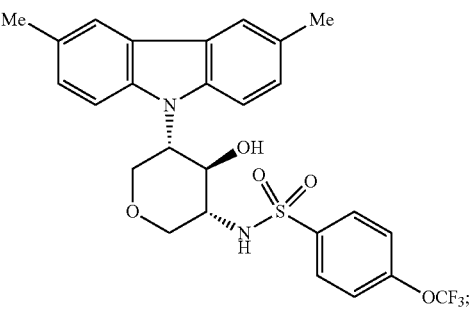
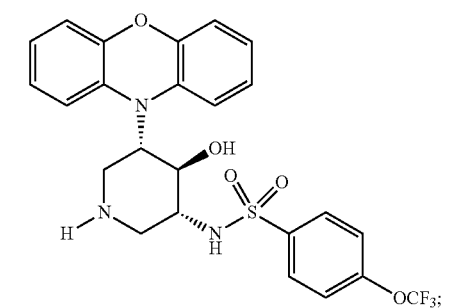
240
-continued
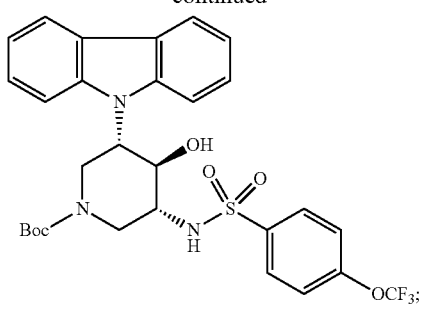
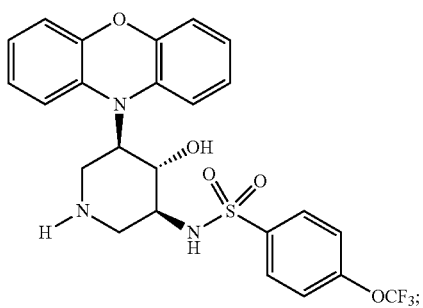
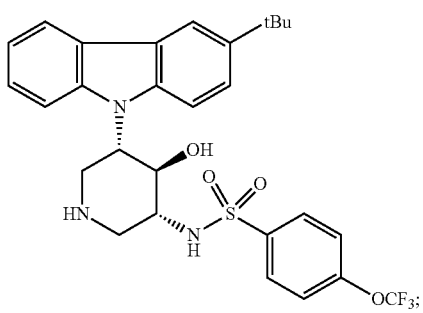
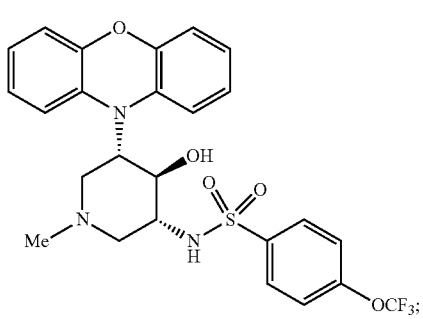
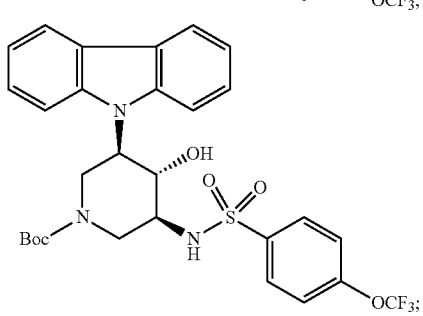

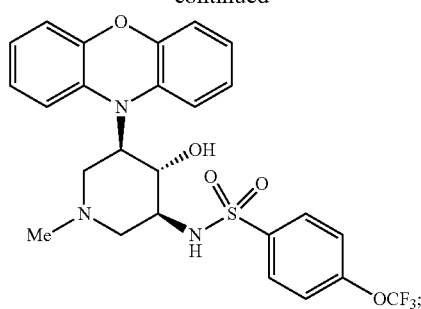
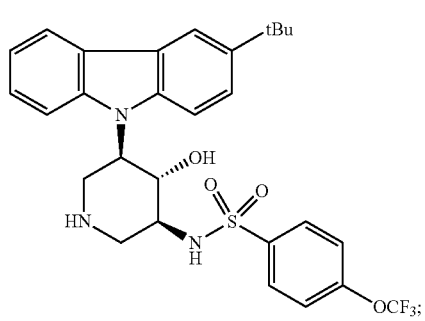
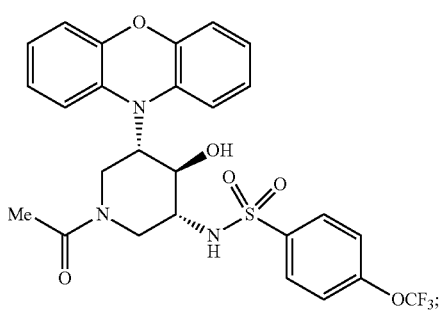
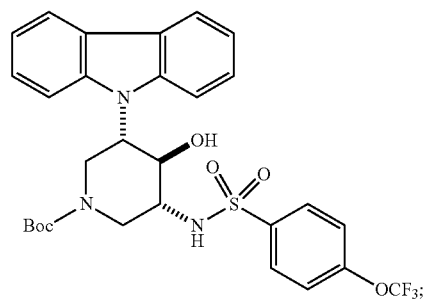
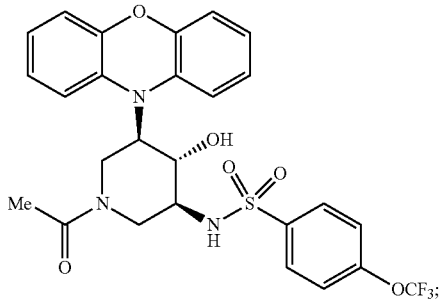
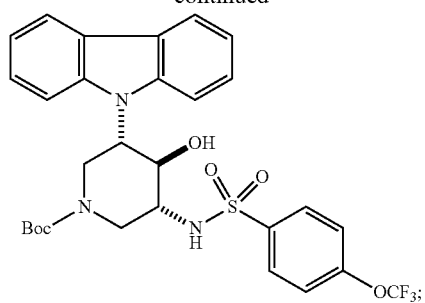
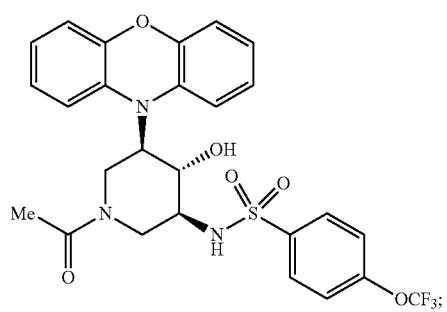
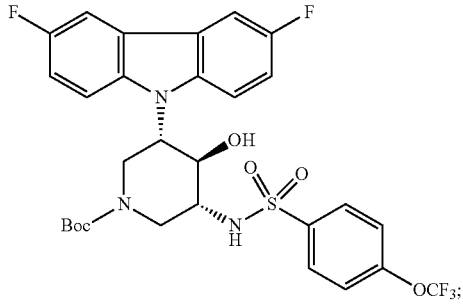
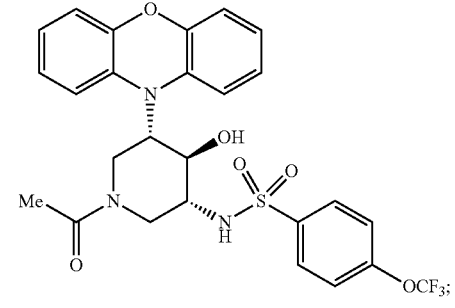
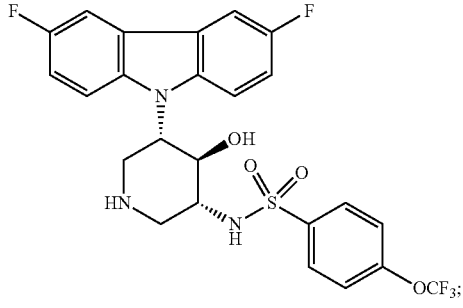

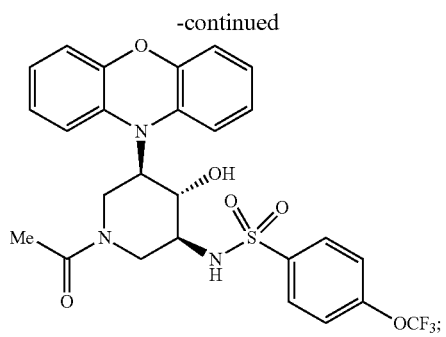
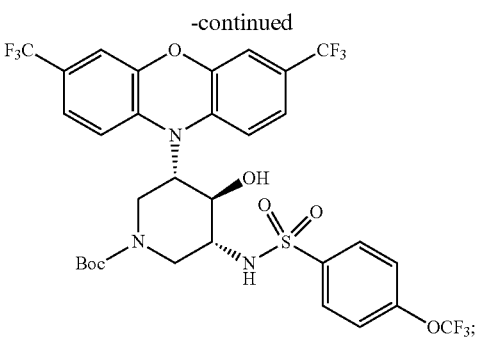
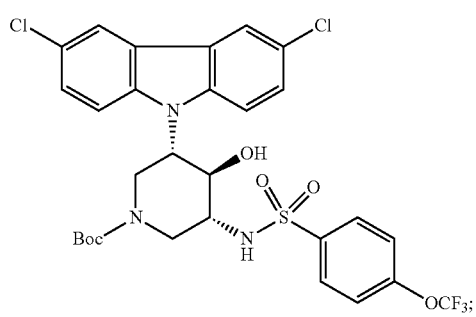
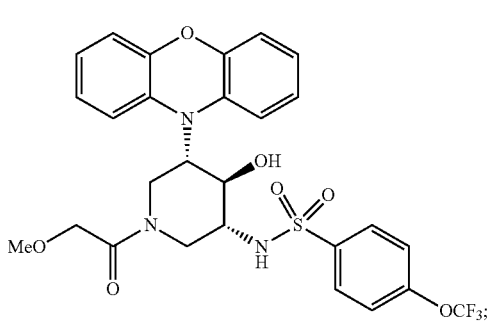
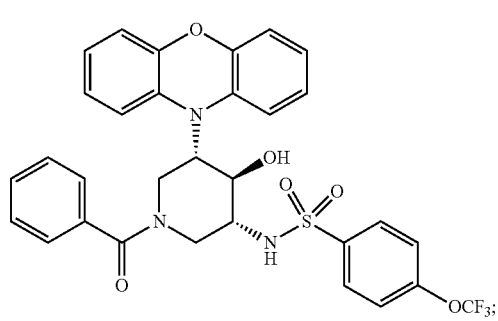
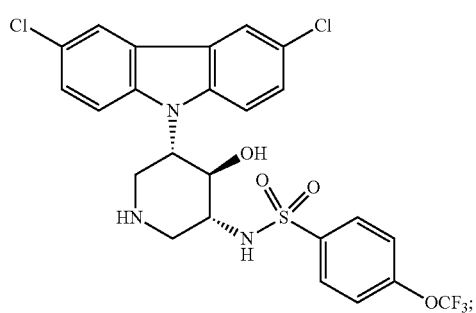
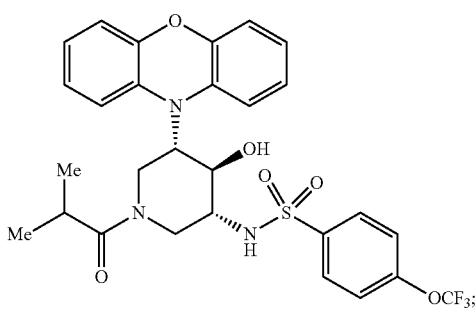

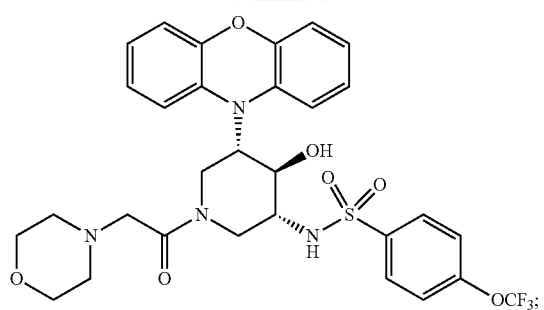
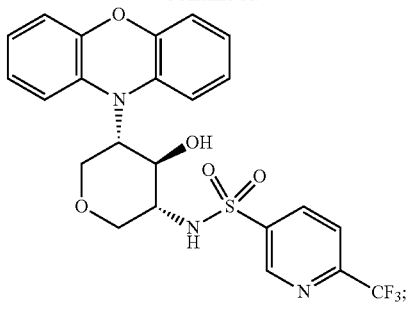
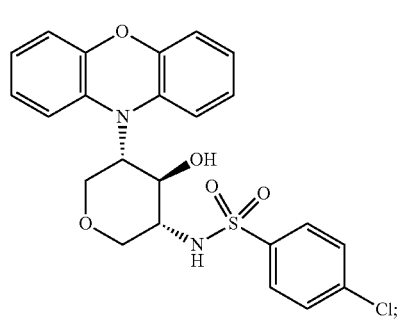
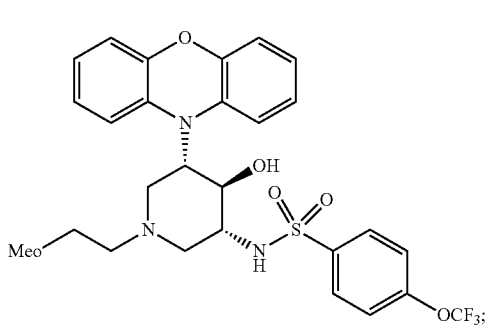
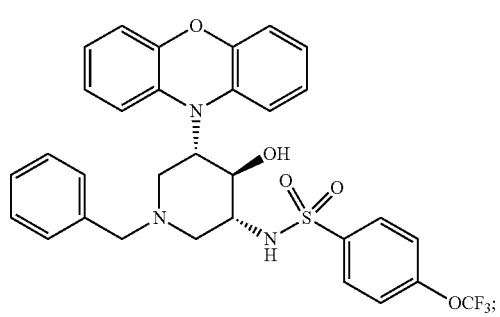
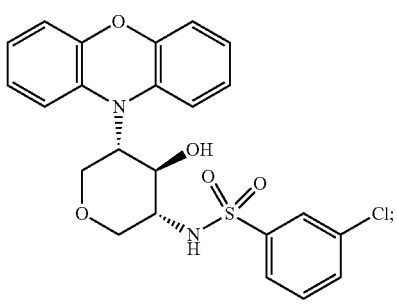
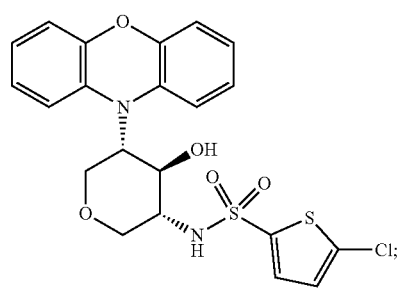
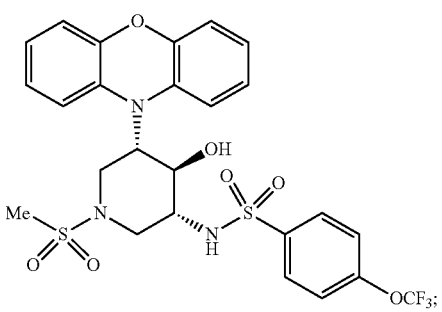
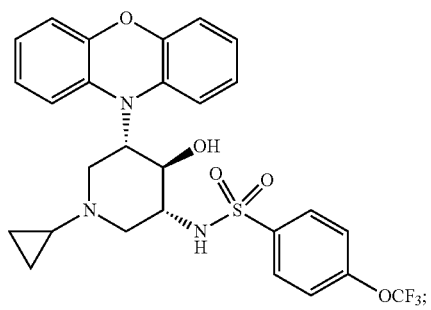
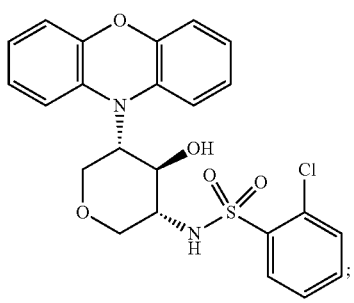

247
-continued
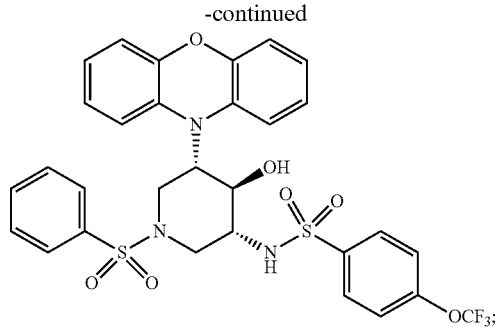
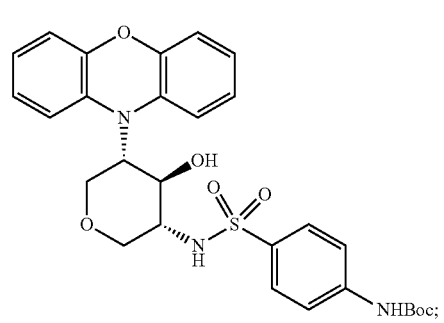
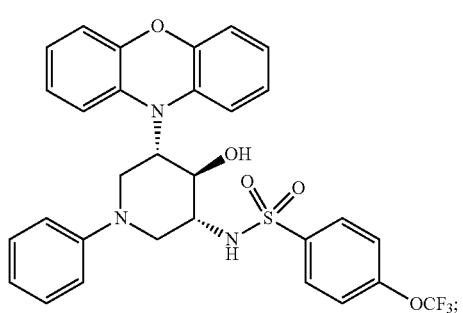
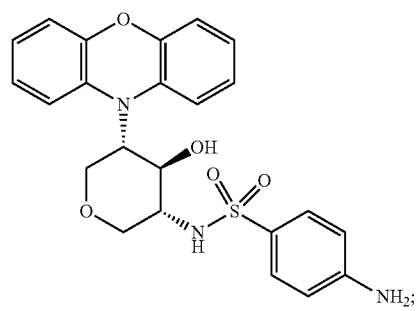
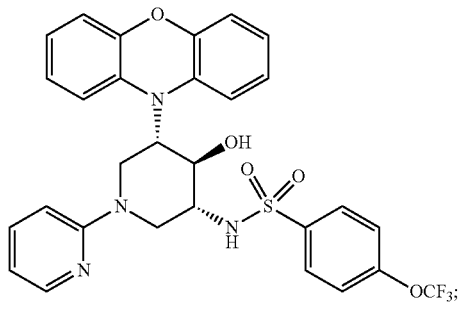
248
-continued
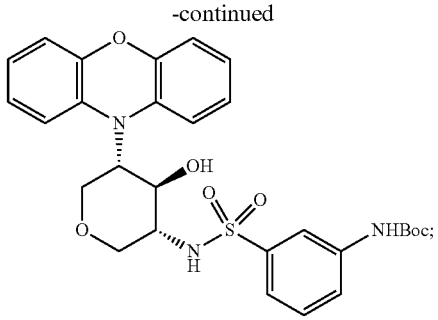
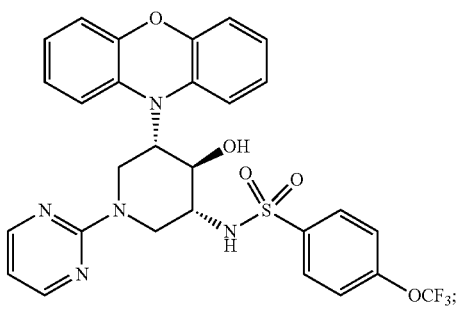
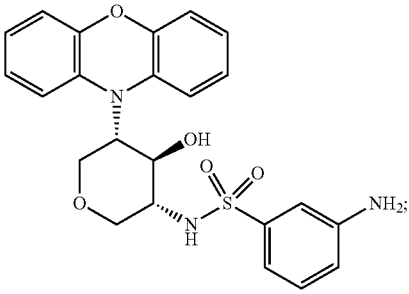
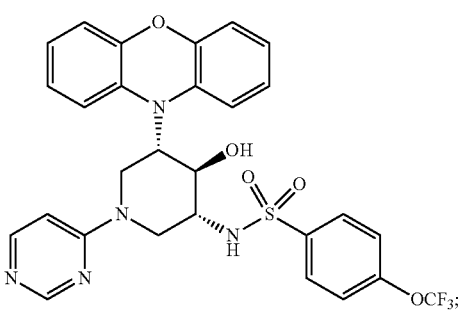
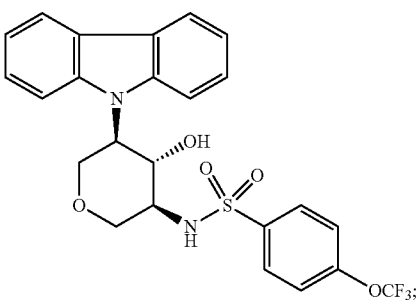

249
-continued
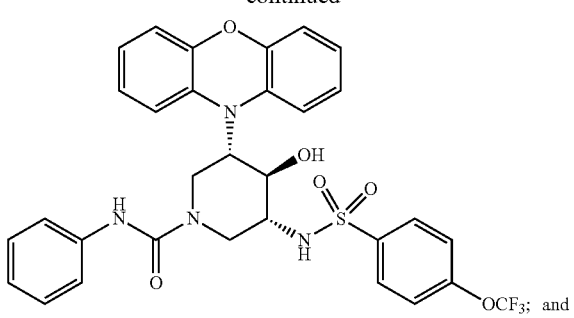
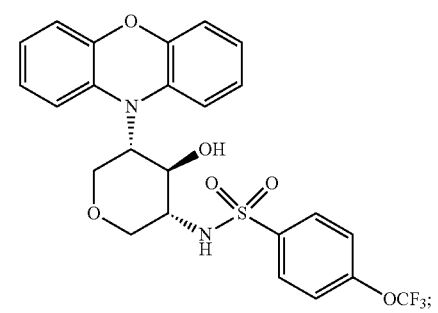
20. A compound according to claim 19 selected from:
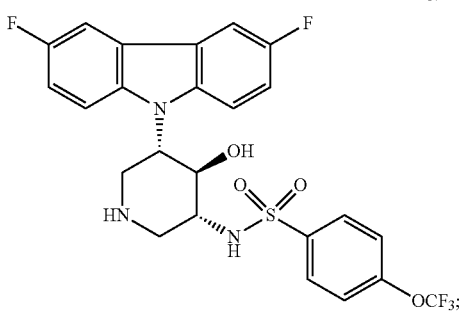
250
-continued
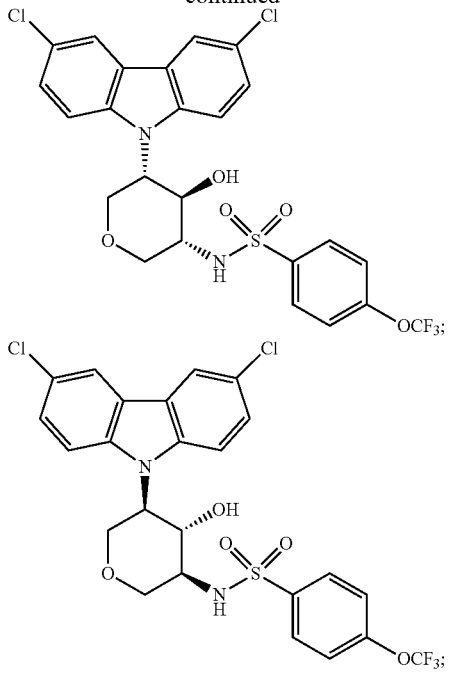
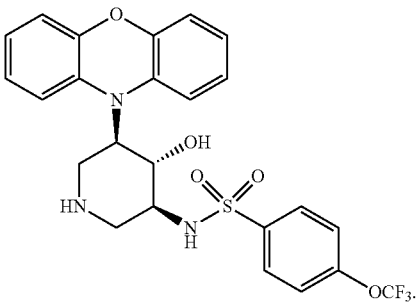
* * * * *

UNITED STATES PATENT AND TRADEMARK OFFICE
CERTIFICATE OF CORRECTION

PATENT NO. : 10,759,790 B2
APPLICATION NO. : 15/758045
DATED : September 1, 2020
INVENTOR(S) : Ohlmeyer et al.

Page 1 of 1

It is certified that error appears in the above-identified patent and that said Letters Patent is hereby corrected as shown below:

Column 227, Line 61: Claim 1, Delete "-$NR^1R^2$, –$C(O)R^1$," and insert -- -$NR^1R^2$, –$OR^1$, –$C(O)R^1$, --

Column 228, Line 36: Claim 1, Delete "-$NR^1C(O)OR^6$, –$C(O)R^1$," and insert -- -$NR^1C(O)OR^6$, –$OR^1$, –$C(O)R^1$, --

Column 228, Line 37: Claim 1, Delete "–$C(O)R^1$, –$SO_2R^1$," and insert -- –$C(O)OR^1$, –$SR^1$, –$SO_2R^1$, --

Signed and Sealed this
Tenth Day of November, 2020

Andrei Iancu
*Director of the United States Patent and Trademark Office*